(12) United States Patent
Brady et al.

(10) Patent No.: US 8,777,976 B2
(45) Date of Patent: Jul. 15, 2014

(54) CLOT CAPTURE SYSTEMS AND ASSOCIATED METHODS

(75) Inventors: Eamon Brady, County Galway (IE); Mahmood Razavi, Irvine, CA (US); David Vale, Galway (IE); John O'Shaughnessy, County Galway (IE)

(73) Assignee: Neuravi Limited, Galaway (IE)

( * ) Notice: Subject to any disclaimer, the term of this patent is extended or adjusted under 35 U.S.C. 154(b) by 0 days.

(21) Appl. No.: 12/737,527

(22) PCT Filed: Jul. 22, 2009

(86) PCT No.: PCT/IE2009/000051
§ 371 (c)(1),
(2), (4) Date: Jan. 21, 2011

(87) PCT Pub. No.: WO2010/010545
PCT Pub. Date: Jan. 28, 2010

(65) Prior Publication Data
US 2011/0125181 A1 May 26, 2011

Related U.S. Application Data

(60) Provisional application No. 61/129,823, filed on Jul. 22, 2008, provisional application No. 61/202,612, filed on Mar. 18, 2009.

(51) Int. Cl.
*A61M 29/00* (2006.01)
*A61B 17/221* (2006.01)
*A61B 17/22* (2006.01)
*A61B 17/00* (2006.01)

(52) U.S. Cl.
CPC ... *A61B 17/22031* (2013.01); *A61B 2017/2212* (2013.01); *A61B 2017/2217* (2013.01); *A61B 17/221* (2013.01); *A61B 2017/22038* (2013.01); *A61B 2017/22035* (2013.01); *A61B 2017/2215* (2013.01); *A61B 2017/22051* (2013.01); *A61B 2017/22094* (2013.01); *A61B 2017/00867* (2013.01)
USPC .......................................... 606/200; 606/127

(58) Field of Classification Search
CPC ...................................................... A61B 17/221
USPC .......................................... 606/113, 127, 200
See application file for complete search history.

(56) References Cited

U.S. PATENT DOCUMENTS

| | | | |
|---|---|---|---|
| 5,011,488 A * | 4/1991 | Ginsburg | 606/159 |
| 5,092,839 A | 3/1992 | Kipperman | |
| 5,171,233 A | 12/1992 | Amplatz | |
| 5,387,219 A | 2/1995 | Rappe | |
| 5,449,372 A | 9/1995 | Schmaltz | |
| 5,658,296 A | 8/1997 | Bates | |
| 5,713,853 A | 2/1998 | Clark | |
| 5,769,871 A | 6/1998 | Mers Kelly | |
| 5,779,716 A | 7/1998 | Cano | |
| 5,810,874 A | 9/1998 | Lefebvre | |
| 5,895,398 A | 4/1999 | Wensel | |
| 5,897,567 A | 4/1999 | Ressemann | |
| 5,904,698 A | 5/1999 | Thomas et al. | |
| 5,911,725 A | 6/1999 | Boury | |
| 5,935,139 A | 8/1999 | Bates | |
| 5,947,995 A | 9/1999 | Samuels | |
| 6,066,158 A | 5/2000 | Engelson | |
| 6,096,053 A | 8/2000 | Bates | |
| 6,099,534 A | 8/2000 | Bates | |
| 6,102,932 A | 8/2000 | Kurz | |
| 6,129,739 A | 10/2000 | Khosravi | |
| 6,146,404 A | 11/2000 | Kim | |
| 6,165,194 A | 12/2000 | Denardo | |
| 6,165,199 A | 12/2000 | Barbut | |
| 6,168,604 B1 | 1/2001 | Cano | |
| 6,179,861 B1 | 1/2001 | Khosravi | |
| 6,203,561 B1 | 3/2001 | Ramee | |
| 6,214,026 B1 | 4/2001 | Lepak | |
| 6,221,006 B1 | 4/2001 | Dubrul | |
| 6,238,412 B1 | 5/2001 | Dubrul | |
| 6,245,087 B1 | 6/2001 | Addis | |
| 6,251,122 B1 | 6/2001 | Tsukernik | |
| 6,264,663 B1 | 7/2001 | Cano | |
| 6,312,444 B1 | 11/2001 | Barbut | |
| 6,348,056 B1 | 2/2002 | Bates | |
| 6,350,271 B1 | 2/2002 | Kurz et al. | |
| 6,383,206 B1 | 5/2002 | Gillick | |
| 6,402,771 B1 | 6/2002 | Palmer | |

| | | |
|---|---|---|
| 6,416,541 B2 | 7/2002 | Denardo |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,530,935 B2 | 3/2003 | Wensel |
| 6,530,939 B1 | 3/2003 | Hopkins |
| 6,544,279 B1 | 4/2003 | Hopkins |
| 6,582,448 B1 | 6/2003 | Boyle |
| 6,592,616 B1 | 7/2003 | Stack |
| 6,602,271 B2 | 8/2003 | Adams |
| 6,610,077 B1 * | 8/2003 | Hancock et al. ............. 606/200 |
| 6,616,679 B1 | 9/2003 | Khosravi |
| 6,638,245 B2 | 10/2003 | Miller |
| 6,656,218 B1 | 12/2003 | Denardo et al. |
| 6,660,021 B1 | 12/2003 | Palmer et al. |
| 6,663,650 B2 | 12/2003 | Sepetka |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,913,612 B2 | 7/2005 | Palmer |
| 6,913,618 B2 | 7/2005 | Denardo et al. |
| 6,989,019 B2 | 1/2006 | Mazzocchi |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,220,271 B2 | 5/2007 | Clubb |
| 7,288,112 B2 | 10/2007 | Denardo et al. |
| 7,306,618 B2 | 12/2007 | Demond |
| 7,323,001 B2 | 1/2008 | Clubb |
| 7,410,491 B2 | 8/2008 | Hopkins |
| 7,452,496 B2 * | 11/2008 | Brady et al. ............. 264/573 |
| 7,534,252 B2 | 5/2009 | Sepetka |
| 7,556,636 B2 | 7/2009 | Mazzocchi |
| 7,594,926 B2 | 9/2009 | Linder |
| 7,618,434 B2 | 11/2009 | Santra |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,828,815 B2 | 11/2010 | Mazzocchi |
| 7,828,816 B2 | 11/2010 | Mazzocchi et al. |
| 7,850,708 B2 | 12/2010 | Pal |
| 7,922,732 B2 | 4/2011 | Mazzocchi |
| 7,927,784 B2 | 4/2011 | Simpson |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 2001/0001315 A1 | 5/2001 | Bates |
| 2001/0016755 A1 | 8/2001 | Addis |
| 2001/0051810 A1 | 12/2001 | Dubrul |
| 2002/0016609 A1 | 2/2002 | Wensel |
| 2002/0022859 A1 | 2/2002 | Hogendijk |
| 2002/0026211 A1 | 2/2002 | Khosravi |
| 2002/0052620 A1 | 5/2002 | Barbut |
| 2002/0068954 A1 | 6/2002 | Foster |
| 2002/0072764 A1 | 6/2002 | Sepetka |
| 2002/0082558 A1 | 6/2002 | Samson |
| 2002/0123765 A1 | 9/2002 | Sepetka |
| 2002/0156455 A1 | 10/2002 | Barbut |
| 2002/0161393 A1 | 10/2002 | Demond |
| 2002/0188276 A1 | 12/2002 | Evans |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0050663 A1 | 3/2003 | Khachin |
| 2003/0144687 A1 | 7/2003 | Brady et al. |
| 2003/0153944 A1 | 8/2003 | Phung |
| 2003/0163064 A1 | 8/2003 | Vrba |
| 2003/0171769 A1 | 9/2003 | Barbut |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0236533 A1 | 12/2003 | Wilson |
| 2004/0068288 A1 | 4/2004 | Palmer |
| 2004/0073243 A1 | 4/2004 | Sepetka |
| 2004/0079429 A1 | 4/2004 | Miller |
| 2004/0133231 A1 | 7/2004 | Maitland |
| 2004/0153118 A1 | 8/2004 | Clubb |
| 2005/0033348 A1 | 2/2005 | Sepetka |
| 2005/0049619 A1 | 3/2005 | Sepetka |
| 2005/0049669 A1 | 3/2005 | Jones |
| 2005/0055033 A1 * | 3/2005 | Leslie et al. ............. 606/127 |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0125024 A1 | 6/2005 | Sepetka |
| 2005/0171566 A1 * | 8/2005 | Kanamaru ............. 606/159 |
| 2005/0216030 A1 | 9/2005 | Sepetka |
| 2005/0216050 A1 | 9/2005 | Sepetka |
| 2005/0288686 A1 | 12/2005 | Sepetka |
| 2006/0058836 A1 | 3/2006 | Bose |
| 2006/0058837 A1 | 3/2006 | Bose |
| 2006/0058838 A1 | 3/2006 | Bose |
| 2006/0155305 A1 | 7/2006 | Freudenthal |
| 2006/0195137 A1 | 8/2006 | Sepetka |
| 2002/0224177 | 10/2006 | Finitsis |
| 2006/0224179 A1 | 10/2006 | Kucharczyk |
| 2007/0156170 A1 | 7/2007 | Hancock |
| 2007/0165170 A1 | 7/2007 | Fukuda |
| 2007/0198028 A1 | 8/2007 | Miloslavski |
| 2007/0198051 A1 * | 8/2007 | Clubb et al. ............. 606/200 |
| 2007/0208367 A1 | 9/2007 | Fiorella |
| 2007/0208371 A1 | 9/2007 | French |
| 2007/0225749 A1 | 9/2007 | Martin |
| 2007/0244505 A1 | 10/2007 | Gilson et al. |
| 2008/0091223 A1 | 4/2008 | Pokorney |
| 2008/0109031 A1 | 5/2008 | Sepetka |
| 2008/0109032 A1 | 5/2008 | Sepetka |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0200946 A1 | 8/2008 | Braun |
| 2008/0215077 A1 | 9/2008 | Sepetka |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275493 A1 | 11/2008 | Farmiga |
| 2008/0312681 A1 | 12/2008 | Ansel |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0292297 A1 | 11/2009 | Ferrere |
| 2009/0292307 A1 | 11/2009 | Razack |
| 2009/0299393 A1 | 12/2009 | Martin |
| 2009/0306702 A1 | 12/2009 | Miloslavski |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |

| | | | |
|---|---|---|---|
| 2010/0268265 A1 | 10/2010 | Krolik et al. | |
| 2010/0318178 A1 | 12/2010 | Rapaport et al. | |
| 2010/0331949 A1 | 12/2010 | Habib | |
| 2011/0009875 A1 | 1/2011 | Grandfield et al. | |
| 2011/0009940 A1 | 1/2011 | Grandfield et al. | |
| 2011/0054514 A1 | 3/2011 | Arcand | |
| 2011/0054516 A1 | 3/2011 | Keegan | |
| 2011/0060359 A1 | 3/2011 | Hannes | |
| 2011/0152920 A1 | 6/2011 | Eckhouse et al. | |
| 2011/0202088 A1 | 8/2011 | Eckhouse et al. | |
| 2011/0276120 A1 | 11/2011 | Gilson et al. | |
| 2012/0041449 A1 | 2/2012 | Eckhouse et al. | |
| 2012/0041474 A1 | 2/2012 | Eckhouse et al. | |
| 2012/0089216 A1 | 4/2012 | Rapaport et al. | |
| 2012/0165858 A1 | 6/2012 | Eckhouse et al. | |
| 2012/0165859 A1 | 6/2012 | Eckhouse et al. | |
| 2013/0144326 A1 | 6/2013 | Brady et al. | |
| 2013/0184739 A1 | 7/2013 | Brady et al. | |
| 2013/0197567 A1 | 8/2013 | Brady et al. | |
| 2013/0345739 A1 | 12/2013 | Brady et al. | |

FOREIGN PATENT DOCUMENTS

| | | | |
|---|---|---|---|
| DE | 10 2010 014778 A1 | 10/2011 | |
| WO | 94/24926 | 11/1994 | |
| WO | 97/27808 | 8/1997 | |
| WO | 99/20335 | 4/1999 | |
| WO | 99/60933 | 12/1999 | |
| WO | 01/21077 | 3/2001 | |
| WO | 02/02162 | 1/2002 | |
| WO | 02/11627 | 2/2002 | |
| WO | 02/43616 | 6/2002 | |
| WO | 02/070061 | 9/2002 | |
| WO | 02/094111 | 11/2002 | |
| WO | 03/002006 | 1/2003 | |
| WO | 03/030751 | 4/2003 | |
| WO | 03/051448 | 6/2003 | |
| WO | 2006/021407 | 3/2006 | |
| WO | 2006/031410 | 3/2006 | |
| WO | 2006/107641 | 10/2006 | |
| WO | 2007/054307 | 5/2007 | |
| WO | 2007/068424 | 6/2007 | |
| WO | 2008/034615 | 3/2008 | |
| WO | 2008/131116 | 10/2008 | |
| WO | 2009/076482 | 6/2009 | |
| WO | 2009/086482 | 7/2009 | |
| WO | WO 2010/010545 A1 | 1/2010 | |
| WO | WO 2010/046897 A1 | 4/2010 | |
| WO | WO 2010/146581 A1 | 12/2010 | |
| WO | WO 2011/013556 A1 | 2/2011 | |
| WO | WO 2011/095352 A1 | 8/2011 | |
| WO | WO 2012/052982 A1 | 4/2012 | |
| WO | WO 2012/081020 A1 | 6/2012 | |
| WO | WO 2012/120490 A2 | 9/2012 | |
| WO | WO 2013/109756 A2 | 7/2013 | |

OTHER PUBLICATIONS

International Search Report of PCT/IE2012/000011, dated Oct. 10, 2012, 3 pages.
Written Opinion and International Search Report, dated Jul. 27, 2011, from international Application No. PCT/IE2011/000026.
International Search Report of PCT/IE2011/000057, dated Feb. 3, 2012.
Advisory Action in co-pending U.S. Appl. No. 13/662,299, dated Jan. 27, 2014 (3 pages).
Office Action in co-pending U.S. Appl. No. 13/662,299, dated Dec. 16, 2013 (10 pages).
Office Action in co-pending U.S. Appl. No. 13/662,299, dated Mar. 12, 2013 (10 pages).
US 6,348,062, 02/2002, Hopkins (withdrawn)

* cited by examiner

*Primary Examiner* — Darwin Erezo
*Assistant Examiner* — Diane Yabut
(74) *Attorney, Agent, or Firm* — Bookoff McAndrews, PLLC

(57) ABSTRACT

A clot capture system for disengaging a clot 2001 from a vessel wall 2002 and removing the clot 2001 from the vessel 202, includes a clot capture device 2140 for placement on a distal side of a clot 2001. The clot capture device 2140 has a retracted delivery configuration and an expanded deployed configuration. The clot removal device has a proximal support frame 2012, and a distal fiber net 2130. The support frame 2012 has a retracted delivery configuration and an expanded deployed configuration. The proximal support frame 2012 in the expanded configuration defines a proximal inlet mouth for engaging a clot 2001 and a net 2130 for confining the clot 2001. An elongate member facilitates capture and/or withdrawal of a clot 2001 from a vessel 2002. The system also includes a clot debonding device 2091 for placement on a proximal side of a clot 2001. The clot debonding device 2091 has a retracted delivery configuration and an expanded deployed configuration and includes a clot engagement element 2112 which defines a distal abutment in the deployed configuration for urging a clot 2001 into the clot capture device 2140.

16 Claims, 91 Drawing Sheets

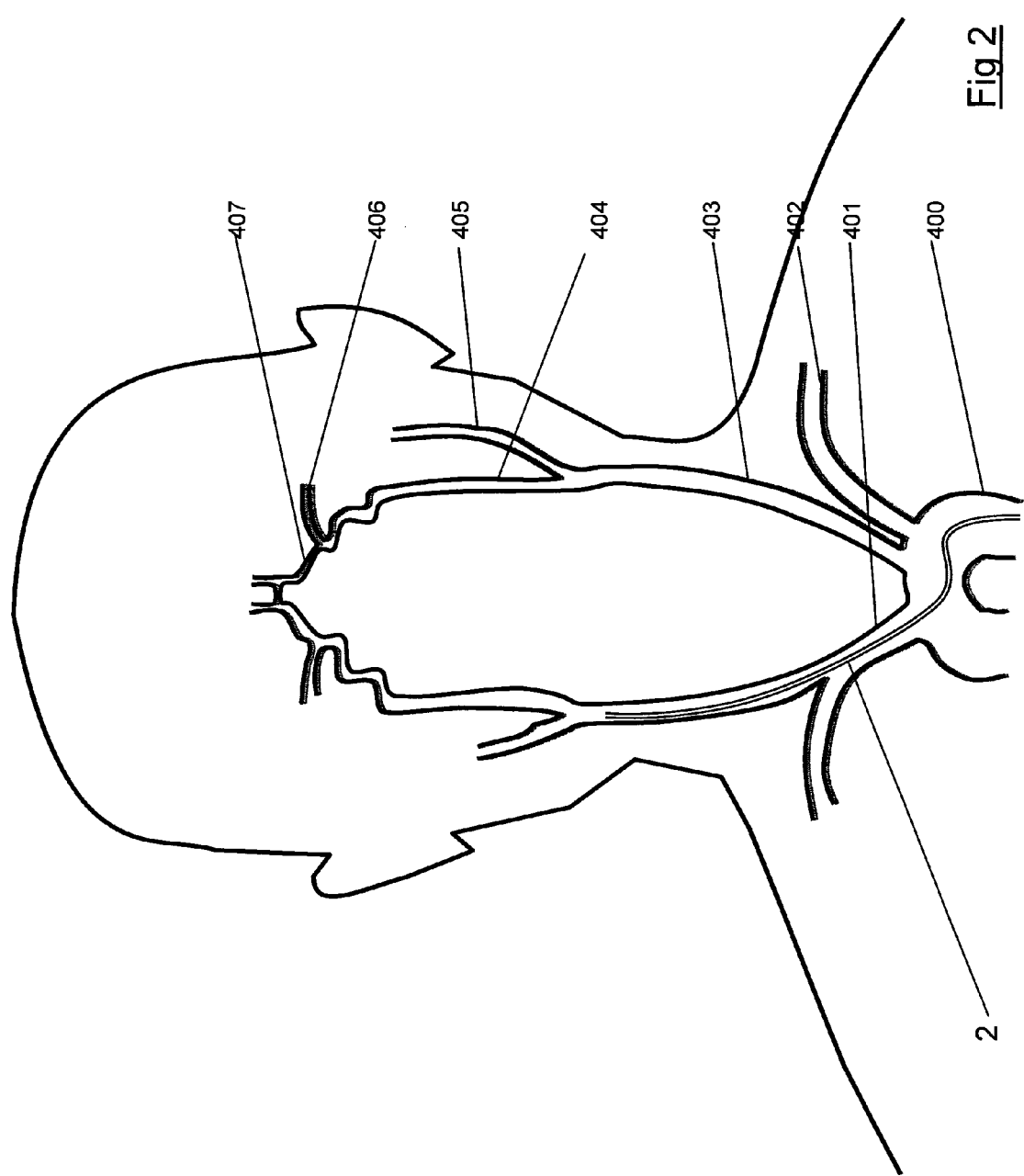

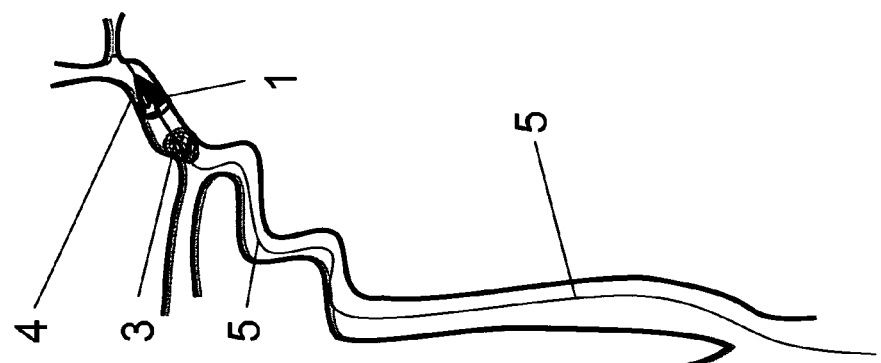
Fig. 3.d
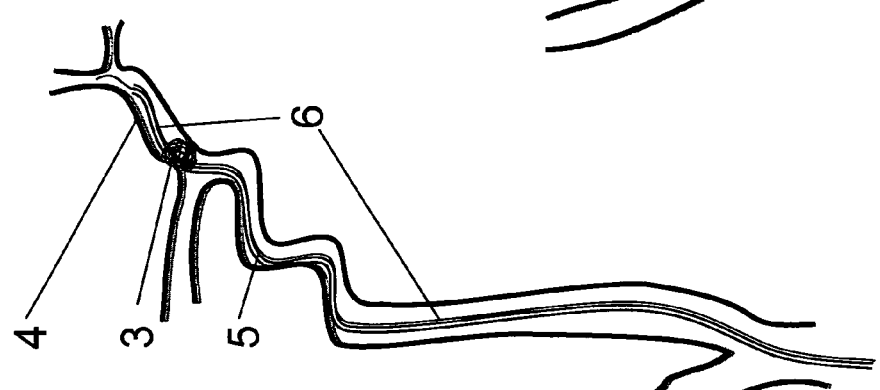
Fig. 3c
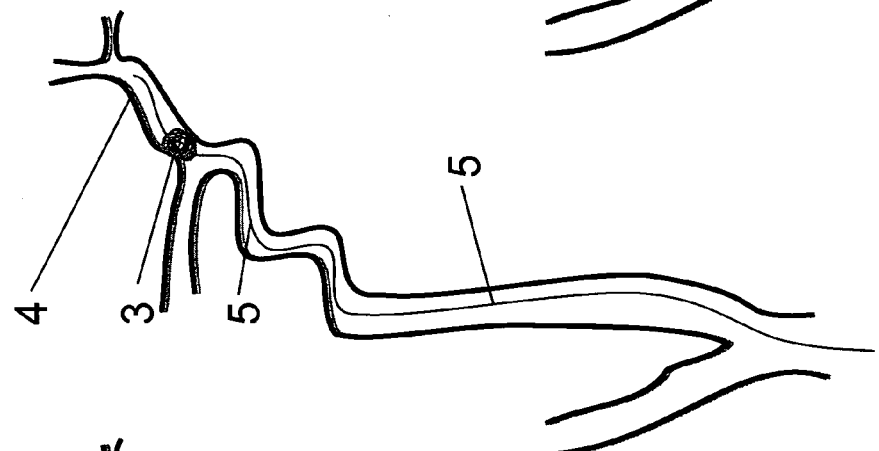
Fig. 3b
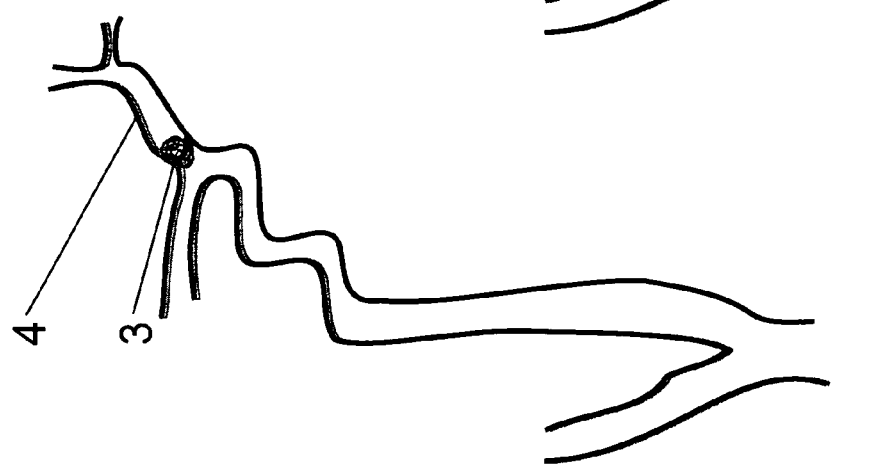
Fig 3a

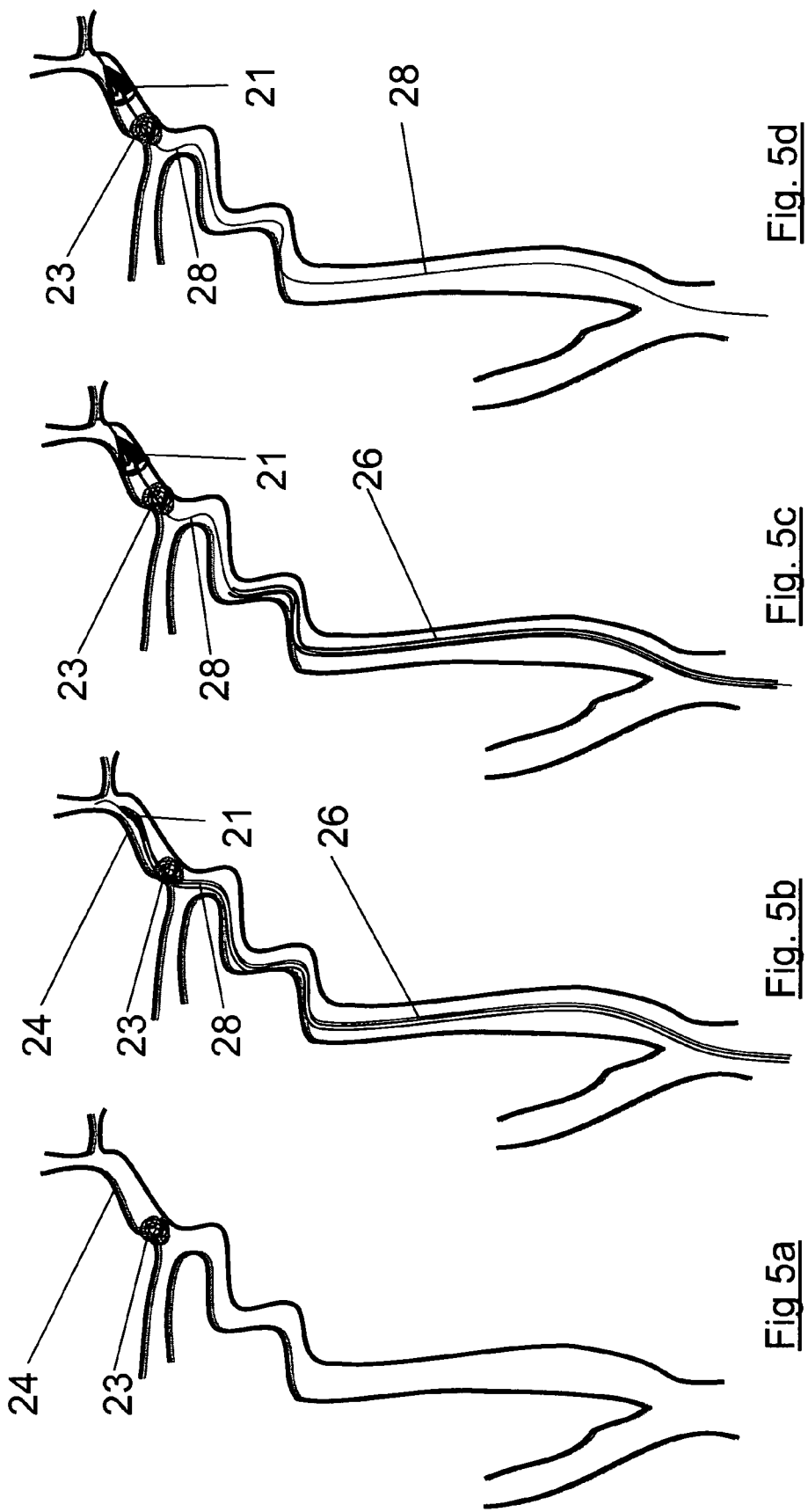

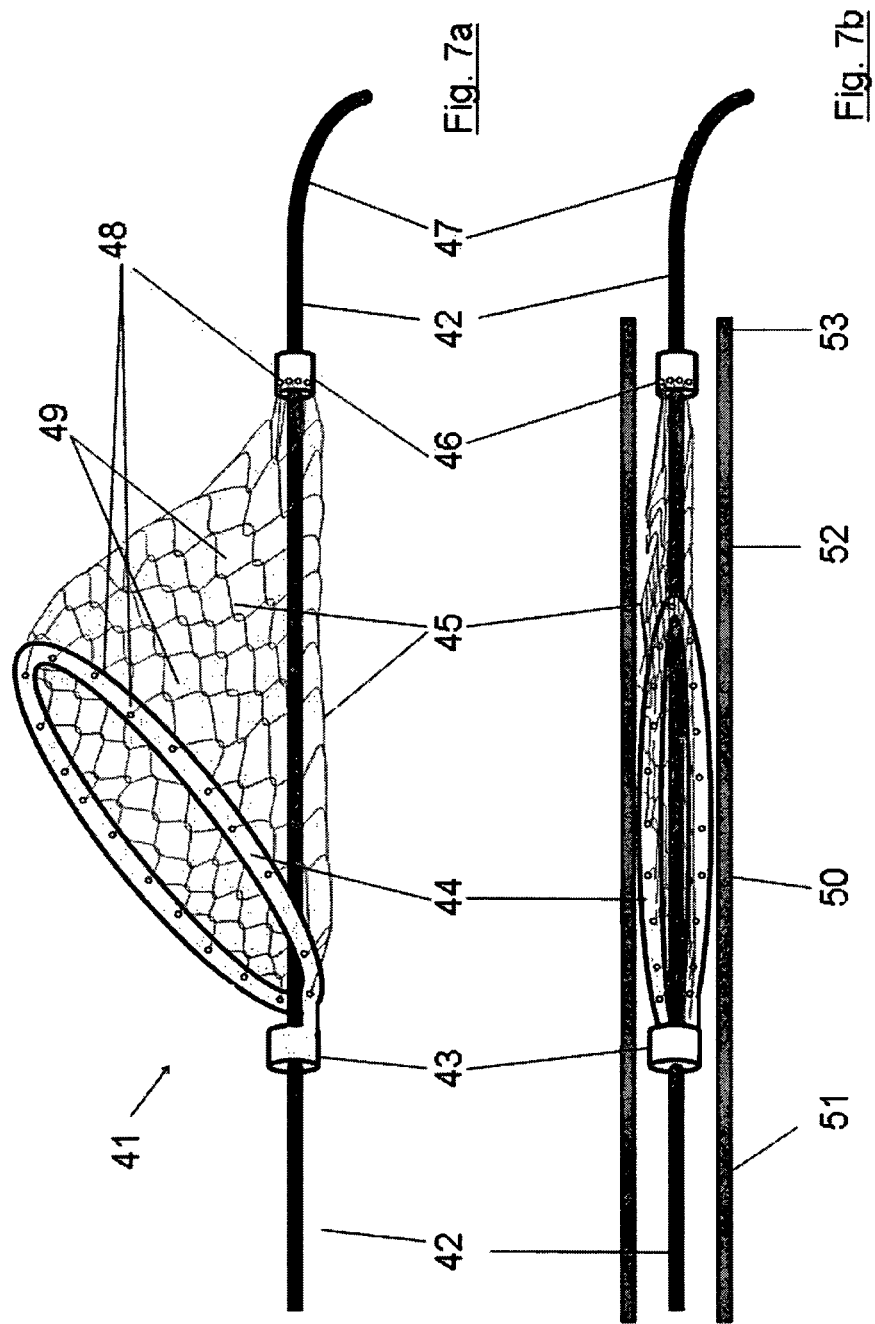

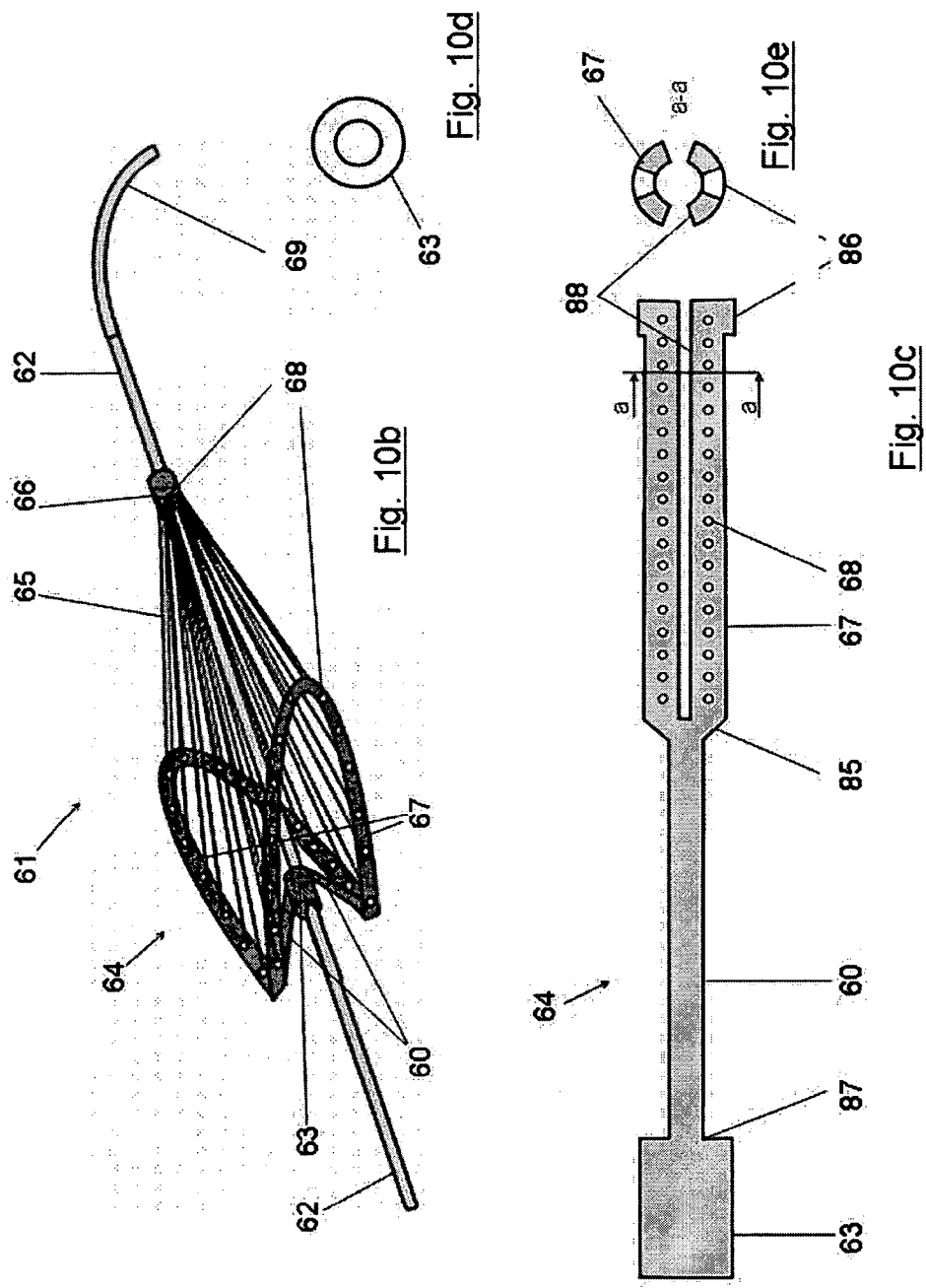

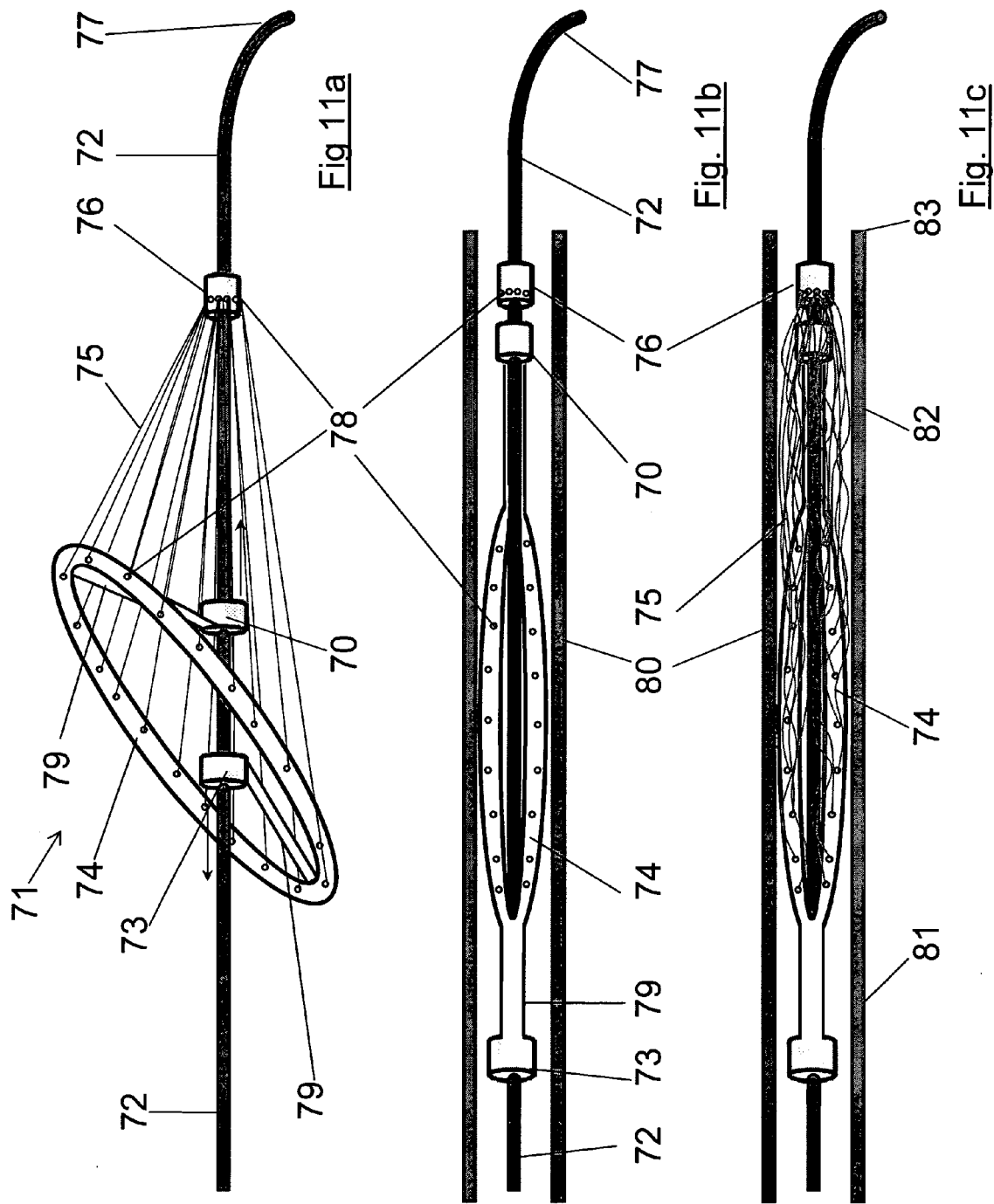

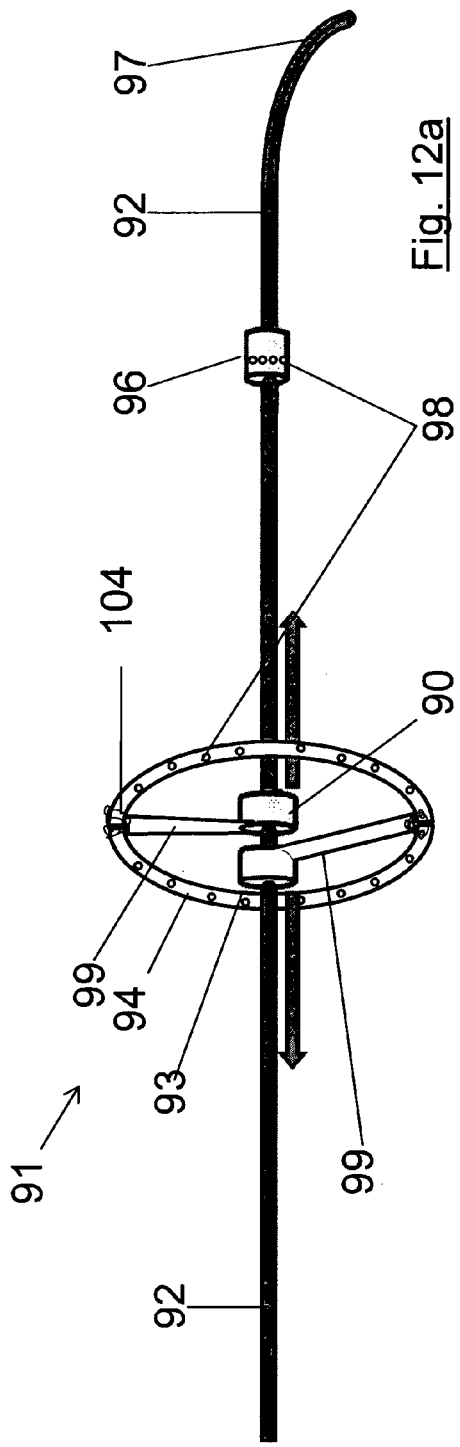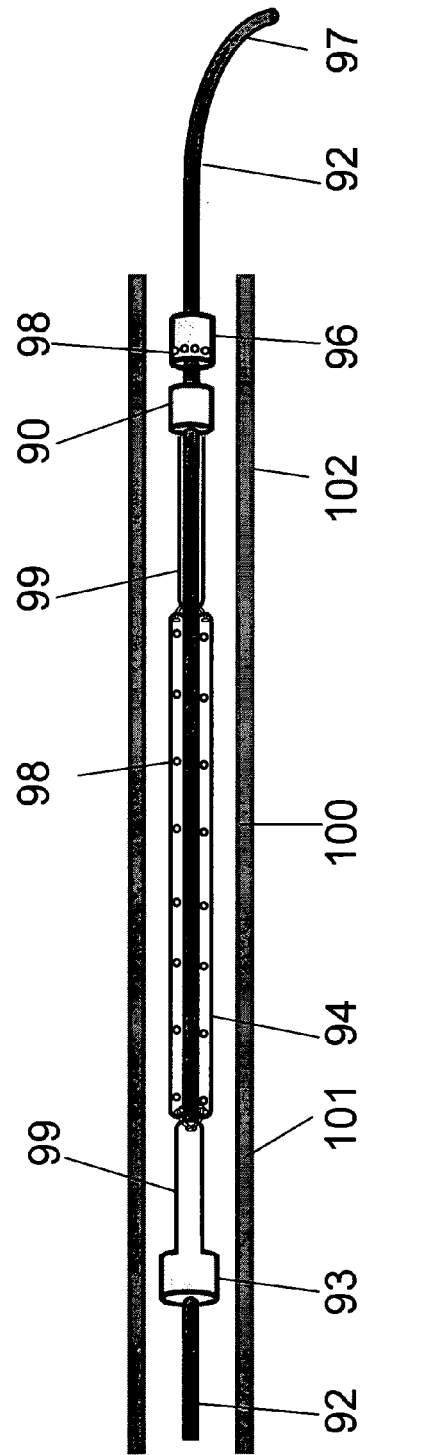
Fig. 12a
Fig. 12b

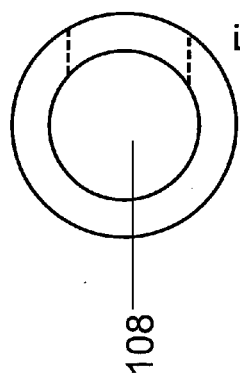
Fig. 13d
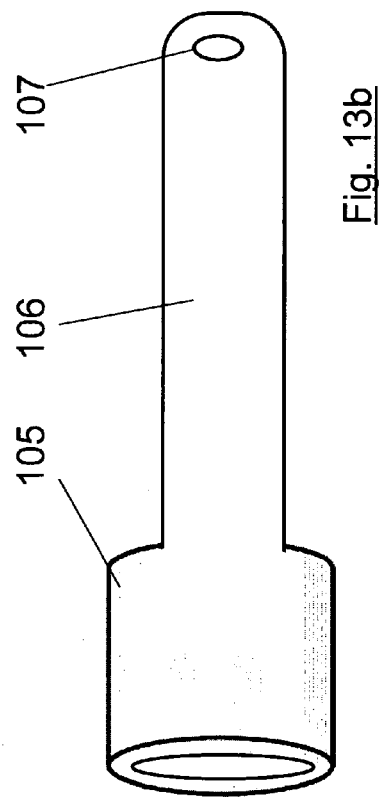
Fig. 13b
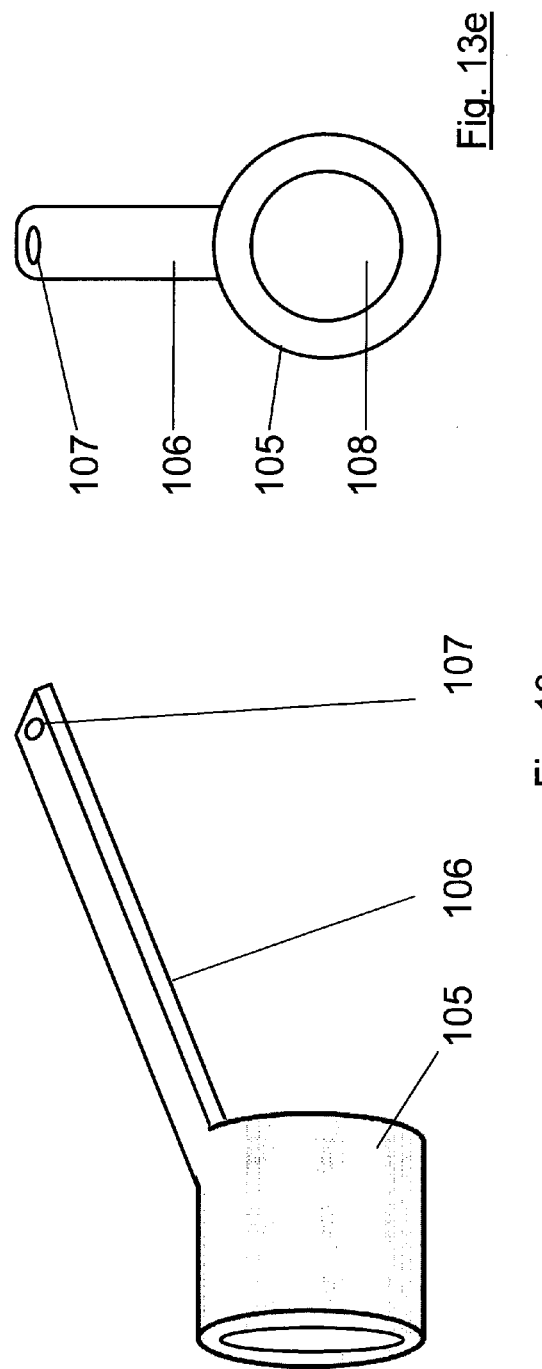
Fig. 13e
Fig. 13c

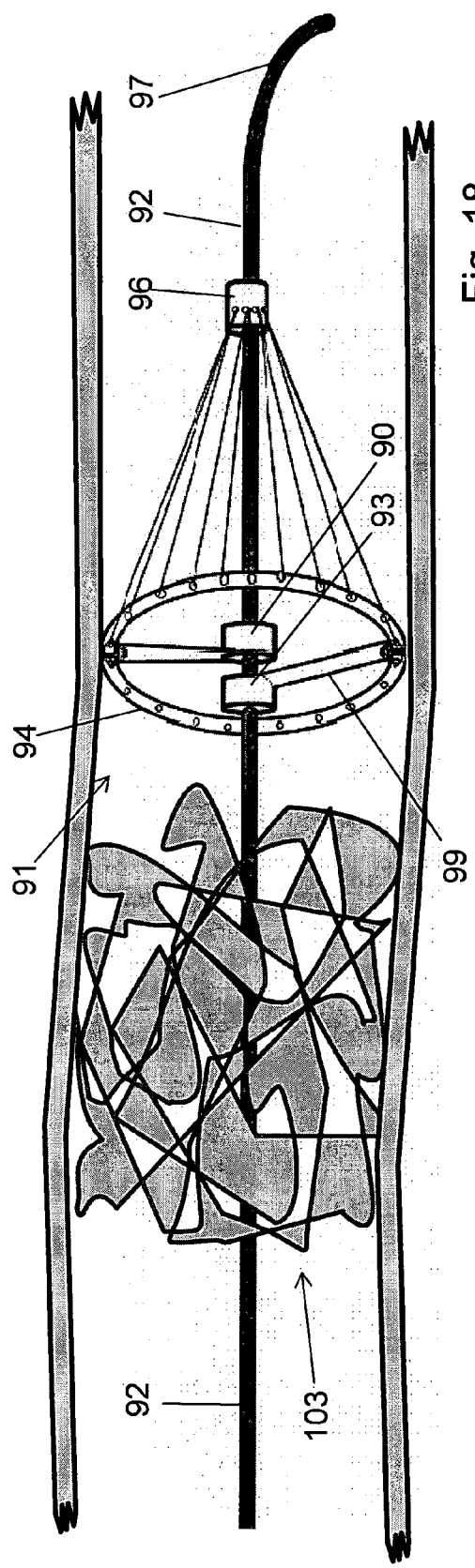
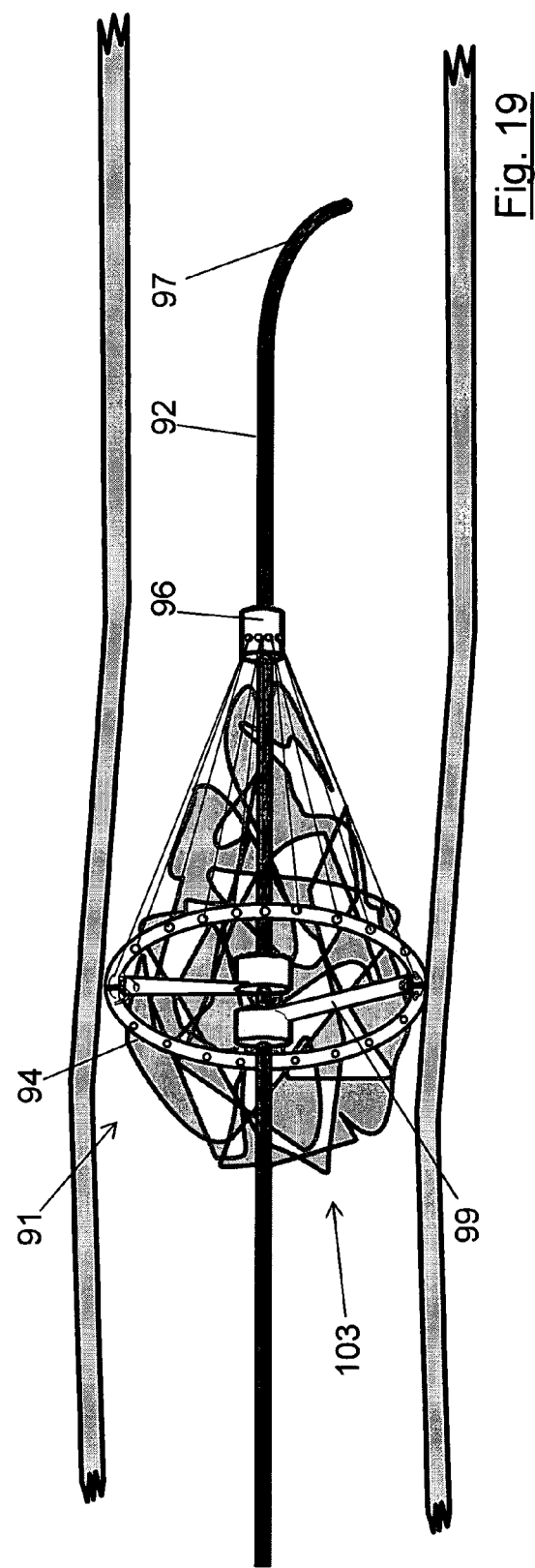
Fig. 18
Fig. 19

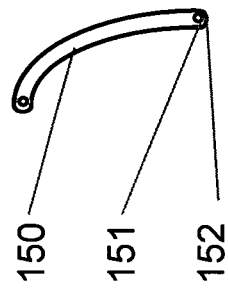
Fig. 20c
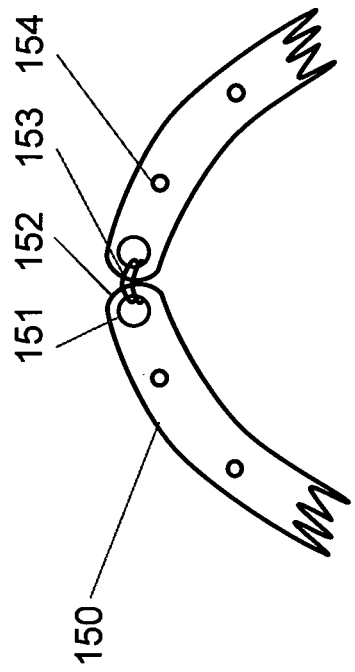
Fig. 20d
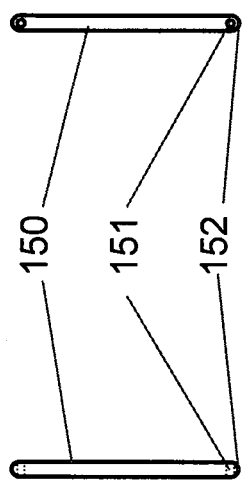
Fig. 20b
Fig. 20a
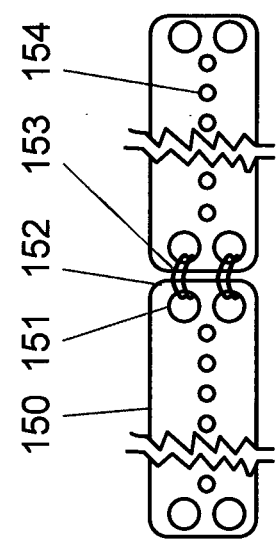
Fig. 20e

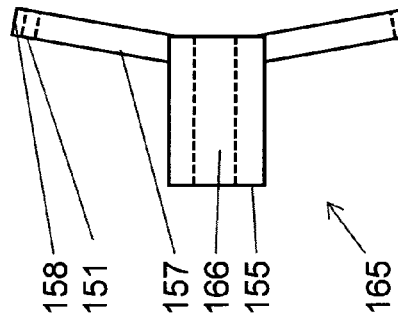
Fig. 20h
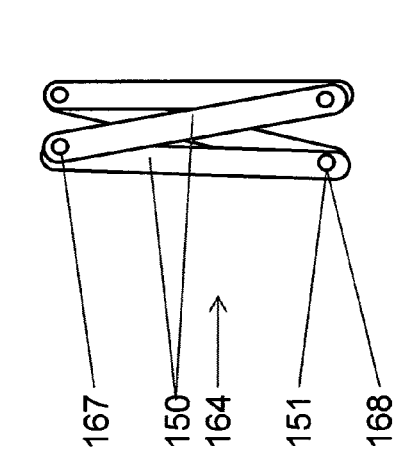
Fig. 20k
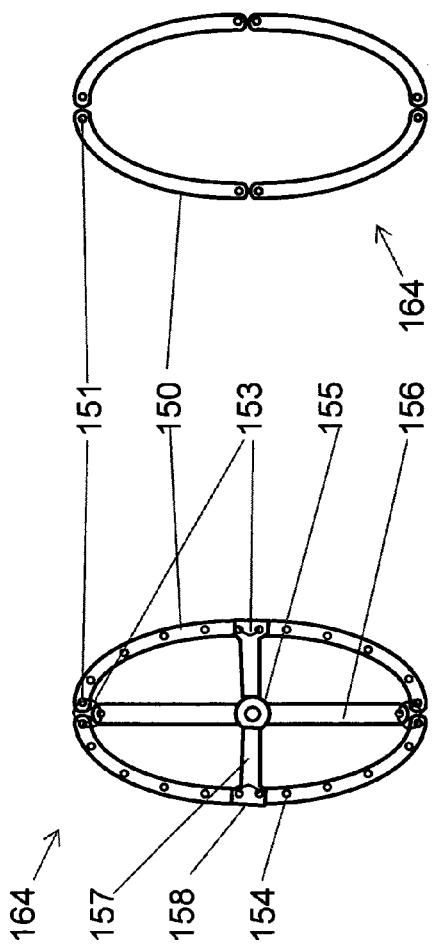
Fig. 20g
Fig. 20f
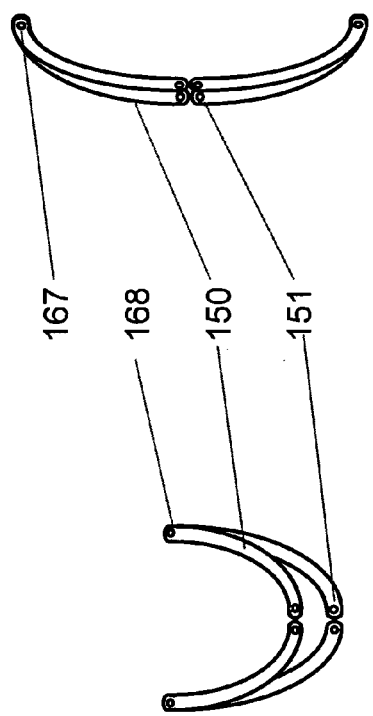
Fig. 20j
Fig. 20i

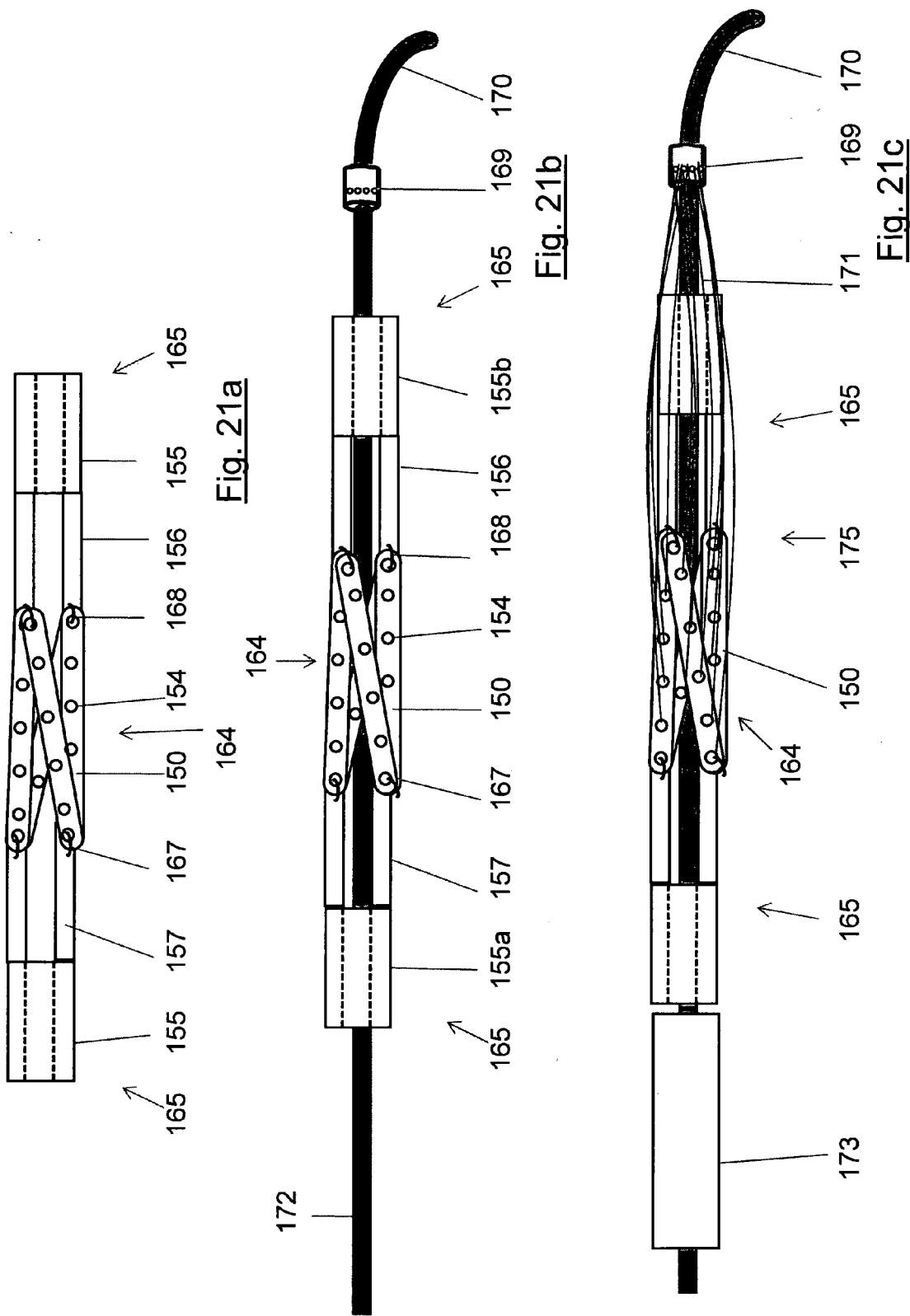

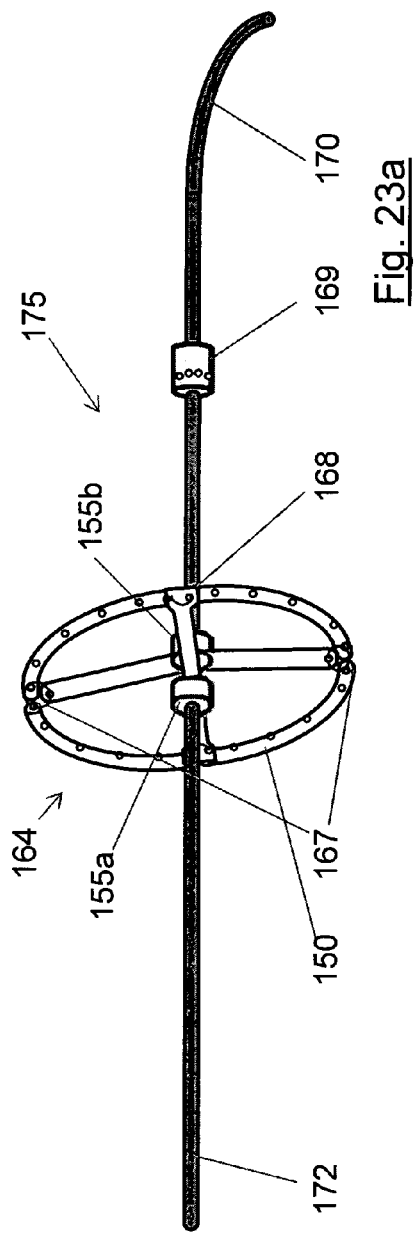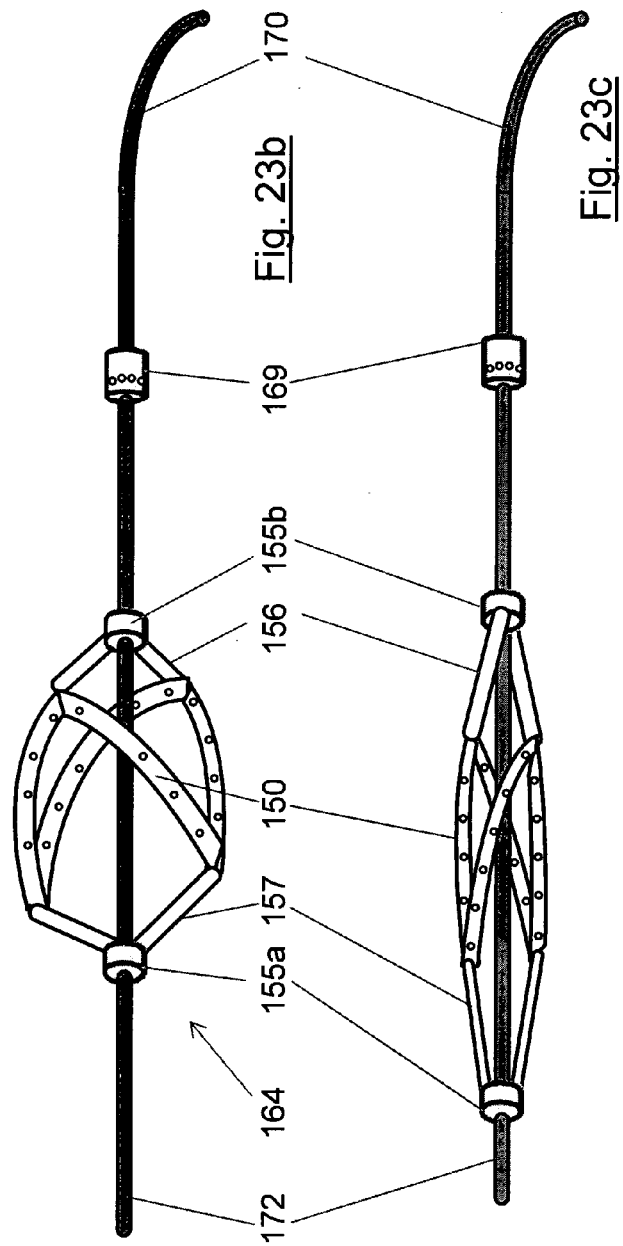

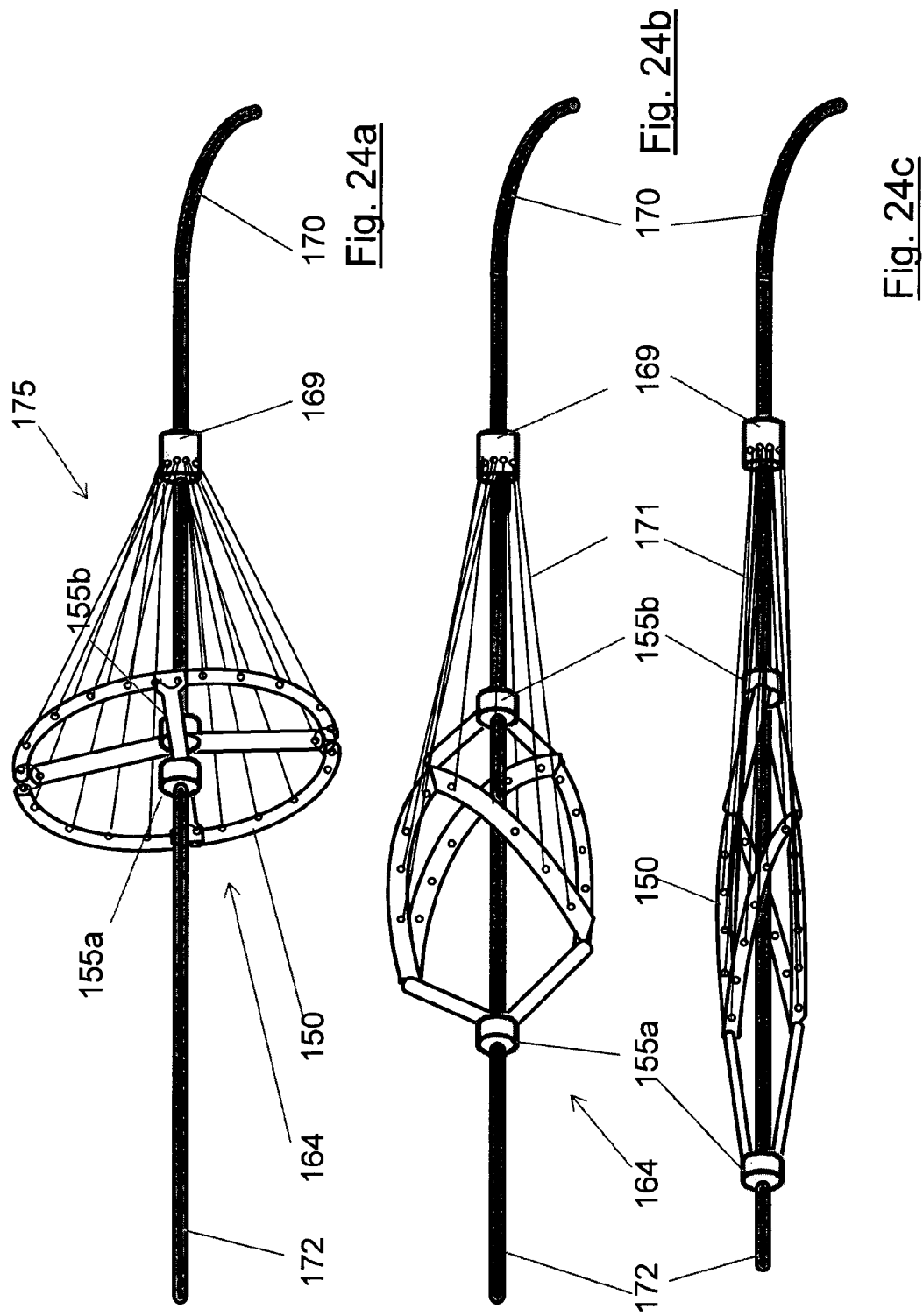

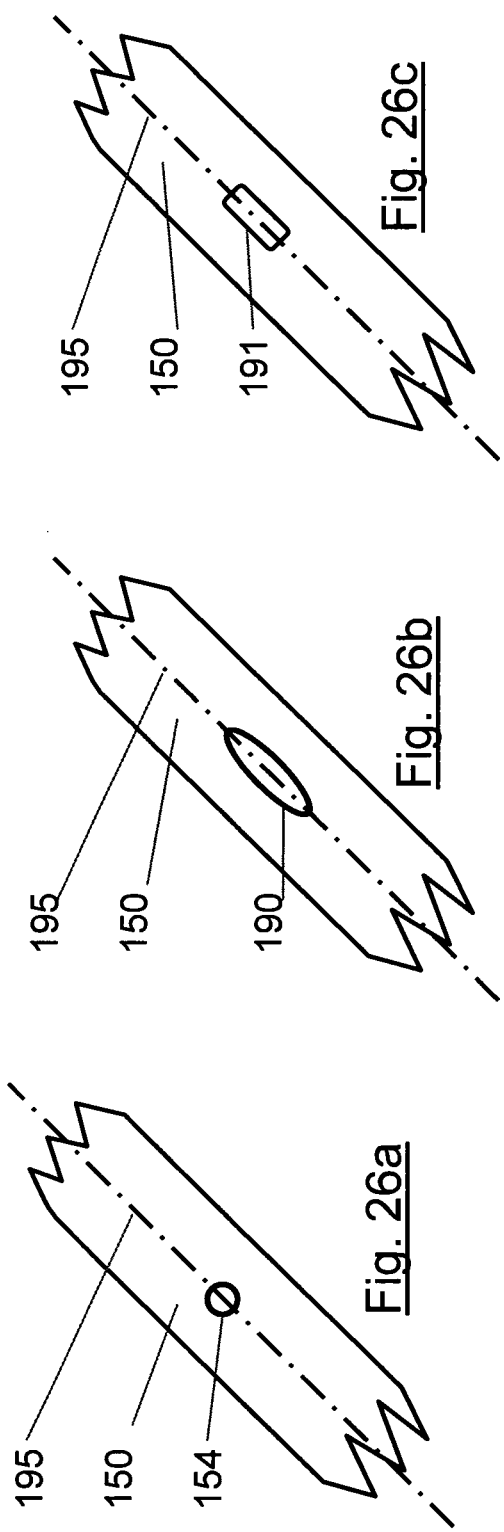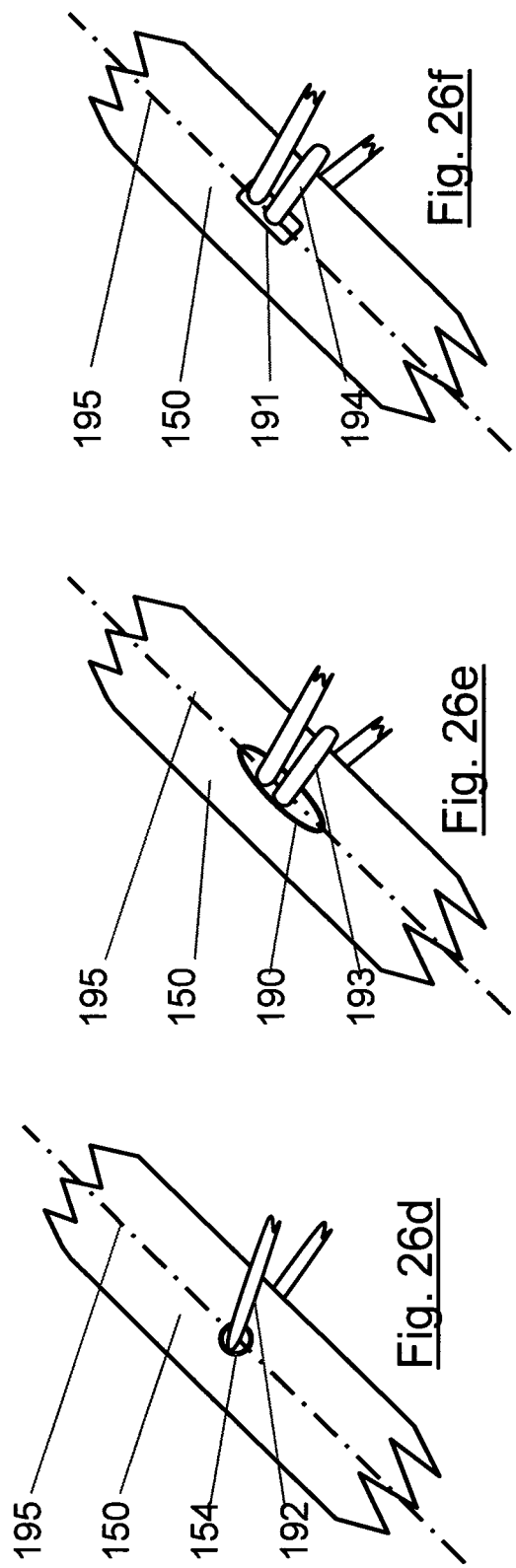

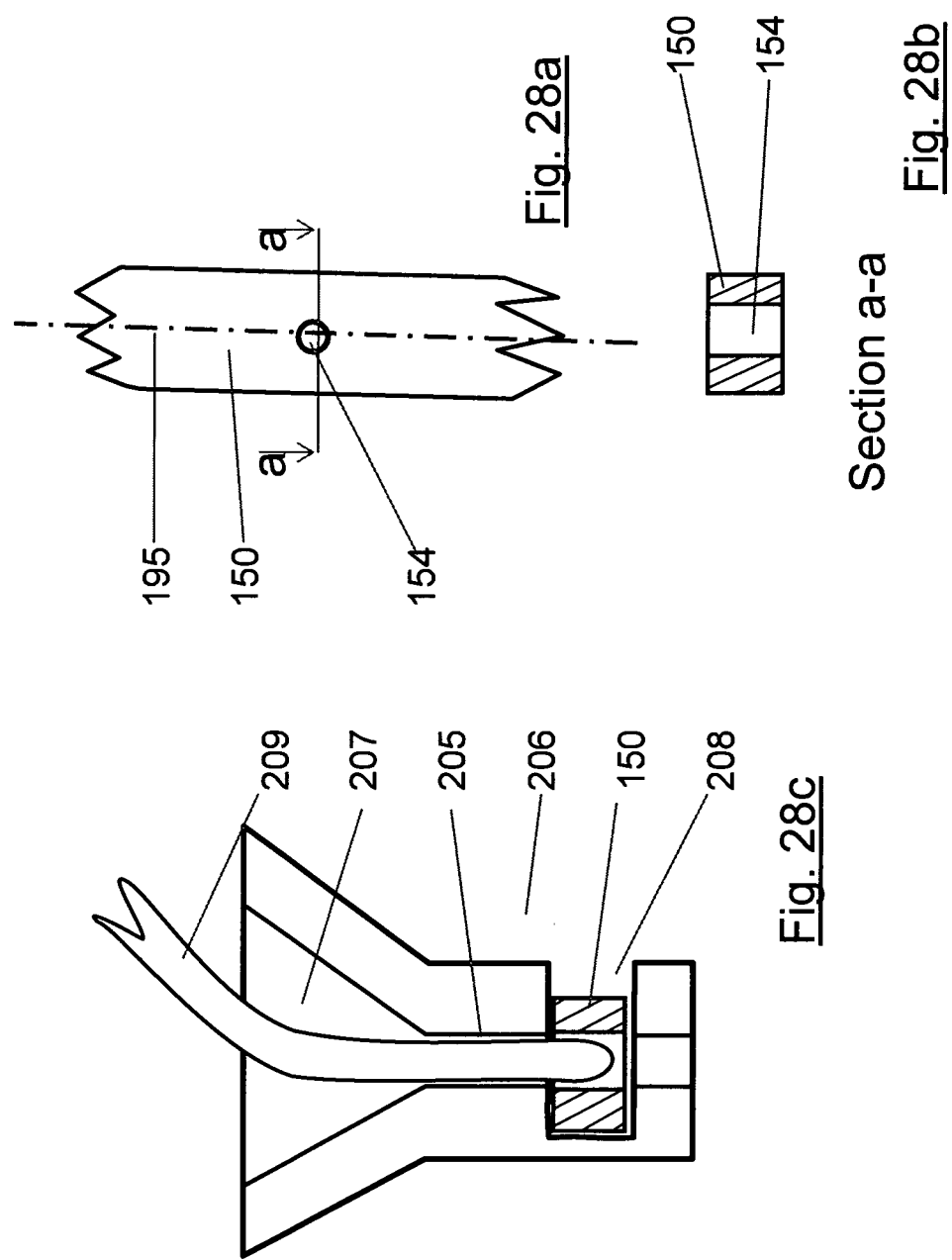

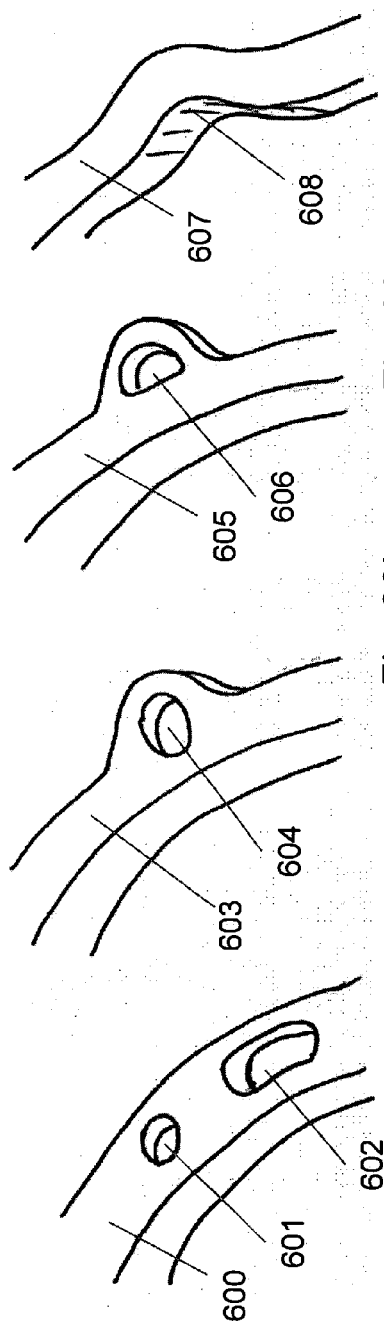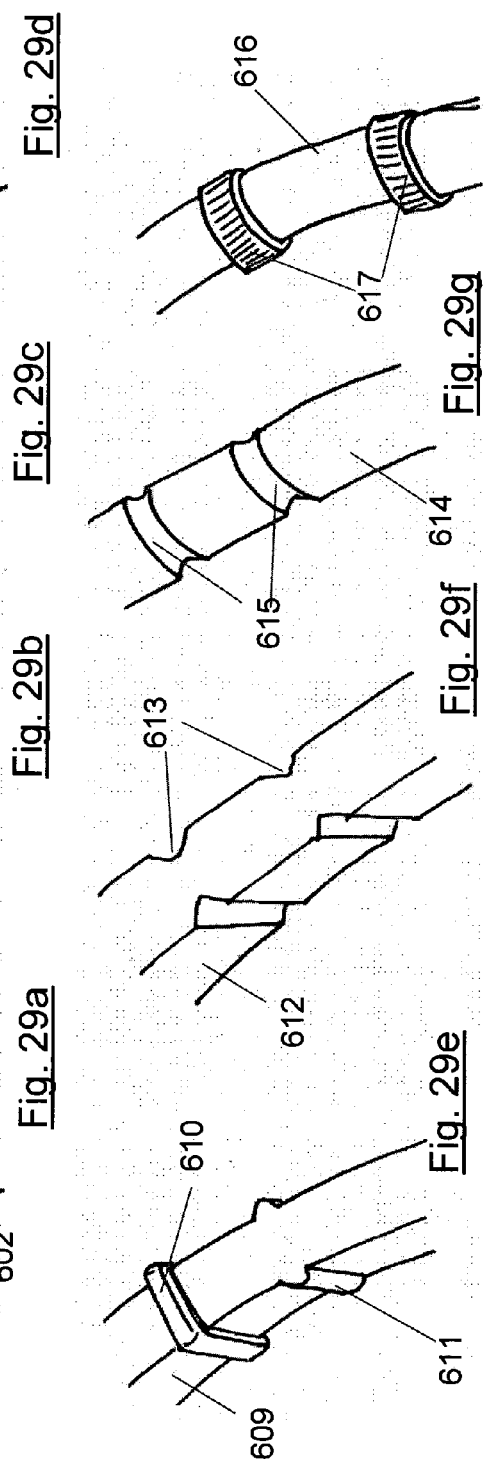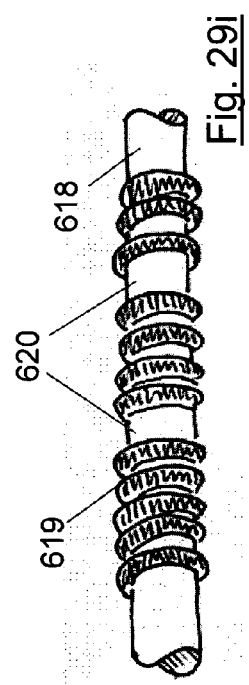

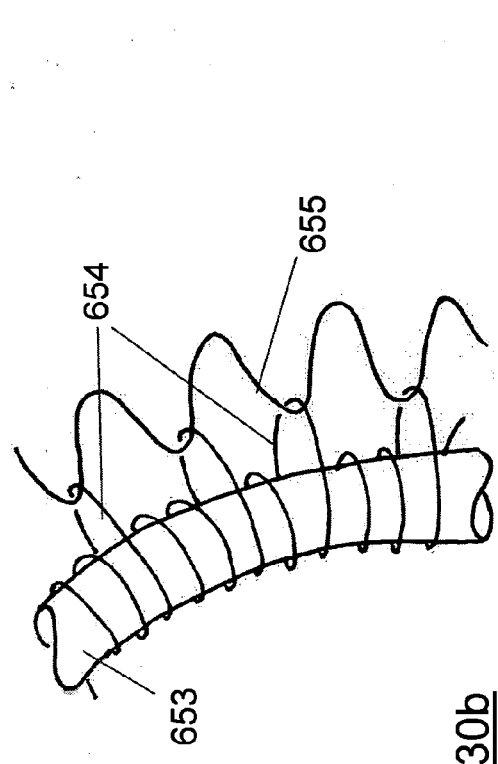
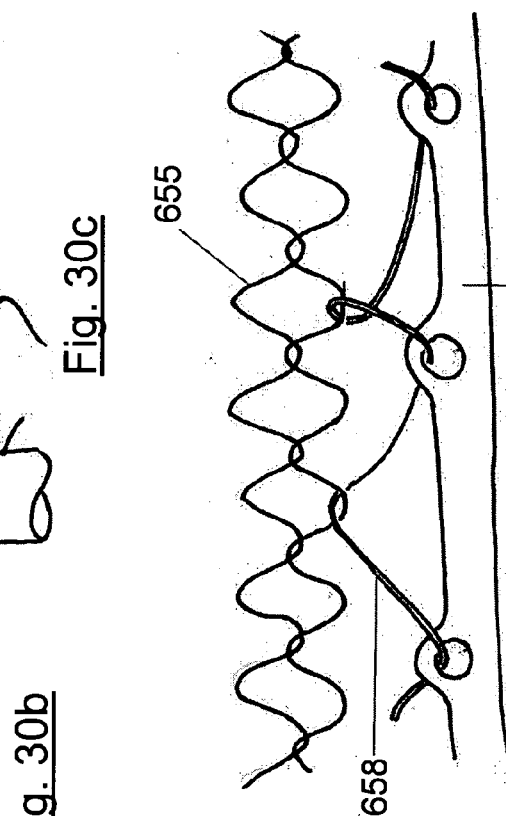
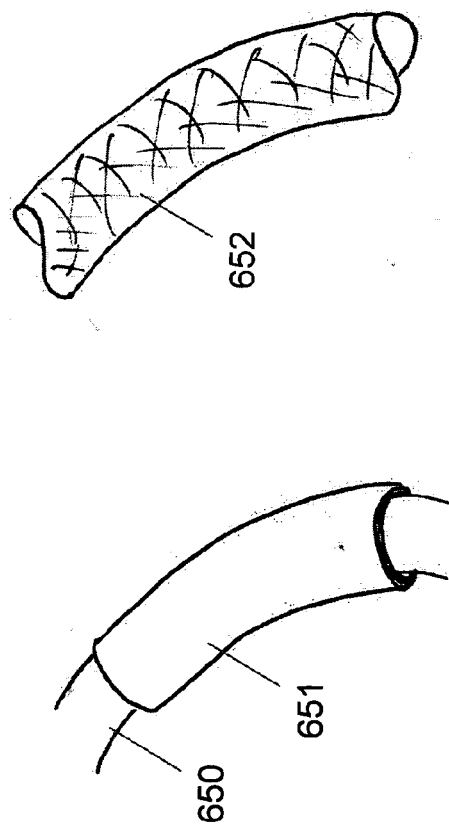
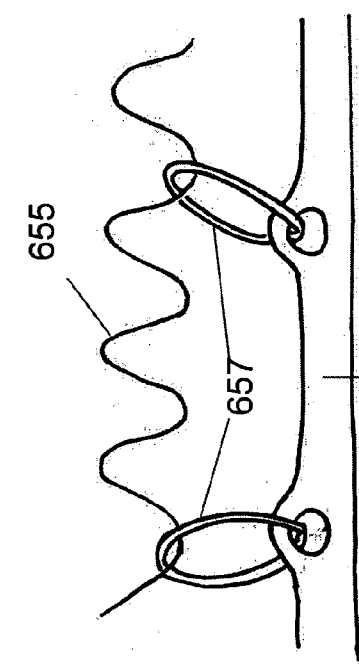

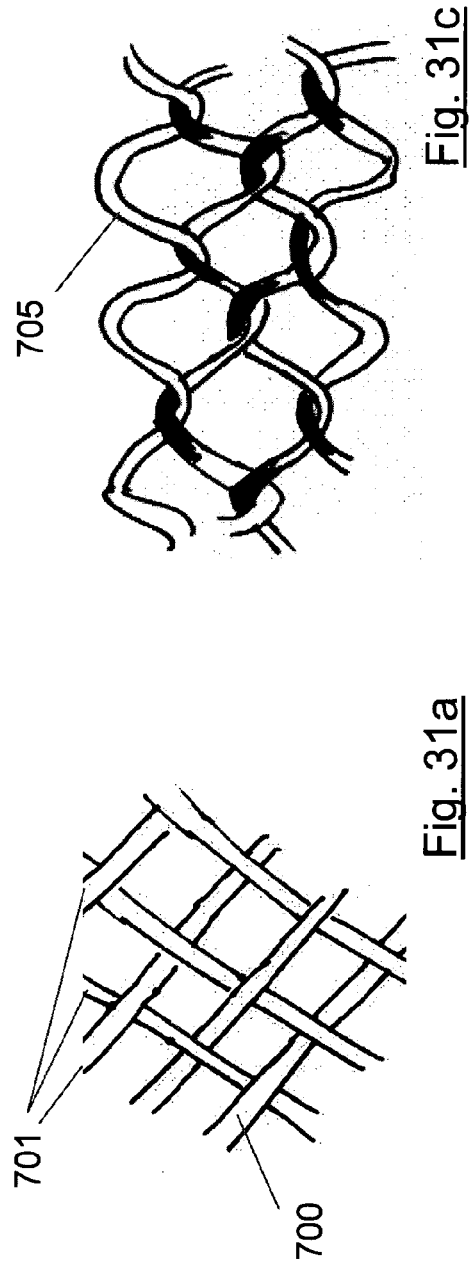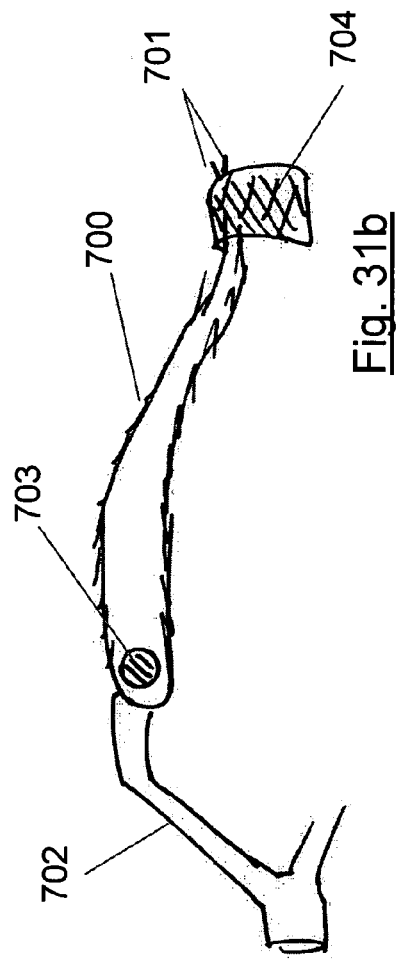
Fig. 31a
Fig. 31b
Fig. 31c

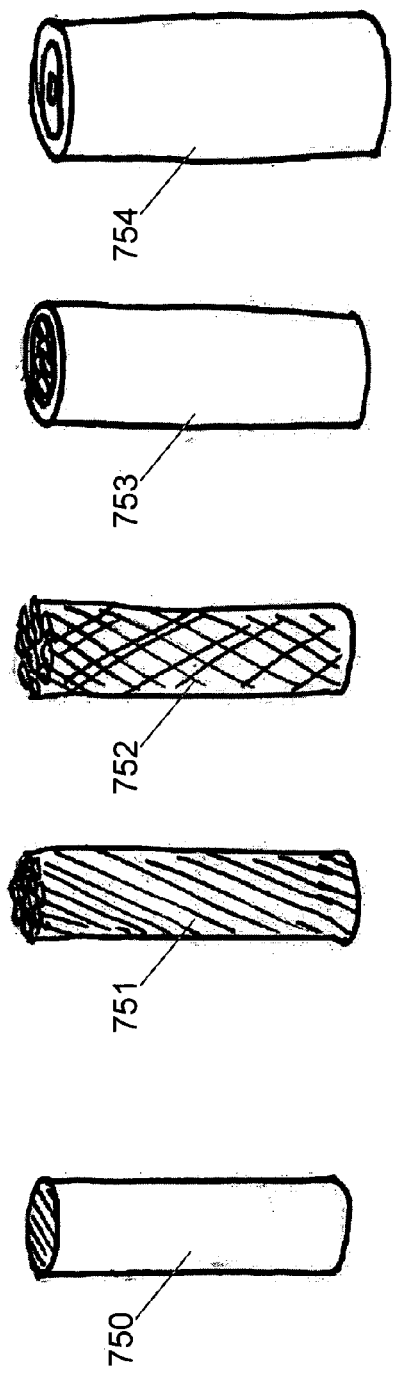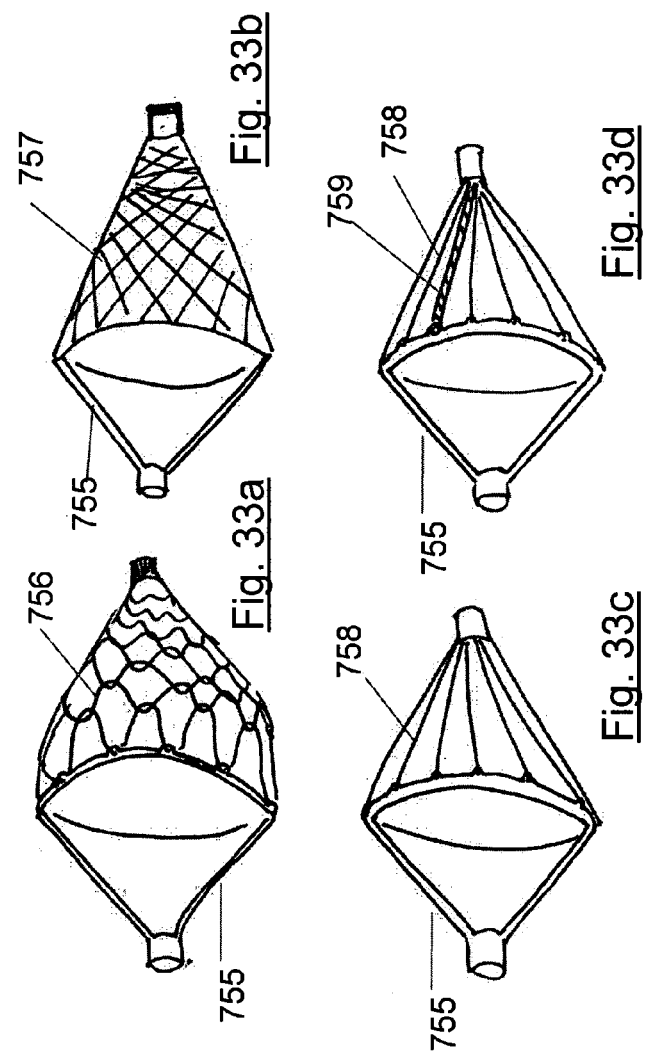

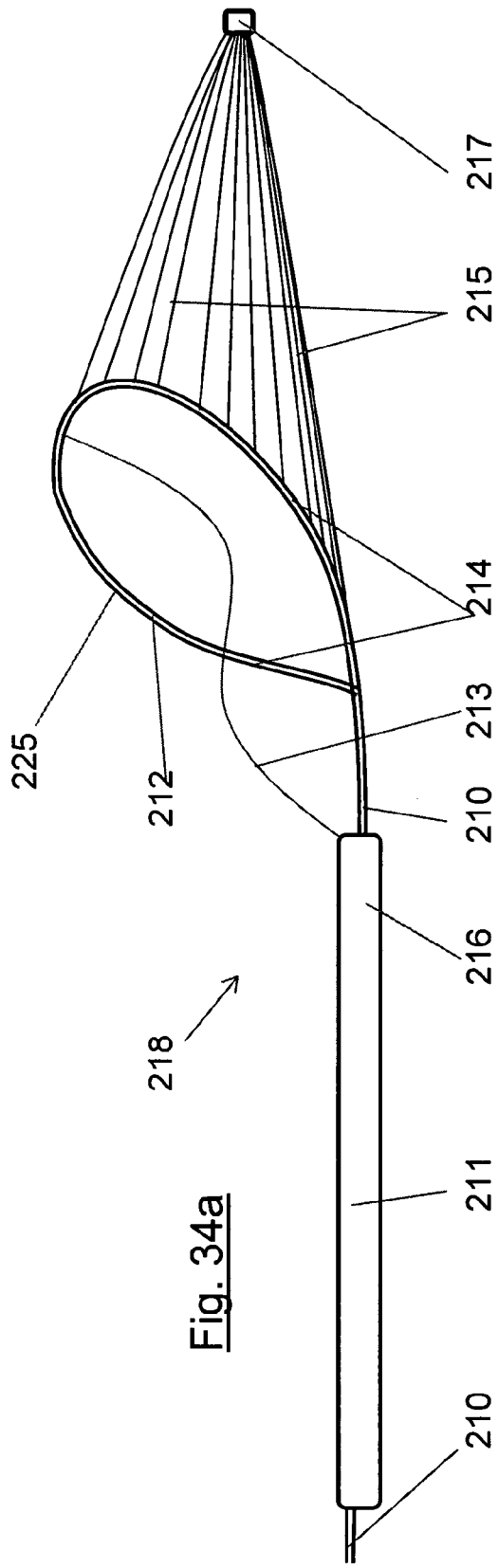
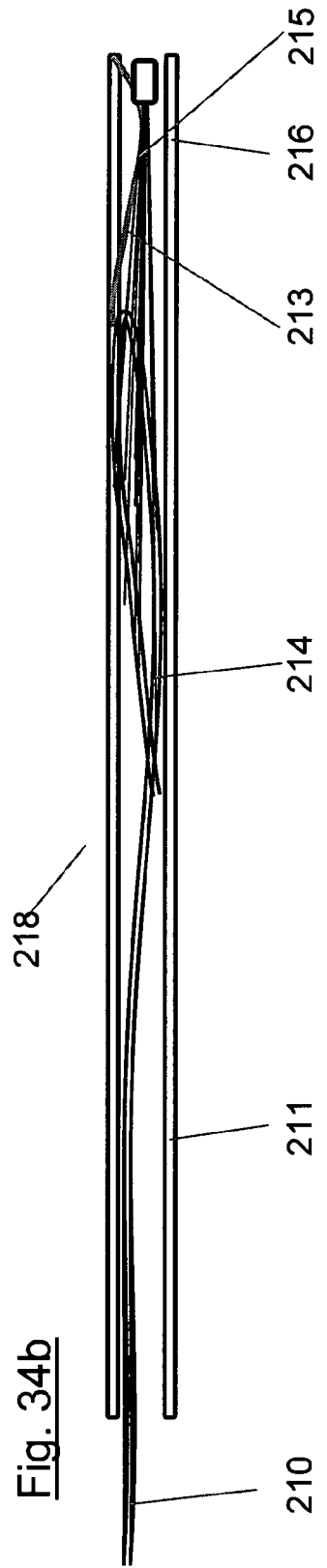
Fig. 34a
Fig. 34b

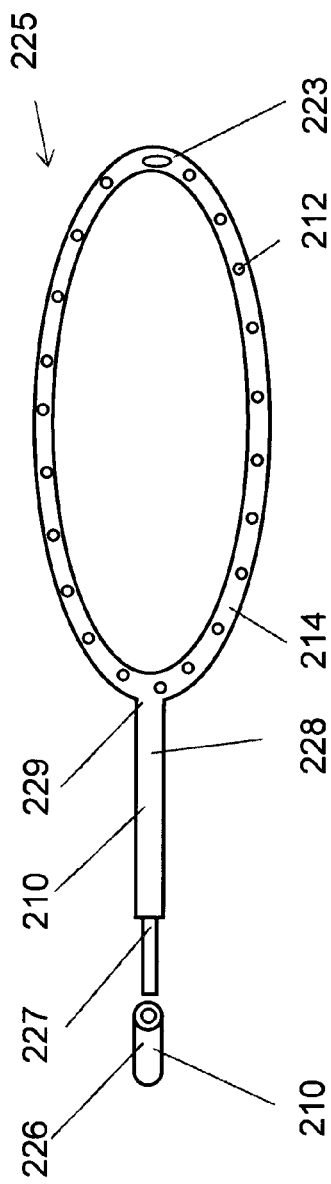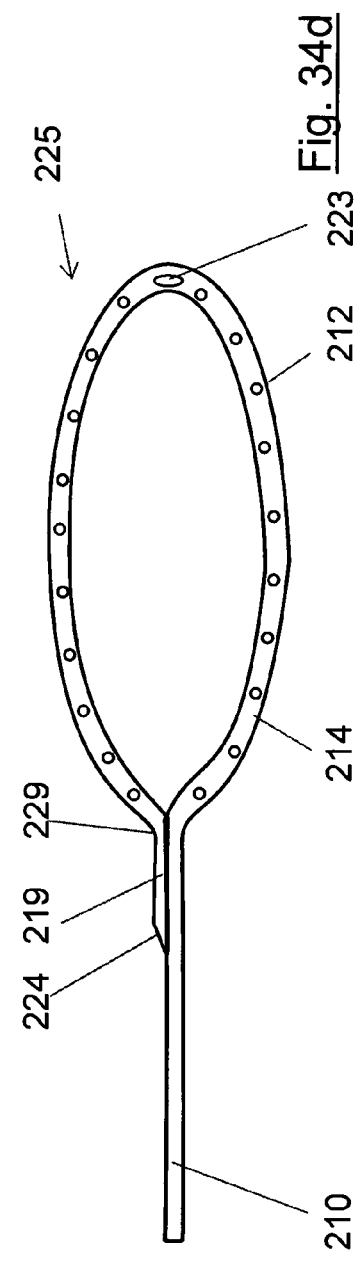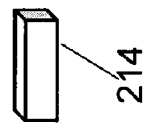

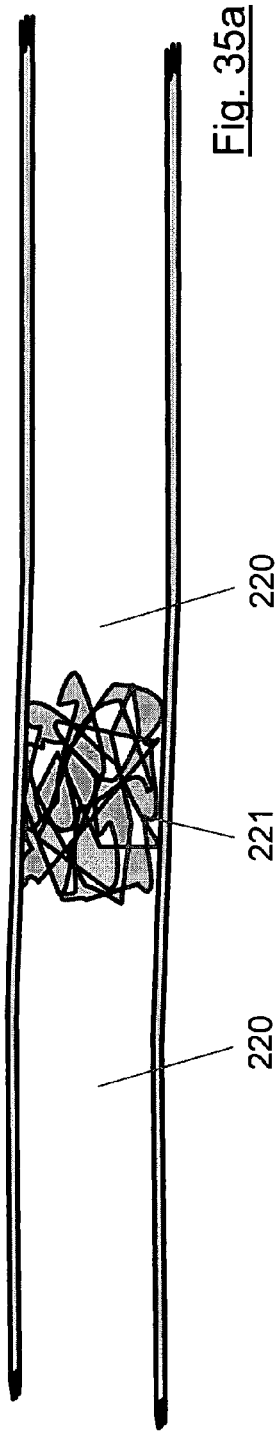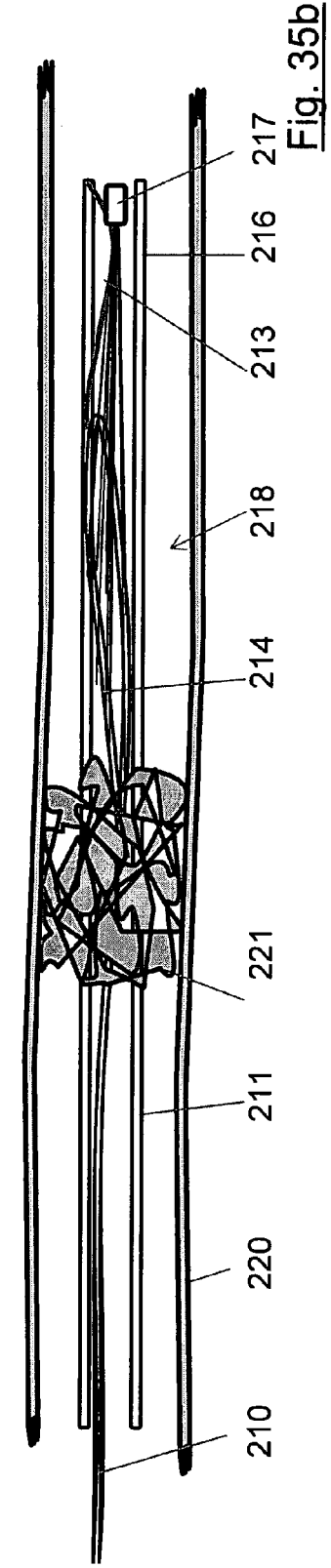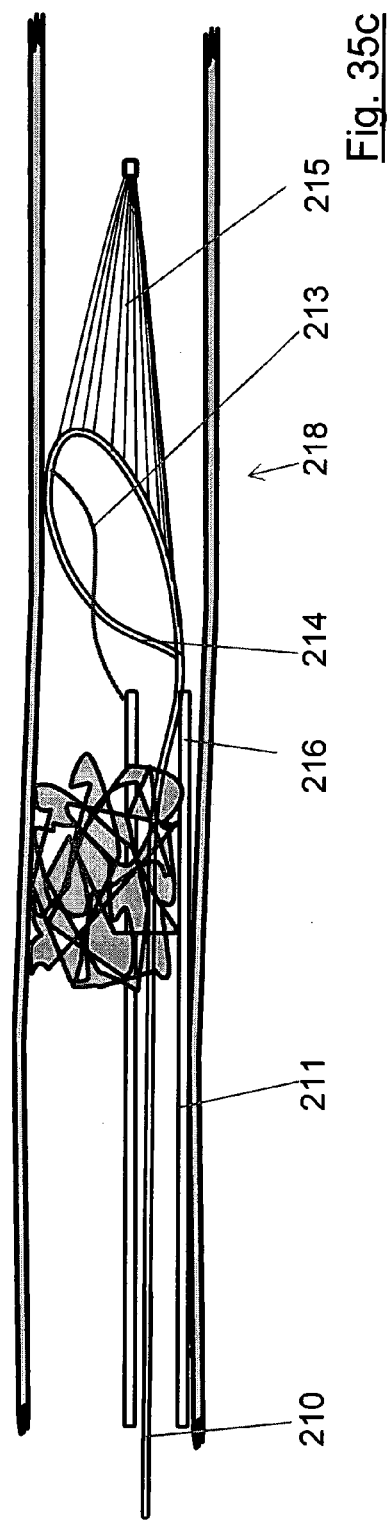

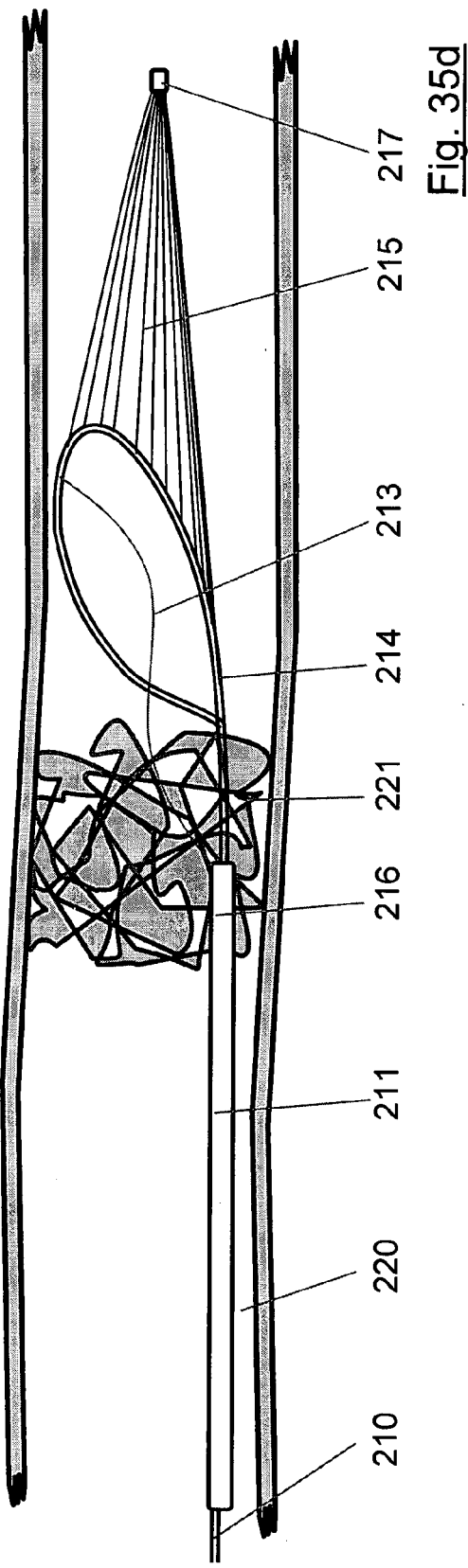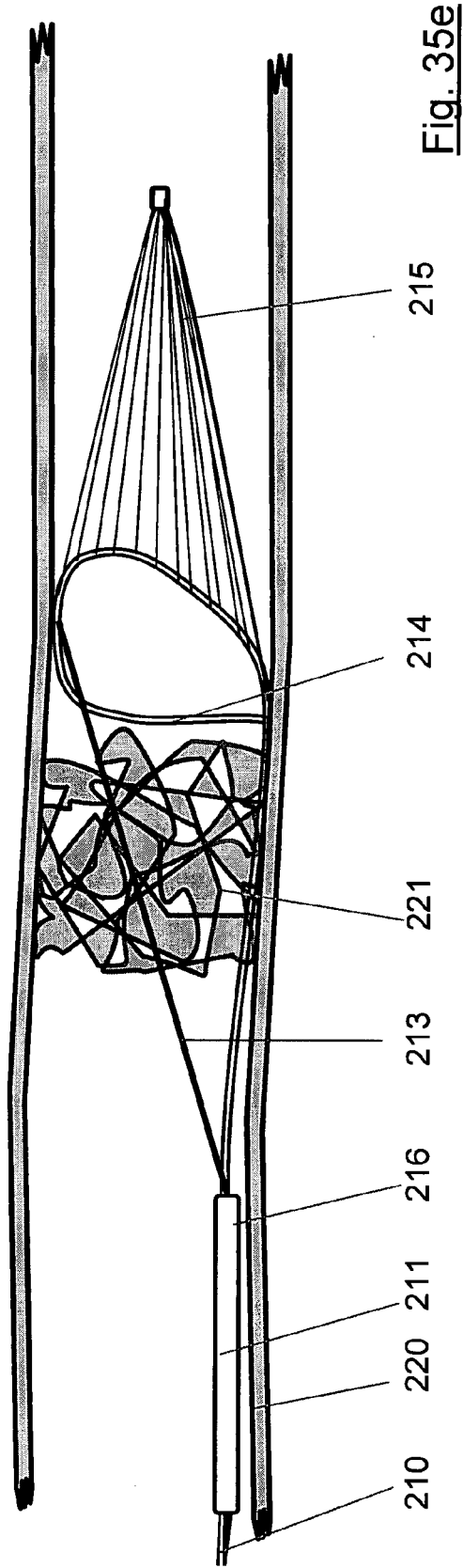

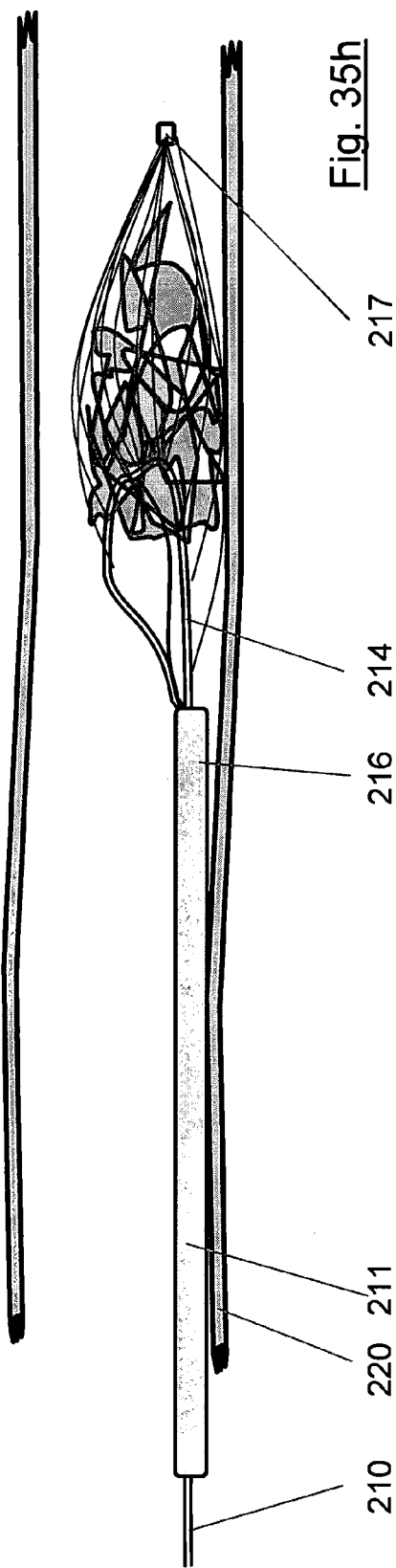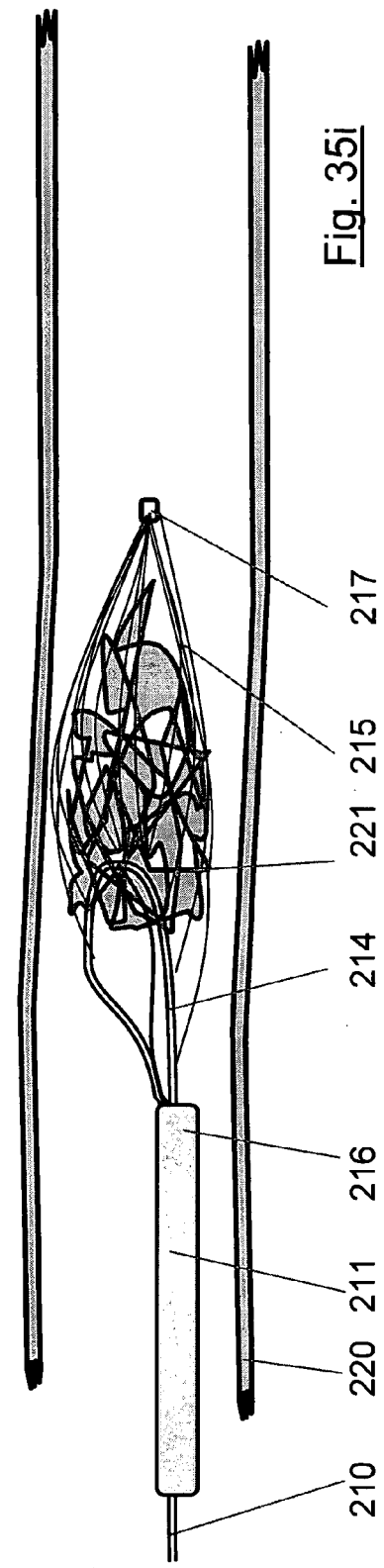

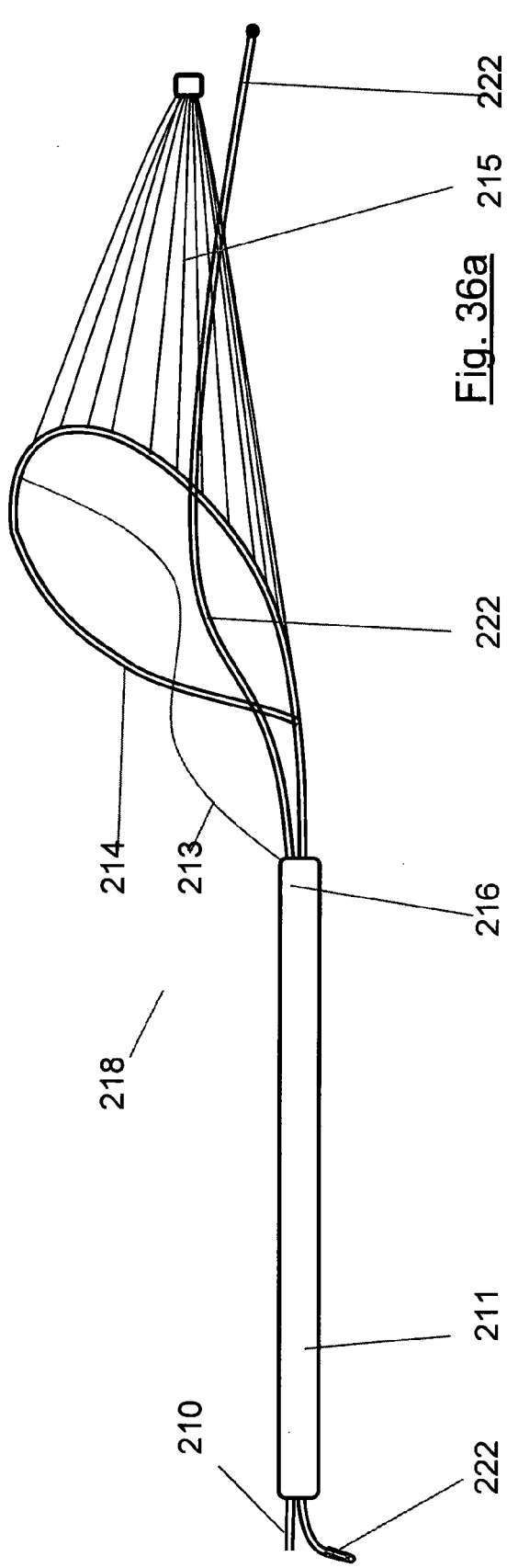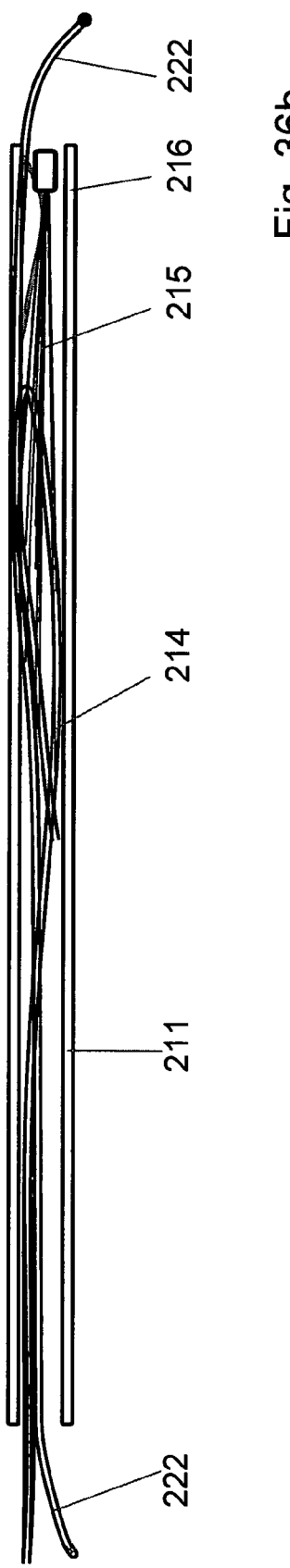
Fig. 36a
Fig. 36b

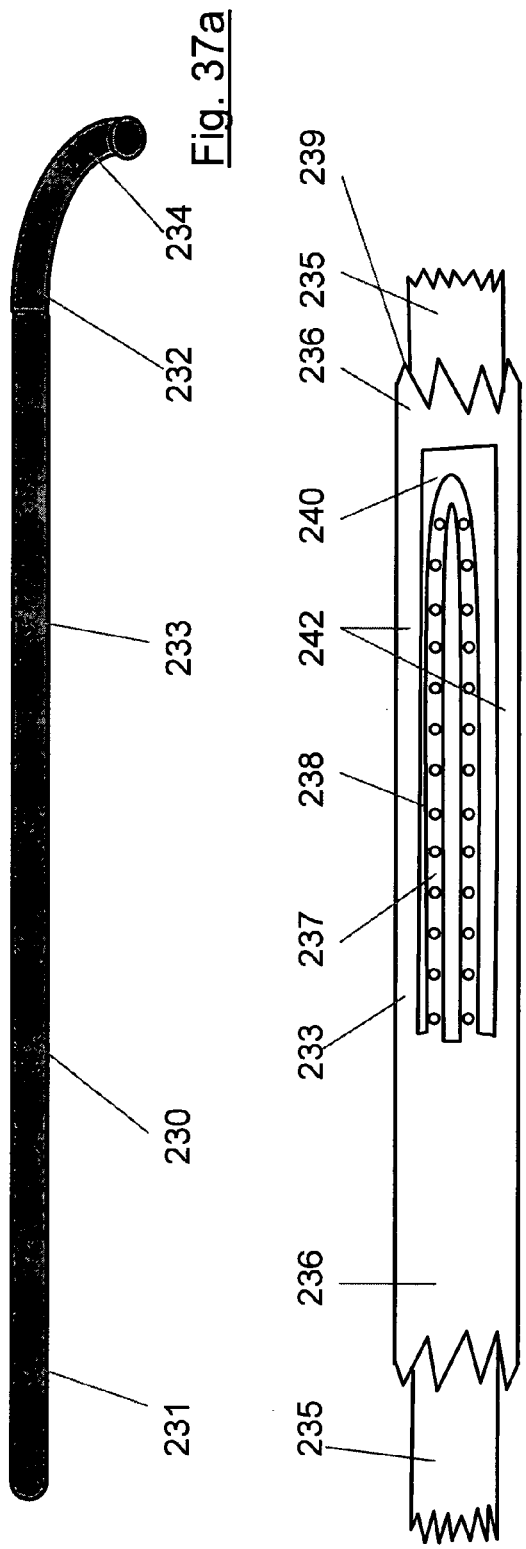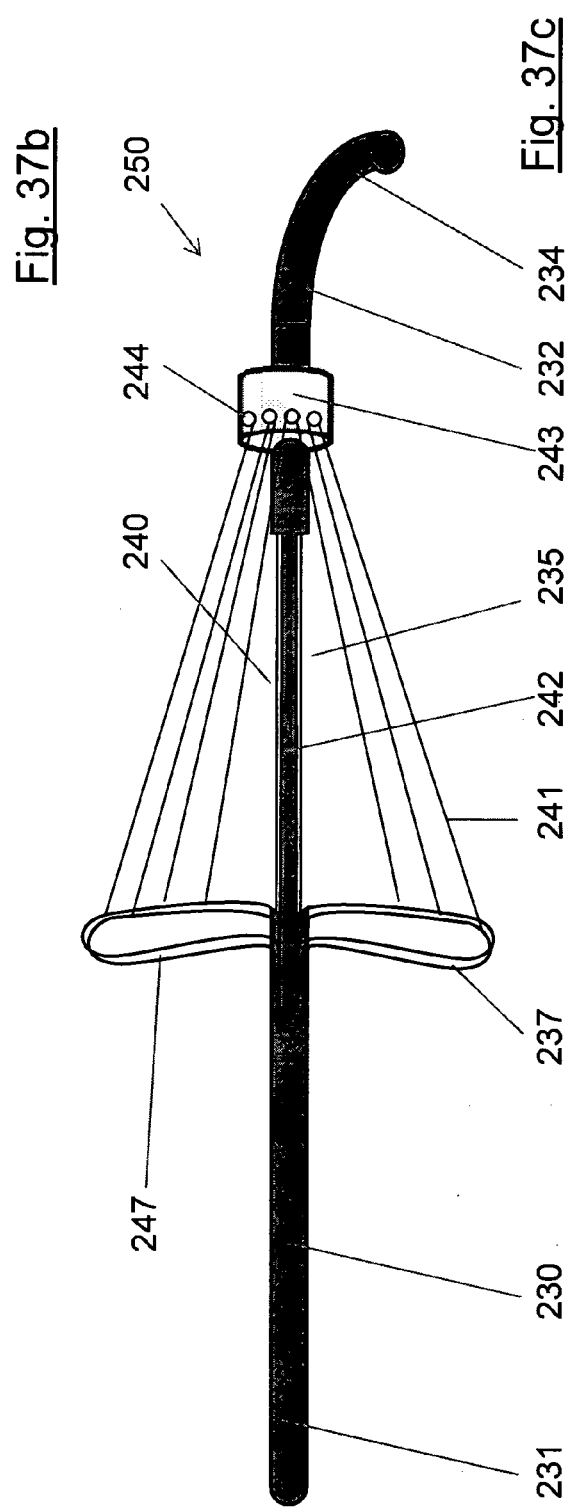

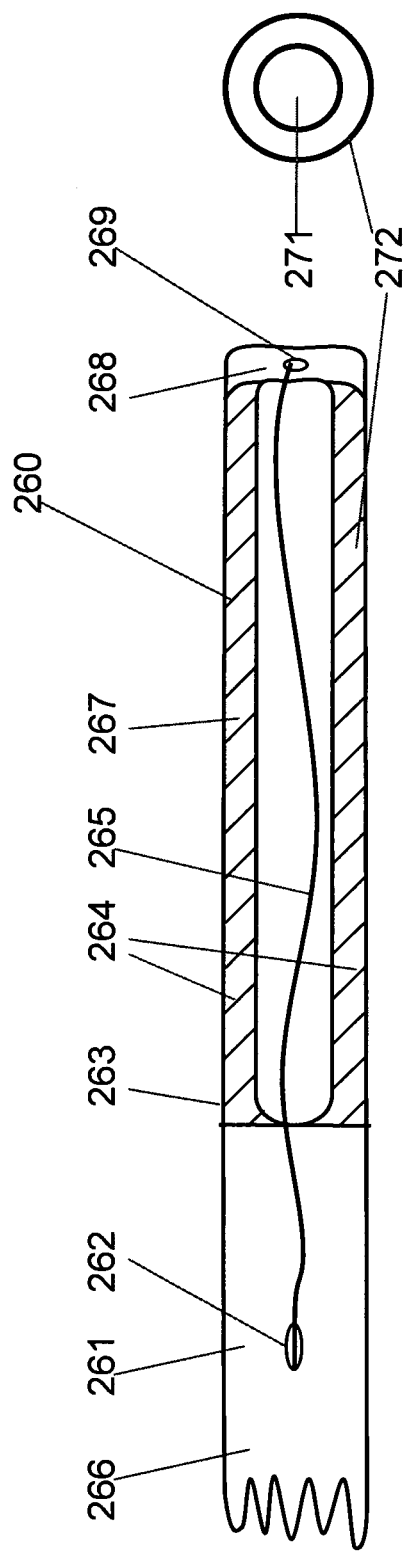
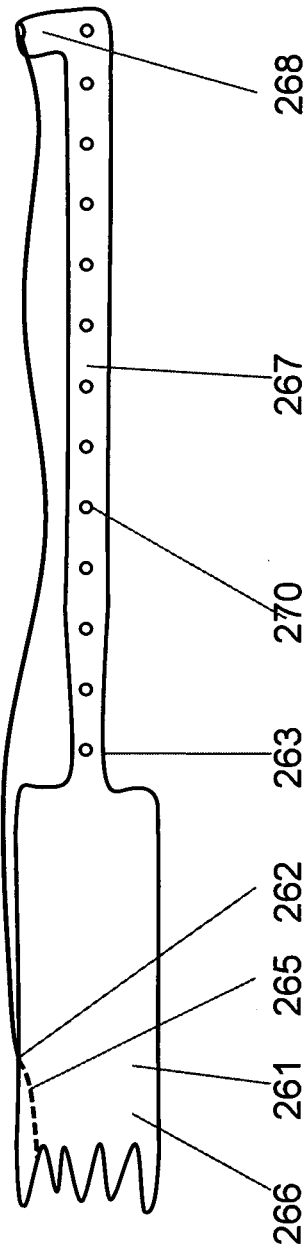
Fig. 38a
Fig. 38b
Fig. 38c

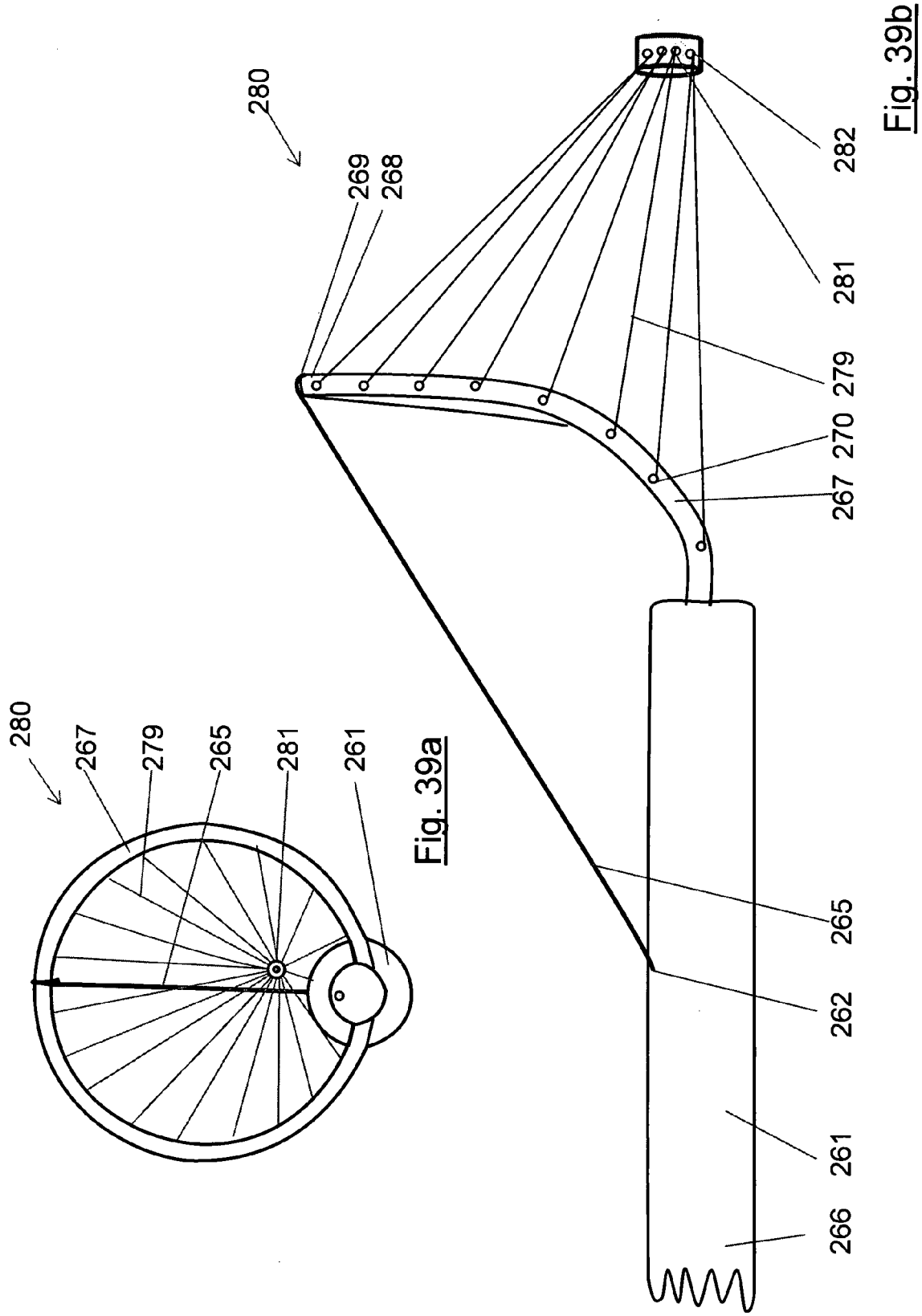

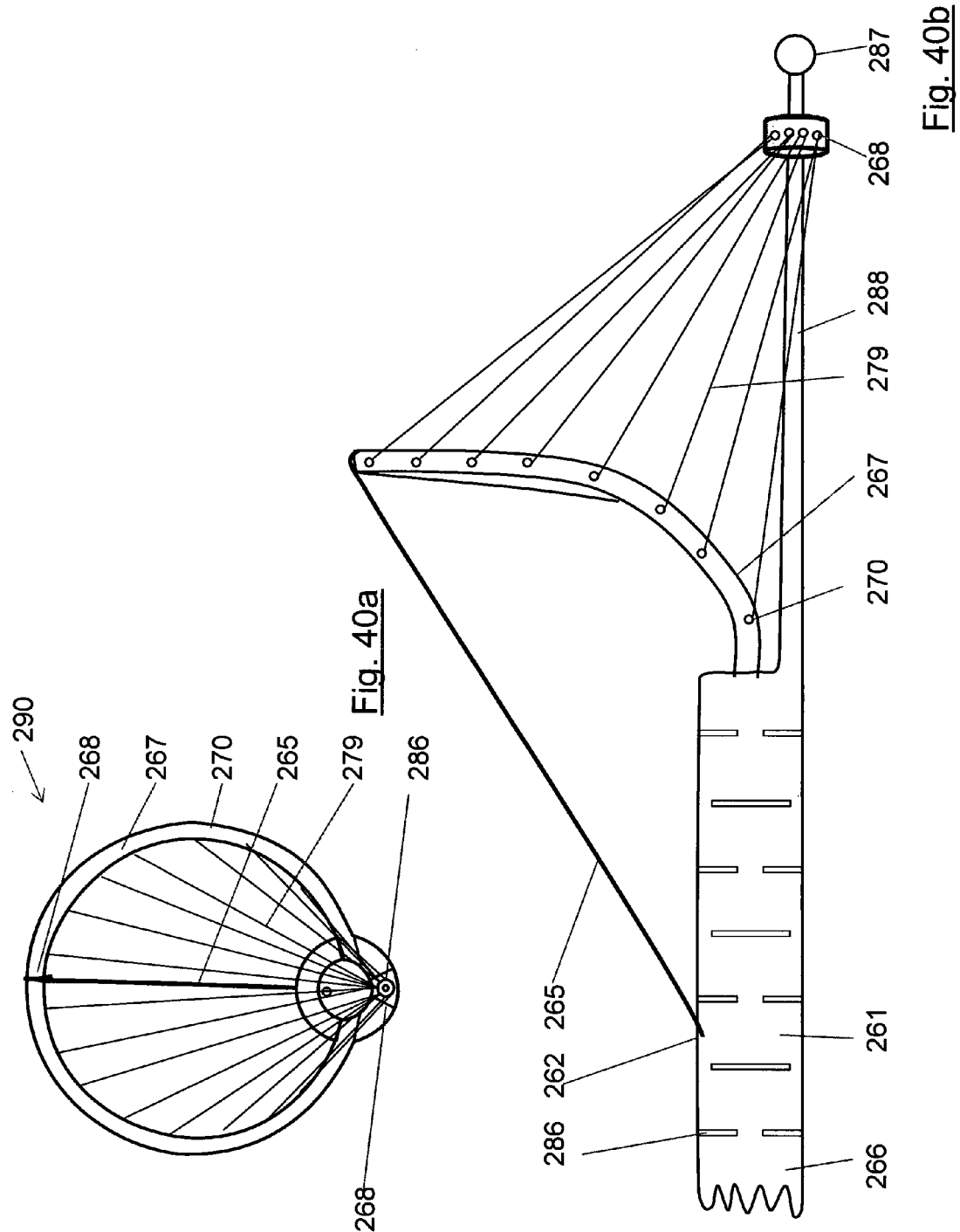

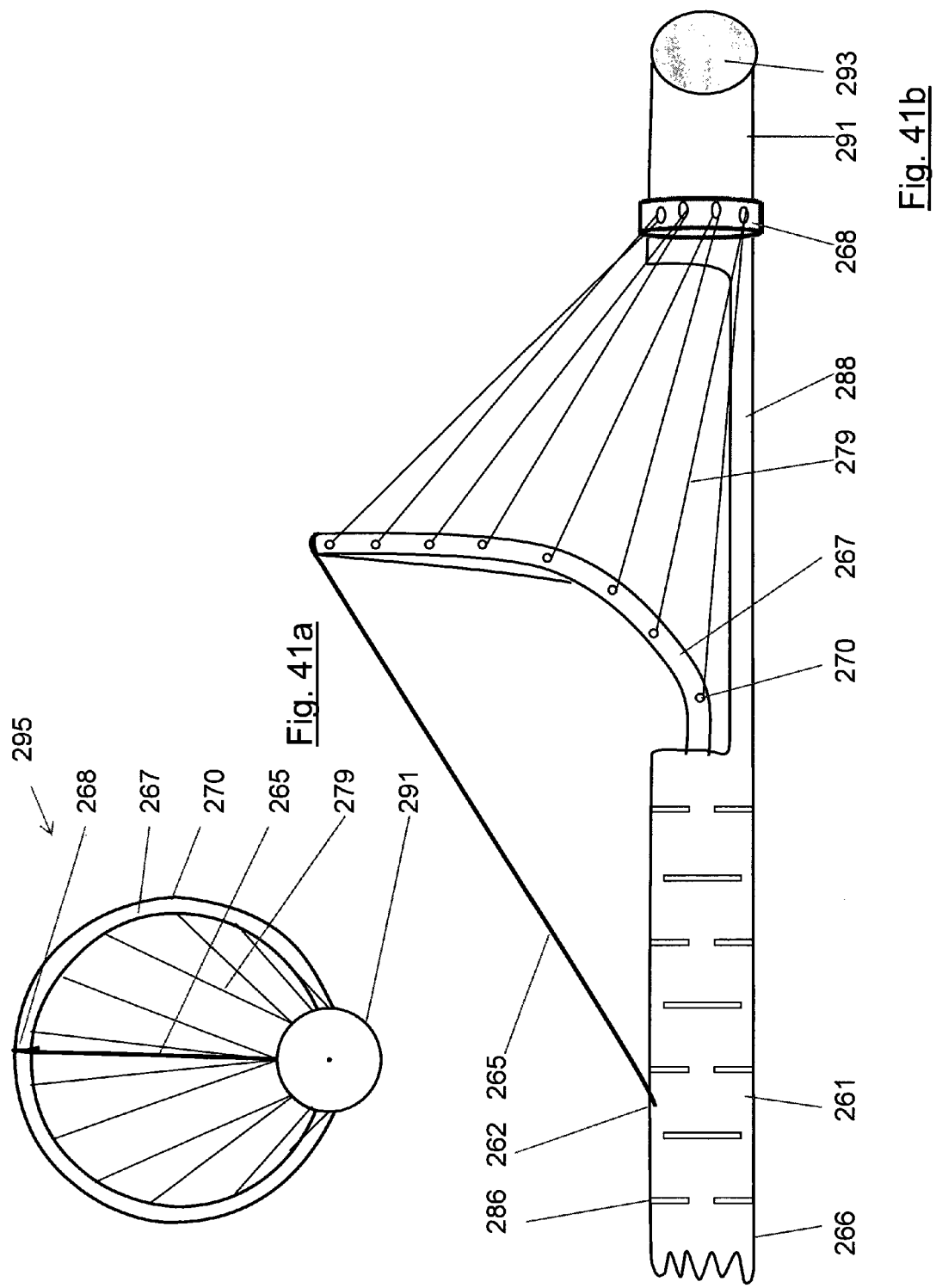

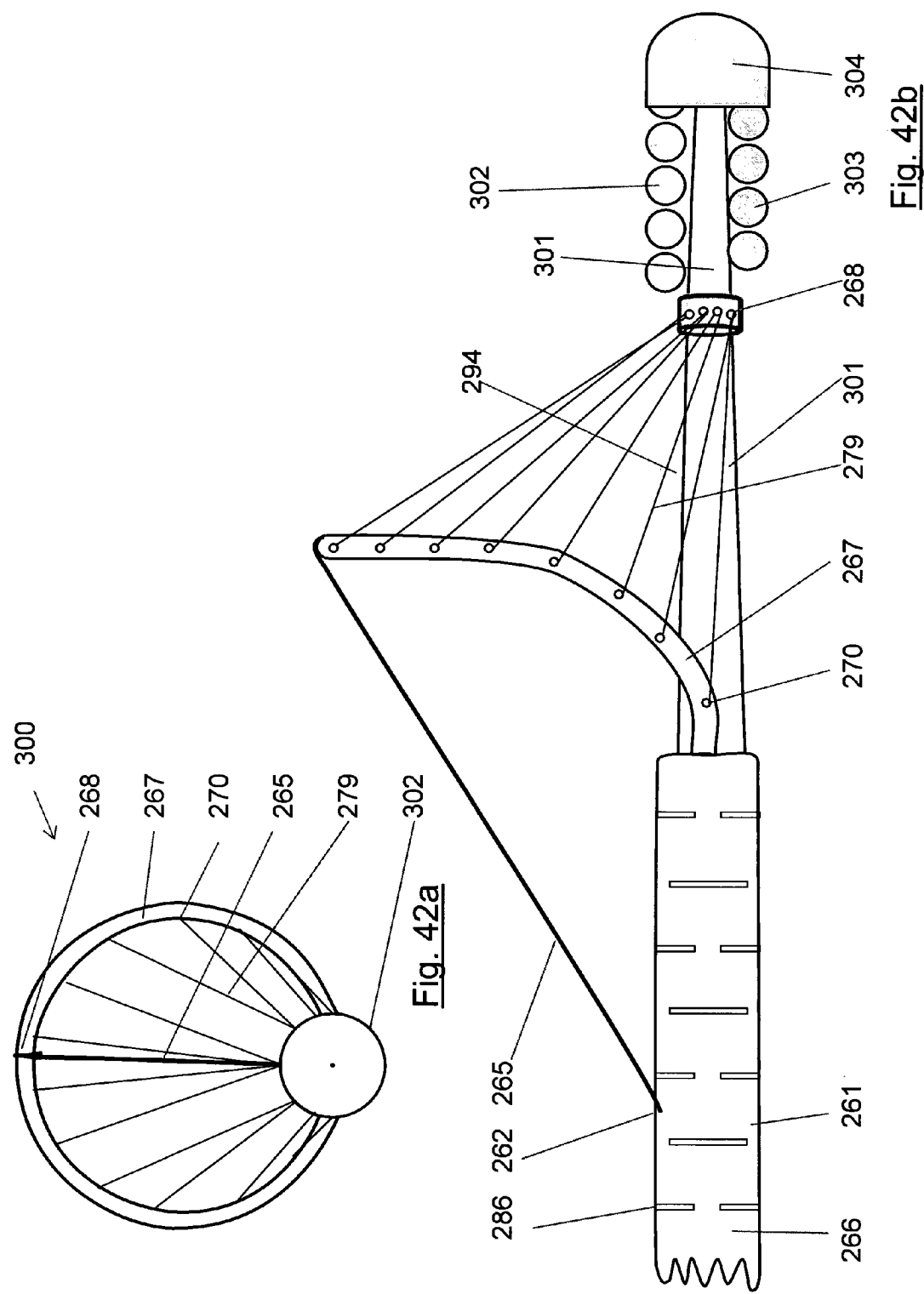

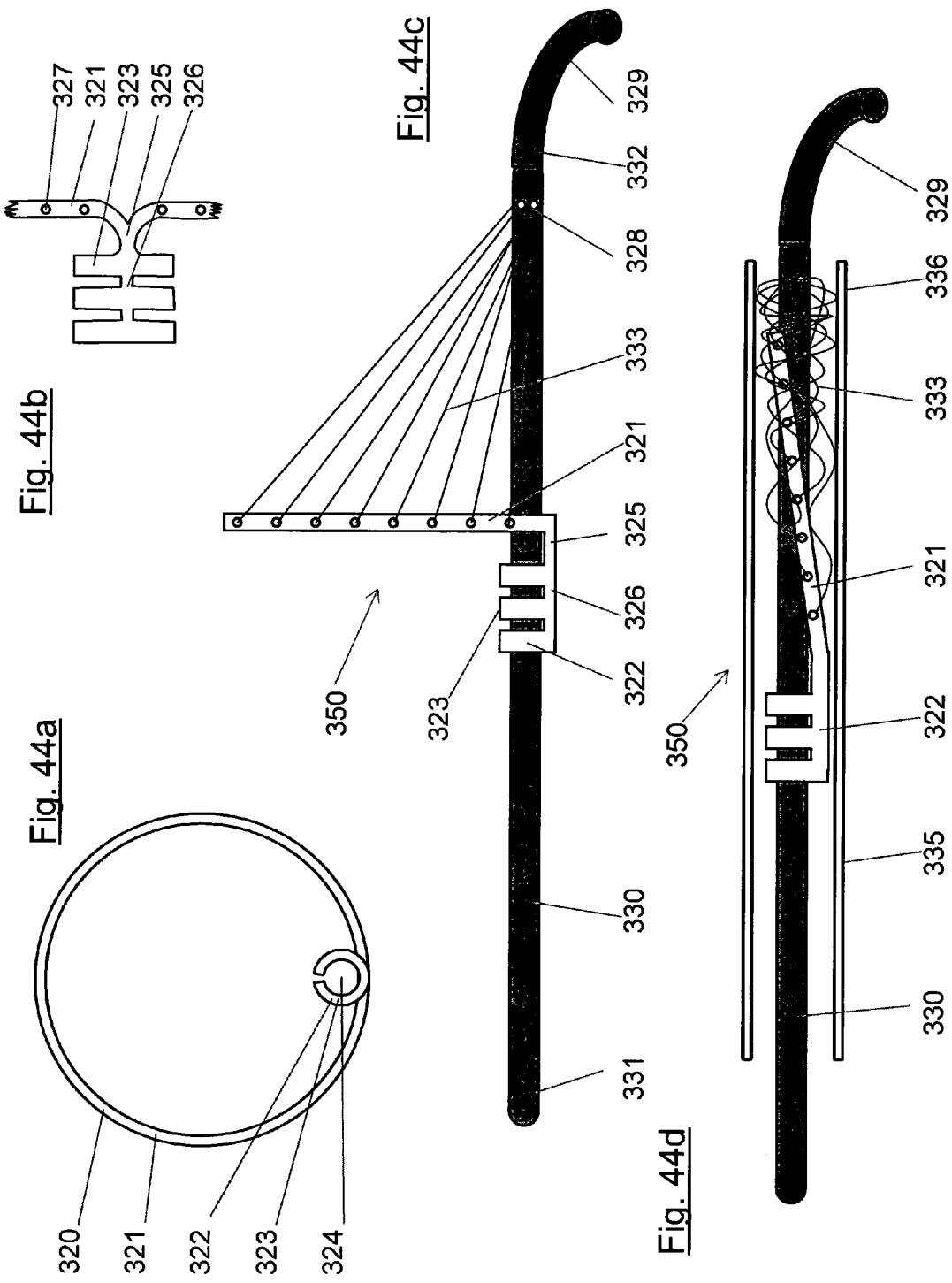

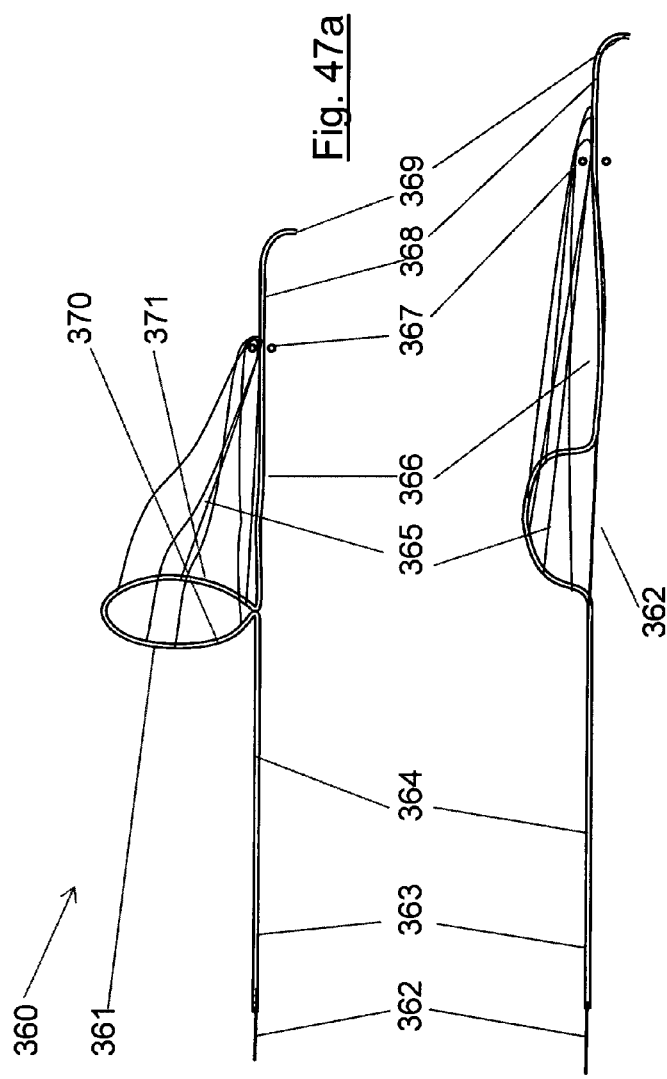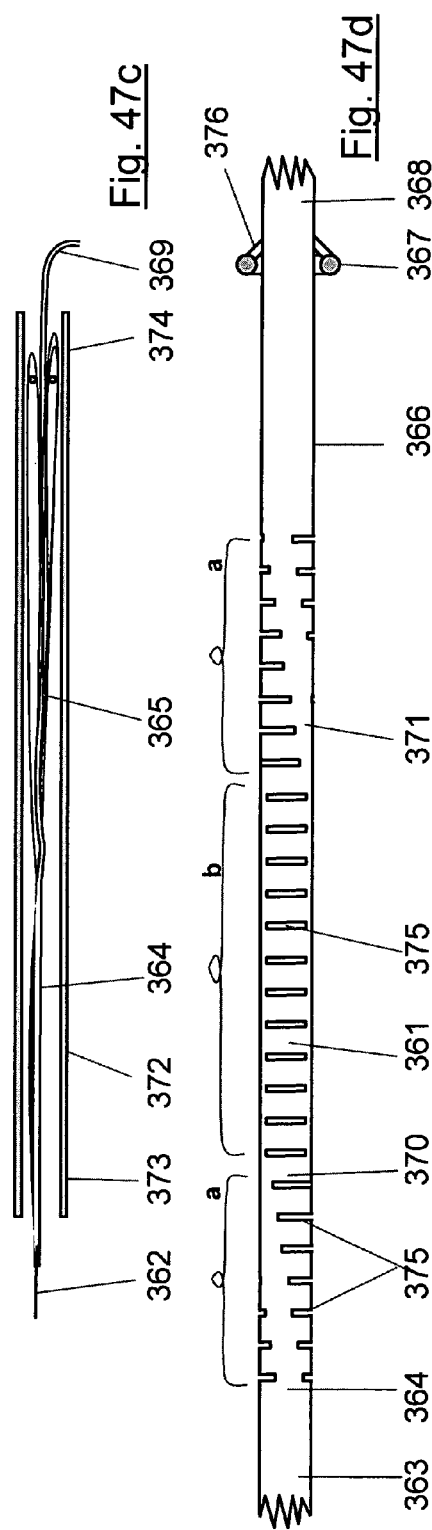

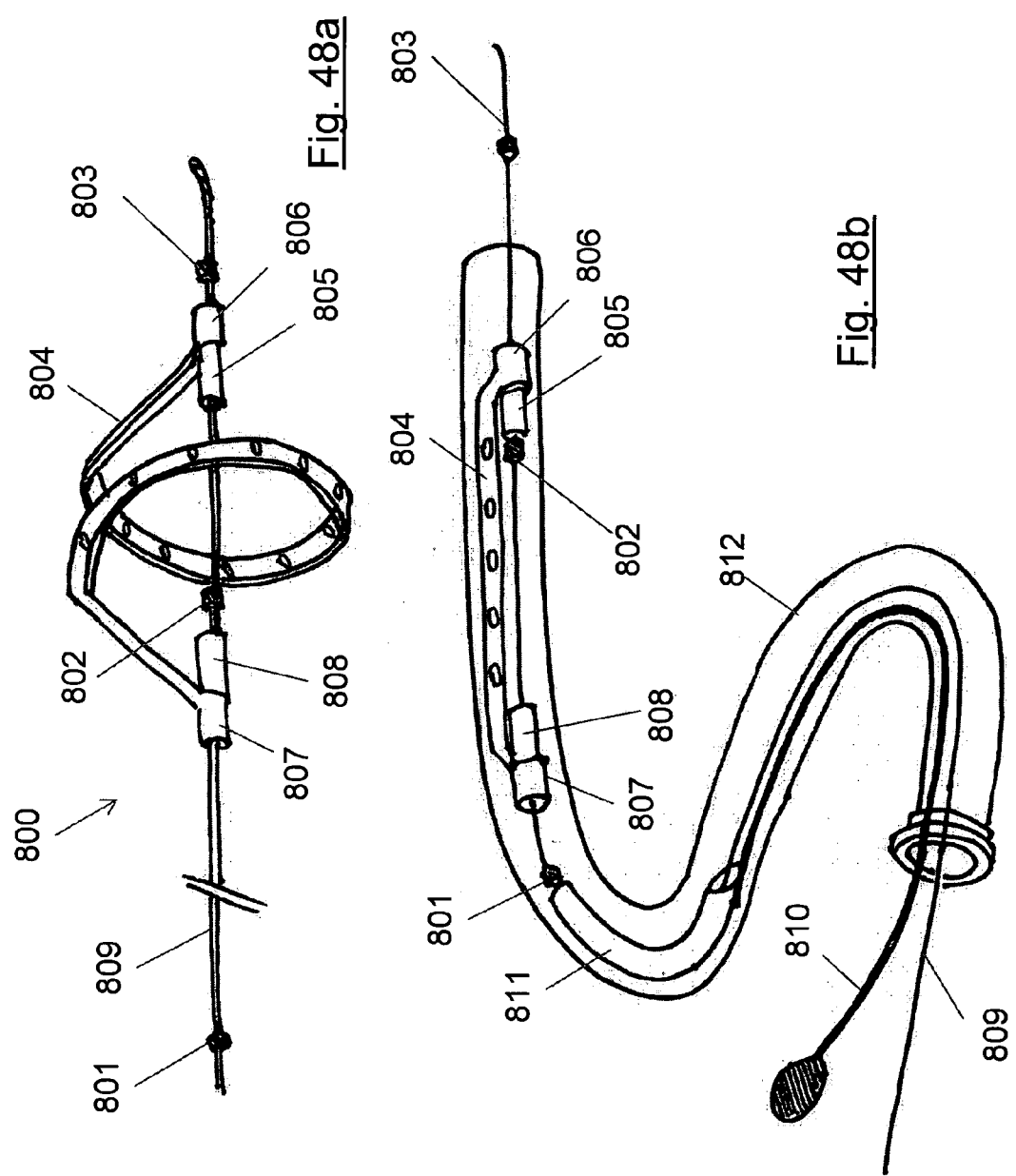

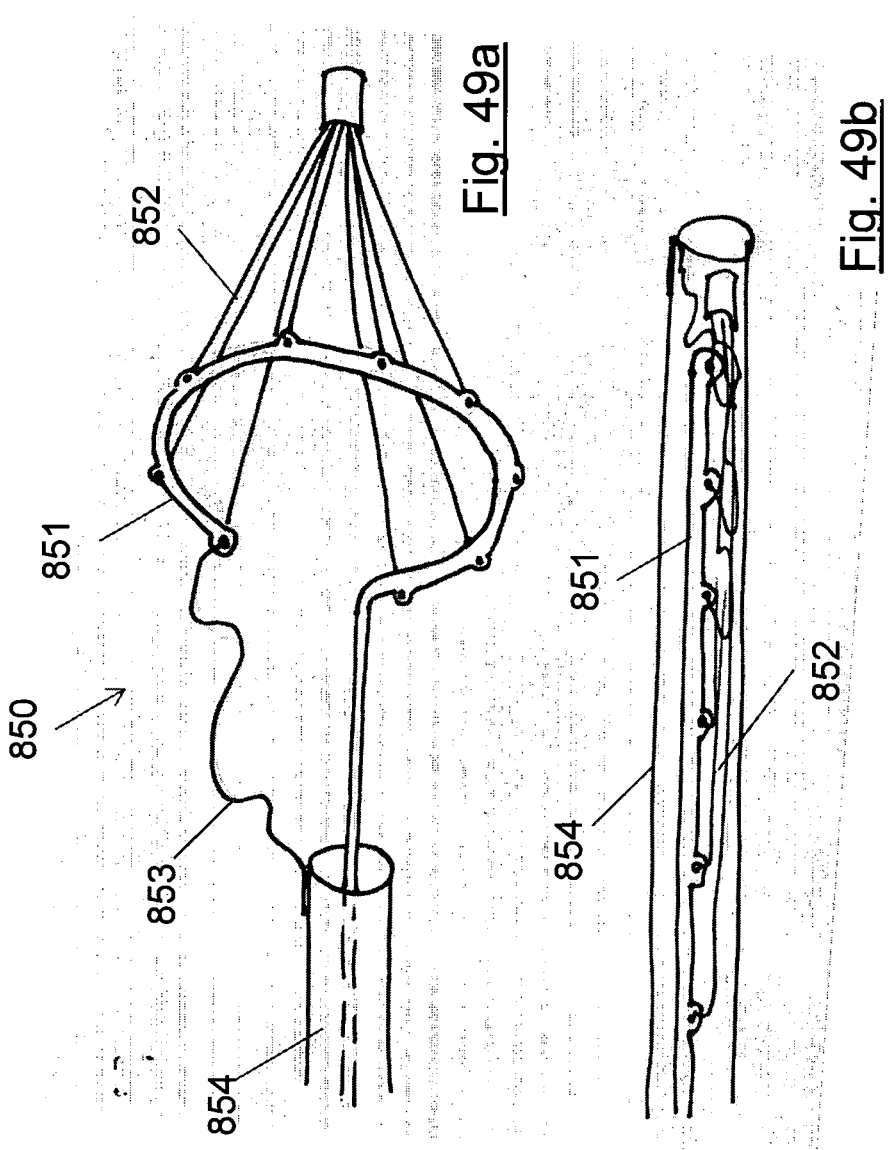

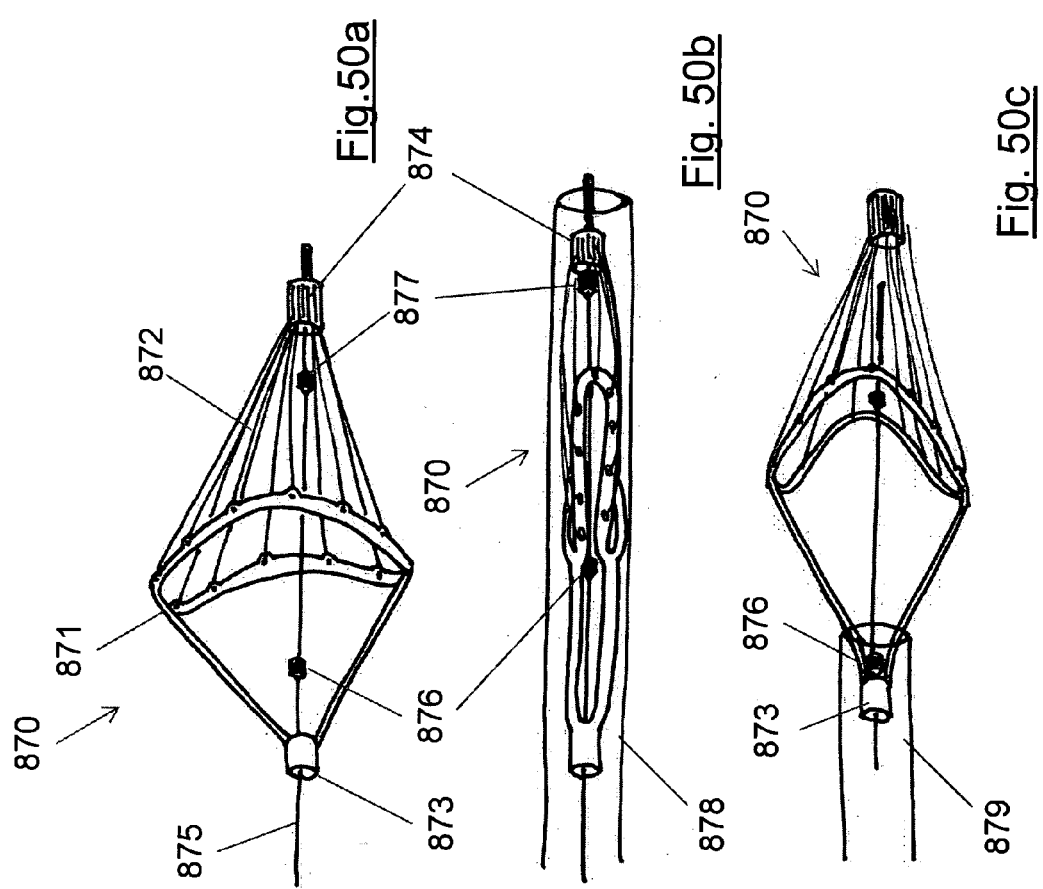

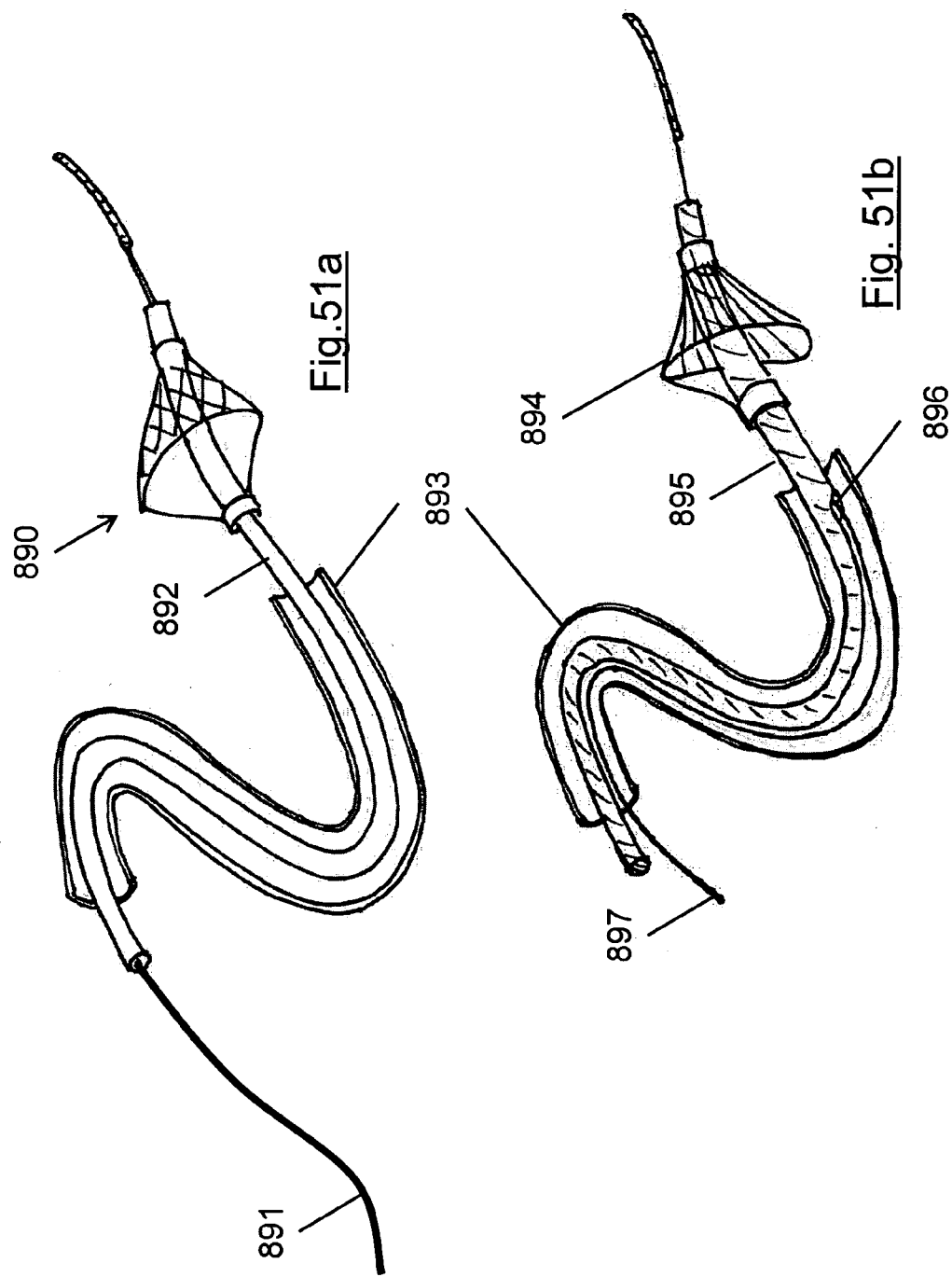

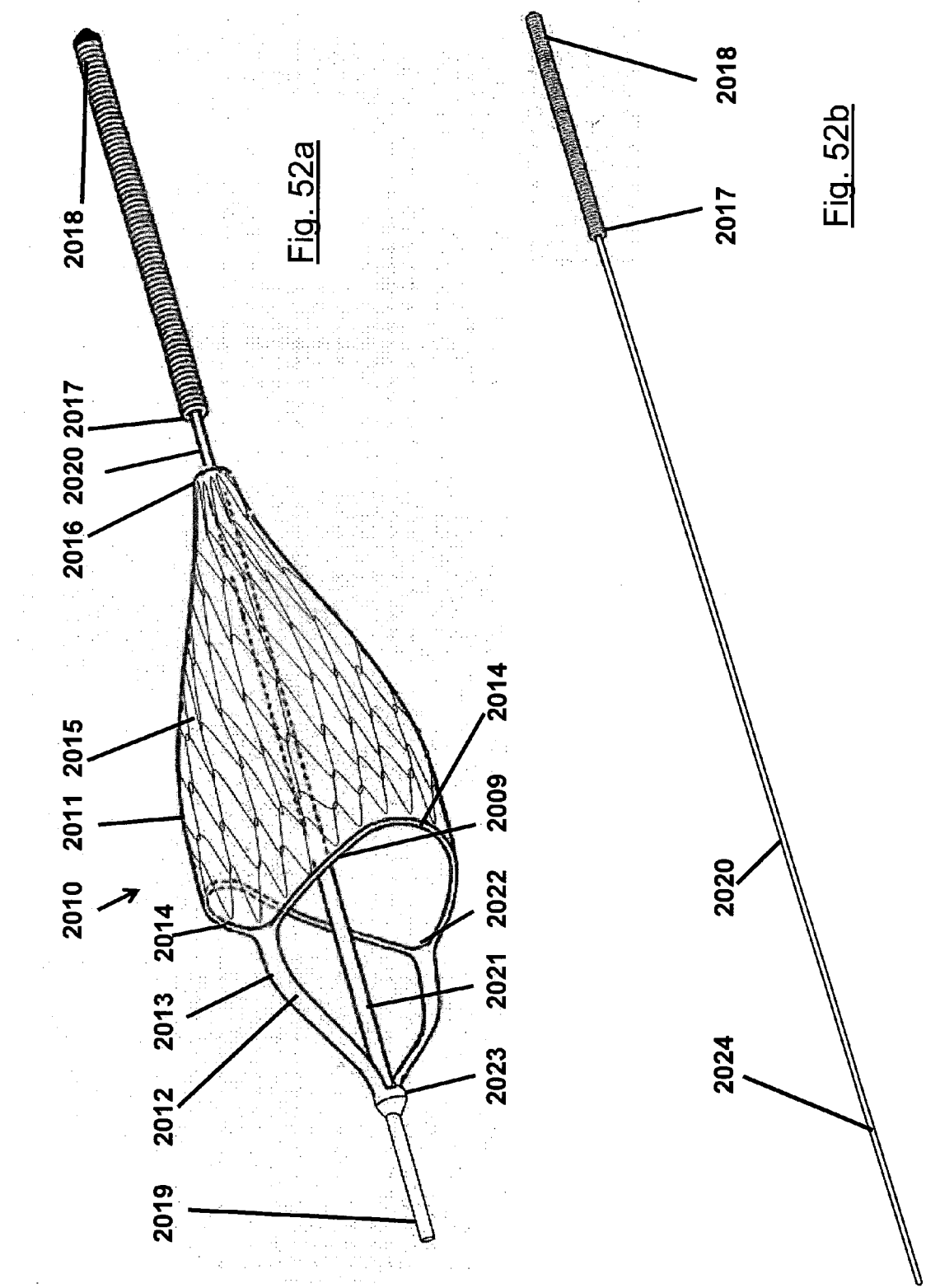

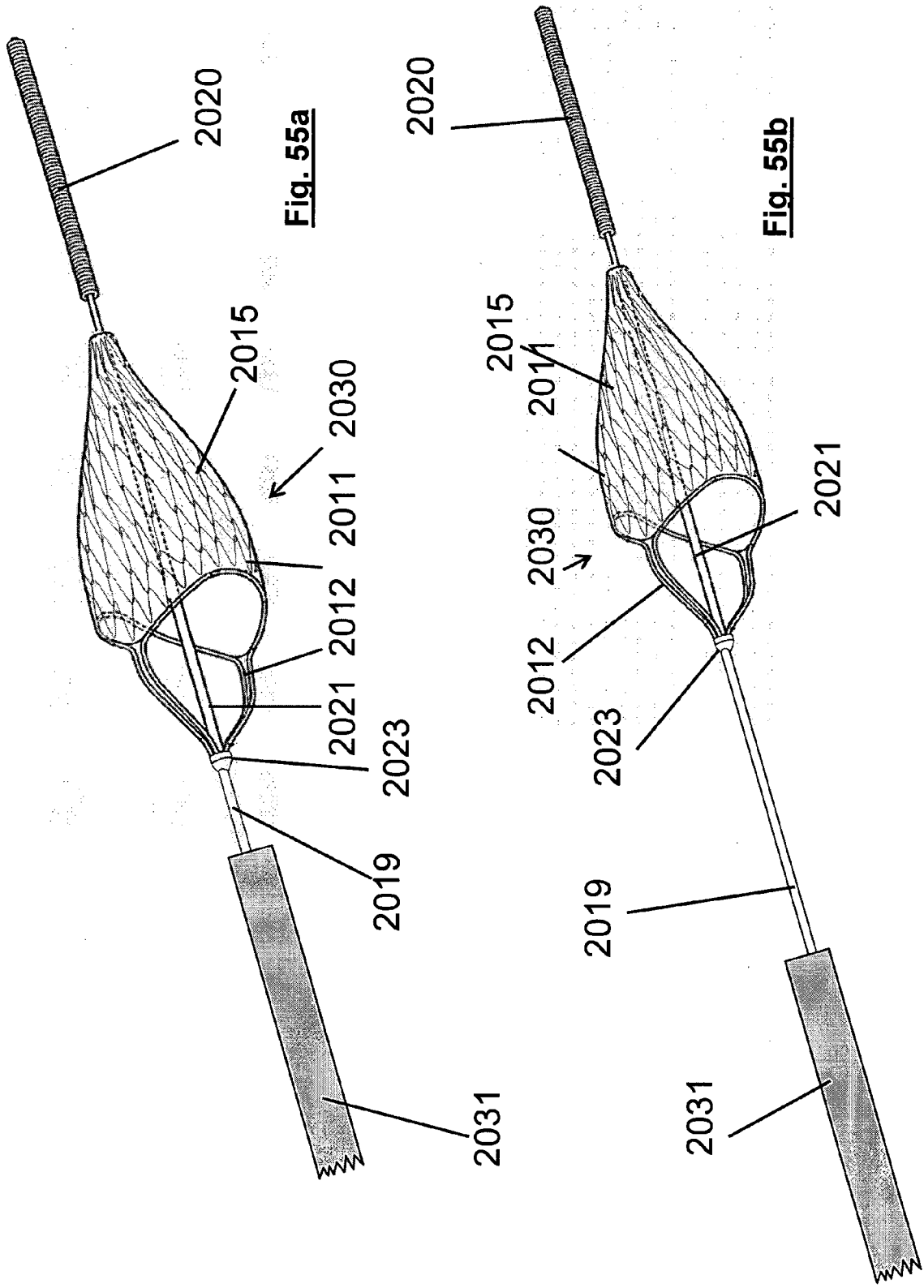

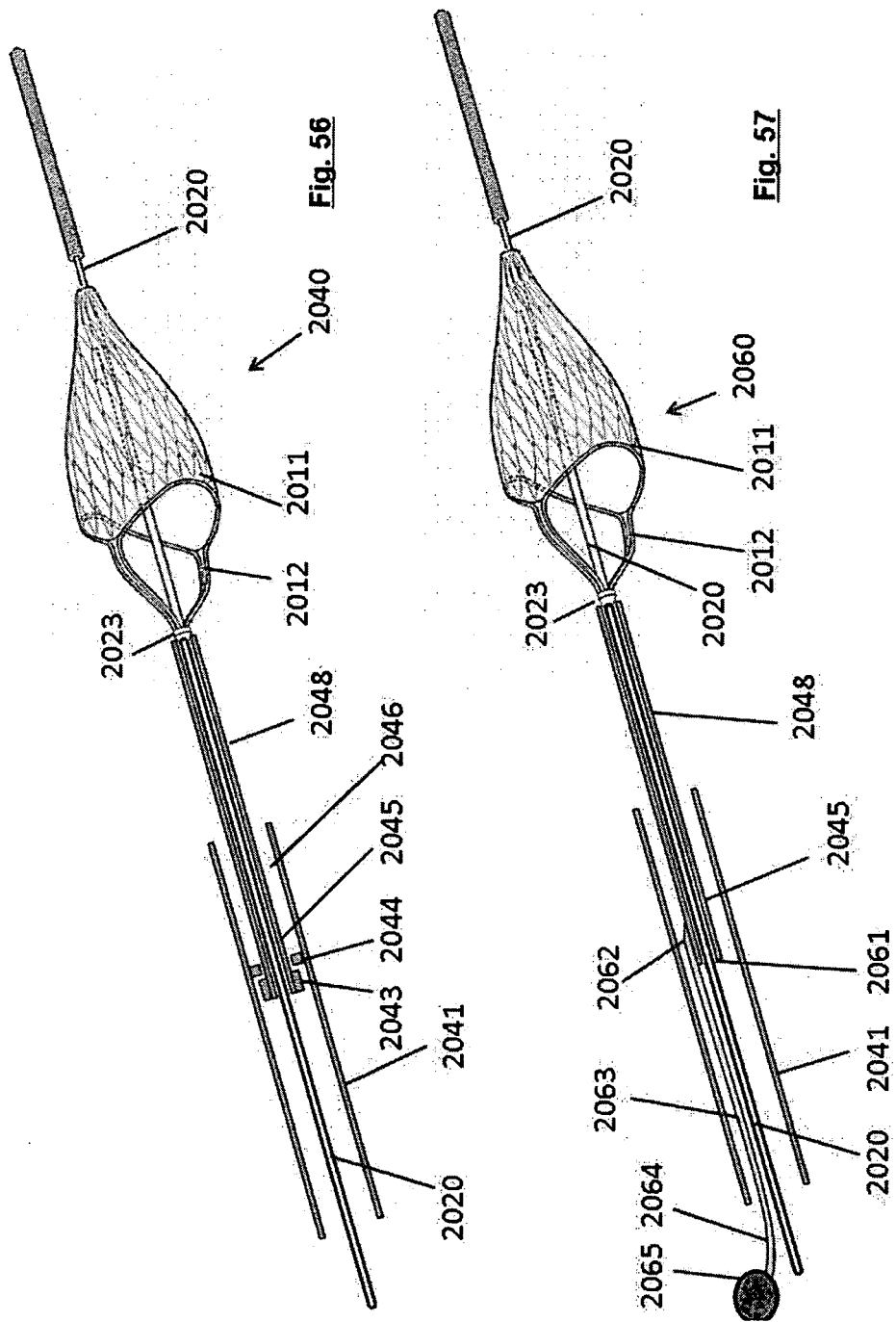

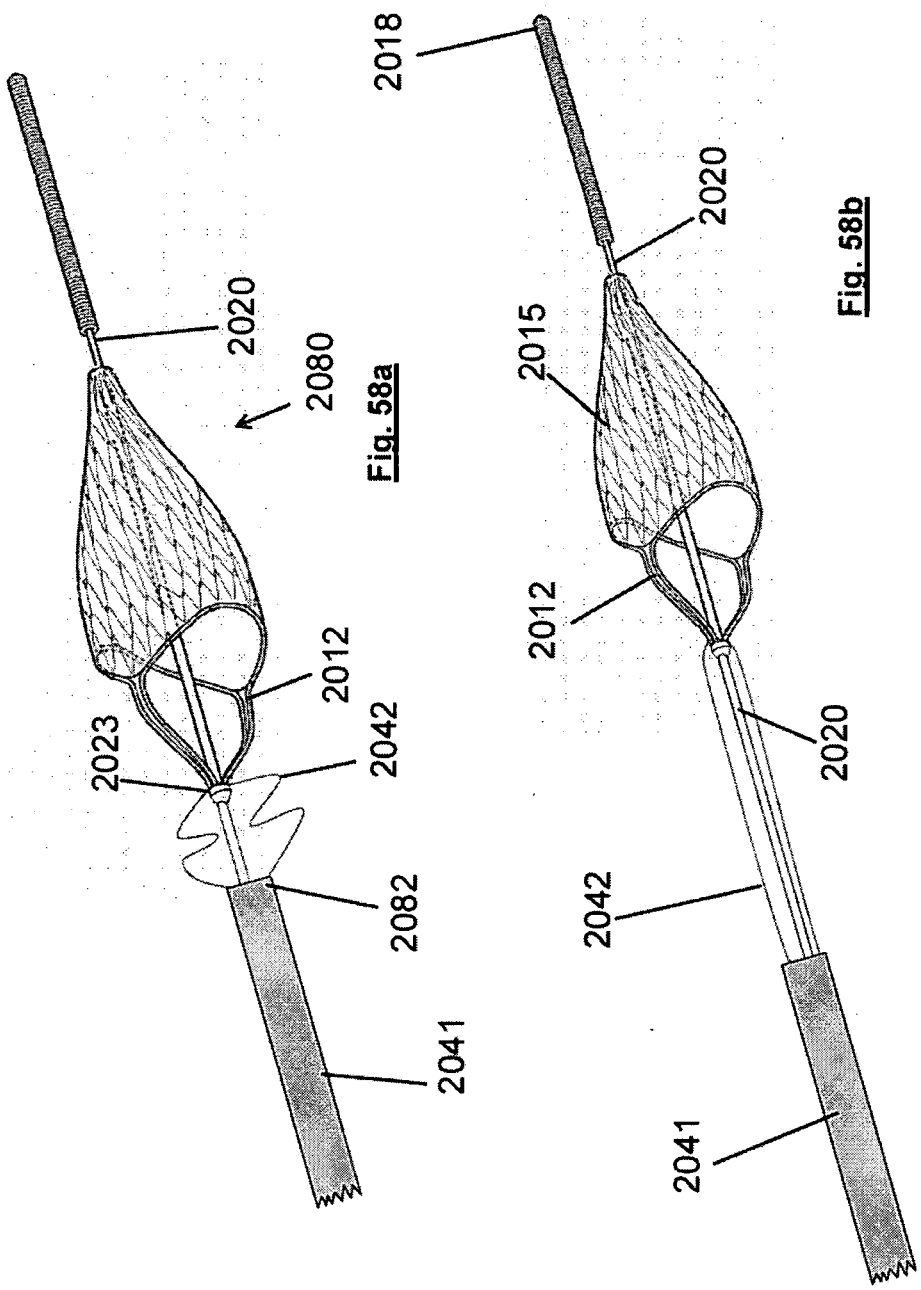

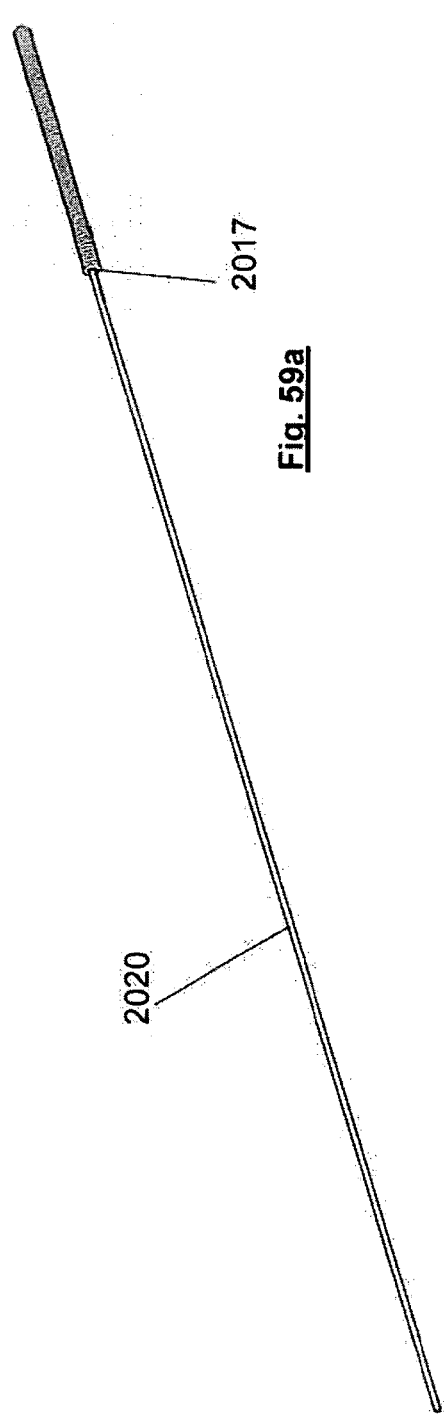
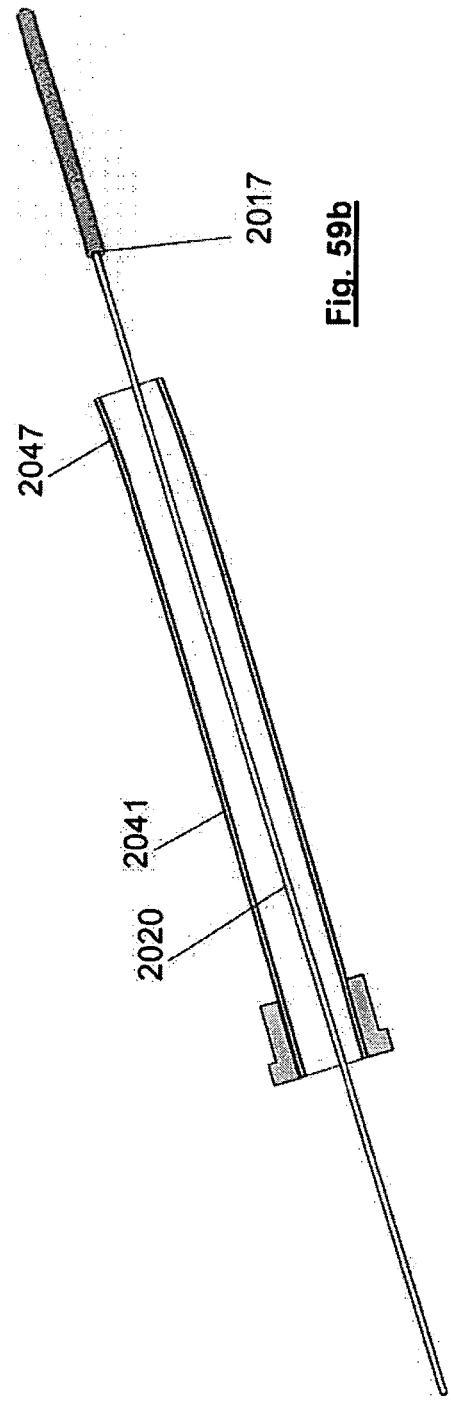
Fig. 59a
Fig. 59b

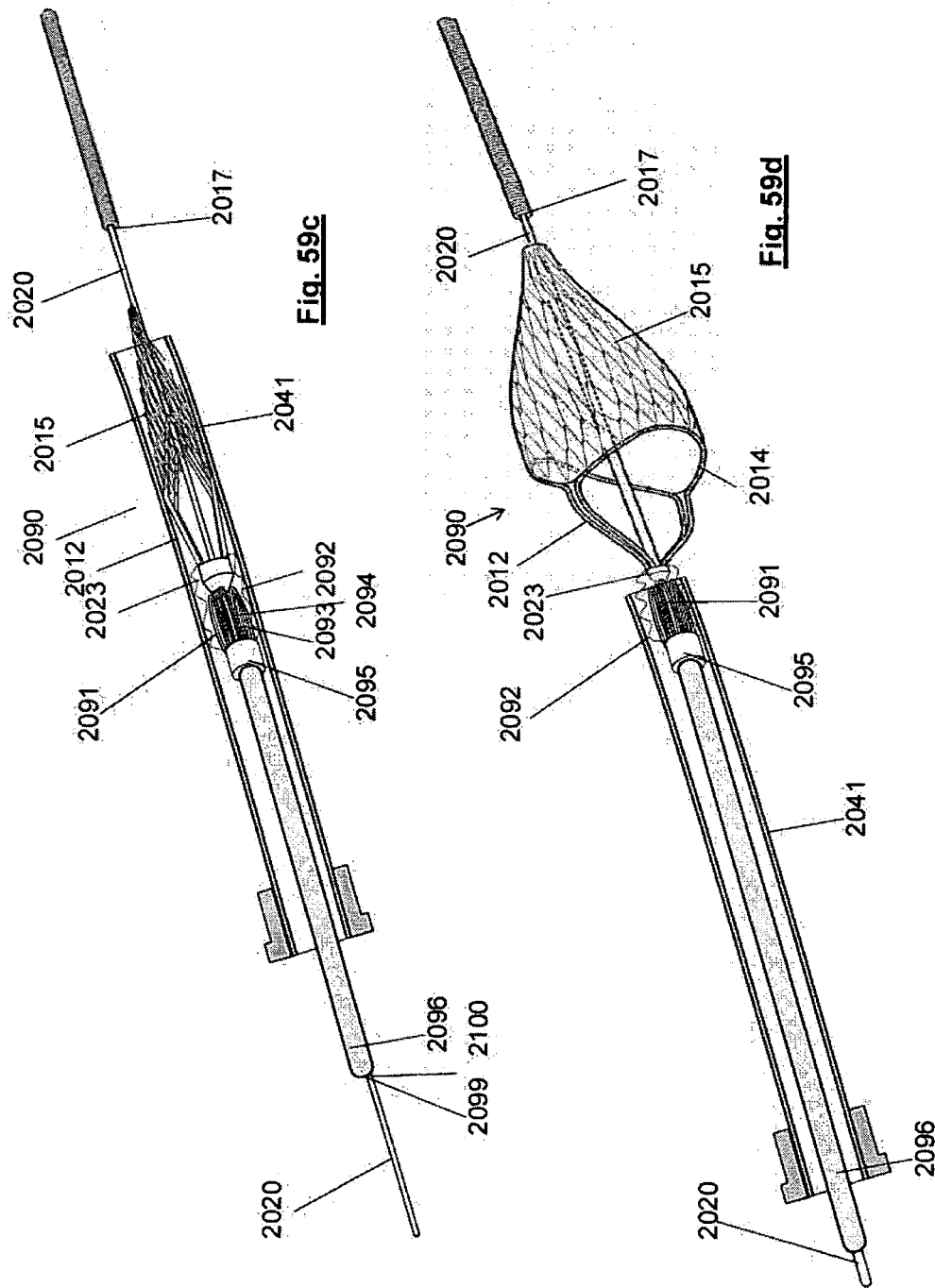

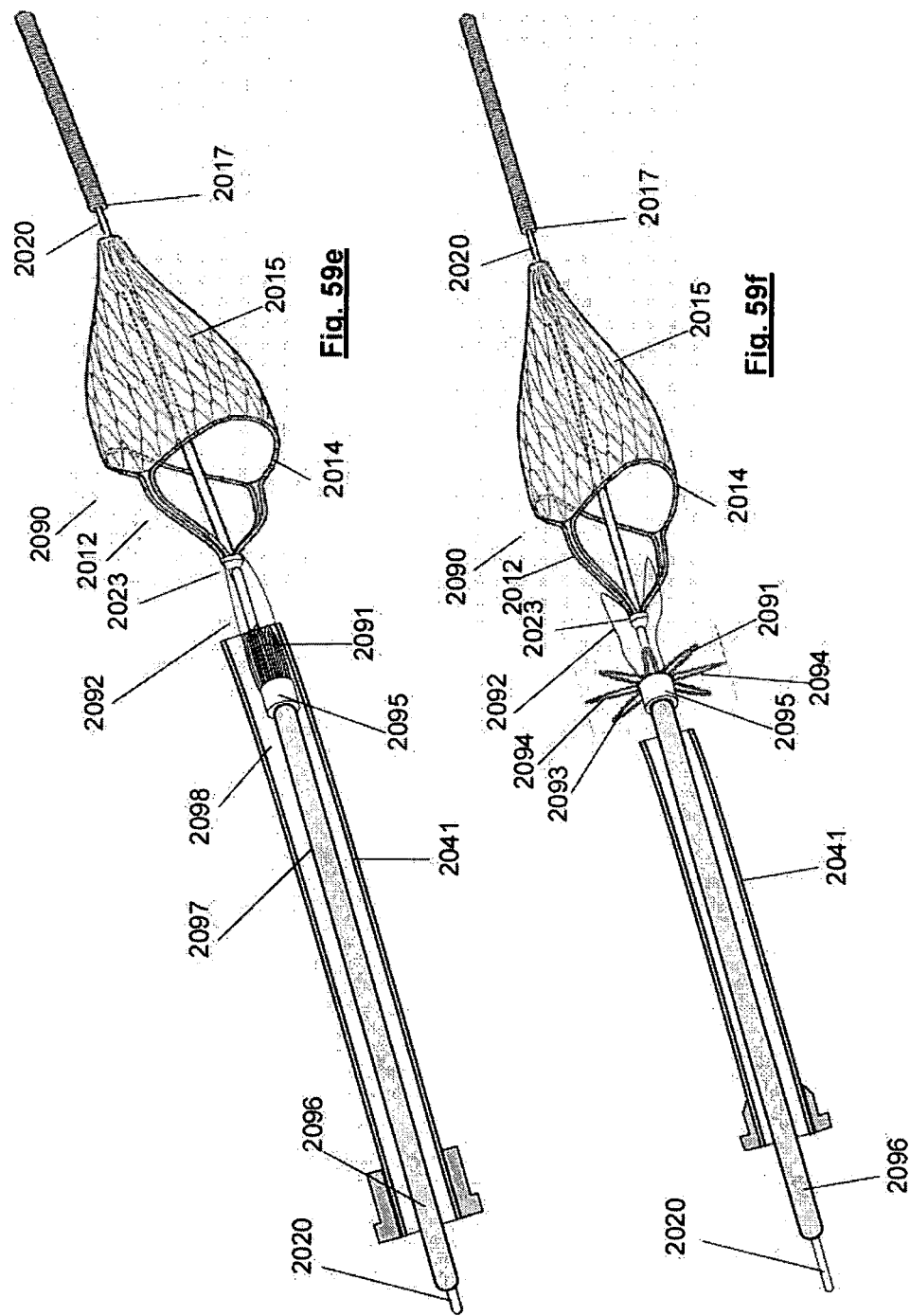

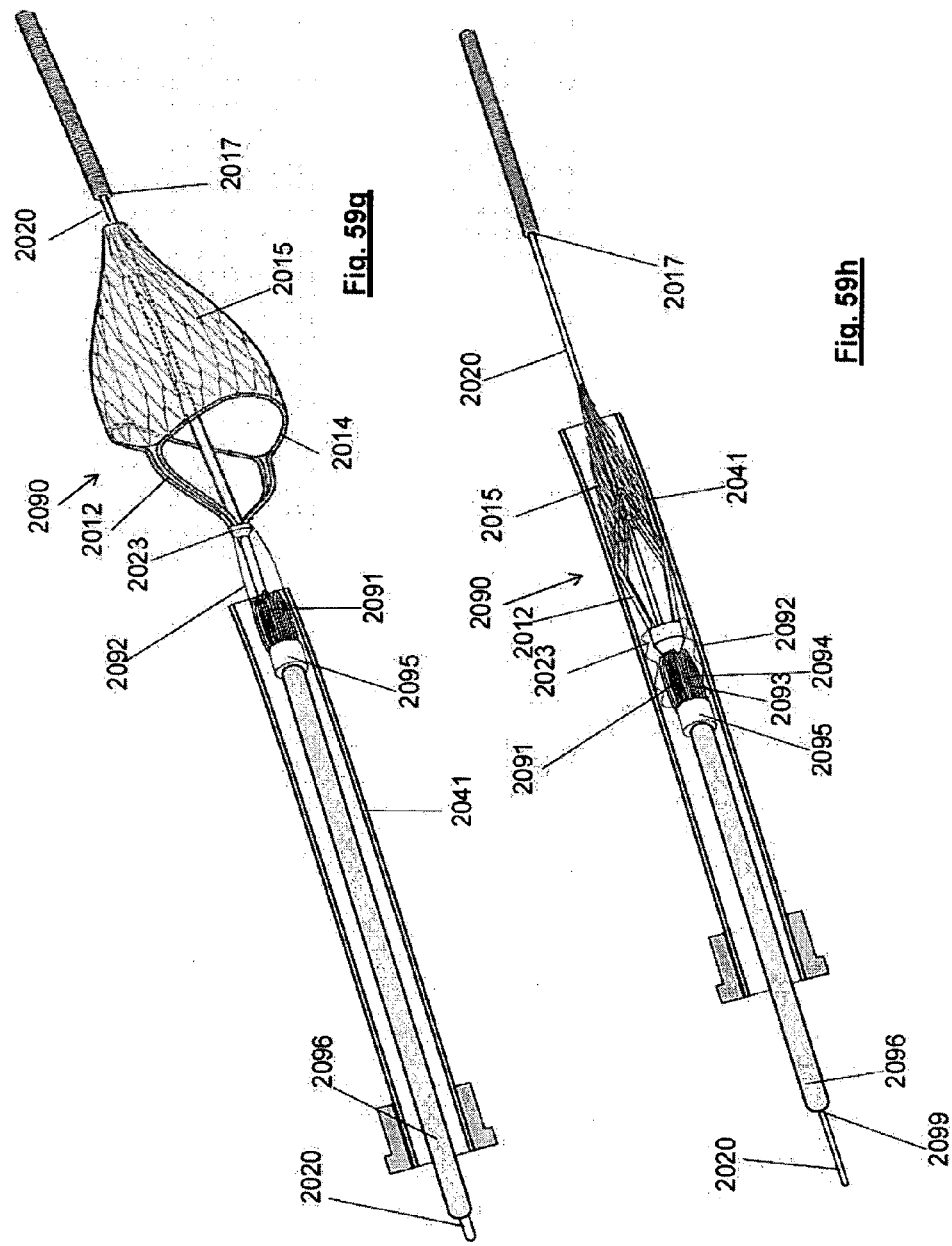

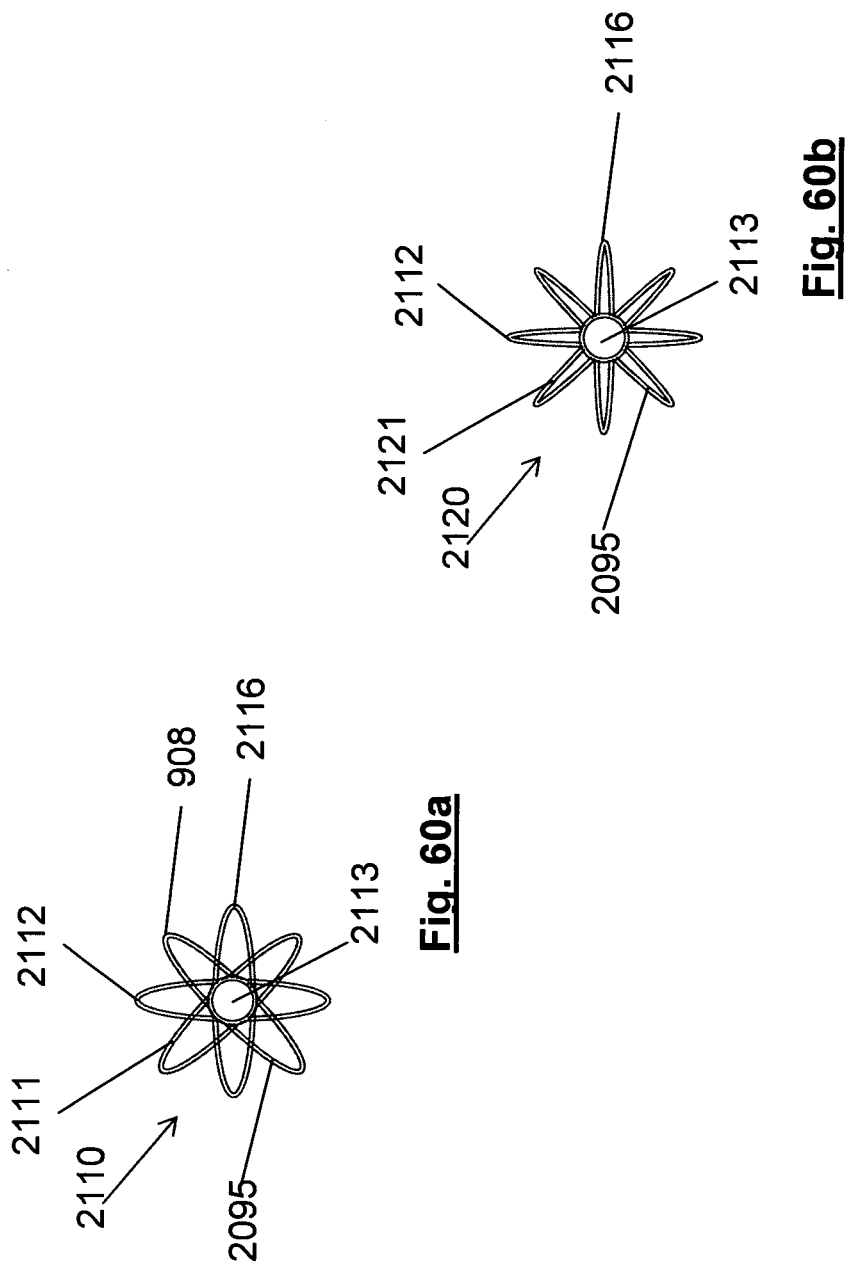

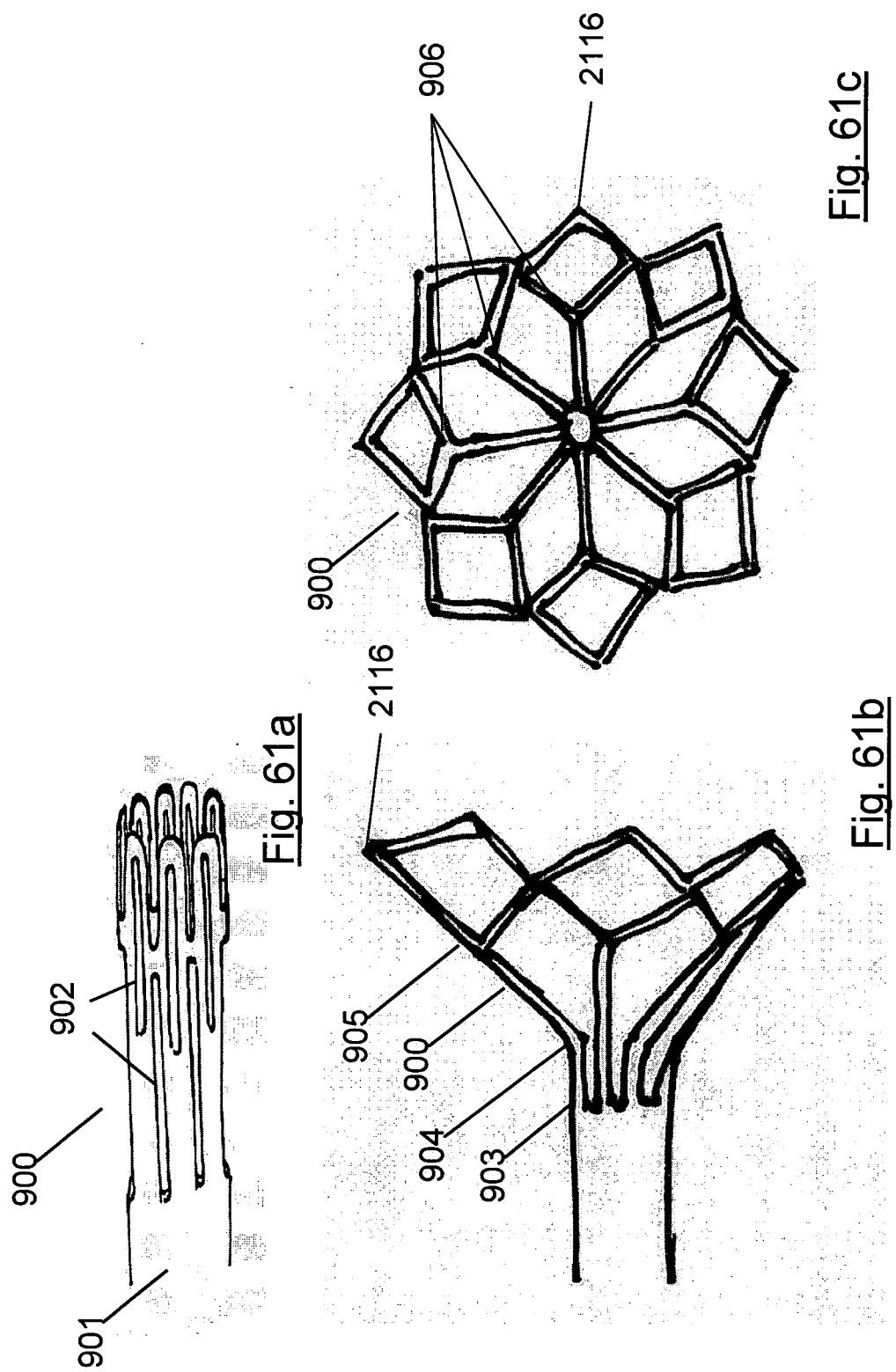

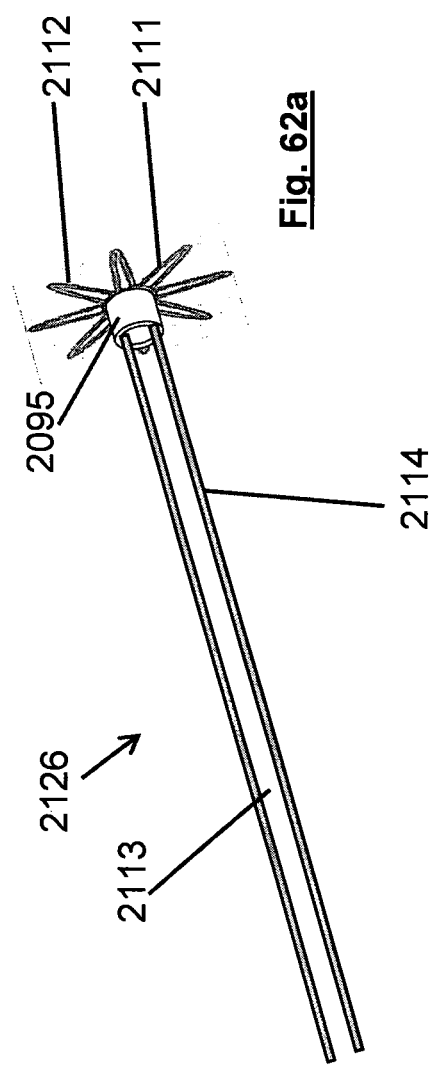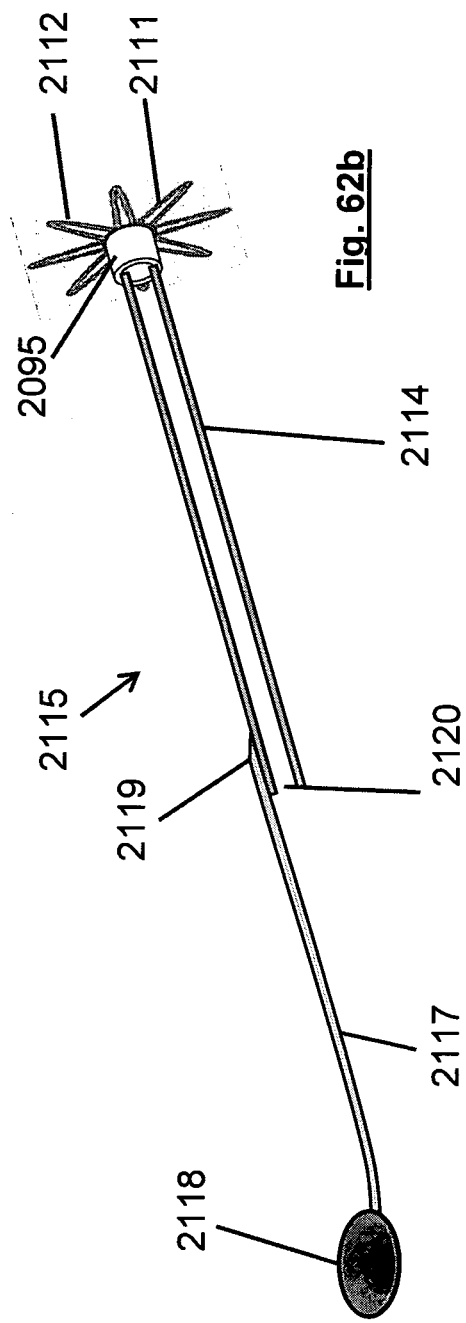
Fig. 62a
Fig. 62b

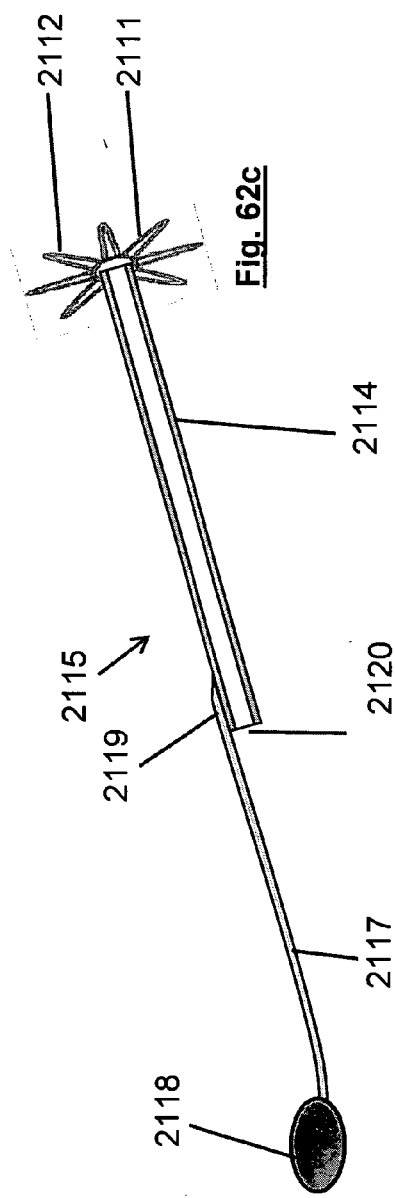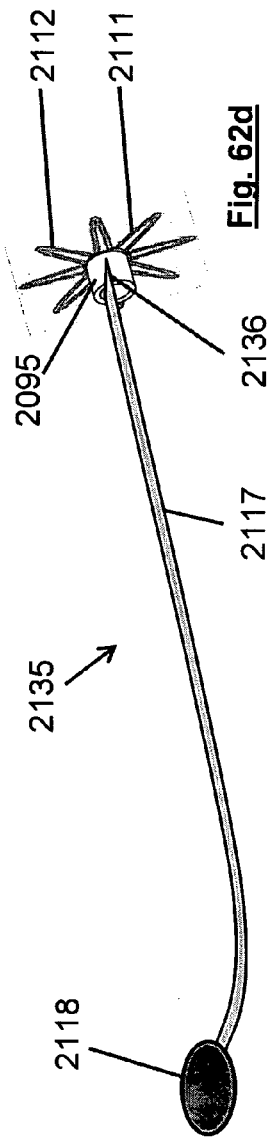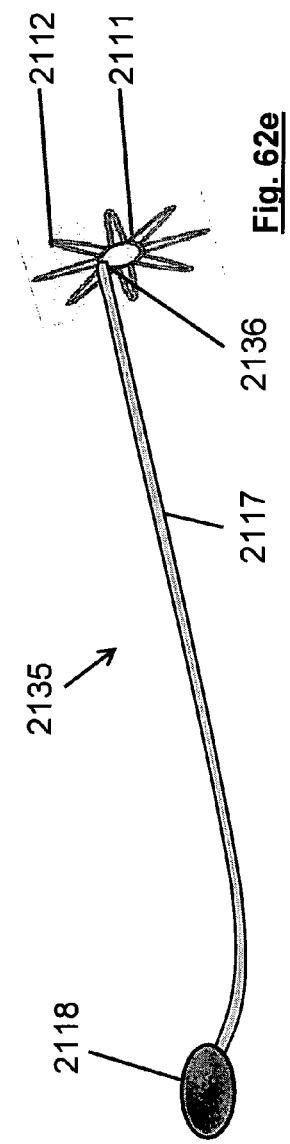

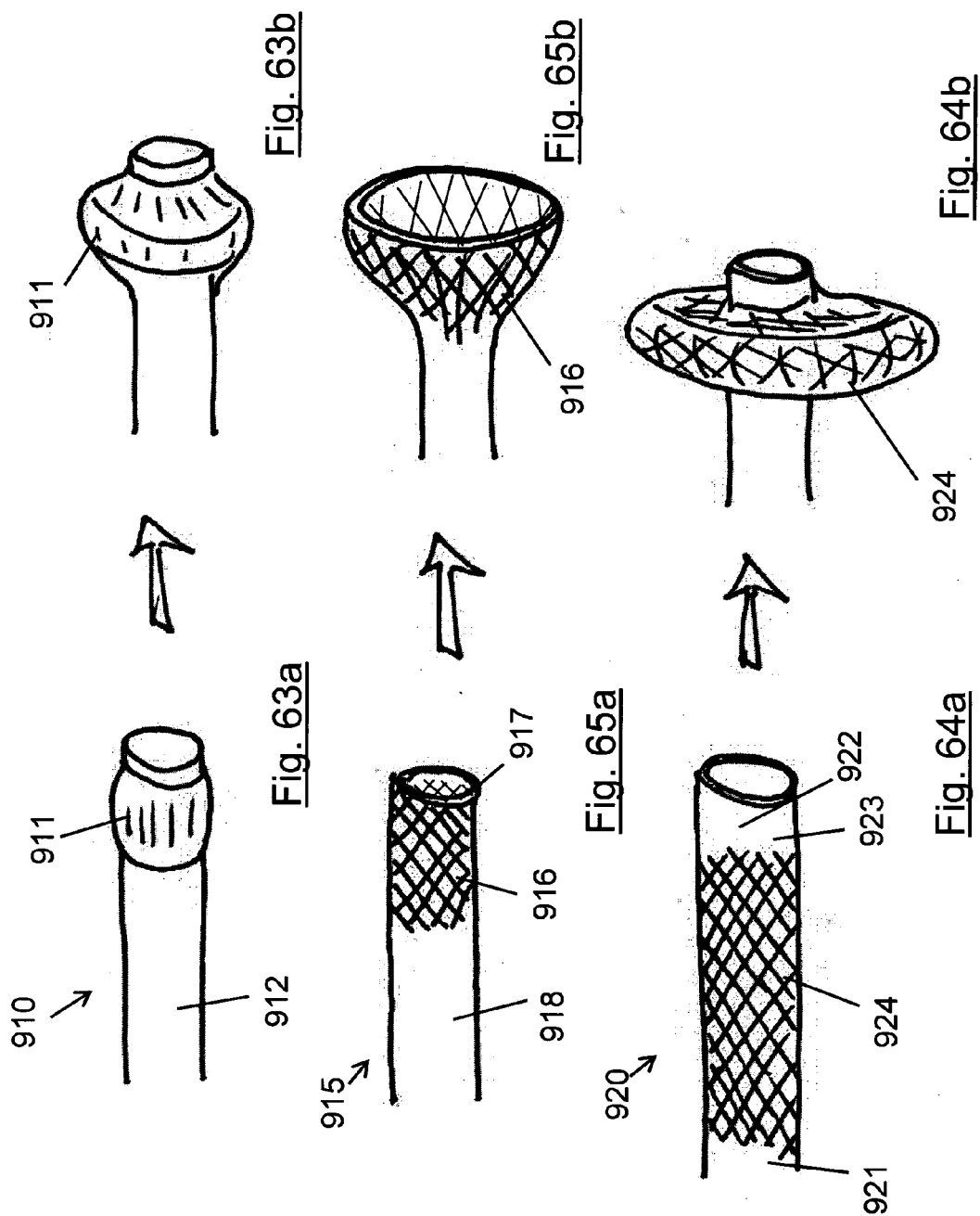

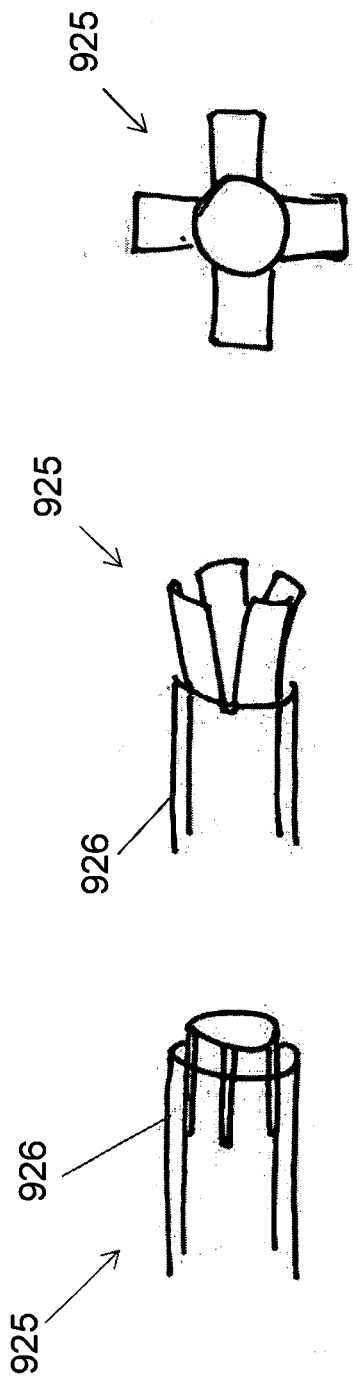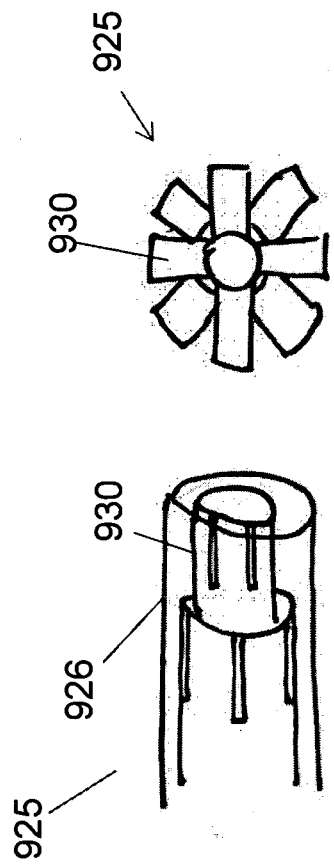

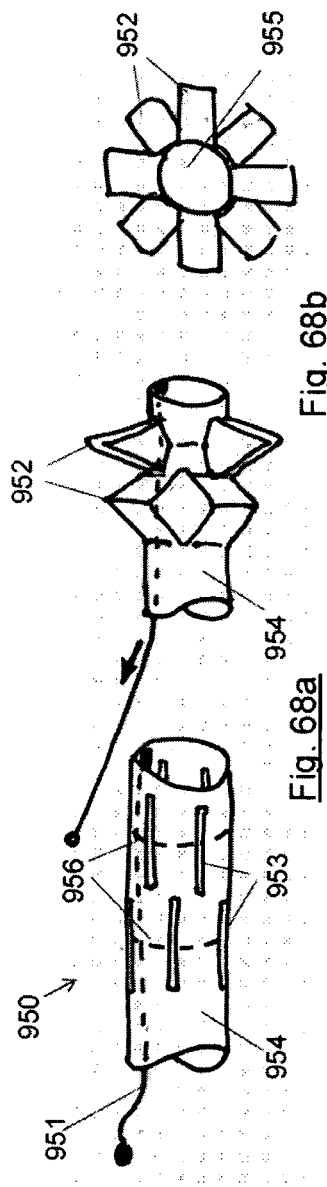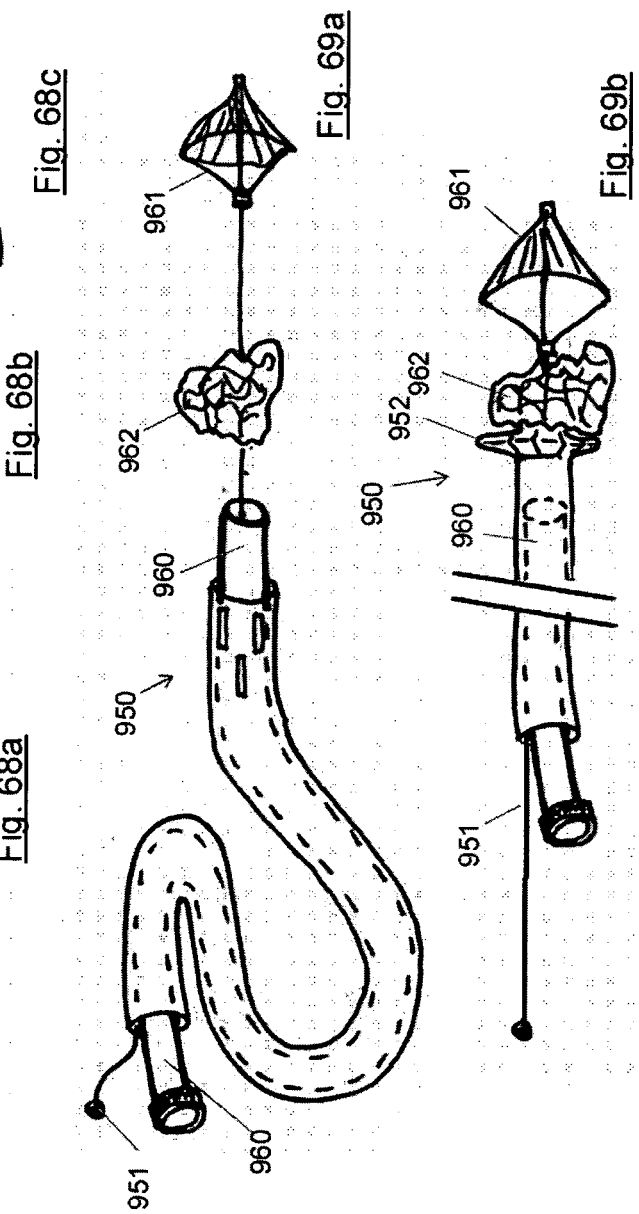
Fig. 68a
Fig. 68b
Fig. 68c
Fig. 69a
Fig. 69b

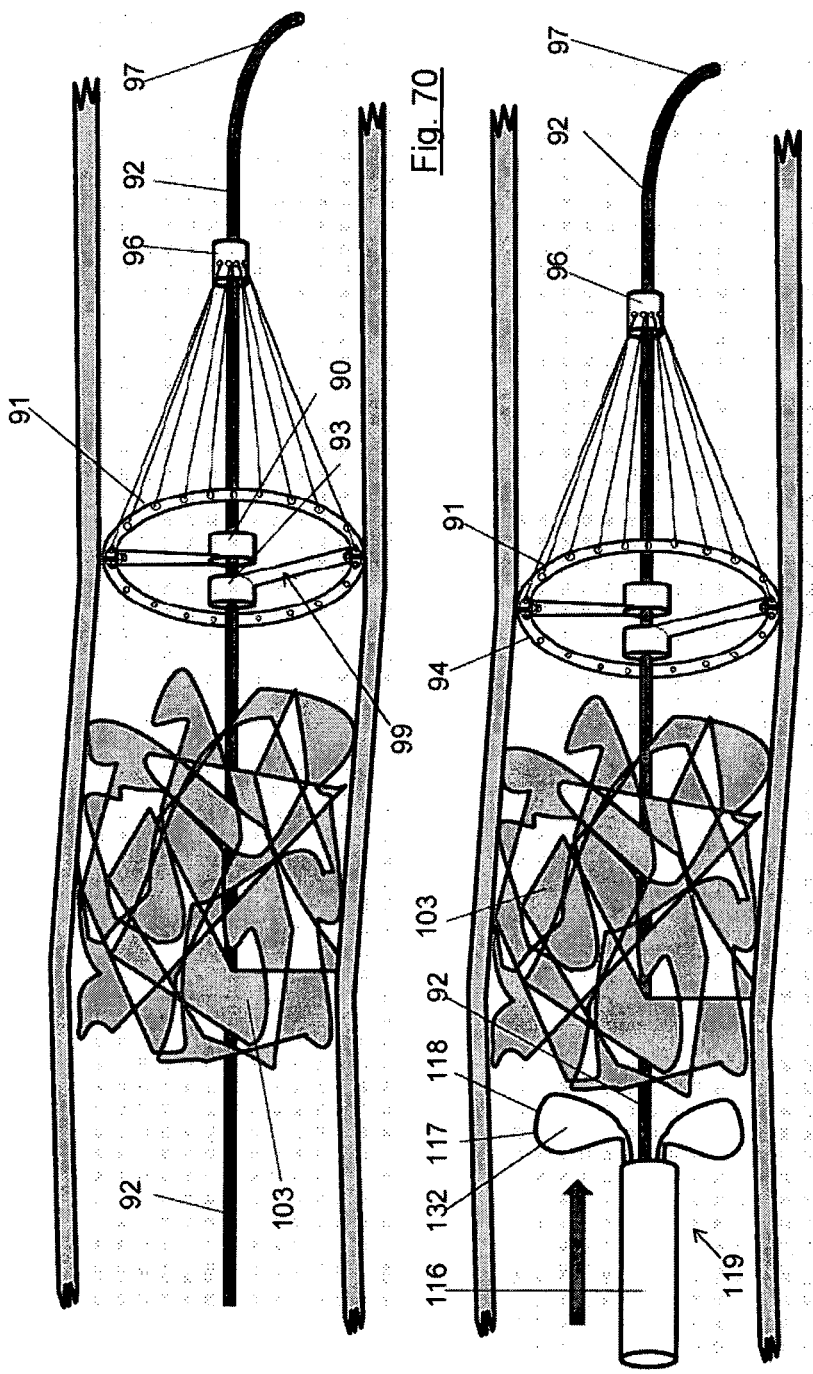

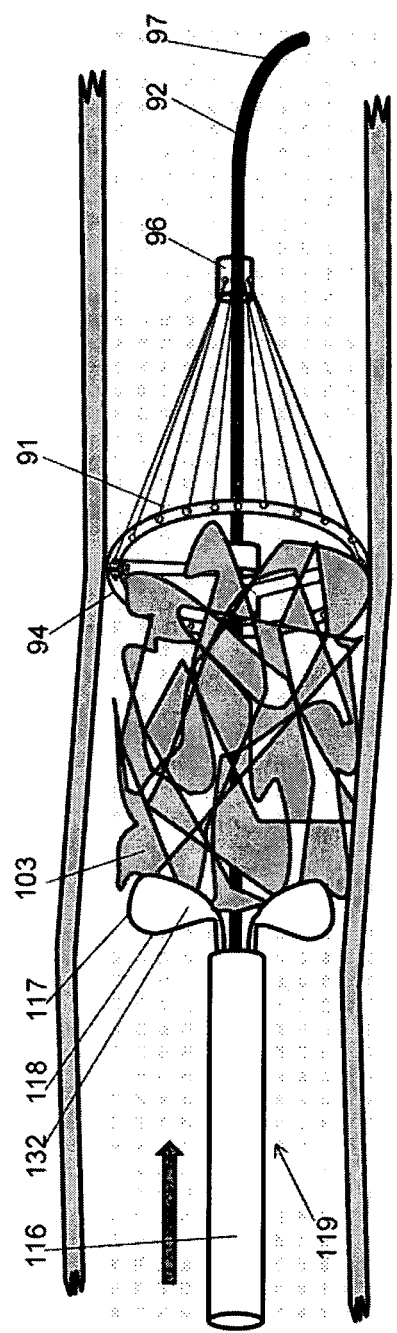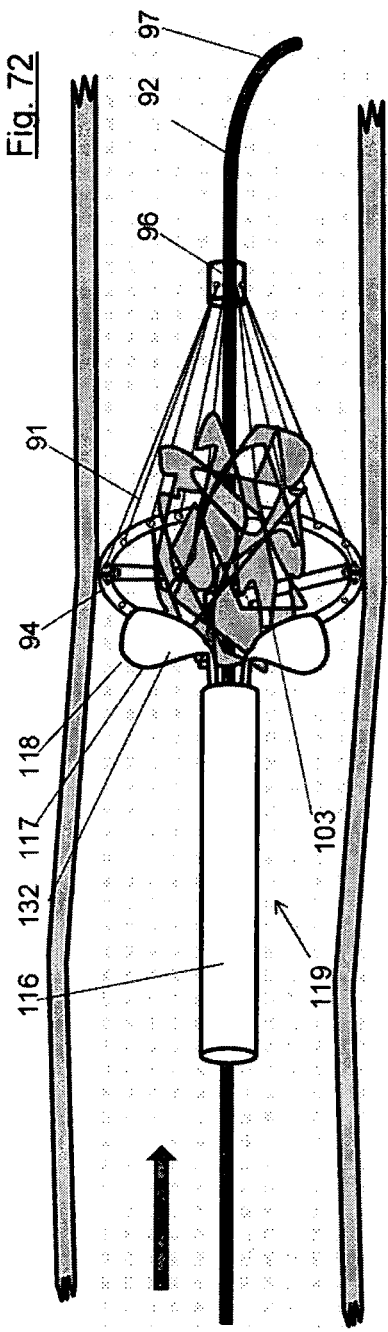

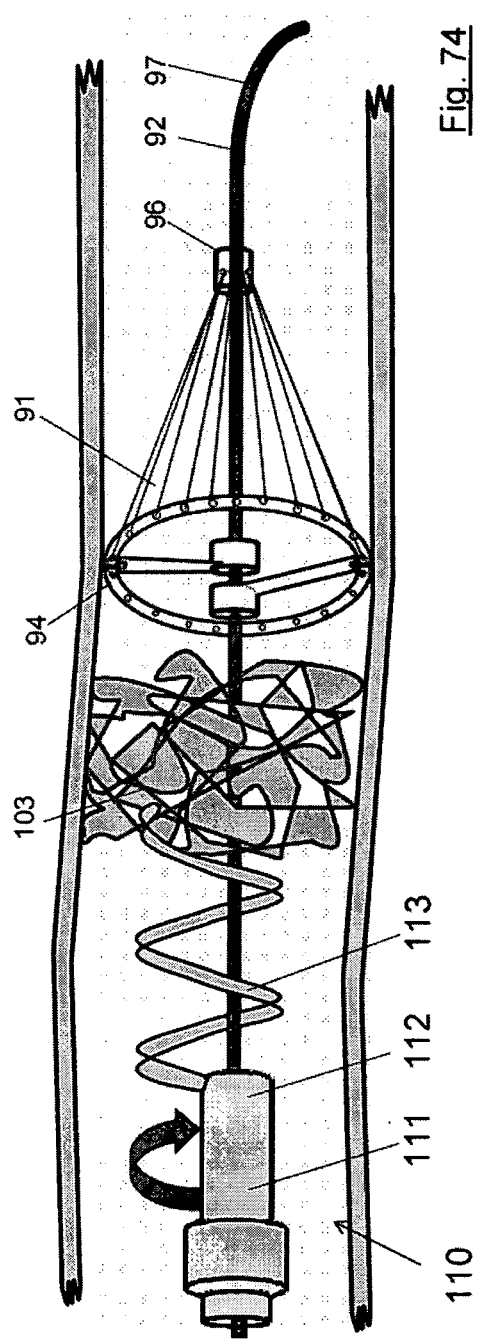
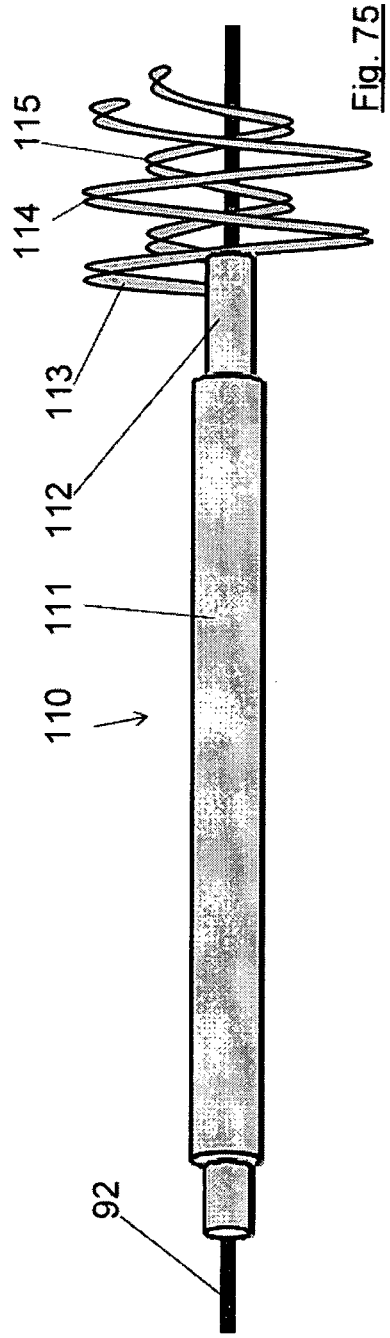
Fig. 74
Fig. 75

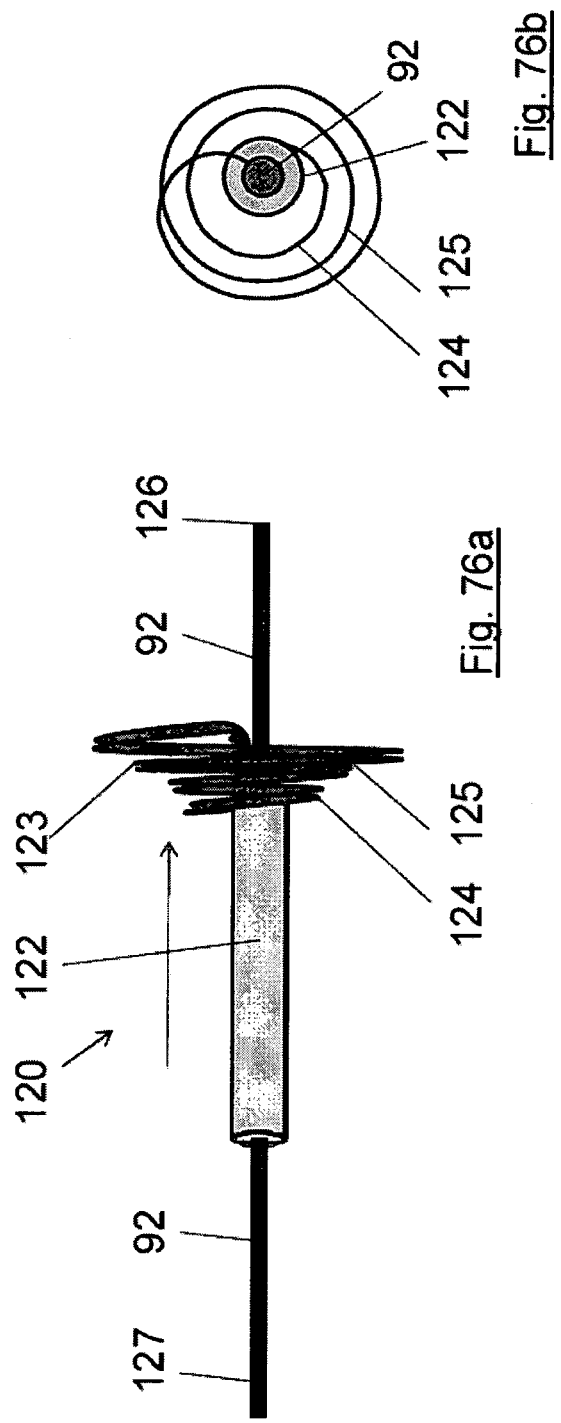

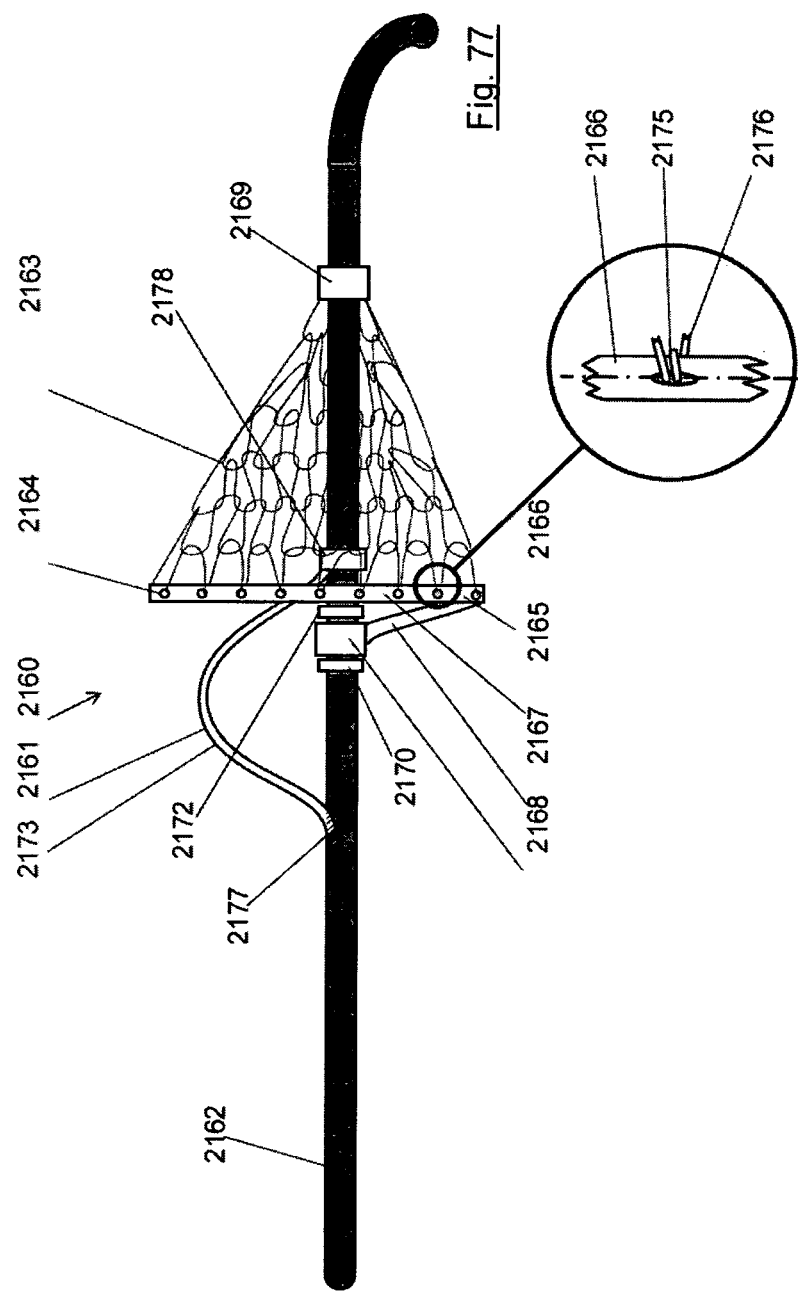

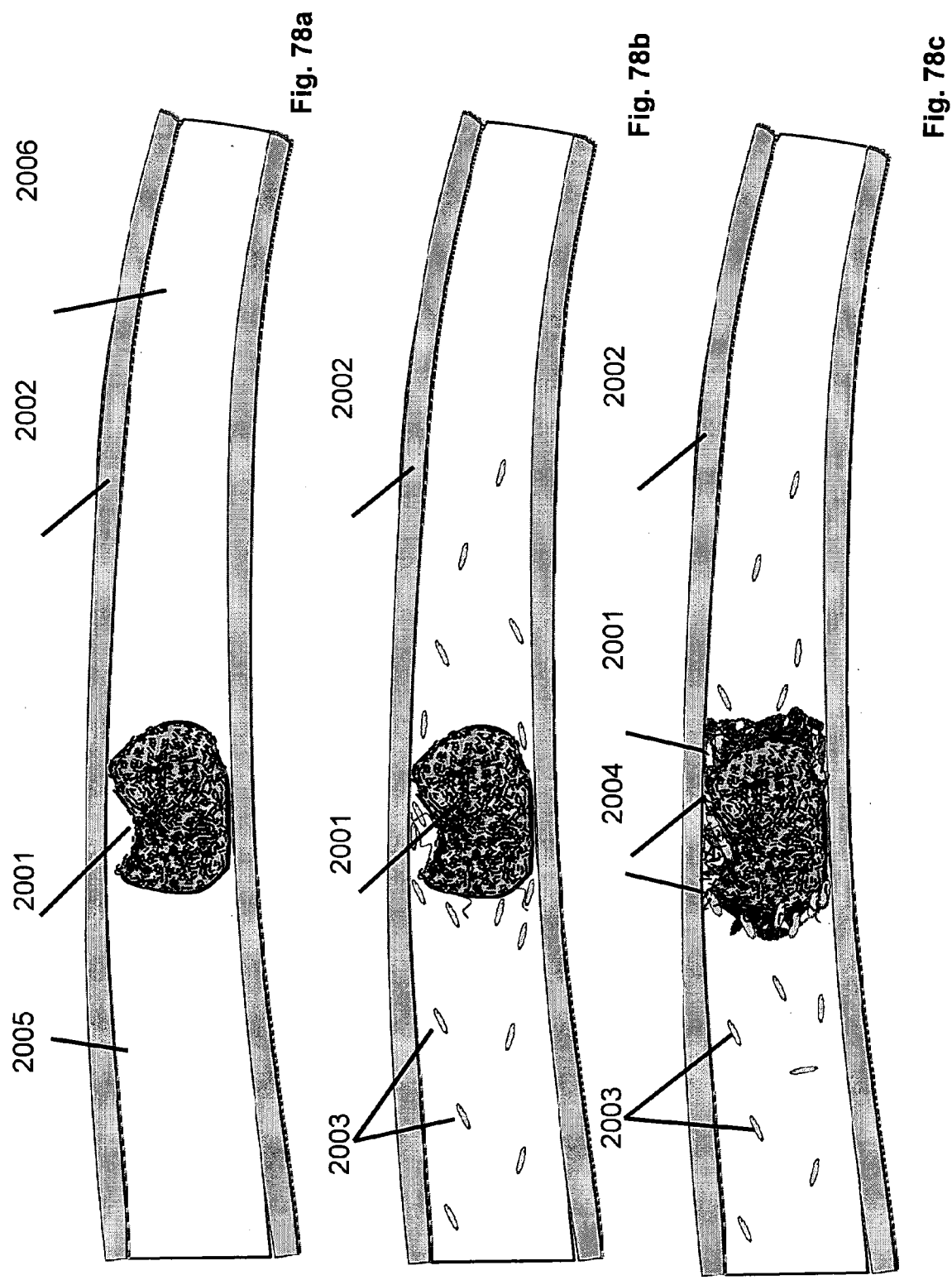

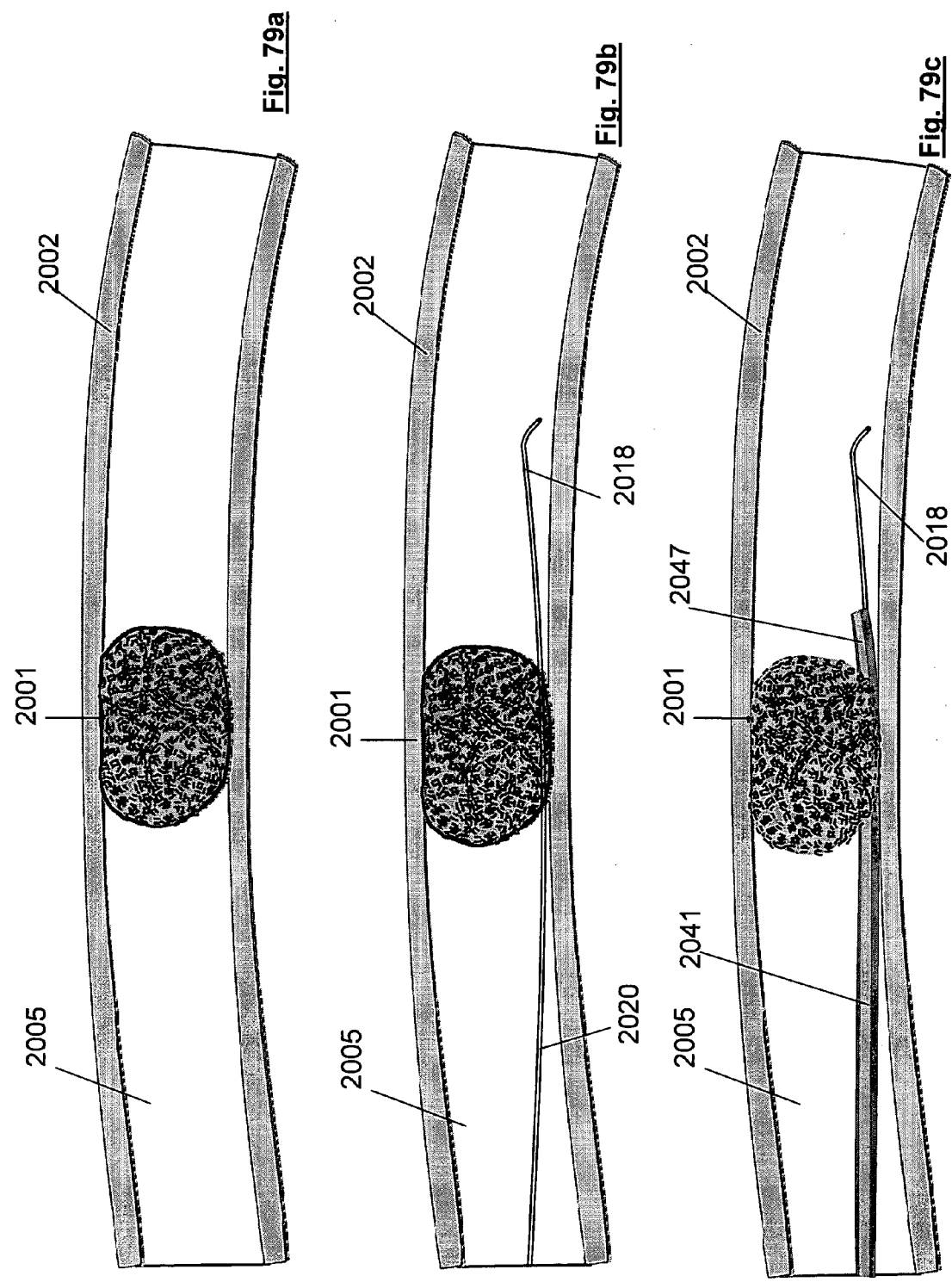

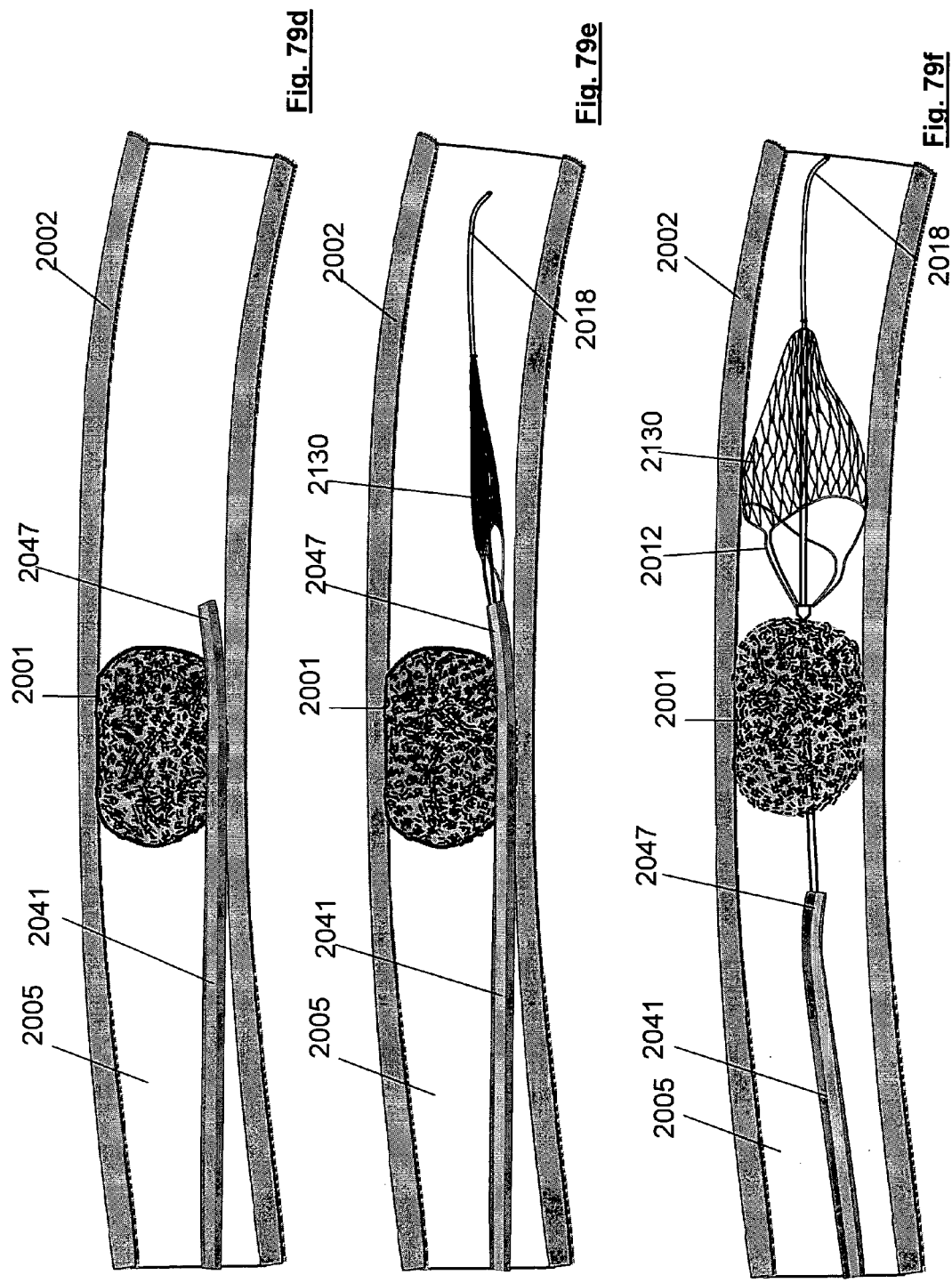

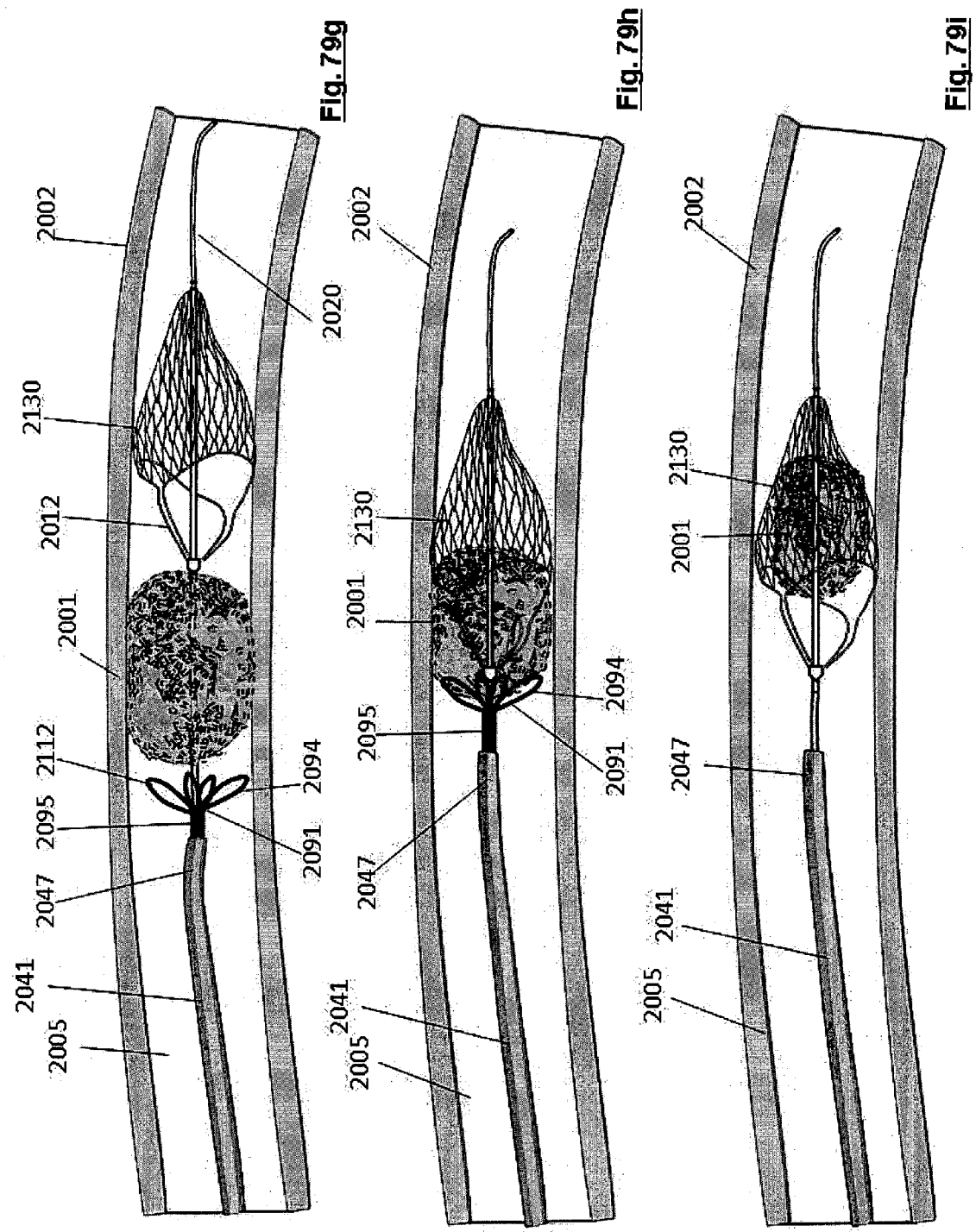

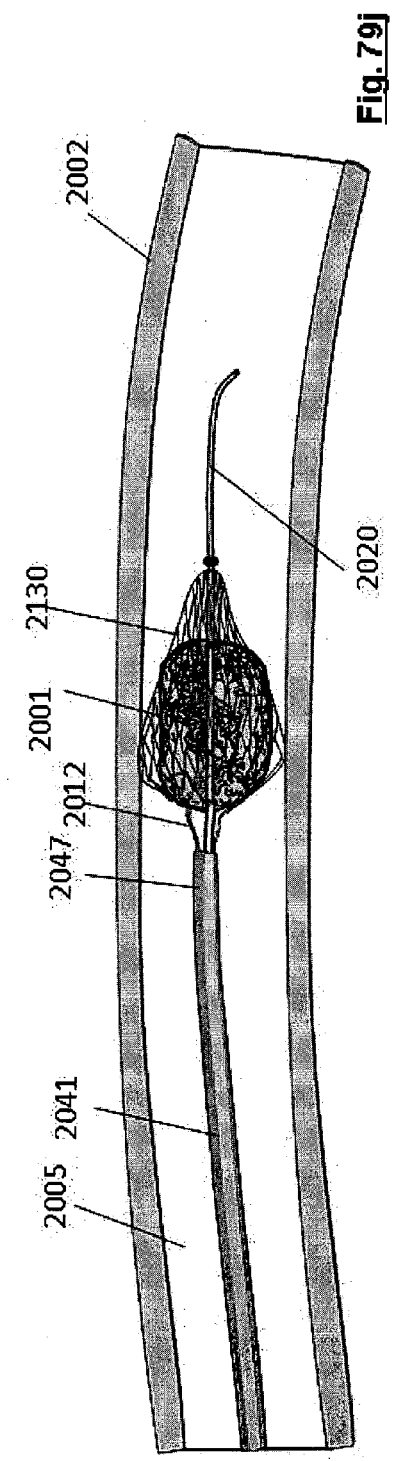
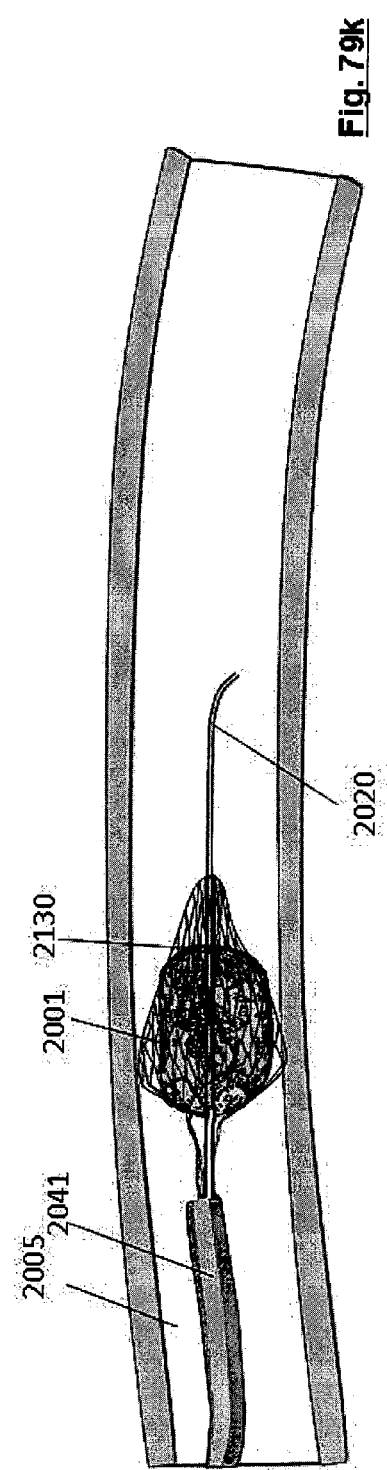
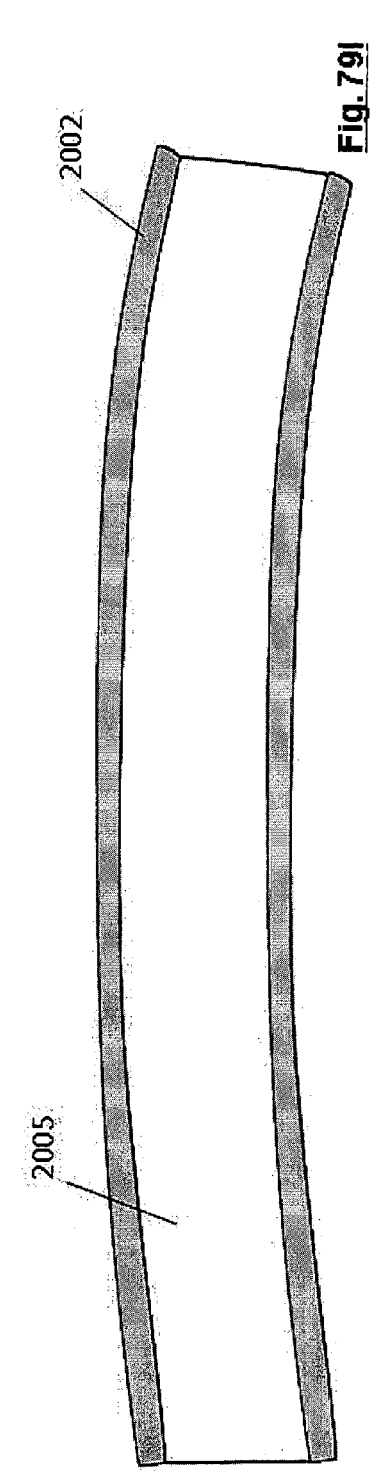

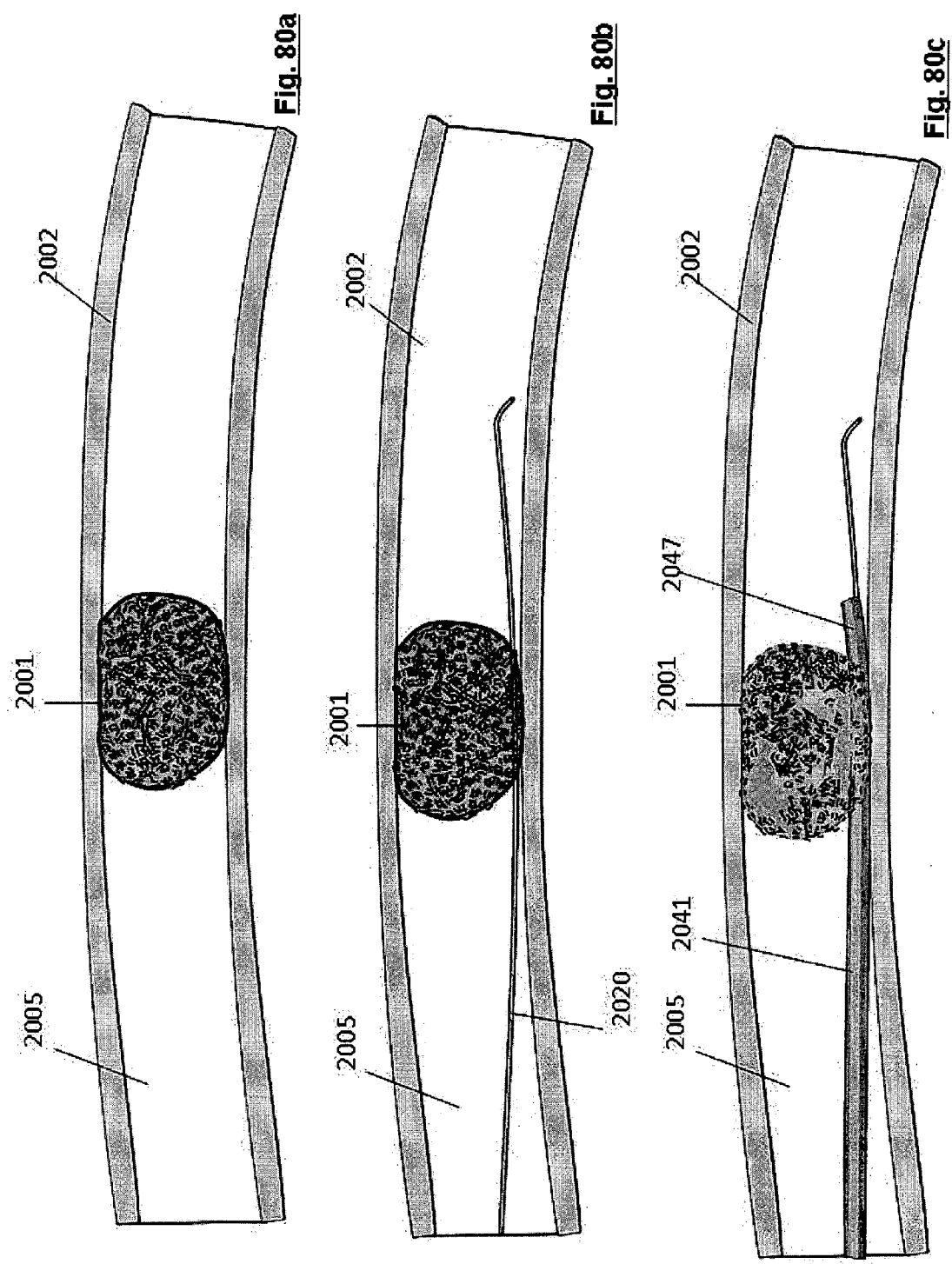

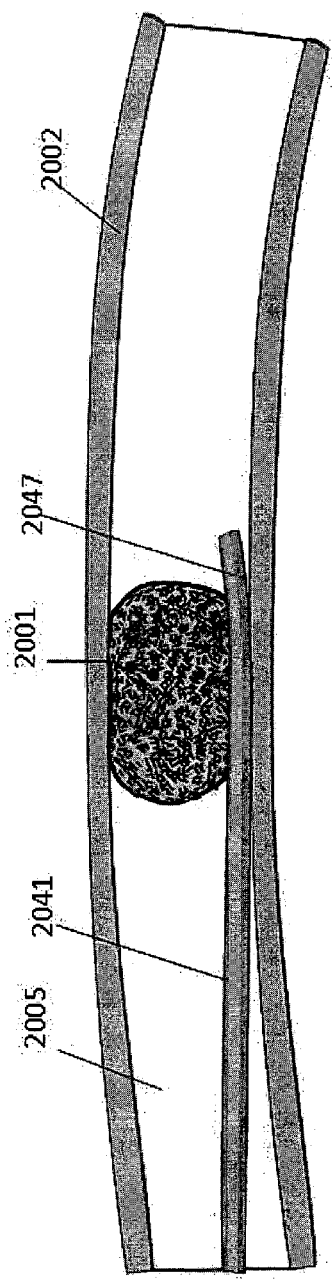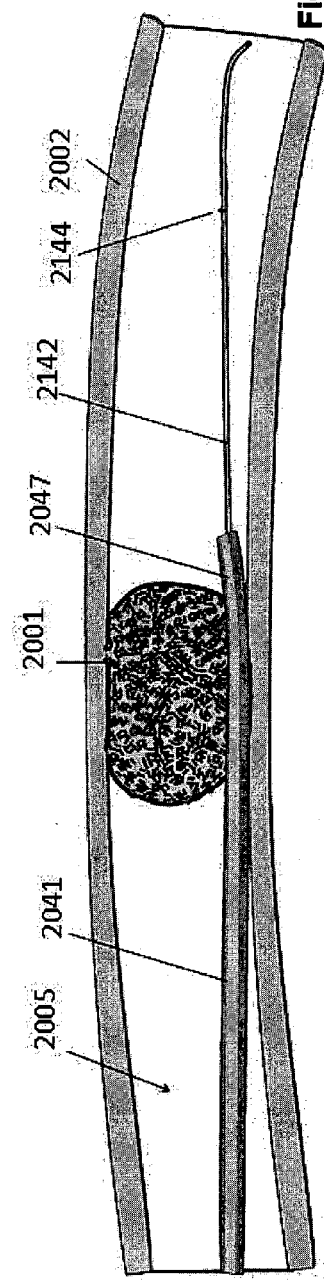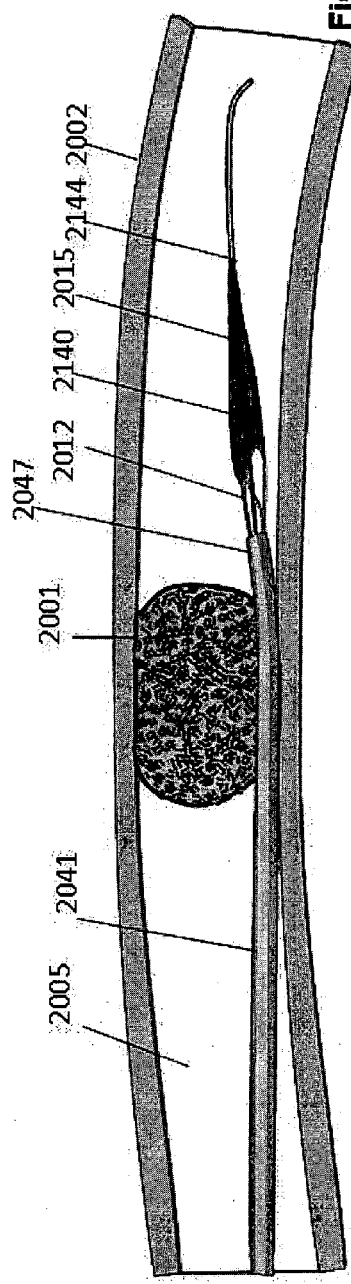

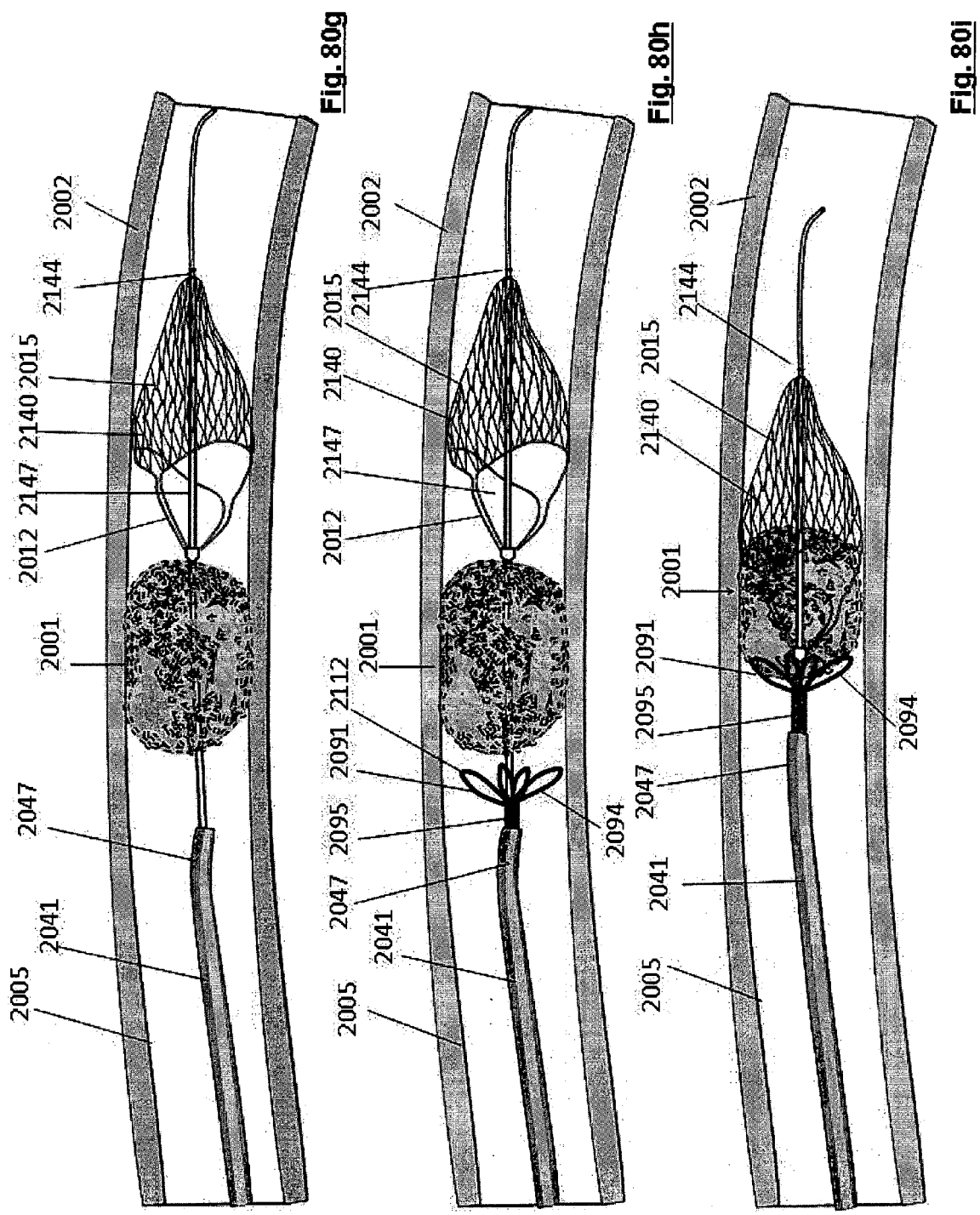

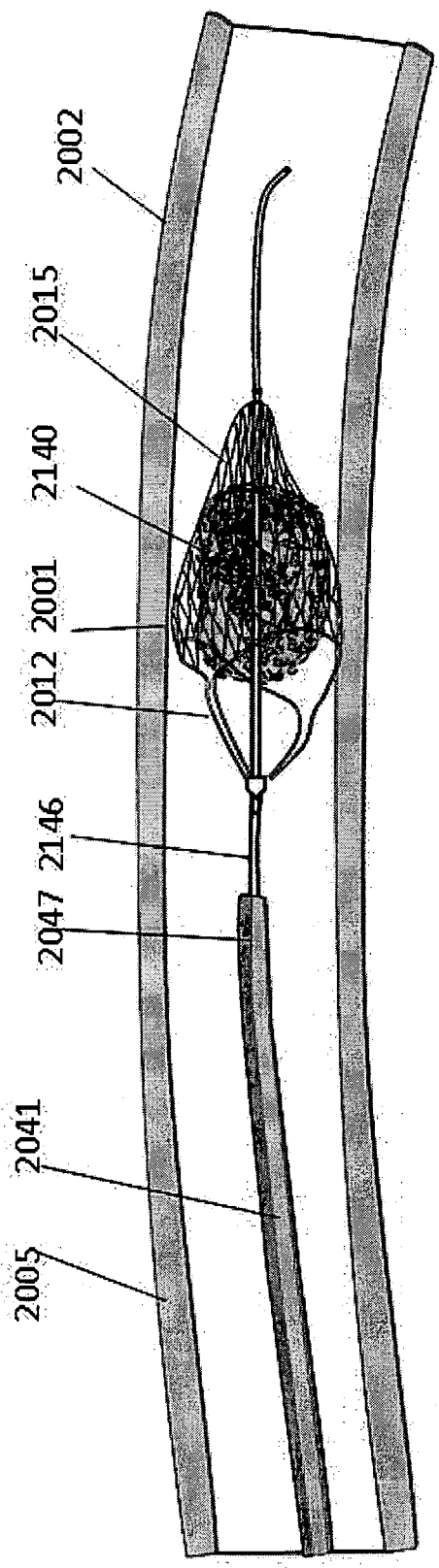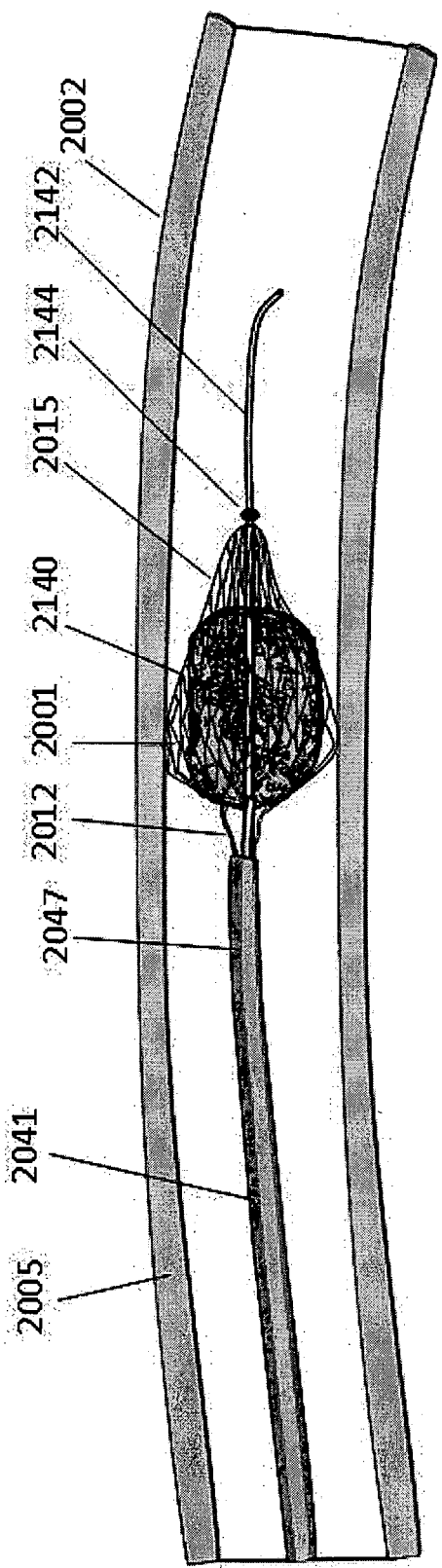

CLOT CAPTURE SYSTEMS AND ASSOCIATED METHODS

This is a national stage of PCT/IE09/000051 filed Jul. 22, 2009 and published in English, claiming benefit of U.S. provisional application No. 61/129,823, filed Jul. 22, 2008, and claiming benefit of U.S. provisional application No. 61/202,612, filed Mar. 18, 2009, hereby incorporated by reference.

INTRODUCTION

The invention relates to devices, and methods of removing acute blockages from blood vessels. The invention especially relates to removing acute obstructions from blood vessels. Acute obstructions may include clot, misplaced devices, migrated devices, large emboli and the like. More particularly the invention relates to removing clot from cerebral arteries in patients suffering acute ischemic stroke.

Accessing the neurovascular bed is difficult with conventional technology as the target vessels are small in diameter, are remote relative to the site of insertion and are highly tortuous. Despite the fact that there are over 600,000 acute ischemic strokes in the US each year, clot retrieval devices are used to treat patients in less than <1% of cases. The reasons for this are that conventional technology is either too large in profile, lacks the deliverability to navigate tortuous vessels or is not effective at removing clot when delivered to the target site.

STATEMENTS OF INVENTION

In accordance with the present invention, device and methods for removing obstructions are described. The invention provides designs and systems for removing clot and other obstructions from the neurovascular arteries and veins as well as other vascular beds.

In one case the invention provides endovascular capture devices which capture obstructive elements and retrieve them from the vessel. The devices of the invention may be used in vessels that are small, tortuous and easily ruptured.

The invention provides a means for removing acute blockages or obstructions from blood vessels. Acute obstructions may include clot, misplaced devices, migrated devices, large emboli and such like. The invention is especially directed at removing clot from cerebral arteries in patients suffering acute ischemic stroke.

The invention provides a clot retrieval device that can be delivered through a micro catheter. The device has sufficient structure to engage the clot. The device provides a means for debonding the clot from the vessel wall. The device further provides means to prevent the fragmentation of the clot and effectively retrieve the clot from the vessel.

There are significant challenges associated with retrieving clot from cerebral vessels including: navigation of the highly tortuous pathways that often exist in the distal internal carotid artery and cerebral arteries, collapsing a device into a profile compatible with the tiny microcatheters typically used in cerebral vessels, disengaging the target clot from the vessel wall without applying painful or harmful forces to the cerebral vessels, and retaining adequate clot retaining scaffolding features in an ultra low profile device to remove the captured clot without fragmentation.

This invention provides a therapeutic device which can be collapsed to a very low profile, and which has a flexible configuration suitable for navigation beyond the Petris portion of the internal carotid artery to restore blood flow by the capture and removal of target clots from the cerebral vasculature. Features and methods that enable disengagement and capture of the target clots which are substantially equivalent in size to the target vessel and to the opening of the clot retrieval device itself are also disclosed.

The invention further provides a device for removing an obstruction from a vessel comprising: an elongate member, a frame with one or more openings and a plurality of fibre segments wherein the elongate element has a proximal end, a distal end and an intermediate segment, and in use the proximal end extends exterior of the patient the intermediate segment extends through the vasculature of the patient to the target vessel and the distal end is positioned in the target vessel with the frame connected to the elongate member adjacent the distal end.

The obstruction to be removed may be clot, with removal of this clot providing the therapeutic benefit of restoring blood flow to the vessel.

The device may comprise a proximal support frame; and a distal fibre net, the support frame having a retracted delivery configuration and an expanded deployed configuration, the proximal support frame in the expanded configuration defining a proximal inlet mouth for engaging or embracing a clot and the net confining the clot; and an elongate member to facilitate capture and/or withdrawal of a clot from a vessel.

The frame may comprise a collapsed state for delivery through the vasculature to the vessel and an expanded state for removing the obstruction from the vessel. The expanded state the frame may comprise a hoop.

The frame may be cut from a metallic tube and the cut frame may comprise a one piece construction. This one piece frame may comprise at least one connector element and a hoop element, and may also comprise a collar.

The frame may be connected to the elongate member and the point of attachment to the elongate member may be spaced apart from the hoop.

The connector element may extend between the points of connection to both the elongate member and the hoop, and may be fixedly connected to the elongate member.

One or more connector elements may be fixed to the elongate member so as to allow rotation between the elongate member and the connector element, or said connector elements may be indirectly fixed to the elongate member.

One or more connector elements may be coupled to a collar and said collar fixed to said elongate member.

The frame may be made of one piece and comprise regions of low strain and regions of high strain, wherein the regions of high strain comprise curved segments to relieve said high strain.

The frame may have an 'as cut' state and an expanded state wherein in the 'as cut' state the frame has a pattern cut through its wall and said pattern defines the collar, one or more connectors, the hoop and the struts that define the hoop.

The frame expanded state may be achieved by expanding the hoop and connector elements to the desired shape for clot retrieval and heat setting the frame in the expanded such that the expanded shape is remembered by the frame and the frame is relaxed in the expanded state.

The connector element may be parallel to the axis of the tube in the as cut state, or may be at an angle to the axis of the metallic tube.

The struts that define the hoop may be parallel to the axis of the tube in the as cut state, or may comprise a helix which traces a pathway around the axis of the tube. Said helix may trace a pathway of not greater than 180 degrees around the axis of the tube.

The cross section of the tube may comprise four quadrants and the at least one first strut and the at least one second strut may be situated either in adjacent quadrants or in the same quadrant over at least a portion of their length in the as cut state.

The hoop may comprise at least one first strut and at least one second strut and said at least one first strut and said at least one second strut may meet at a junction element and said junction element may be at the end of said at least one first and second struts. The at least one first strut and the at least one second strut may be diametrically opposite when the frame is in the as cut state.

The cut pattern of the junction element may comprise a smooth inner curve and a smooth outer curve.

The at least one first strut and the at least one second strut and the junction element may comprise a common neutral axis of bending in the as cut configuration.

The shape defined by the neutral axis of the at least one first strut and at least one second strut may be substantially linear and the shape defined by the neutral axis of the junction element may be curved.

The radius of curvature of the neutral axis of the junction element may be greater when the junction element is in the expanded state than when the junction element is in the as cut state.

The frame may comprise a collar, one or more connector elements and a hoop, and said collar may be fixed to the elongate member. Said collar may be slidable relative to the elongate member, and said elongate member may comprise at least one stop to limit the translation of the collar.

The distal end of the elongate member may comprise a frame, or the elongate member may comprise a shaped section adjacent its distal end and said shaped section comprises the frame.

The elongate member may comprise a tube and the elongate member and the frame may be integral.

The elongate member may comprise a guidewire.

The bending stiffness of the elongate member may decrease along the length of the elongate member.

The elongate member may comprise a plurality of circumferential slots adjacent its distal end, said slots reducing the bending stiffness of the elongate member. The distance between said slots may vary along the length of the elongate member.

The elongate member may comprise at least one continuous helical slot adjacent the distal end of the elongate member to reduce the bending stiffness of the elongate member.

The bending stiffness of the elongate member may decrease gradually along the length of the distal segment of the elongate member. Also the diameter of the elongate member may be less in the distal segment than in the proximal segment.

The elongate member may comprise a solid wire, a wire with a coating, a wire and an outer tube, a wire and a outer coil, a tubular member and an inner core, a tubular member and an inner cable, or a tubular member and an inner tube.

The elongate member may be offset relative to the axis of the vessel when the frame is in the expanded configuration, or the elongate member may be substantially concentric with the axis of the vessel when the frame is expanded in the vessel, or the elongate member may be adjacent the wall of the vessel when the frame is in the expanded configuration in the vessel.

The frame may comprise a collapsed state for delivery through the vasculature to the vessel and an expanded state for removing the obstruction from the vessel. The expanded state of the frame may comprise a hoop.

The wire of the hoop may comprise a round wire, a square wire, a rectangular wire, an elliptical wire a flattened wire or a multifilament.

The elongate member may comprise a wire and the distal segment of said wire is formed into a hoop. The distal end of said wire may be fixed to the wire in order to close the hoop. The fixing of the wire distal end to the wire may comprise a weld joint, a solder joint, an adhesive joint, a bifilar joint, a coupling, a compression joint, a snap fit, or an interlock.

The hoop may comprise a single piece hoop cut from a metallic tube or from a metallic sheet.

The distal section of the elongate member may comprise a tube and said hoop may be integral with said tube.

The elongate member distal end may comprise a machined section. The elongate member distal end machined section may comprise a hoop.

The elongate member cross-section may comprise four quadrants and the hoop may comprise at least two struts, each extending from a separate quadrant. The first strut may extend from said first quadrant and said second strut extend from said third quadrant. The first and second struts may be diametrically opposite. The first strut may extend from said first quadrant and said second strut may extend from said second quadrant. The first strut may extend from said first quadrant and said second strut may extend from said first quadrant.

The struts may comprise a plurality of net attachment features.

The hoop of the frame may be expanded by inserting a pin between the struts and heat treating the frame to set the shape. This pin diameter may be similar to the diameter of the target vessel.

The hoop may be cut from a large diameter tube, the diameter of which is similar to the diameter of the target vessel. Alternatively the hoop may be integral with the elongate member.

A plurality of connector elements may be attached to the hoop. This plurality of connector elements may be connected to the hoop at a series of spaced apart junction points around the circumference of the hoop and said spacings may be substantially equal.

In its expanded state the hoop may define an opening, and said opening may be elliptical or circular in shape, and may be similar in size to the cross-sectional area of the target vessel. The axis of the elongate member may pass through this opening created in the hoop in its expanded state.

The connector element may extend at least partially radially inward from the hoop and be connected to the collar, or the connector element may extend radially inward and proximally from the hoop and be connected to the collar, or the connector element may extend radially inward and distally from the hoop and be connected to the collar.

In the collapsed state the hoop may lie substantially parallel the elongate member, or may lie at an angle of approximately 90 degrees to the axis of the elongate member.

In the expanded state the hoop may make an angle of greater than 90 degrees to the axis of the elongate member, or may make an angle of less than 90 degrees to the axis of the elongate member. The angle between the hoop and the elongate member may be between 45 degrees and 135 degrees. The angle between the hoop and the elongate member may be between 60 degrees and 120 degrees. The angle between the hoop and the elongate member may be between 80 degrees and 100 degrees.

The hoop may comprise a number of struts wherein said struts are rectangular, square or circular in cross-section. The struts may be interconnected. These interconnections may be at the strut ends and said interconnections may comprise curved crown elements.

In the collapsed state said the curved crown elements may connect strut segments that are substantially parallel, or may connect strut segments that are angled relative to one another.

The hoop may comprise a plurality of curved segments. The plurality of curved segments of the hoop may be configured to from a single plane, or may be configured to form two planes with the curved segments interconnecting at a point of intersection of the planes.

The plurality of curved segments may comprise a plurality of struts and said plurality of struts may form a substantially circular hoop when viewed along the axis of the elongate member.

The frame may comprise at least two openings in the expanded state each opening defining an opening for the capture of clot. The two openings may comprise a circular shape.

Each opening may be defined by a strut section and a body strut section wherein the strut section comprises two radially projecting struts and the body strut section comprises a curved strut wherein the radius of curvature of said body strut section is substantially similar to the target vessel size for the device.

The body strut section may connect the ends of the two projecting radial struts. The two substantially parallel wires may be connected to each other at at least one end.

The elongate member may extend in use from the target vessel through the vasculature of the patient and further extend exterior of the patient.

The elongate member may comprise a distal end, said distal end may terminate adjacent the frame collar, or may terminate at the distal junction of the capture fibres. Or the distal end may terminate distal of said frame and net and comprise a soft atraumatic tip.

The elongate member may comprise an inner lumen said inner lumen may extend from the proximal end of the elongate member at least to an area adjacent the frame.

The elongate member may comprise an exit port, said exit port located in the distal region of the elongate member.

The elongate member may comprise an inner core and an outer tube. Said inner core may comprise a wire and said wire may comprise a tapered distal end. The inner core wire may comprise an atraumatic distal end.

The distal end of the inner core wire may be associated with the distal fibre junction. The fibre junction may be adjacent to the core wire. The fibre junction may be tethered to the core wire.

The fibre junction may be integral with the distal segment of the inner core, or may be moveable relative to the inner core, or may be moveable by the inner core.

The inner core may comprise a coil. This coil may be a radiopaque coil.

The frame may comprise at least one collar. The collars may be fixed relative to the elongate member, or the collars may be slidable relative to the elongate member.

The frame may comprise a first collar and a second collar. Said first collar may be fixed relative to the elongate member and said second collar may be slidable relative to said elongate member.

The collar may be integral with at least one first strut and the collar and first strut may comprise a collapsed state for delivery through the vasculature and an expanded state for capturing and removing said occlusive material.

The at least one integral collar strut may define an area of bending and said area of bending may comprise a relaxed state and a strained state wherein in the frame expanded state the area of bending is in the relaxed state and in the frame collapsed state the area of bending is in the strained state.

The frame may comprises at least one proximal connector strut and at least one distal connector strut where said at least one proximal connector strut is connected to the hoop at a point which is spaced apart from the point of connection of the at least one distal connector strut.

The cross-sectional dimensions of the connector struts may be different to the cross-sectional dimensions of the hoop struts.

The device may further comprise a third collar distal of previously mentioned first and second collars.

The frame may further comprise a formed collar wherein the collar comprises a C shaped section. This C shaped section may be formed by cutting a segment of the large diameter tube, and forming the tube section such that it's radius of curvature is greatly reduced and heat treating the section so as to permanently set the formed shape.

Any or all of these collars may comprise at least one longitudinal slot extending along at least a portion of the length of the collar, and/or at least one circumferential slot extending partially around the circumference of the collar.

The plurality of fibres may constitute a capture net, said net comprising a series of fibre segments arranged to create a three dimensional clot capture net. The net may be connected to the frame at a plurality of points or engagement features around the circumference of the frame.

The capture net may comprise a knitted, braided or crocheted structure, or may comprise a series of longitudinal fibre segments. This structure may comprise a tube. This tube may be cylindrical or conical in shape.

The net comprises an inner layer and an outer layer. The inner layer and the net outer layer may be integral The net may be connected to the frame with a fibre. The net may partially encircle the frame.

The net may comprise a fibre junction wherein a plurality of fibre segments are connected. The capture net may comprise a series of fibre segments extending between the frame and this fibre junction. The fibre junction may be spaced apart from the frame and the fibre segments may define a basket for restraining clot that has been debonded from the vessel.

The clot capture system may have a capture net wherein the net comprises a proximal end and a distal end, the proximal end of the net being attached to the frame. The capture net may have a low density structure where the area ratio of the fibres to the capture net pores is <20%.

At least one of the plurality of high tensile fibres may have an ultimate tensile strength of at least 1500 MPa, or at least 2000 MPa, or at least 2500 MPa, or 3000 MPa or greater.

At least one of the plurality of high tensile fibres may comprise polymer fibers such as Ultra High Molecular Weight Polyethylene or Kevlar, or metal fibers such as 302 stainless steel, 304 stainless steel, other stainless steels, MP35N, L604, 35N LT, or Nitinol.

Wherein a metal fiber is used it may be cold worked to at least 50%.

An Ultra High Molecular Weight Polyethylene (UHMWPE) fiber may comprise a Dyneema, Celanese, Spectra or a Tekmilon fibre.

The frame may comprise a plurality of attachment points around its circumference, and the capture net may be secured to the frame at a plurality of points around the circumference of the frame.

The attachment features may be integral with the frame struts and comprise localised changes to the cross section of the struts. The localised change in cross section may comprise a hole in the strut wherein the hole is circular, oblong, elliptical, curved and the hole may be in the centre of the strut or is offset. The hole may extend through the wall of the frame.

The localised change in cross section may comprise a notch, a recess, a depression, or a groove in the outer surface of the strut of the frame. The attachment points may comprise a plurality of such localised changes in cross section. The plurality of attachment points may be spaced equally around the circumference of the frame.

The plurality of attachment points may comprise holes in the struts and said holes may be less than 50 microns in diameter, or less than 30 microns in diameter, or less than 25 microns in diameter, or less than 20 microns in diameter.

The holes may not be fully cylindrical, but may be less than 50 microns in one dimension, or less than 30 microns in one dimension, or less than 25 microns in one dimension, or less than 20 microns in one dimension.

The frame and holes may be polished by a polishing process selected from sand blasting or electropolishing or chemical etching.

The device may further comprise a fibre junction where a plurality of fibre segment ends are connected. This fibre junction may comprise a knot, a weld, an adhesive joint, a site of attachment, a laminated junction, a coupling, a bonded joint or an assembly joint.

The device may further comprise a distal collar and said distal collar may comprise a junction for a number of fibres of the fibre net.

The distal collar may comprise a reception space and said reception space may be configured to restrain the ends of said fibre segments.

The distal collar reception space may comprise an annular space, said annular space sized to allow fibres to be received in the space.

The distal collar reception space may comprise at least one hole wherein said hole is sized to receive at least one fibre. The distal collar reception space may also comprise a plurality of holes, said plurality of holes being sized to receive one or more fibres.

The distal collar reception space may comprise a feature such as a hole, a groove or an annular space in the wall of the collar wherein said feature is sized to receive at least one fibre. This feature may also be located between the collar and the elongate member.

The device may comprise an expansion cable which may be connected to the frame and extend in use exterior of the patient.

The expansion cable may comprise a relaxed state and a tensioned state wherein in the relaxed state the expansion cable exerts no force on the frame and in the tensioned state the expansion cable exerts an expansion force on the frame. This expansion force may assist in the expansion of the frame.

The expansion cable in use may extend from exterior of the patient through a lumen in the elongate member, through an exit port located in the distal region of the elongate member and terminate at a point of connection with the frame.

The expansion cable may comprise a polymeric or metallic cable, and may be a monofilament or multifilament. The material of the expansion cable may be a polymer, such as a polyester, Ultra high molecular weight polyethylene, a fluoropolymer, a nylon, or Kevlar, or may be metallic such as a stainless steel or nitinol, or may be a mixture of the above or may possess similar properties to the above.

The frame may comprise an expanded configuration and a collapsed configuration and may be naturally biased towards the collapsed configuration and may further comprise a restraining system, which allows the frame to be stored in the collapsed state (during delivery) by interconnecting elements of the frame to one another.

The restraining system may comprise restraining one or more struts to each other.

The restraining system may comprise restraining a frame hoop in a collapsed state substantially parallel with the axis of the elongate member.

The elongate member may comprise an inner core extending distal of the collar of the frame, and the restraining system may comprise fixing the hoop to the inner core in a collapsed state.

The frame may comprise a supporting strut extending distally from the collar and substantially parallel to the axis of the collar, and the restraining system may comprise fixing the hoop to the supporting strut in a collapsed state.

The supporting strut may comprise an engagement feature allowing the supporting strut and the hoop and/or a connector element to be fastened to the supporting strut.

The device may further comprise a micro-delivery catheter comprising a reception space and a shaft. This reception space may extend proximally wherein the frame and net are configured to be received in the reception space in the collapsed state for delivery to the site of occlusion. The reception space may comprise a tubular element.

The collar or collars of the frame may be mounted on a tubular member and the tubular member may be moveable relative to the guidewire. The tubular member may be connected to a control wire and said control wire may extend proximally to the user, allowing the user to move the frame relative to the guidewire, or the tubular member may extend proximally to the user, allowing the user to move the frame relative to the guidewire.

The frame of this invention may also compromise hinges and may comprise a plurality of struts with one or more hinges connecting at least a pair of said struts. The expansion of the frame from its collapsed state to its expanded state may comprise an articulation of one or more of these hinges. Said hinges may be configured to articulate without significant resistance.

The at least one pair of struts may comprise a first strut and a second strut and the first strut may comprise a first point wherein said first point is spaced apart from the hinge. The at least one hinge may be configured such that said first point is restricted to move through a segment of a substantially circular arc when said hinge is articulated. The at least one hinge may be configured such that said first point is restricted to move through a set of points defining a substantially spherical surface when said hinge is articulated.

The at least one hinge may each comprise a first strut and a second strut, the first and second struts comprising hinge attachment features and said first and second struts being coupled by a hinge coupling element.

The hinge attachment features may comprise a hole, a mounting, a loop, a cut profile or a formed shape.

The hinge coupling may comprise a monofilament fibre, a multifilament fibre, a pin, a loop, a C section, a ring, a tether, or an articulating coupling.

The hinge attachment feature may comprise a hole and the hinge coupling may comprise a fibre wherein said fibre is looped through the hole in said first and second struts so as to fix said struts to one another while allowing said struts to articulate in at least one direction.

The frame may comprise a hoop and at least one connector strut. This hoop may comprise a plurality of hoop struts. The at least one hinge may comprise a pair of hoop struts. The at least one hinge may comprise a hoop strut and a connector strut.

The frame may comprise a compound hinge wherein more than two struts are hinged relative to each other. The compound hinge may comprise three struts. The compound hinge may comprise two hoop struts and a connector strut.

The at least one connector strut may be connected to the elongate member. The connection between the connector strut and the elongate member may comprise a hinge. The connection between the connector strut and the elongate member may comprise a collar wherein said collar connects the connector strut to the elongate member.

The frame may comprise an arrangement of hinges and said hinges may comprise movement freedoms and movement constraints and said movement freedoms and movement constraints may be arranged such that the frame moves progressively between a collapsed state and an expanded state when activated and between an expanded state and a collapsed state when deactivated.

The frame may be expanded by advancing or retracting at least a part of the elongate member. The elongate member may be connected to at least one strut and advancing or retracting a portion of the elongate member may cause the articulation of the at least one hinge and the frame expands.

The elongate member may comprise a first portion and a second portion and the elongate member first portion may be connected to an at least one first strut and the elongate member second portion may be connected to at least one second strut and relative movement between the elongate member first portion and the elongate member second portion may cause expansion or collapse of the frame depending on the direction of relative motion.

The elongate member may comprise an inner shaft and an outer tubular member and said outer member may be slidable relative to said inner shaft. Movement of the outer tubular member relative to the inner shaft may cause the frame to expand and/or collapse.

Any of the frames disclosed herein may be expanded by the release of stored energy. Said stored energy may comprise the release of stored elastic energy wherein at least one element of the frame comprises an elastic component and said elastic component is restrained in a strained state during delivery. Upon removal of said constraint said elastic component relaxes to its unstrained state and in so doing the frame is expanded.

The elastic component may comprise a nitinol component, a shape memory component, an elastic component or a superelastic component.

The elastic component may comprise a hoop strut, a connector strut, a connector or a combination of these elements or a junction between these elements.

This invention also comprises a clot debonding device which may be used in conjunction with the clot retrieval designs described herein. The clot debonding device is designed to assist in the removal of obstructions from a vessel by providing an abutment surface which may be used to appose one side of the obstruction so that a force may be applied to the other side of the obstruction without said force being transmitted to the vessel in which the obstruction is placed. It therefore enables a clot retrieval device or other similar device to more effectively engage and capture clot or other such vessel obstructions.

It will be appreciated that such a device also has applications beyond its use with the clot retrieval device described herein. Such a clot debonder may be effectively used to aid the disengagment and removal of vessel obstructions in conjunction with other clot retrieval devices or thrombectomy devices or aspiration devices.

The invention further provides a clot capture system for disengaging a clot from a vessel wall and removing the clot from the vessel, the clot capture system comprising: a clot capture device for placement on a distal side of a clot, the clot capture device having a retracted delivery configuration and an expanded deployed configuration; and a clot debonding device for placement on a proximal side of a clot, the clot debonding device having a retracted delivery configuration and an expanded deployed configuration and comprising a clot engagement element which defines a distal abutment in the deployed configuration for urging a clot into the clot capture device.

It will be understood that the above mentioned clot capture device may be any of the clot retrieval device embodiments previously described herein, and the clot capture system may comprise any combination of the permutations described below with those of the clot retrieval devices described above.

The abutment area of the clot debonding device may be configured to engage with the clot in its expanded configuration. The engagement of the abutment area with the clot may comprise a relative movement between the abutment area and the clot and said relative movement may at least partially disengage the clot from the vessel. The relative movement between the abutment area and the clot may comprise an axial movement or a rotational movement or a combination of both movements of the abutment area.

The clot retrieval device may be configured to engage the clot from a distal end and the clot debonding device may be configured to engage the clot from a proximal end. The clot debonding device may thus be configured to apply a debonding force to the clot to disengage the clot from the vessel, and the clot retrieval device may be configured to apply a reaction force to the clot wherein the reaction force is applied substantially in the opposite direction to the debonding force and the combination of said forces disengages the clot from the vessel wall.

The clot retrieval device may comprise an engagement element and a reception space said engagement element may be configured to engage the clot from a distal end and said reception space may be configured to receive said disengaged clot and to allow the removal of said clot from the vasculature.

The clot debonding device may be configured to at least partially protect the blood vessel from the forces of clot debonding.

The clot engagement element may extend substantially the width of the mouth of the capture device in the deployed configuration.

The clot debonding device is movable relative to the clot capture device in the deployed configuration.

The clot engagement element may have a longitudinal axis and the distal abutment may extend radially of the longitudinal axis. The longitudinal axis may be a substantially central axis and the distal abutment may extend radially outwardly of the substantially central axis, or the longitudinal axis may be an offset axis and the distal abutment may extend radially outwardly of the offset axis.

The engagement element may comprise an axially extending region and a radially extending region. The engagement element may further comprise a circumferential region extending from the radial region. The engagement element may also comprise a transition region between the axial region and the radial region.

The clot debonding device may comprise an axially extending collar.

The clot capture device may define an inlet mouth in the deployed configuration and the clot engagement element may extend substantially the width of the inlet mouth of the clot capture device.

The clot debonding device may be slidable relative to the clot capture device.

The clot debonding device may be rotatable relative to the clot capture device.

In the deployed configuration, the clot capture device may be located distal of the clot debonding device.

The clot capture device and the clot debonding device may be independently movable.

The clot capture system may comprise an elongate member. The clot capture system may comprise a first elongate member associated with the clot capture device. The clot capture system may comprise a second elongate member associated with the clot debonding device. The first elongate member may comprise a guidewire, and said guidewire may comprise a stop. This stop may comprise a distal stop.

The second elongate member may comprise a proximal shaft. The clot debonding device may be mounted to the proximal shaft. The clot bonding device may be fixedly mounted to the proximal shaft.

The clot capture system may comprise a delivery catheter for the clot capture device.

The system may further comprise a first access catheter and a second access catheter, the distal end of said first access catheter being placed in a proximal vessel and the distal end of said second access catheter being placed in a distal vessel wherein the second access catheter is delivered to said distal vessel through the lumen of said first access catheter. Said first access catheter may comprise a guide catheter or a guide sheath and said second access catheter may comprise a delivery catheter or a microcatheter, wherein the clot retrieval device is configured to be delivered through the second access catheter.

The clot debonding device may comprise a lumen extending from its distal end and a proximal shaft connected either directly or by a collar to the expandable engagement element. The clot debonding device may be configured as a rapid exchange catheter.

The distal end of the clot debonding device may comprise an abutment surface in the collapsed state for advancement of the clot retrieval basket through a catheter lumen.

The expandable engagement element may expand radially outward from a central axis and may comprise an inflatable element, a self expanding element, a shape memory element, a super elastic element, a remotely activated element, a coil or spring element.

The expandable engagement element may comprise a balloon, an inflatable cuff, a plurality of struts, a slotted section, a cell structure, a plurality of wire segments, a helical coil, a flare, a ring, a braided section, or a hoop.

The expandable engagement element may comprise a slotted tubular member, or a number of overlapping coaxial slotted tubular members. The slotted tubular members may be self expanding or may be expanded by retraction of an actuation element connected to their distal end.

The expandable engagement element may comprise elements which expand into a generally helical configuration, such as a coiled element which at least partially uncoils to expand from one diameter to a second larger diameter.

The expandable engagement element may comprise a number of curved wire struts or segments, which may have points of inflection, and/or which may be configured to create closed or open cells, or a mixture of both.

The expandable engagement element of the clot debonder may be made from a shape memory alloy or a super elastic alloy such as Nitinol, or from another metal such as stainless steel, or from a polymer such as PEEK, Nylon, PE or Polyimide.

The expandable engagement element may comprise a plurality of struts or segments cut from a tube. Said struts or segments cut from a tube with slots that run substantially parallel to the longitudinal axis of the tube, or with slots that are not parallel to the longitudinal axis of the tube. Said struts or segments may overlap or may be non non-overlapping.

The engagement element may comprise a collapsed state wherein the engagement struts are aligned with the axis of the clot debonder and said plurality of struts comprise a tubular structure.

Said plurality of struts may be close packed in the delivery configuration.

In the expanded state the engagement element is preferably configured to transmit axial force of the user to the clot. The engagement element may comprise an engagement surface and said engagement surface may comprise a distally facing surface. In one embodiment the engagement surface comprises an annular surface. With this embodiment the engagement surface may have an outer diameter and an inner diameter. The outer diameter may be substantially the same or smaller than the diameter of the vessel. The outer diameter may be substantially the same or smaller than the diameter of the clot. The inner diameter may be substantially the same or larger than the diameter of the guidewire.

In one embodiment the engagement surface comprises a flared surface. In another embodiment the engagement surface comprises a plurality of struts said struts configured to apply pressure to the clot over a substantial portion of the cross-section of the vessel. In one embodiment the engagement surface is configured to apply an axial displacement to the entire body of the clot. The engagement surface of the clot debonding device may be configured to prevent clot fragmentation during debonding and capture.

In one embodiment the engagement element comprises a plurality of elongate struts. In the delivery configuration the elongate struts may be substantially aligned with the axis of the vessel. In the expanded configuration the struts may project radially outward from the axis of the clot debonder. In one embodiment the struts are interconnected. The struts may comprise regions of bending.

In one embodiment the struts of the engagement element comprise an outer ring member and a plurality of radial struts connected to said outer ring member. In another embodiment the strut arrangement of the engagement element comprises a plurality of cells. Each cell boundary may be defined by a strut. In another embodiment the engagement element comprises an outer ring member. The outer ring may comprise a plurality of struts configured in a circumferential ring. The engagement element may comprise an inner ring member. The inner ring member may be connected to or separate of the outer ring member. In one embodiment the outer ring member is connected to the collar by a plurality of radial struts. In one embodiment the outer ring member comprises a plurality of zig zag strut elements.

In one embodiment the struts are cut from a nitinol tube. The tube may comprise a cut pattern. The cut pattern may comprise a plurality of longitudinal slots and a plurality of struts. In one embodiment the cut pattern comprises a plurality of curved segments interconnecting said struts.

In another embodiment the engagement element comprises a plurality of wires. The wires may comprise a collapsed state and an expanded state. In the collapsed delivery state the wires may be substantially aligned with the axis of the vessel. In the expanded state the wires may project radially outwardly of the axis of the clot debonding device.

In the fully expanded state the engagement element may comprise an outer rim. The outer rim may comprise a plurality of curved segments.

In another embodiment the engagement element comprises a plurality of shaped wires. Each shaped wire may comprise a first wire end and a second wire end. The first wire ends and second wire ends may be fixed to a tubular member. The wire segment may comprise a first radial curve adjacent the collar and a second circumferential curve. The circumferential curve in the wire may comprise an atraumatic vessel interface.

In one embodiment the engagement element comprises an axial strut segment, a curved strut segment and a radial strut segment. With this embodiment the engagement element may be connected to a tubular member at the proximal end of the axial strut section. The struts of the axial segment may be oriented substantially parallel to the axis of the clot debonding device. The engagement element may comprise an immediate segment distal of the axial segment. The intermediate segment may comprise the radial curve. The intermediate section may comprise most of the engagement surface. The intermediate section may provide a high area surface for the transmission of force to the clot.

The clot debonding element may be designed to transmit force over the entire surface of the clot. The clot debonding element may be configured to debond the clot in one piece. The clot debonder may be configured such that the clot does not snag on its surface. The clot debonder may be configured to push the clot into the opening of the clot capture basket.

The clot debonder engagement element may be configured such that upon withdrawal it disengages from the clot without snagging, or fragmenting the clot and without removing the clot from the capture basket.

The connection between the wire and the collar may be configured so as to orient the wire parallel to the axis of the clot debonding device. The connection between the collar and the wire may comprise a hole in the collar. Immediately distal of the collar the wire may comprise a curve. The wire may be radially curved so as to create an abutment surface. The body of the wire may be substantially radial relative to the axis of the clot debonder. The clot engagement element may comprise a plurality of radial wire segments configured to deliver and distribute pressure to one face of the clot. The wires may comprise a second curved segment. This second curved segment may define an outer rim of the clot engagement element. The curved segment may also present an atraumatic surface to the vessel. This second curved segment may be curved in the circumferential direction.

The clot engagement element may comprise radial and circumferential engagement elements and may transmit force to the clot in a manner similar to that of a piston.

In another embodiment the struts or wires of the engagement element comprise an articulation region. The engagement element may assume the expanded state by an articulation of the struts or wires about the articulation region.

The invention also provides a method for removing clot from a vessel involving a clot capture device that comprises a frame, a net and an elongate member such as a wire and is capable of being advanced through a microcatheter comprising the steps of: advancing a crossing guidewire through the vasculature and across the clot, advancing a microcatheter over the guidewire such that the tip of the microcatheter is across the clot, removing the crossing guidewire from the microcatheter, advancing through the lumen of the microcatheter a collapsed clot capture device, deploying the clot capture device distal of the tip of the microcatheter, expanding the clot capture device distal of the microcatheter, retracting the clot capture device and engaging with the clot, applying a force to the clot over at least a portion of the outer circumference of the clot, applying shearing forces to the clot, disengaging the clot from the wall of the vessel, capturing the clot within the clot capture basket, removing the clot capture basket and the clot from the patient and taking a final angiogram of the recannalized vessel.

The step of removing the clot capture basket may comprise at least partially collapsing the basket and/or applying compressive forces to the clot.

The clot capture device may comprise a frame, a wire and a net wherein the frame is expandable and the net is attached to the frame and the frame is at least partially fixed to the guidewire.

The invention provides a further method for removing clot from a vessel involving a clot capture device that comprises a frame and a net and is capable of being advanced through a microcatheter and is further advancable relative to a guidewire comprising the steps of: advancing a guidewire through the vasculature and across the clot, advancing a microcatheter over the guidewire such that the tip of the microcatheter is across the clot, advancing the frame and net in a collapsed state over the guidewire, deploying the frame and net from the distal end of the microcatheter, expanding the frame and net distal of the clot, retracting the frame and net and engaging with the clot, applying a force to the clot over at least a portion of the outer circumference of the clot, applying shearing forces to the clot, disengaging the clot from the wall of the vessel, encircling at least a portion of the clot with the frame, restraining fragments of the clot with the net, removing the frame and net from the patient and taking a final angiogram of the recannalized vessel.

The clot capture device may comprise an advancement element and the step of advancing the frame and net over the guidewire may comprise advancing the advancement element parallel of and relative to the guidewire.

The invention provides a further method for removing clot from a vessel involving a clot capture device that comprises a frame, a net and an elongate wire and is capable of being advanced through a guide catheter comprising the steps of: advancing a guidewire through the vasculature and across the clot, advancing a guide catheter into the target vessel and positioning the tip of the guide catheter proximal of the clot, advancing the clot capture device in a collapsed state through the guide catheter, advancing the frame and net and the distal portion of the elongate wire across the clot, deploying the frame and net distal of the clot, expanding the frame and net distal of the clot, retracting the elongate wire with the frame and net attached, applying a force to the clot over at least a portion of the outer circumference of the clot, disengaging the clot from the wall of the vessel, encircling at least a portion of the clot with the frame, restraining fragments of the clot with the net, removing the frame and net from the patient, taking a final angiogram of the recannalized vessel.

The invention also provides a further method for removing clot from a vessel involving a clot capture device that comprises a basket and a debonding element, the capture basket comprising a collapsed state for delivery through the vasculature and an expanded state for the capture of clot, the clot debonding element comprising a collapsed delivery state and an expanded state the method comprising the steps of: advancing a guidewire through the vasculature and across the clot, advancing a microcatheter over the guidewire such that the tip of the microcatheter is across the clot, advancing the basket through the microcatheter, deploying the basket from the distal end of the microcatheter, expanding the basket distal of the clot, retracting the microcatheter until the tip of the micro catheter is proximal of the clot, retracting the basket and engaging with the clot, advancing the clot debonder through the microcatheter, deploying the clot debonder proximal of the clot, advancing the clot debonder to engage with the clot from the proximal side, retracting the basket while holding the clot debonder steadfast, disengaging the clot from the wall of the vessel without applying force to the vessel wall distal of the occlusion, disengaging the clot from the wall of the vessel, encircling at least a portion of the clot with the frame, retracting the clot debonder, collapsing the clot debonder inside the lumen of the microcathater, restraining fragments of the clot with the basket, removing the basket and the clot from the patient and taking a final angiogram of the recannalized vessel.

The above methods may include applying a force to the clot over at least a portion of the outer circumference of the clot, and/or applying shearing forces to the clot and/or collapsing the clot debonder inside the lumen of the guide catheter and/or expanding the clot debonder at the distal end of the microcatheter.

The step of expanding the clot debonder may comprise inflating the clot debonder, or inflating a sac at the distal end of the clot debonder.

The step of expanding the clot debonder may comprise removing an outer restraint from clot debonder and allowing the clot debonder to self-expand. The step of removing this restraint may comprise removing a pod from over the clot debonder.

The step of removing the restraint may comprise retracting the distal end of the microcatheter from over the clot debonder.

The invention further discloses a method for removing clot from a vessel comprising the steps of: providing a clot capture device comprising a basket and a debonding element, the capture basket comprising a collapsed state for delivery through the vasculature and an expanded state for the capture of clot, the clot debonding element comprising a collapsed delivery state and an expanded state; advancing the basket through the vasculature in the collapsed state; deploying the basket distal of the clot; advancing the clot debonder through the vasculature; deploying the clot debonder proximal of the clot; engaging the basket and/or the clot debonder with the clot; disengaging the clot from the wall of the vessel; capturing the clot in the basket; and removing the clot from the vasculature.

BRIEF DESCRIPTION OF THE DRAWINGS

The invention will be more clearly understood from the following description of some embodiments thereof, given by way of example only, with reference to the accompanying drawings, in which:

FIG. 2 shows some of the anatomy of arteries above the aortic arch leading to the brain;

FIG. 3a shows part of the cerebral circulation with an obstructive clot positioned in the Anterior Cerebral Artery, distal of the Middle Cerebral Artery branch;

FIG. 3b shows a guidewire being placed across the obstructive clot;

FIG. 3c shows a micro-catheter with the clot retrieval device of the invention crossing the obstructive clot;

FIG. 3d shows the micro-catheter removed with the clot retrieval device placed distal of the obstructive clot;

FIG. 5a shows a target vessel with an occlusive clot;

FIG. 5b shows a micro delivery catheter with a clot retrieval device collapsed within a distal lumen of the micro delivery catheter, the micro delivery catheter being advanced across the occlusive thrombus, the clot retrieval device having a guidewire that extends proximally and distally;

FIG. 5c shows the micro delivery catheter being removed with the clot retrieval device deployed in the target vessel distal of the occlusive clot with the guidewire extending across the lesion and proximal to the user;

FIG. 5d shows the clot retrieval device deployed in the target vessel distal of the occlusive clot with the guidewire extending across the lesion and proximal to the user;

FIG. 7a shows a clot retrieval device in its expanded capture state;

FIG. 7b shows the clot retrieval device of FIG. 7a inside a micro delivery catheter in its collapsed delivery state;

FIG. 11a shows a clot retrieval device in its expanded capture state;

FIG. 11b shows the clot retrieval device of FIG. 11a inside a micro delivery catheter in its collapsed delivery state with the capture fibers removed (for illustration);

FIG. 11c shows the clot retrieval device of FIG. 11a inside a micro delivery catheter in its collapsed delivery state;

FIG. 12a shows a clot retrieval device in its expanded capture state without capture fibers being shown (for illustrative purposes);

FIG. 12b shows a clot retrieval device of FIG. 12a inside a micro delivery catheter in its collapsed delivery state with the capture fibers removed (for illustration);

FIG. 13b shows a view of a collar and strut arrangement for use with a number of frame designs of the invention;

FIG. 13c shows another view of a collar and strut arrangement for use with a number of frame designs on the invention;

FIG. 13d shows an end view of a collar and strut arrangement for use with a number of frame designs of the invention with the strut in its collapsed state;

FIG. 13e shows an end view of a collar and strut arrangement for use with a number of frame designs on the invention with the strut in its expanded state;

FIG. 18 shows a clot retrieval device in the deployed configuration distal of an occlusive clot;

FIG. 19 shows a clot retrieval device being withdrawn proximally to capture a clot;

FIG. 20a shows a first side view of a strut of the hinged frame of a clot retrieval device;

FIG. 20b shows a second side view of a strut of the hinged frame of a clot retrieval device;

FIG. 20c shows a strut of the hinged frame of a clot retrieval device. The strut has a preset curved shape;

FIG. 20d shows the joining of the ends of two struts in the construction of a hinged frame;

FIG. 20e shows a hinged frame with four struts forming a ring and four support elements supporting the frame;

FIG. 20f shows four struts of a hinged support frame configured into a ring;

FIG. 20g shows how the hinged support frame can collapse about the X axis;

FIG. 20h shows how the hinged support frame can collapse about the Y axis;

FIGS. 20i-k shows how hinges allow the support frame to collapse;

FIG. 21a shows a clot retrieval device with a hinged frame in the expanded configuration;

FIG. 21b shows a clot retrieval device with a hinged frame in the partially collapsed configuration FIG. 21c shows a clot retrieval device with a hinged frame in the fully collapsed configuration;

FIG. 23a shows a clot retrieval device with a hinged frame in the expanded configuration;

FIG. 23b shows a clot retrieval device with a hinged frame in the partially collapsed configuration;

FIG. 23c shows a clot retrieval device with a hinged frame in the fully collapsed configuration;

FIG. 24a shows a clot retrieval device with a hinged frame in the fully expanded configuration;

FIG. 24b shows a clot retrieval device with a hinged frame in the partially collapsed configuration;

FIG. 24c shows a clot retrieval device with a hinged frame in the fully collapsed configuration;

FIG. 26a shows an eyelet for capture fibre attachment to a strut;

FIG. 26b shows an eyelet for capture fibre attachment to a strut;

FIG. 26c shows an eyelet for capture fibre attachment to a strut;

FIG. 26d shows an eyelet in a strut section with a capture fibre in situ;

FIG. 26e shows an eyelet in a strut section with a capture fibre in situ;

FIG. 26f shows an eyelet in a strut section with a capture fibre in situ;

FIG. 28a shows a segment of a strut of a clot retrieval device;

FIG. 28b shows a cross section of a strut;

FIG. 28c shows a fixture for assembling capture fibres to struts;

FIG. 29a shows two eyelets for capture fibre attachment to a strut;

FIG. 29b shows an eyelet for capture fibre attachment to a strut;

FIG. 29c shows an eyelet for capture fibre attachment to a strut;

FIG. 29d shows a strut with curvature to define a capture fiber attachment location;

FIG. 29e shows a strut with raised features to define a capture fiber attachment location;

FIG. 29f shows a strut with recessed features to define a capture fiber attachment location;

FIG. 29g shows a strut with recessed features to define a capture fiber attachment location;

FIG. 29h shows a strut with bands to define a capture fiber attachment location;

FIG. 29i shows a strut with coils to define a capture fiber attachment location;

FIG. 30a shows a strut with a sleeve to create a capture fiber attachment location;

FIG. 30b shows a strut with a coating to create a capture fiber attachment location;

FIG. 30c shows a strut and a capture net with a connecting fiber joining the two;

FIG. 30d shows a strut and a capture net with connecting rings joining the two;

FIG. 30e shows a strut and a capture net with a connecting fiber joining the two;

FIG. 31a shows a capture net of a woven or braided construction;

FIG. 31b shows a capture net of a knitted construction;

FIG. 31c shows a sectional side view of the capture net of FIG. 31a or FIG. 31b inverted and mounted on a frame;

FIG. 32a shows a monofilament capture fiber;

FIG. 32b shows a multifilament twisted capture fiber;

FIG. 32c shows a multifilament braided capture fiber;

FIG. 32d shows a multifilament capture fiber with a cover sleeve;

FIG. 32e shows a multilayer capture fiber;

FIG. 33a shows a frame with a capture net with a porosity gradient;

FIG. 33b shows a frame with a capture net with a porosity gradient;

FIG. 33c shows a frame with capture fibers with a porosity gradient;

FIG. 33d shows a frame with capture fibers with a stiffening fiber;

FIG. 34a shows a clot retrieval device in the fully expanded configuration;

FIG. 34b shows a clot retrieval device in the collapsed configuration inside a catheter;

FIG. 34c shows a ring and guidewire of a clot retrieval device;

FIG. 34d shows a ring and guidewire of a clot retrieval device;

FIG. 34e shows a portion of a guidewire of a clot retrieval device;

FIG. 34f shows a portion of a guidewire of a clot retrieval device;

FIG. 35a shows a vessel with an obstructive clot;

FIG. 35b shows a clot retrieval device crossing an obstructive clot;

FIG. 35c shows a clot retrieval device being deployed in a vessel;

Figure 35F:
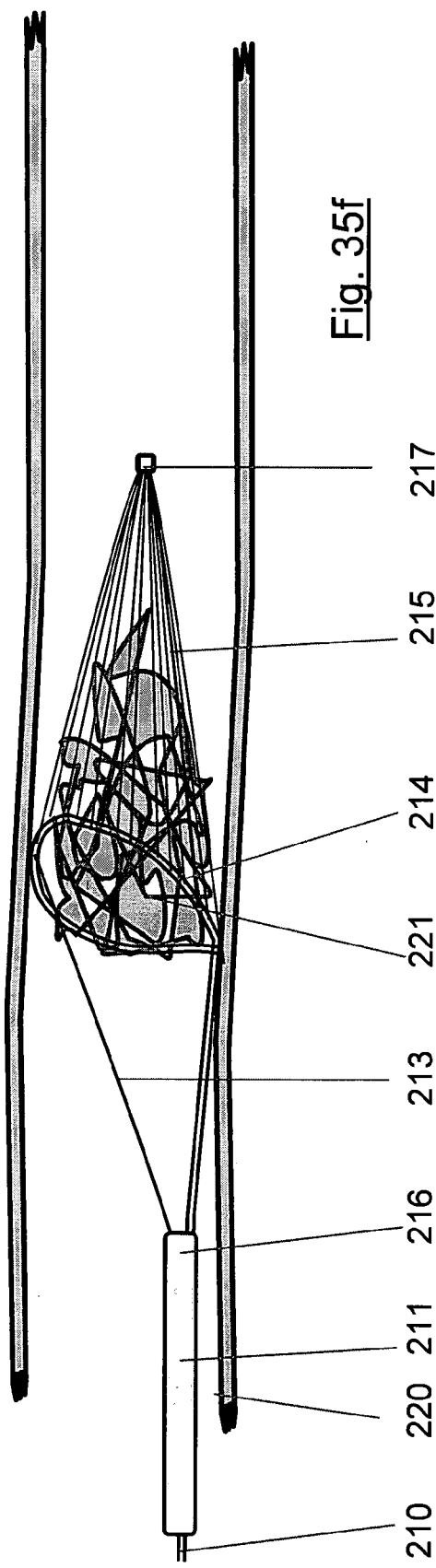
Figure 35G:
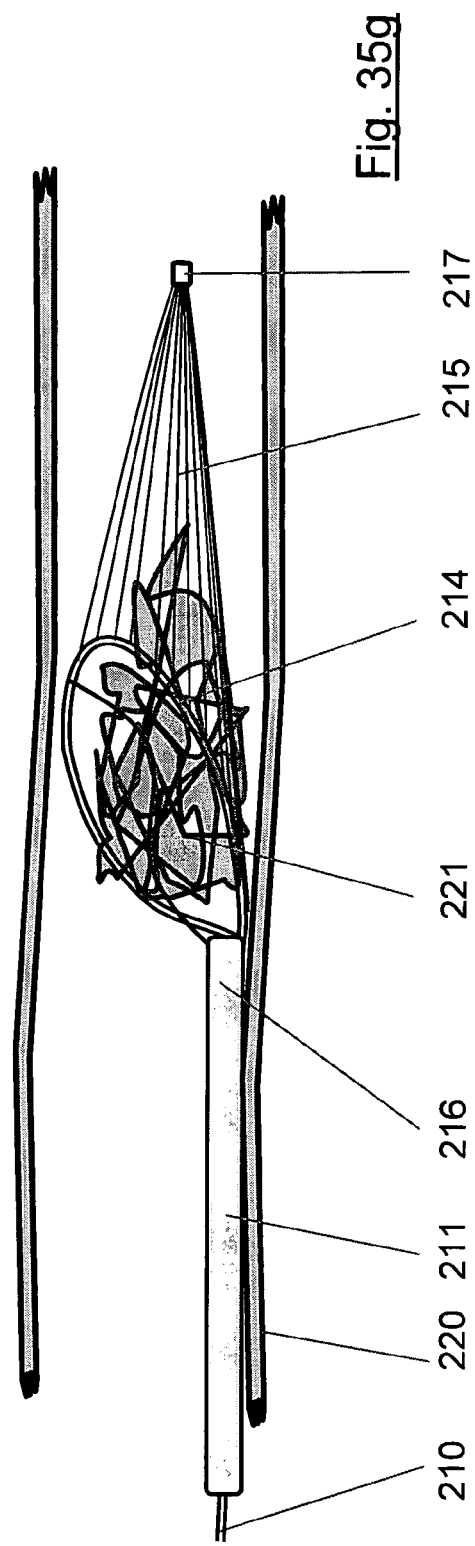
Figures 37D, 37E:
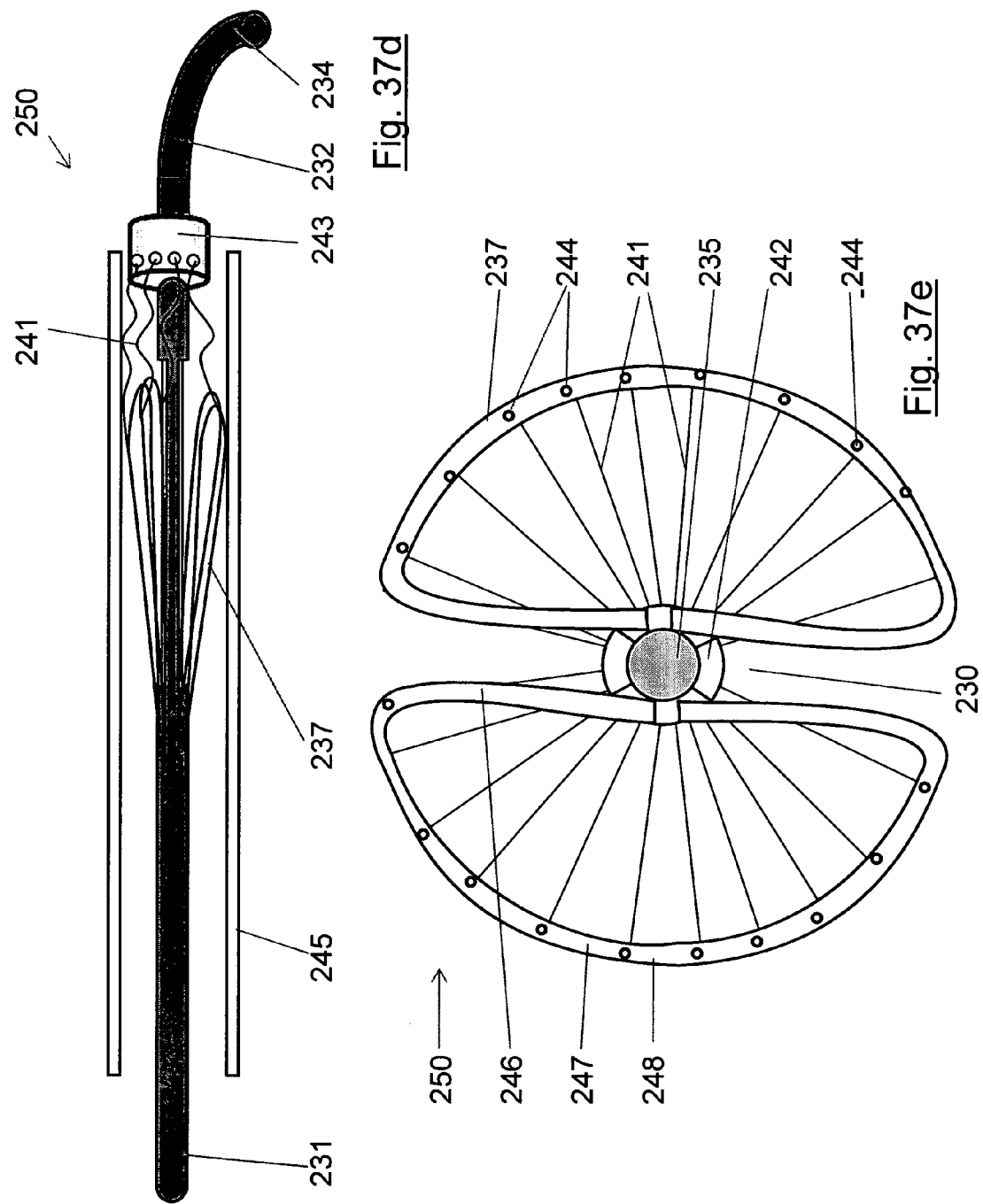
Figure 39C:
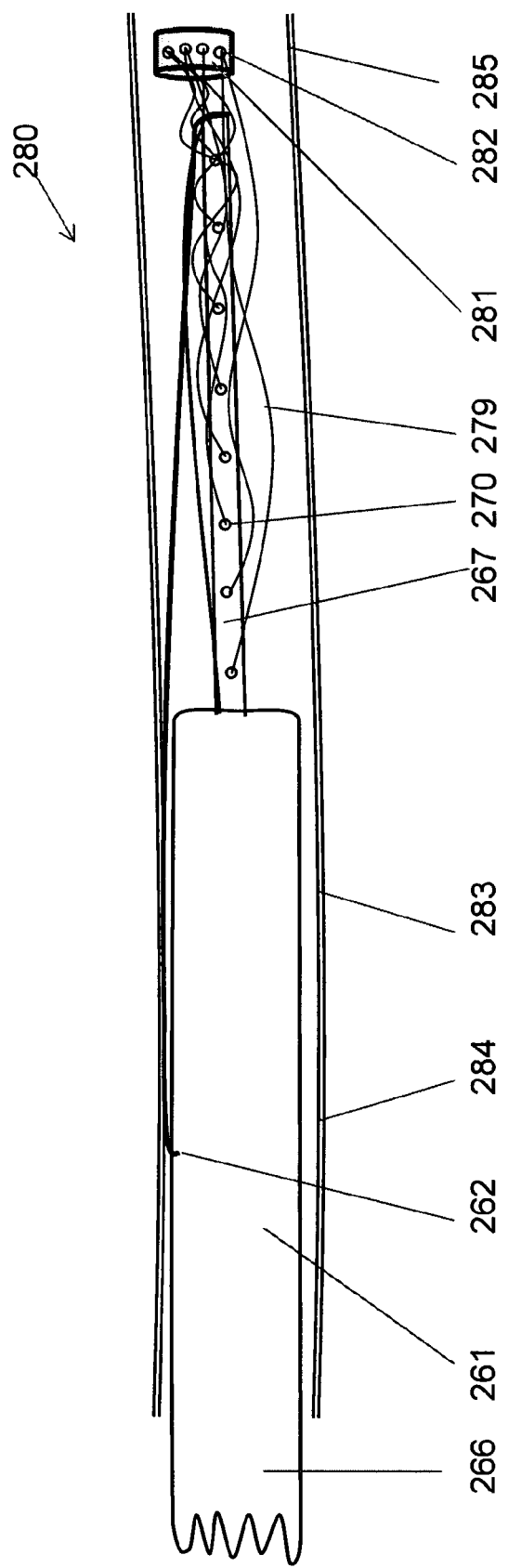
Figure 45A:
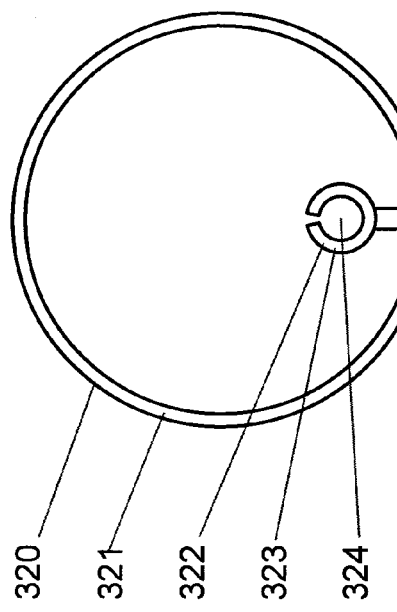
Figure 45B:
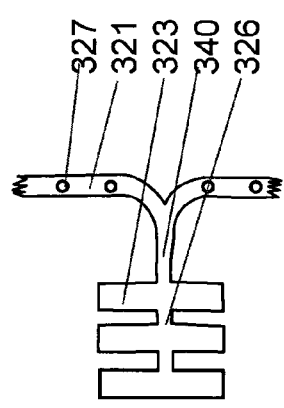
Figure 45C:
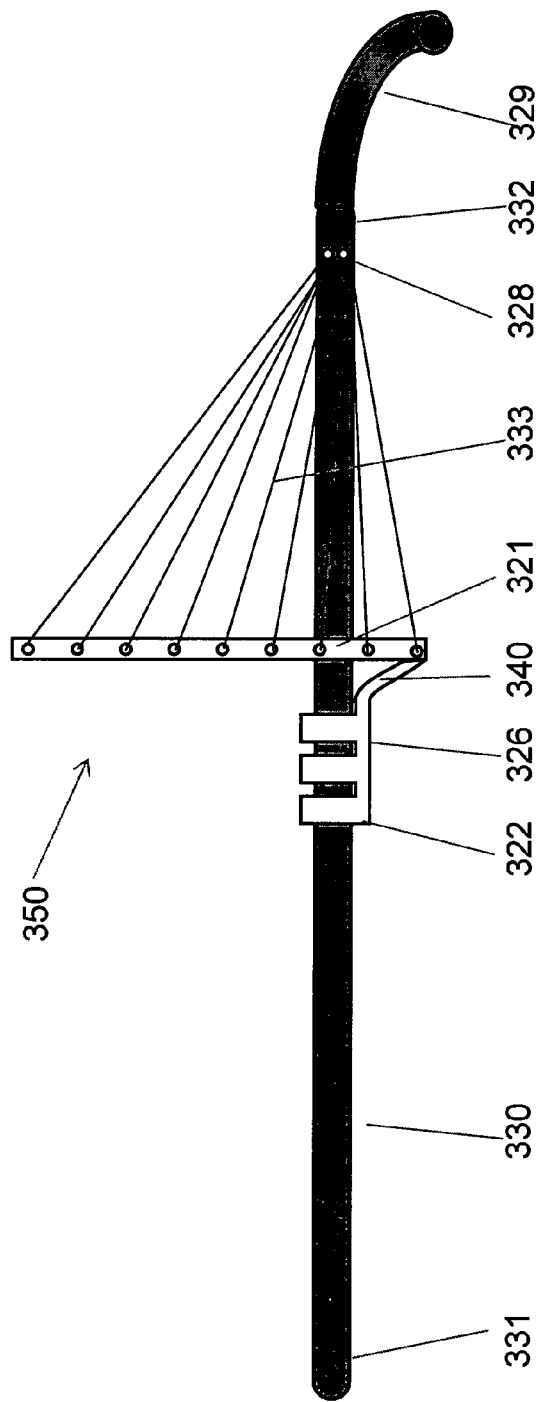
Figure 46:
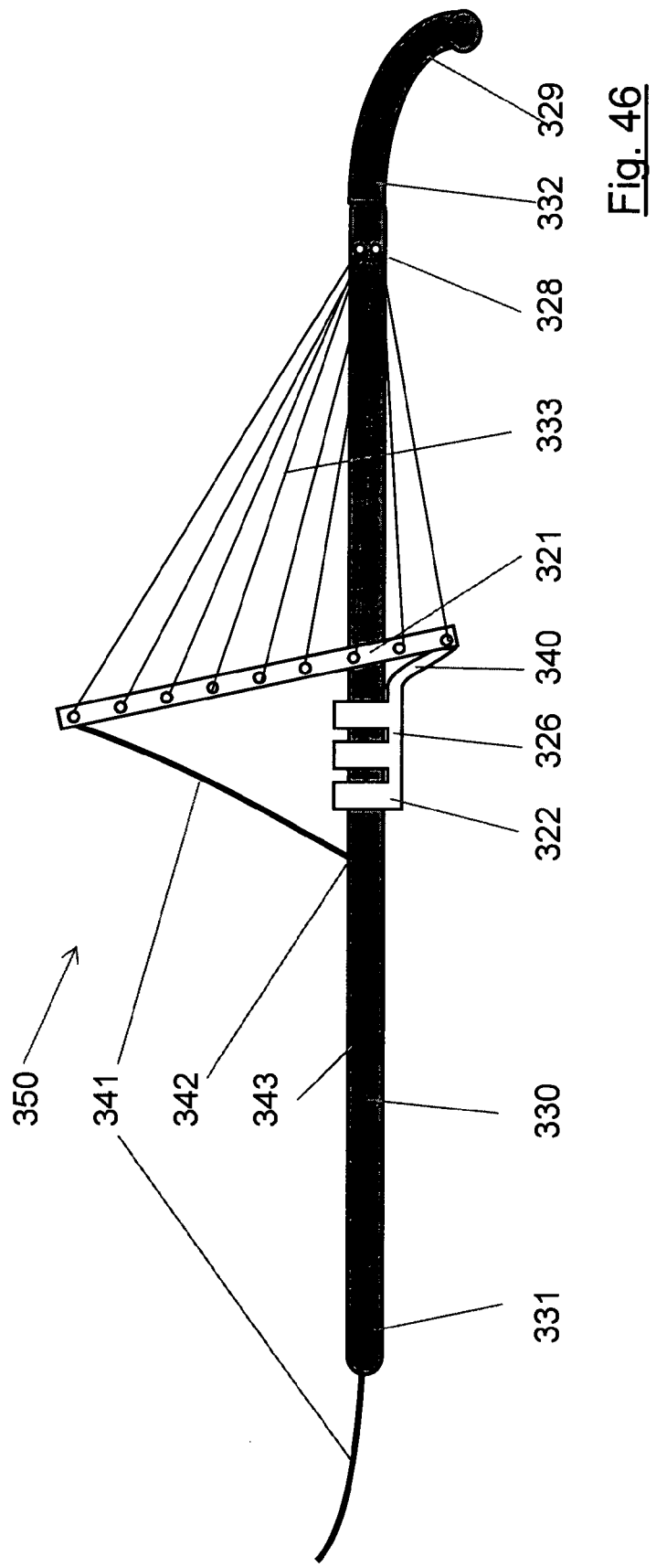
Figure 53:
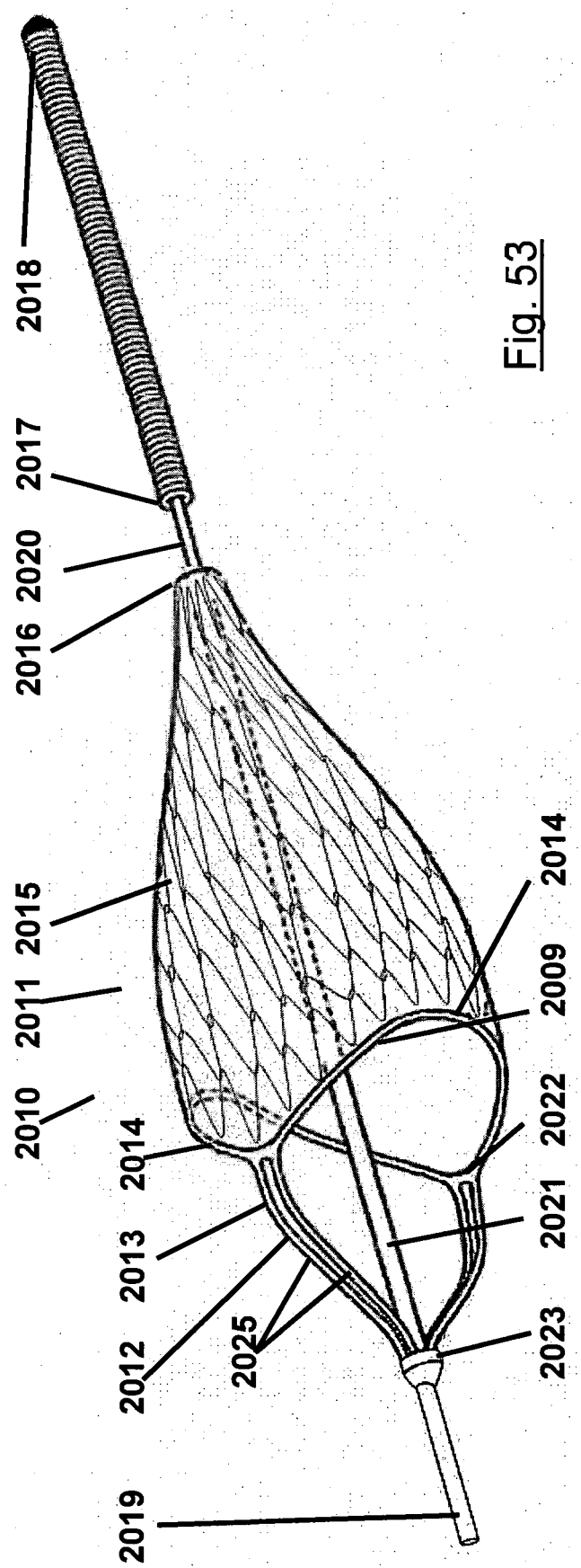
Figure 54:
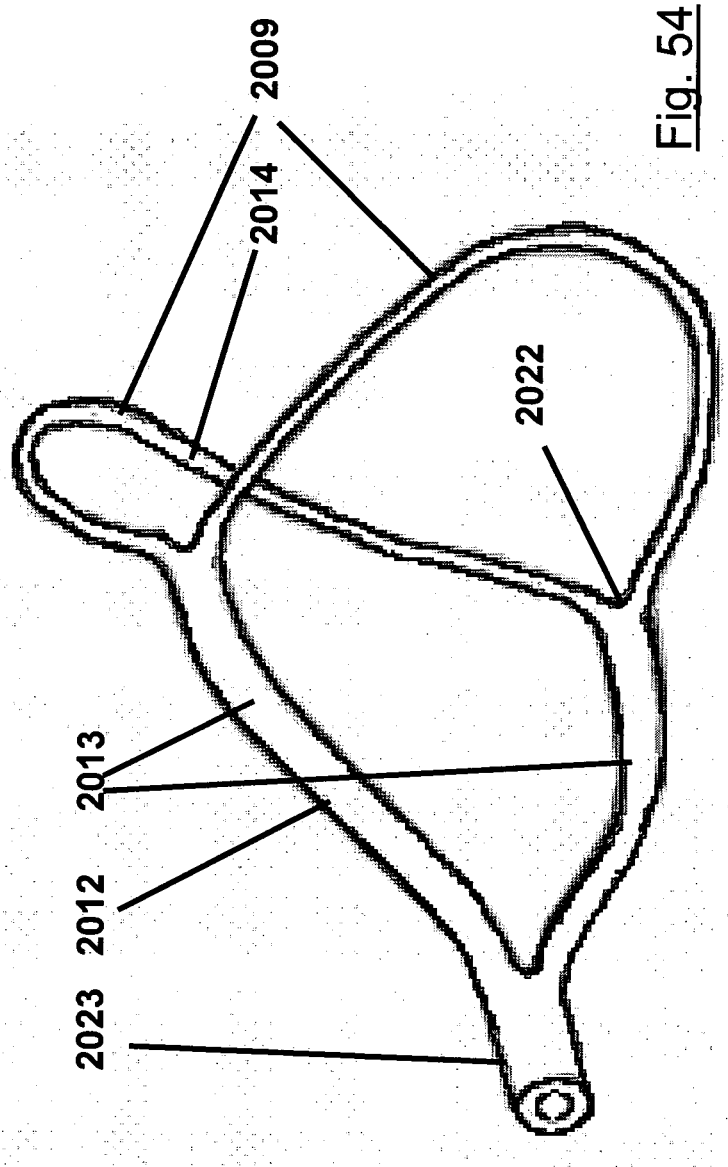
Figure 80L:
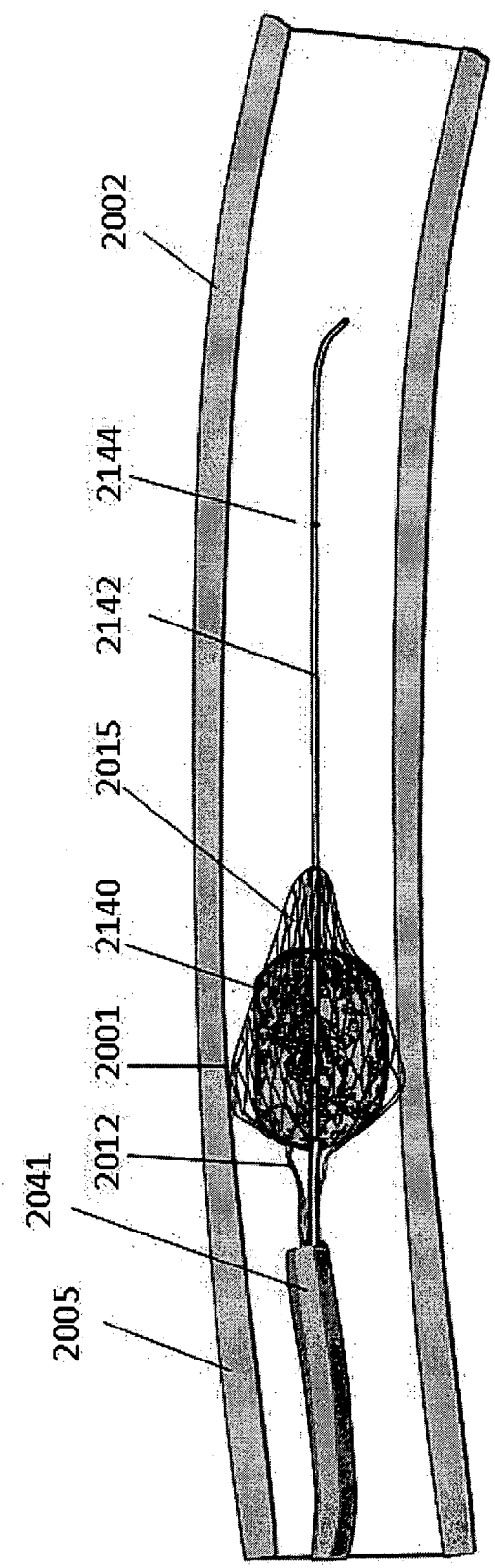
Figure 80M:
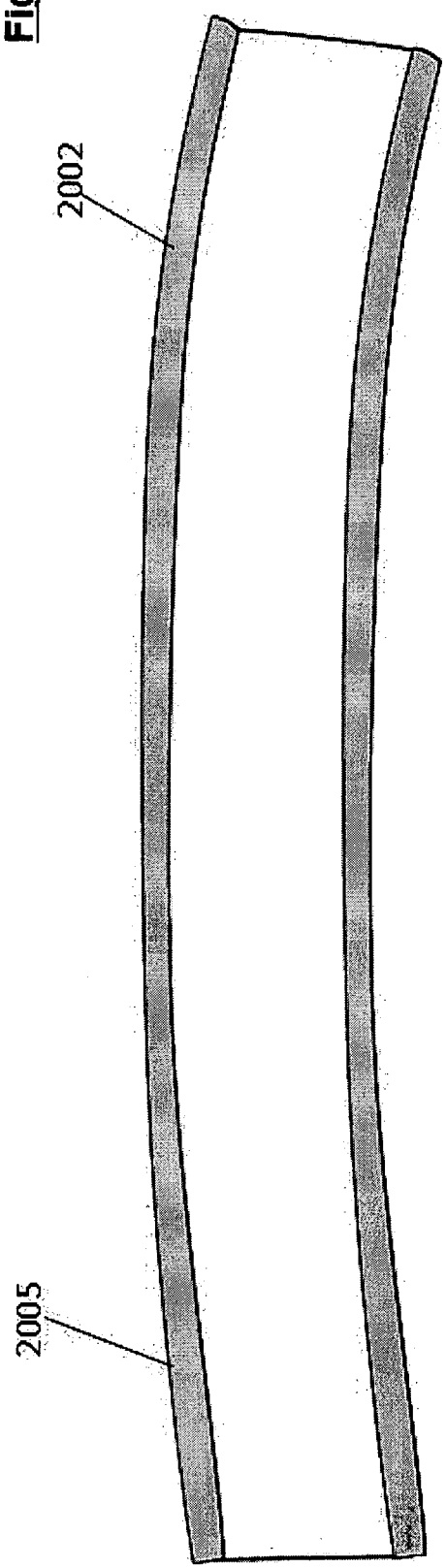

FIG. 35d shows a clot retrieval device deployed in a vessel;

FIG. 35e shows a clot retrieval device fully expanded in a vessel;

FIG. 35f shows a clot retrieval device capturing an obstructive clot;

FIG. 35g shows a clot retrieval device being collapsed;

FIG. 35h shows a clot retrieval device partially collapsed;

FIG. 35i shows a clot retrieval device being removed from a vessel;

FIG. 36a shows a clot retrieval device in the expanded configuration;

FIG. 36b shows a clot retrieval device in the collapsed delivery configuration;

FIG. 37a shows a conventional guidewire;

FIG. 37b shows a portion of a guidewire modified to create a clot retrieval device;

FIG. 37c shows a clot retrieval device in the expanded state;

FIG. 37d shows a clot retrieval device in the collapsed delivery configuration;

FIG. 37e shows an end view of a clot retrieval device;

FIG. 38a shows a portion of a guidewire modified to create a clot retrieval device;

FIG. 38b shows a portion of a guidewire modified to create a clot retrieval device;

FIG. 38c shows a cross sectional view of a guidewire modified to create a clot retrieval device;

FIG. 39a shows an end view of a clot retrieval device;

FIG. 39b shows a clot retrieval device in the expanded configuration;

FIG. 39c shows a clot retrieval device in the collapsed delivery configuration;

FIG. 40a shows an end view of a clot retrieval device;

FIG. 40b shows a clot retrieval device in the expanded configuration;

FIG. 41a shows an end view of a clot retrieval device;

FIG. 41b shows a clot retrieval device in the expanded configuration;

FIG. 42a shows an end view of a clot retrieval device;

FIG. 42b shows a clot retrieval device in the expanded configuration;

FIG. 43a shows a clot retrieval device in the expanded configuration;

FIG. 44a shows an end view of a frame design of a clot retrieval device;

FIG. 44b shows a view of a portion of frame of a clot retrieval device;

FIG. 44c shows a clot retrieval device in the expanded configuration;

FIG. 44d shows a clot retrieval device in the delivery configuration;

FIG. 45a shows an end view of a frame design of clot retrieval device;

FIG. 45b shows a view of a portion of frame of a clot retrieval device;

FIG. 45c shows a clot retrieval device in the expanded configuration;

FIG. 46 shows a clot retrieval device in the expanded configuration;

FIG. 47a shows a clot retrieval device in the expanded configuration;

FIG. 47b shows a clot retrieval device in the partially collapsed configuration;

FIG. 47c shows a clot retrieval device in the delivery configuration;

FIG. 47d shows a view of a portion of frame section of a clot retrieval device;

FIG. 48a shows a clot retrieval frame mounted on a guidewire;

FIG. 48b shows the device of FIG. 48a and a delivery device housed in a microcatheter;

FIG. 49a shows a clot retrieval device and a delivery catheter;

FIG. 49b shows the device of FIG. 49a loaded within its delivery catheter;

FIG. 50a shows a clot retrieval device;

FIG. 50b shows the device of FIG. 50a loaded within a catheter;

FIG. 50c shows the device of FIG. 50a partially withdrawn into a retrieval catheter;

FIG. 51a shows a clot retrieval device positioned over a full length guidewire;

FIG. 51b shows a clot retrieval device positioned over a rapid exchange length guidewire;

FIG. 52a shows a clot retrieval device;

FIG. 52b shows a guidewire of the clot retrieval device of FIG. 2a;

FIG. 53 shows another clot retrieval device;

FIG. 54 shows a frame cut from a hypotube for use as the frame of a clot retrieval device;

FIG. 55a shows another clot retrieval device delivered through a microcatheter;

FIG. 55b shows another clot retrieval device delivered through a microcatheter;

FIG. 56 shows a detailed view of the distal end of a clot retrieval device and a microcatheter delivery system;

FIG. 57 shows a detailed view of the distal end of another clot retrieval device and a microcatheter delivery and retrieval system;

FIG. 58a shows a detailed view of the distal end of another clot retrieval device and a microcatheter delivery and retrieval system;

FIG. 58b shows a detailed view of the clot retrieval device of FIG. 58a in another configuration;

FIG. 59a shows a guidewire with a step at the distal, the tip of the guidewire is placed in a vessel (not shown);

FIG. 59b shows a microcatheter being advanced over the guidewire;

FIG. 59c shows the clot retrieval device being delivered through the microcatheter and over the wire, a clot debonding device is also being advanced through the microcatheter;

FIG. 59d shows the clot retrieval device deployed from the distal end of the microcatheter and expanded in the vessel (not shown);

FIG. 59e shows the clot retrieval device deployed from the distal end of the microcatheter and the microcatheter advanced proximally;

FIG. 59f shows the clot debonding element deployed from the microcatheter;

FIG. 59g shows the clot debonding element retrieved back into the distal end of the microcatheter;

FIG. 59h shows the clot retrieval device collapsed back into the pod of the microcatheter;

FIGS. 60a and 60b show end views of clot debonding elements;

FIG. 61a shows a side view of an unexpanded clot debonding element;

FIG. 61b shows a side view of the expanded clot debonding element from FIG. 61a;

FIG. 61c shows an end view of the expanded clot debonding element from FIG. 61a;

FIG. 62a shows an end view of another clot debonding element;

FIG. 62b shows a side view of a clot debonding device;

FIG. 62c shows a side view of another clot debonding device;

FIG. 62d shows a side view of yet another clot debonding device;

FIG. 62e shows a side view of an alternative clot debonding device;

FIG. 63a shows a side view of the end of an unexpanded clot debonding catheter;

FIG. 63b shows a side view of the end of an expanded clot debonding catheter from FIG. 63a;

FIG. 64a shows a side view of the end of an unexpanded clot debonding catheter;

FIG. 64b shows a side view of the end of an expanded clot debonding catheter from FIG. 64a;

FIG. 65a shows a side view of the end of an unexpanded clot debonding catheter;

FIG. 65b shows a side view of the end of an expanded clot debonding catheter from FIG. 65a;

FIG. 66a shows a side view of the end of an unexpanded clot debonding catheter;

FIG. 66b shows a side view of the end of a partially expanded clot debonding catheter from FIG. 66a;

FIG. 66c shows an end view of the expanded clot debonding catheter from FIG. 66a;

FIG. 67a shows a side view of the end of an unexpanded clot debonding catheter;

FIG. 67b shows an end view of the expanded clot debonding catheter from FIG. 67a;

FIG. 68a shows a side view of the end of an unexpanded clot debonding catheter;

FIG. 68b shows a side view of the end of a partially expanded clot debonding catheter from FIG. 68a;

FIG. 68c shows an end view of the expanded clot debonding catheter from FIG. 68a;

FIG. 69a shows the clot debonding catheter from FIG. 68a mounted over a microcatheter prior to deployment proximal to a clot and clot retrieval device;

FIG. 69b shows the clot debonding catheter from FIG. 69a post deployment;

FIG. 70 shows a clot retrieval device in the deployed configuration distal of an occlusive clot;

FIG. 71 shows a collector device being used with a clot retrieval device;

FIG. 72 shows a collector device with deployed elements being used to advance clot into a clot retrieval device;

FIG. 73 shows the collector device in an advanced position with most of the clot inside the clot retrieval device;

FIG. 74 shows an alternative clot advancement device;

FIG. 75 shows a clot advancement device with two coil elements;

FIG. 76a shows a side view of another clot advancement device;

FIG. 76b shows an end view of the clot advancement device of FIG. 76a;

FIG. 77 shows another clot retrieval device with an integral clot debonding element;

FIG. 78a shows an artery or vein with an occlusive clot acutely lodged in the vessel, the occlusive clot reduces or prevents distal blood flow;

FIG. 78b shows the occlusive clot of FIG. 78a with platelets being activated at the site of occlusion;

FIG. 78c shows bonds formed between the occlusive clot and the vessel wall;

FIG. 79a shows a vein or artery with an occlusive clot lodged therein;

FIG. 79b shows an occlusive clot with the tip of a guidewire advanced across the occlusive clot;

FIG. 79c shows a microcatheter advanced over the guidewire such that its tip is distal of the occlusive clot;

FIG. 79d shows the microcatheter tip distal of the occlusive clot with the guidewire removed;

FIG. 79e shows a clot retrieval device being advanced through the lumen of the microcatheter;

FIG. 79f shows the clot retrieval device expanded with the microcatheter partially withdrawn;

FIG. 79g shows a clot debonding element advanced through the microcatheter and in the deployed state;

FIG. 79h shows the clot being engaged by both the clot retrieval device and the clot debonding element;

FIG. 79i shows the clot captured in the net of the clot retrieval device with the clot debonding element removed through the lumen of the microcatheter;

FIG. 79j shows the clot retrieval device with the frame partially collapsed and the clot captured in the net;

FIG. 79k shows the clot retrieval device, the microcatheter and the captured clot being removed from the vessel;

FIG. 79l shows the vessel recannalized;

FIG. 80a shows a vein or artery with an occlusive clot lodged therein;

FIG. 80b shows an occlusive clot with the tip of a guidewire advanced across the occlusive clot;

FIG. 80c shows a microcatheter advanced over the guidewire such that its tip is distal of the occlusive clot;

FIG. 80d shows the microcatheter tip distal of the occlusive clot with the guidewire removed;

FIG. 80e shows a stepped guidewire advanced through the lumen of the microcatheter;

FIG. 80f shows a clot retrieval device being advanced through the lumen of the microcatheter and over the guidewire;

FIG. 80g shows the clot retrieval device expanded with the microcatheter partially withdrawn;

FIG. 80h shows a clot debonding element advanced through the microcatheter and in the deployed state;

FIG. 80i shows the clot being engaged by both the clot retrieval device and the clot debonding element;

FIG. 80j shows the clot captured in the net of the clot retrieval device with the clot debonding element removed through the lumen of the microcatheter;

FIG. 80k shows the clot retrieval device with the frame partially collapsed and the clot captured in the net;

FIG. 80l shows the clot retrieval device, the microcatheter and the captured clot being removed from the vessel; and FIG. 80m shows the vessel recannalized.

DETAILED DESCRIPTION

The present invention is related to an apparatus and methods for the removal of obstructions in vessels. More particularly the present invention relates to devices and methods for the removal of obstructive clot from cerebral vessels.

Figure 1:
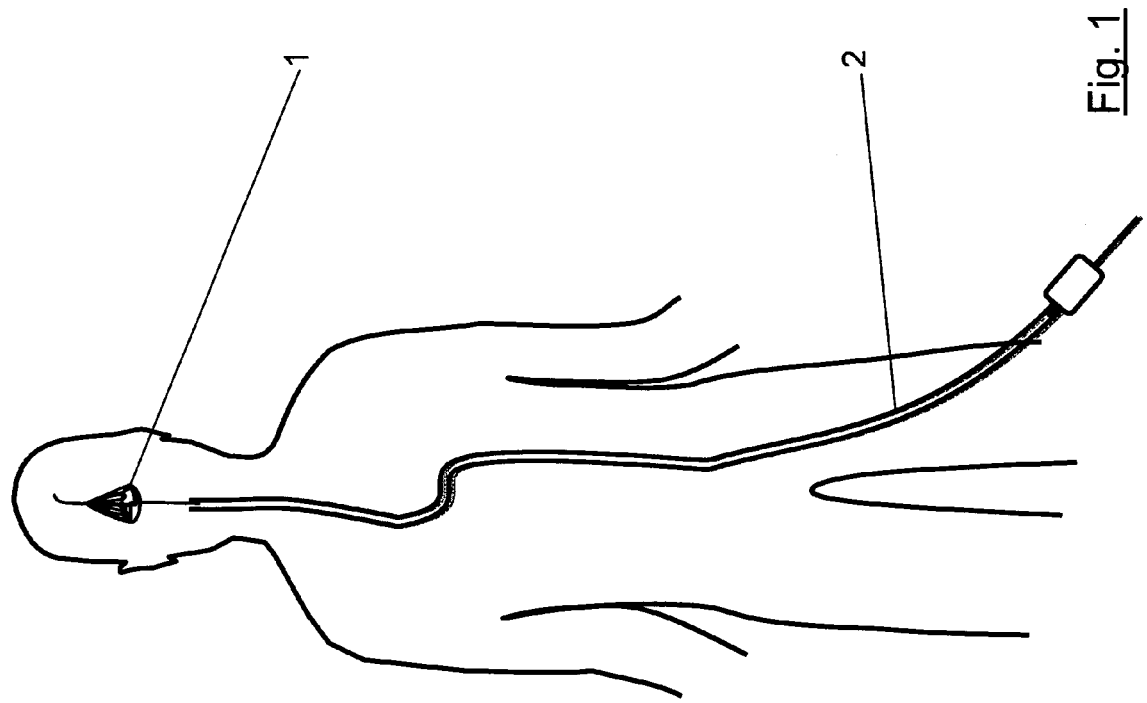
FIG. 1 shows a patient catheterized via femoral access with a clot retrieval device positioned in a cerebral vessel using the arterial system for its delivery.

With reference to FIG. 1 there is shown a schematic representation of the catheterization of a patient with a clot retrieval device 1 according to the invention. The patient is catheterized via the femoral artery with a catheter 2 in accordance with standard interventional technique.

FIG. 2 shows a schematic representation of some of the arteries supplying blood to the brain. The arteries shown are on the anterior circulation. Vessel 400 is the Aorta. Vessel 401 is the brachiocephalic artery. Vessel 402 is the subclavian artery. Vessel 403 is the common carotid artery. Vessel 404 is the internal carotid artery. Vessel 405 is the external carotid artery. Vessel 406 is the middle cerebral artery. Vessel 407 is the anterio-cerebral artery. A catheter 2 is shown with its distal end in the common carotid artery. In the more detailed drawings of the invention the details of the access site will not be shown but in general access and delivery is in accordance with FIG. 1 and/or FIG. 2. It will be appreciated that the devices and methods disclosed in this invention relate to all of femoral access, radial access, direct stick access, carotid access even where only one variation is shown or described.

Figure 3G:
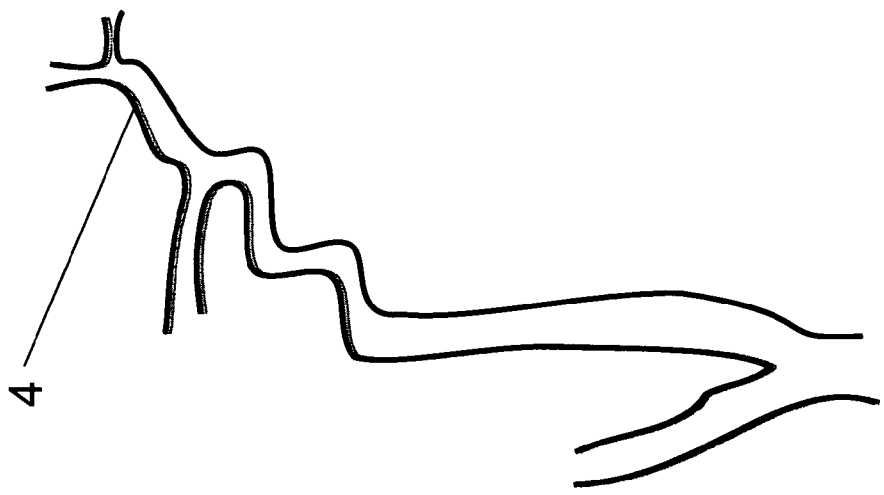
FIG. 3g shows the target vessel with the obstructive clot and devices completely removed.
Figure 3F:
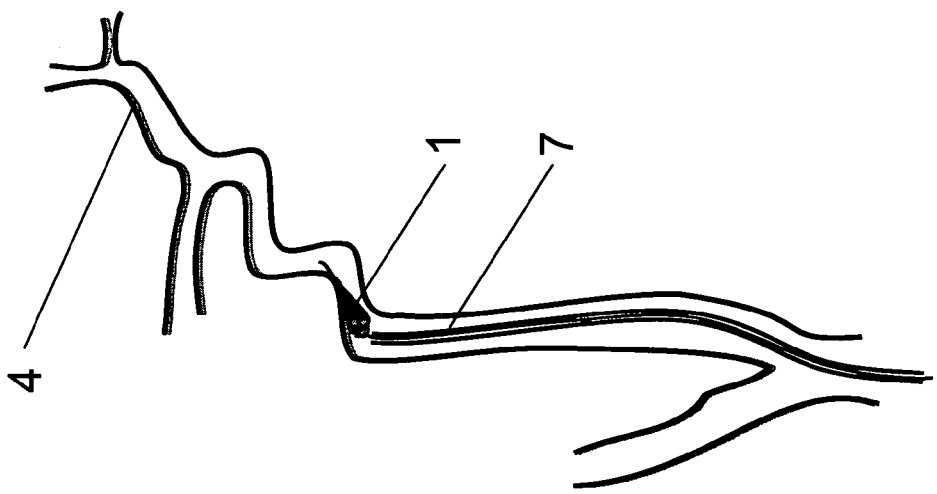
FIG. 3f shows the clot retrieval device, the captured occlusive clot and the removal catheter being removed from the vessel.
Figure 3E:
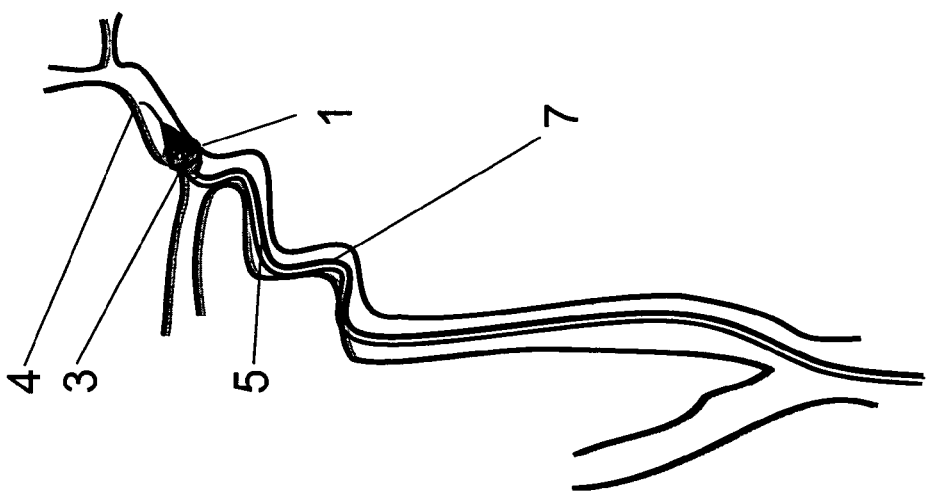
FIG. 3e shows the clot retrieval device being advanced proximally and capturing the obstructive clot with a removal catheter advanced from the proximal side.

Now with reference to FIG. 3a to FIG. 3g a first method of using the devices of the invention is highlighted. FIG. 3a shows an obstructive clot 3 located on a cerebral vessel 4. The first step in treating this obstruction is to cross the obstruction 3 with a guidewire 5. The guidewire 5 is inserted into the arterial system through conventional techniques and is advanced to the obstruction. The tip of the guidewire 5 is advanced across the obstruction 3, FIG. 3b. A micro delivery catheter 6 can then be advanced over the guidewire 5 and across the obstructive clot 3. The clot retrieval device 1 is expanded in the target vessel distal of the clot 4. The micro delivery catheter is withdrawn until its tip is proximal of the occlusive clot. Alternatively it can be completely removed from the patient. The clot retrieval device is positioned at the distal end of guidewire 5 and is fixed thereto. The obstructive clot 3 is captured in the device by advancing the device proximally (FIG. 3e). A removal catheter 7 is advanced over the guidewire 5 to assist in the removal of the clot 3. The removal catheter 7 may be a micro-catheter, a guide catheter, a sheath or a special recovery catheter. Aspiration may be employed through the lumen of the recovery catheter to assist in clot removal. FIG. 3g shows the target vessel reannalised after the removal of the obstructive clot 3.

FIG. 3a shows part of the cerebral circulation with an obstructive clot 3 positioned in the Anterior Cerebral Artery 4, distal of the Middle Cerebral Artery branch.

FIG. 3b shows a Guidewire 5 being placed across the obstructive clot 3.

FIG. 3c shows a micro-catheter 6 with the clot retrieval device 1 of the invention crossing the obstructive clot 3.

FIG. 3d shows the micro-catheter removed with the clot retrieval device 1 placed distal of the obstructive clot 3.

FIG. 3e shows the clot retrieval device 1 being advanced proximally and capturing the obstructive clot 3 with a removal catheter 7 advanced from the proximal side.

FIG. 3f shows the clot retrieval device 1, the captured occlusive clot 3 and the removal catheter 7 being removed from the vessel.

FIG. 3g shows the target vessel 4 with the obstructive clot and devices completely removed.

Figure 4C:
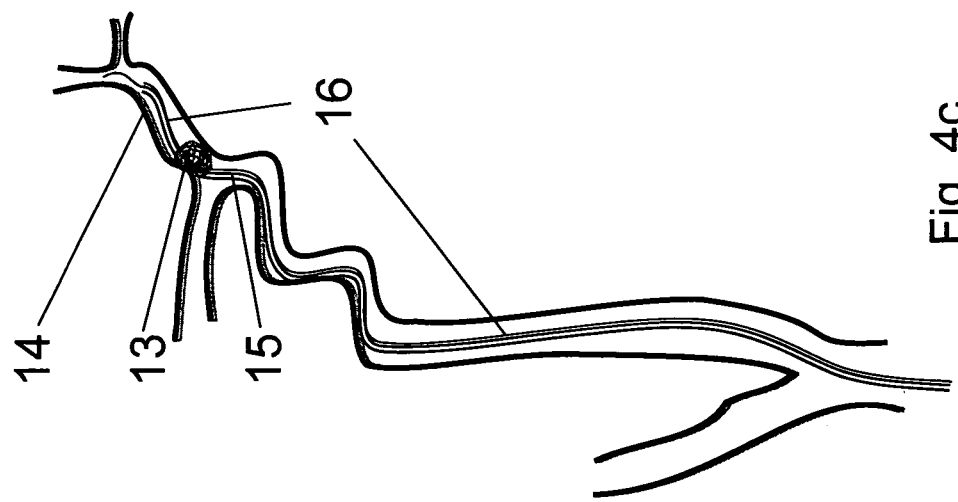
FIG. 4c shows a micro-catheter advanced over the guidewire until its distal end is across the obstructive clot.
Figure 4B:
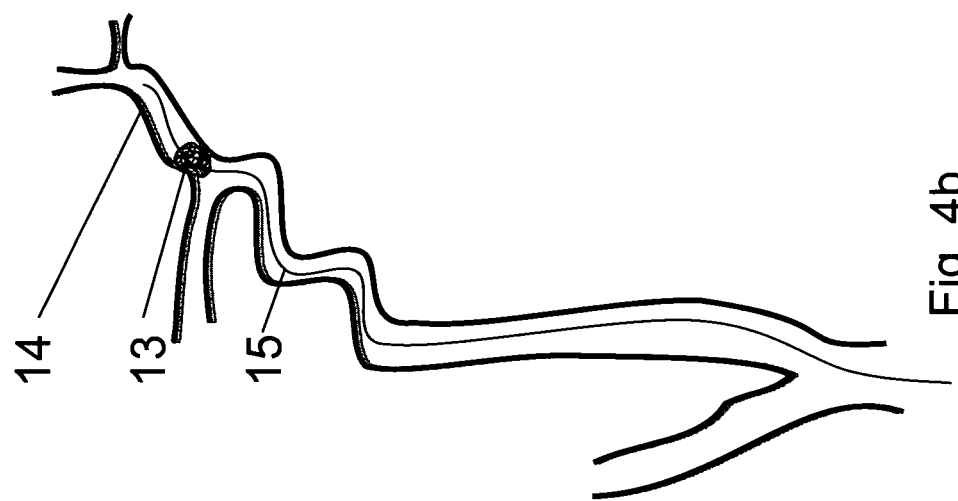
FIG. 4b shows a guidewire with its distal tip across the obstructive clot.
Figure 4A:
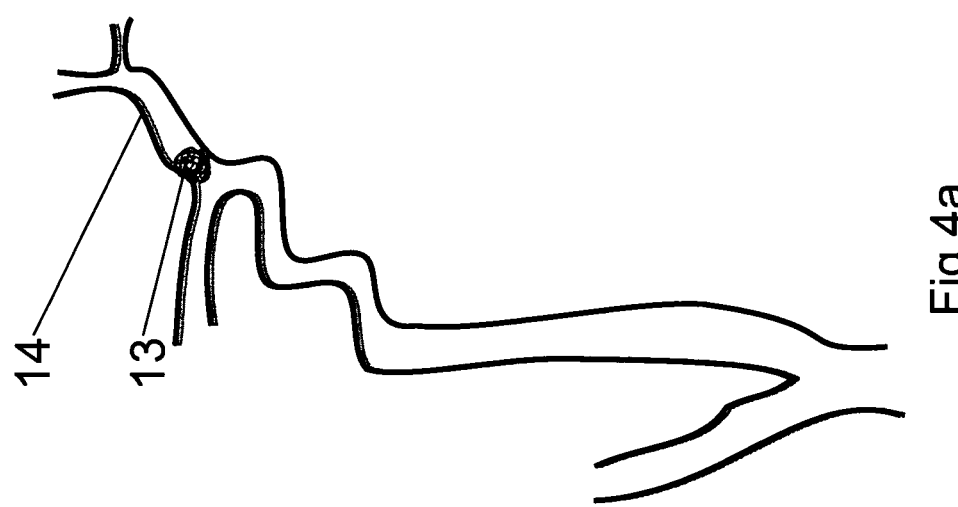
FIG. 4a shows a target vessel with an occlusive clot.
Figure 4F:
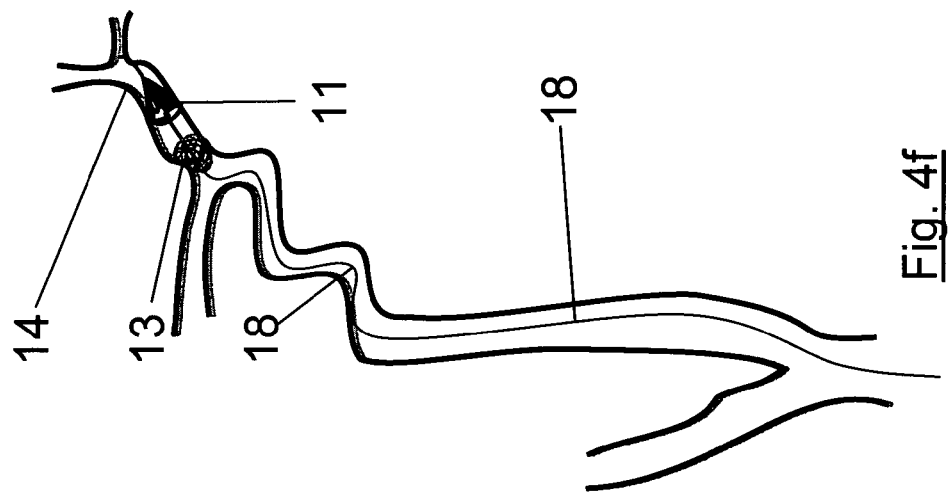
FIG. 4f shows the clot retrieval device deployed distal of the occlusive clot.
Figure 4E:
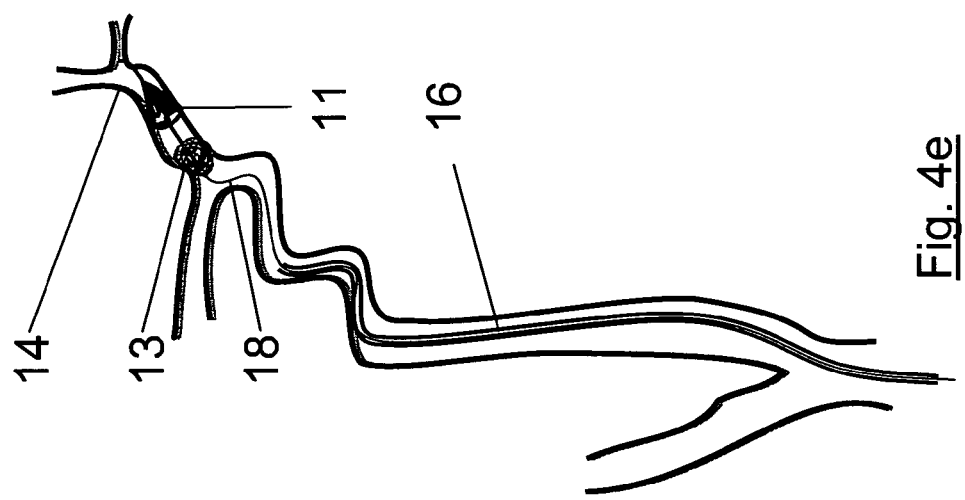
FIG. 4e shows clot retrieval device deployed distal of occlusive clot with the micro-catheter being withdrawn, the clot retrieval device being connected to a wire and the proximal end of the wire exiting the patient and being controlled by a physician.
Figure 4D:
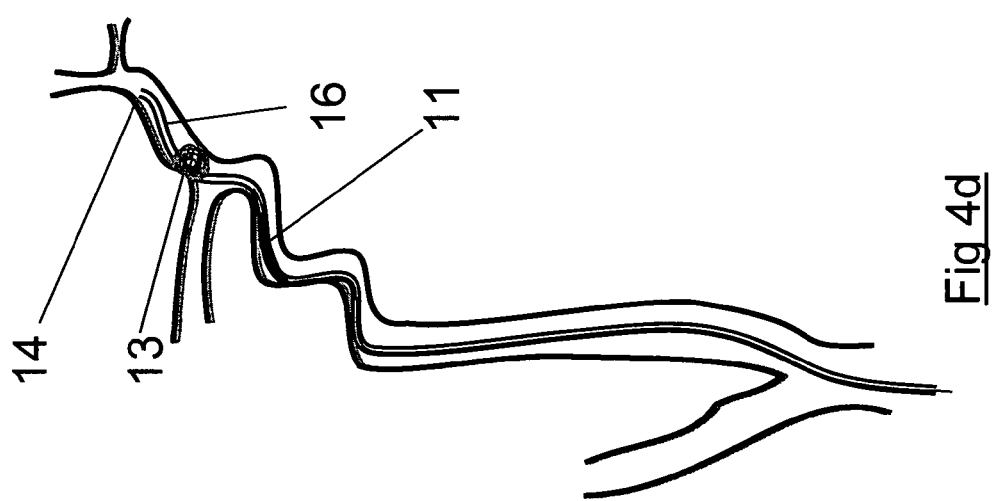
FIG. 4d shows the preplaced micro-catheter with its distal end across occlusive clot and a clot retrieval device being advanced through its inner lumen.
Figure 4I:
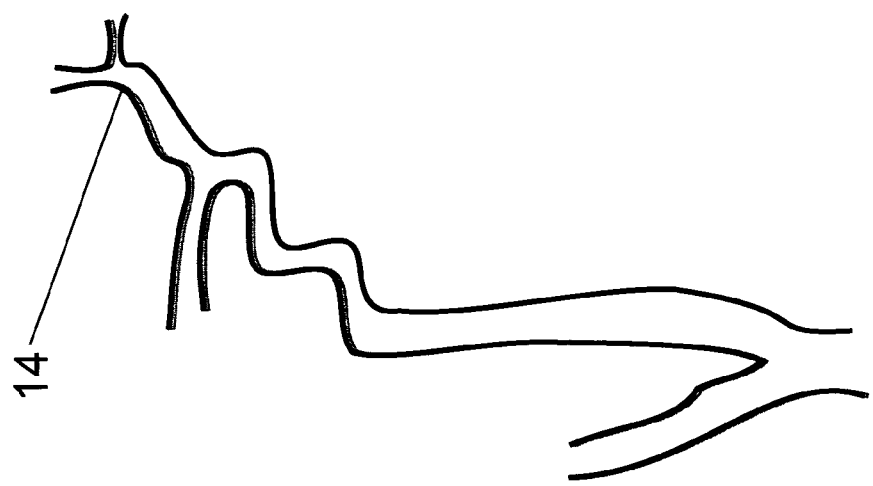
FIG. 4i shows the target vessel with the obstructive clot and devices completely removed.

With reference to FIG. 4a to FIG. 4i another method of employing the clot retrieval devices of this invention is described. With this method an access guidewire 15 is used to cross the obstructive clot 13. A micro catheter 16 is advanced over the access guidewire 15 and across the clot 13. The access guidewire 15 is removed from the lumen of the micro-catheter 16. A clot retrieval device 11 is advanced through the lumen of the micro-catheter 16 in a collapsed state. It will be appreciated that the clot retrieval device was collapsed in order to access the proximal end of the lumen of the micro-catheter 16. The clot retrieval device 11 expands distal of the tip of the micro-catheter 16 and clot 13. The micro-catheter 16 is advanced proximally until its tip is proximal of the clot. Alternatively the micro-catheter 16 can be removed from the patient (as shown FIG. 4d). The clot retrieval device 11 is advanced proximally with the aid of guidewire 18 to capture the obstructive clot 13. The guidewire 18 of the clot retrieval device 11 extends proximally of the expanded section of the device 11 and allows the physician to control the clot retrieval device 11. A removal catheter 17 is advanced over the guidewire 18 to assist in the removal of the clot 13. The removal catheter 17 may be the same micro-catheter that was used to deliver the clot removal device or it may be different size micro-catheter, or a guide catheter, or a sheath or a balloon catheter or a special recovery catheter. The recovery catheter 17 may also be used by the physician to assist with the clot capture by preventing the clot 13 from migrating proximally. Aspiration may be employed through the lumen of the recovery catheter to assist in clot removal. FIG. 4*i* shows the target vessel recannalised after the removal of the obstructive clot 13.

FIG. 4*a* shows a target vessel 14 with an occlusive clot 13.

FIG. 4*b* shows a guidewire 15 with its distal tip across the obstructive clot 13.

FIG. 4*c* shows a micro-catheter 16 advanced over the guidewire 15 until its distal end is across the obstructive clot 13.

FIG. 4*c* shows the preplaced micro-catheter 16 with its distal end across occlusive clot 13 and a clot retrieval device 11 being advanced through its inner lumen, guidewire 18 having being removed from the microcatheter.

FIG. 4*d* shows clot retrieval device 11 deployed distal of occlusive clot 13 with the micro-catheter 16 being withdrawn. Clot retrieval device is connected to wire 18 and proximal end of wire 18 exits the patient and is controlled by the physician.

FIG. 4*e* shows the clot retrieval device 11 deployed distal of occlusive clot 13 with the micro-catheter being removed.

FIG. 4*f* shows the clot retrieval device 11 deployed distal of occlusive clot 13.

Figure 4H:
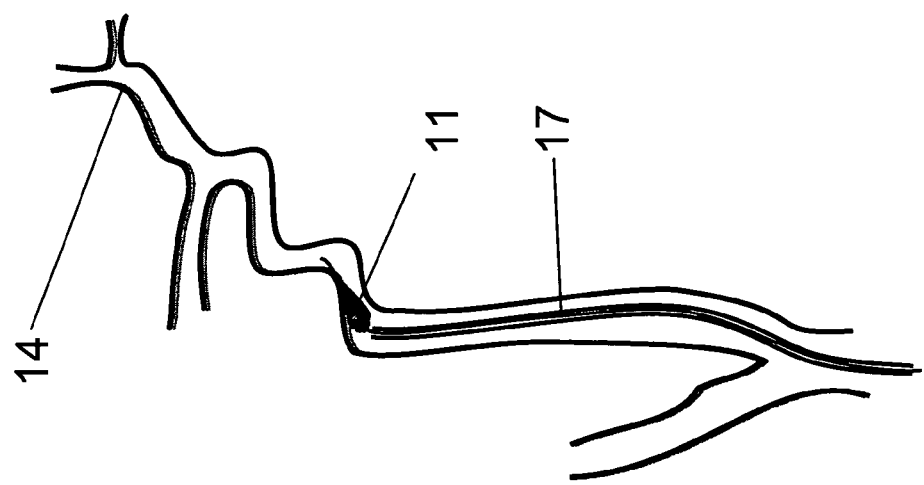
FIG. 4h shows the clot retrieval device, the captured occlusive clot and the removal catheter being removed from the vessel.
Figure 4G:
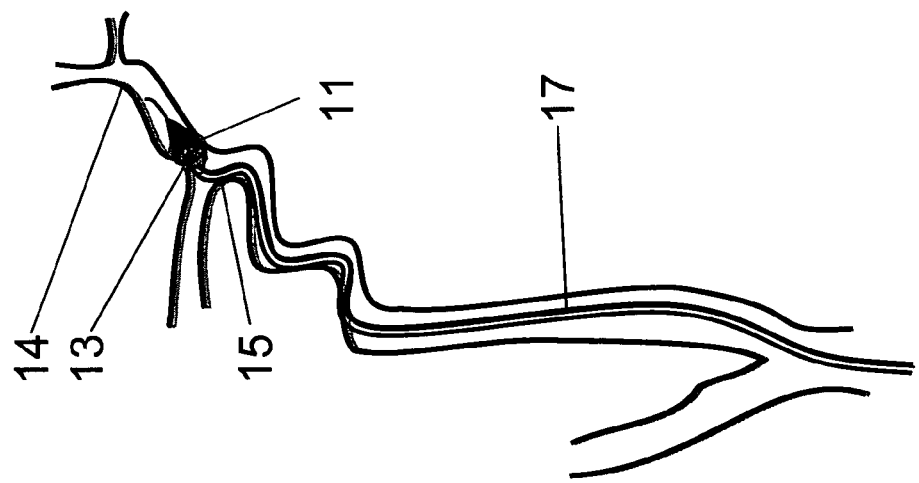
FIG. 4g shows the clot retrieval device being advanced proximally and capturing the obstructive clot with a removal catheter advanced from the proximal side.

FIG. 4*g* shows the clot retrieval device 11 being advanced proximally and capturing the obstructive clot 13 with a removal catheter 17 advanced from the proximal side.

FIG. 4*h* shows the clot retrieval device 11, the captured occlusive clot 13 and the removal catheter 17 being removed from the vessel.

FIG. 4*i* shows the target vessel 14 with the obstructive clot 13 and devices completely removed.

Referring now to FIG. 5*a* to FIG. 5*g* another method of employing the clot retrieval devices of this invention is described. With this method the obstructive clot 23 in target vessel 24 is crossed directly with a clot retrieval micro-delivery catheter 26. The clot retrieval micro delivery catheter 26 has a reception space at its distal end and the collapsed capture device 21 resides in this reception space during delivery. In one embodiment the distal end of the guidewire 28 of the clot retrieval device 21 extends distally of the micro-delivery catheter 26 and assists the device in crossing the occlusive clot 23. When the distal end of the micro-delivery catheter is across the clot 23, the clot retrieval device 21 is deployed and the micro delivery catheter 26 advanced proximally.

The clot retrieval device 21 is advanced proximally with the aid of guidewire 28 to capture the obstructive clot 23. The guidewire 28 of the clot retrieval device 21 extends proximally of the expanded section of the device 21 and allows the physician to control the clot retrieval device 21. A removal catheter 27 is advanced over the guidewire 28 to assist in the removal of the clot 23. The removal removes the clot and capture device as described above.

FIG. 5*a* shows a target vessel 24 with an occlusive clot 23.

FIG. 5*b* shows a micro delivery catheter 26 with a clot retrieval device 21 collapsed within a distal lumen of the micro delivery catheter. The micro delivery catheter is advanced across the occlusive thrombus 23. The clot retrieval device 21 has a Guidewire 28 that extends proximally and distally.

FIG. 5*c* shows micro delivery catheter 26 being removed with the clot retrieval device 21 deployed in the target vessel 24 distal of the occlusive clot 23 with Guidewire 28 extending across the lesion and proximal to the user.

FIG. 5*d* shows the clot retrieval device 21 deployed in the target vessel 24 distal of the occlusive clot 23 with guidewire 28 extending across the lesion and proximal to the user.

Figure 5G:
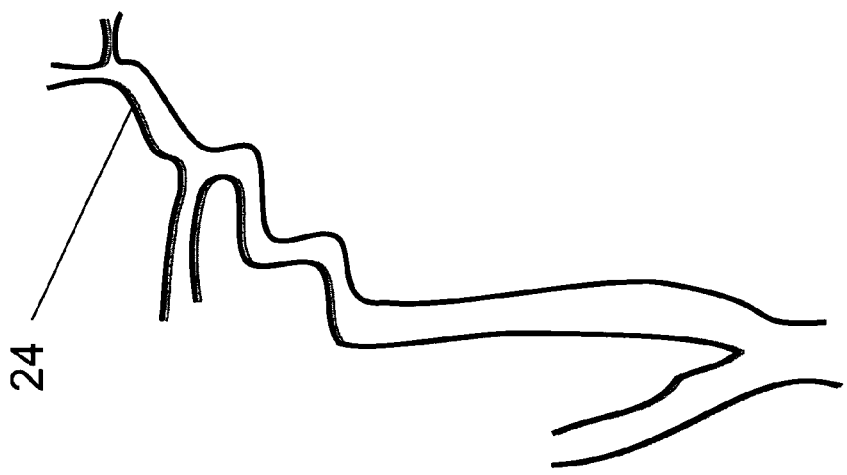
FIG. 5g shows the target vessel with the obstructive clot and devices completely removed.
Figure 5F:
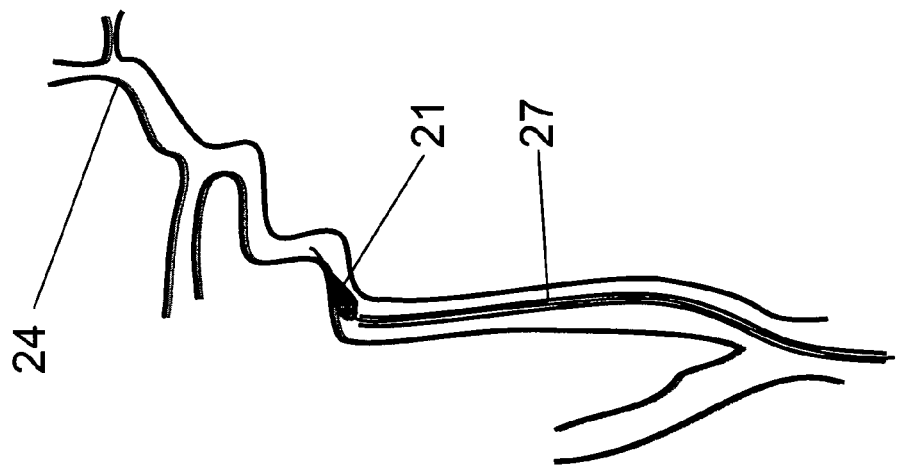
FIG. 5f shows the clot retrieval device, the captured occlusive clot and the removal catheter being removed from the vessel.
Figure 5E:
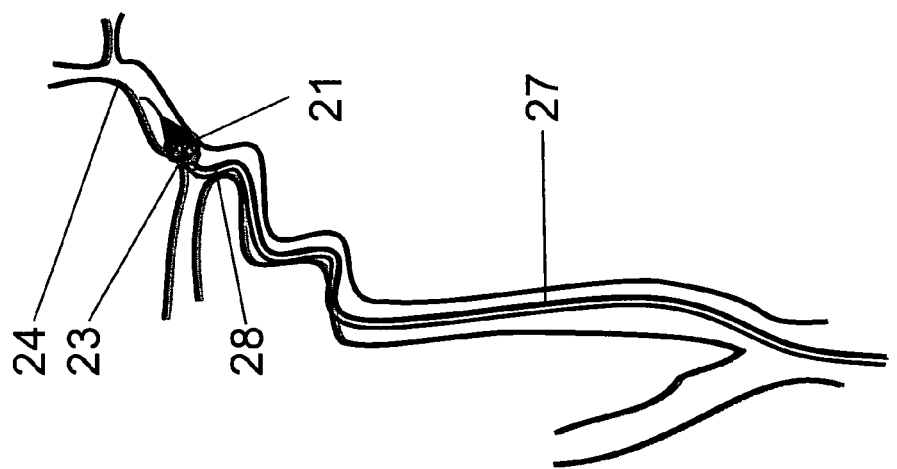
FIG. 5e shows the clot retrieval device being advanced proximally and capturing the obstructive clot with a removal catheter advanced from the proximal side.

FIG. 5*e* shows the clot retrieval device 21 being advanced proximally and capturing the obstructive clot 33 with a removal catheter 27 advanced from the proximal side.

FIG. 5*f* shows the clot retrieval device 21, the captured occlusive clot 23 and the removal catheter 27 being removed from the vessel.

FIG. 5*g* shows the target vessel 24 with the obstructive clot 23 and devices completely removed.

In one embodiment (not shown) the removal catheter comprises a balloon catheter wherein the guidewire lumen of the balloon catheter is larger than the guidewire diameter. The distal end of the balloon catheter lumen provides a reception space for a portion of the collapsed clot capture device. The balloon may be inflated during the clot capture step to prevent the clot from migrating proximally.

Figure 6:
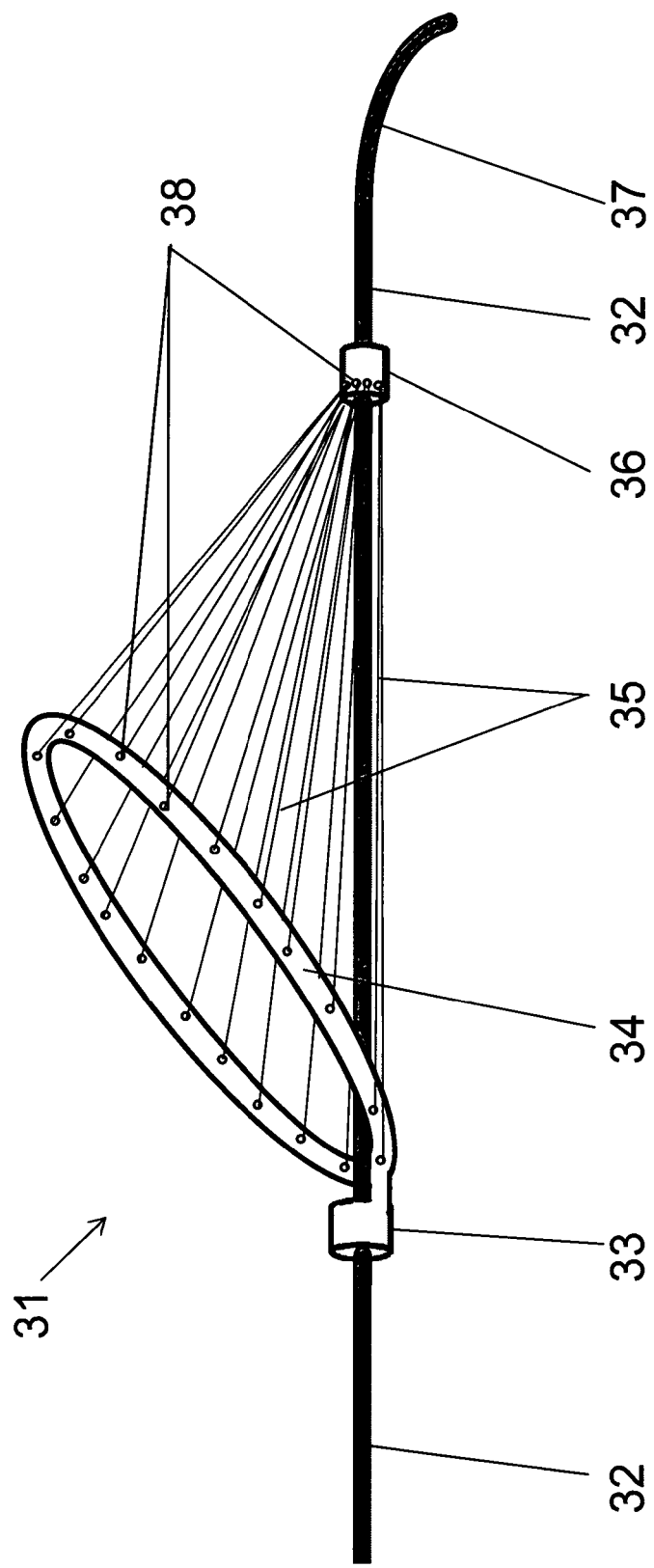
FIG. 6 is a detailed view of the distal end of a clot retrieval device in its expanded clot capture state.

With reference to FIG. 6 an example of the clot retrieval device of this invention is shown. The device 31 comprises a frame 34, a proximal collar 33, a distal collar 36, capture fibers 35, and a guidewire 32. Frame 34 comprises a metallic elliptical hoop. The hoop 34 is subtended at an acute angle relative to the guidewire 32 in the expanded configuration. In the collapsed state the hoop 34 sits substantially parallel to the guidewire 32. The frame 34 further comprises eyelets 38 that allow for a low profile interconnection between the capture fibers 35 and the frame 34. The eyelets 38 are shown as circular eyelets positioned substantially in the center of the struts. Multiple eyelets are located around the frame. Corresponding eyelets 38 are located on distal collar 36. The capture fibers are looped through the eyelets either in a simple single loop or using multiple loops. Where two or more loops are employed the loops act like a knot and prevent fiber slippage. In the embodiment shown the capture fibers 35 are not interconnected with each other but form straight line connections between the frame and the distal collar. This configuration means that there are no knots or fiber overlaps in the entire capture net which improves the wrapping profile of the device. In one embodiment the fibres are looped through the eyelets of the collar and the eyelets of the frame and this avoids the need for knots thus reducing the profile. The eyelets 38 of the distal collar 36 are arranged around the circumference of the distal collar 36. In one embodiment the distal collar is fixed to the guidewire 32. In another embodiment the distal collar 36 is slidable relative to the guidewire 32. In another embodiment the distal collar is rotatable relative to the guidewire. The proximal collar and the frame are preferably connected. In one embodiment the proximal collar and the frame are integral. In another embodiment both the frame and collar are machined from a hypotube. In this embodiment the hypotube diameter corresponds to that of the collar and the frame is laser cut in a configuration that corresponds closely to the shape of the frame when it is collapsed for delivery. The proximal hypotube is mechanically connected to the wire. This mechanical connection allows the memory in the metal to act to generate an angle between the frame and the guidewire in its expanded state. In one embodiment the mechanical connection comprises a closely tolerance fit between the collar inner diameter and the wire. In another embodiment the collar is fixed to the wire. It may be fixed by gluing, welding, or other well known means. The tip 37 of guidewire 32 is soft and flexible to allow the delivery system (not shown) to steer through the anatomy.

With reference to FIG. 7*a* another clot capture device 41 of the invention is shown. This device employs a similar arrangement to the device of FIG. 6, however in this instance the capture fibers 45 are interconnected. It will be noted that the fibers 45 are connected in a series of interconnecting loops 49. These loops 49 can be crafted by hand and have the advantage of avoiding the need for knots, bonds or other features that will significantly impact the profile of the device in the delivery configuration. The loops mean that the interconnected fibres can slide relative to one another and this allows the net to change its shape in response to an irregularly shaped clot. Alternatively the net may be knitted or braided so as to create a regular net structure. With both knitting and braiding it is also possible to create fibre interconnections without rigidly fixing the fibres at the cross over points. Attachment fibres are used to connect the net to the frame. In one case the proximal collar 43, distal collar 46 and guidewire 42 have similar features to those of FIG. 6.

The clot capture device of FIG. 7a is shown in the delivery configuration in FIG. 7b. The frame 44 lies substantially parallel to the guidewire 42 inside the lumen of delivery catheter 50. The delivery catheter 50 comprises a proximal shaft 51, a distal shaft 52 and a distal tip 53. The clot retrieval device sits inside a reception space at the distal end of the delivery catheter 50. The distal tip of the delivery catheter is preferably a soft tip material. The proximal end 51 of the delivery catheter 50 extends back to the user. In one embodiment the delivery catheter is a rapid exchange catheter.

In another embodiment the shaft 50 comprises a loading system. The distal tip 53 of the shaft 50 is engaged with the proximal end of a micro-catheter. The micro-catheter has had its distal end preplaced at a target treatment site. With the distal tip 53 engaged with the proximal end of the micro-catheter the clot retrieval element 41 is advanced into the lumen of the micro-catheter. When the proximal collar 43 has entered the micro-catheter the shaft 50 can be removed and the clot retrieval device 41 advanced through the micro catheter to the target location. It will be appreciated that the features of the loading system described with respect to the clot retrieval device 41 could be applied to other clot retrieval devices of the invention. It will also be appreciated that the method steps described can be applied with the methods described in FIGS. 3 to 5.

Figure 8B:
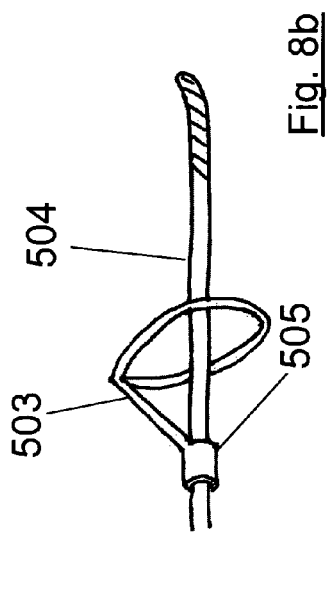
FIG. 8b shows a clot retrieval device frame attached to a guidewire.
Figure 8D:
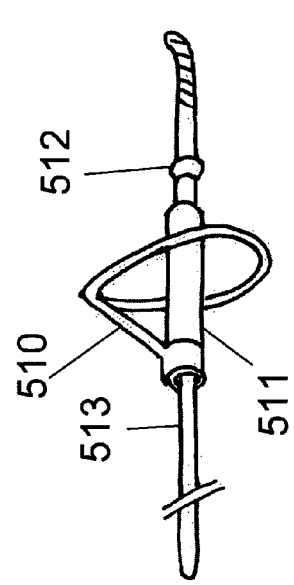
FIG. 8d shows a clot retrieval device frame connected to a tubular element mounted proximal to a stop on a guidewire.
Figure 8F:
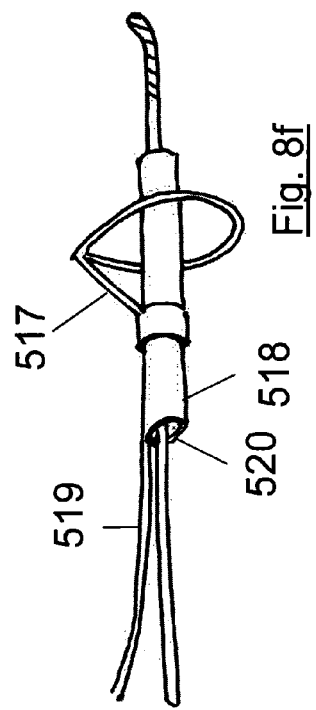
FIG. 8f shows a clot retrieval device frame connected to a tubular element with an exit port and proximal shaft, mounted on a rapid exchange guidewire.
Figure 8A:
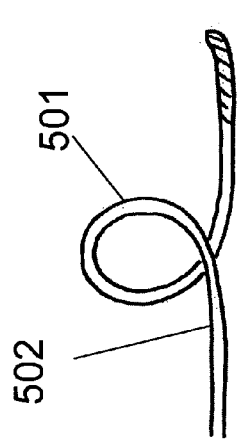
FIG. 8a shows a clot retrieval device frame constructed from a guidewire.
Figure 8C:
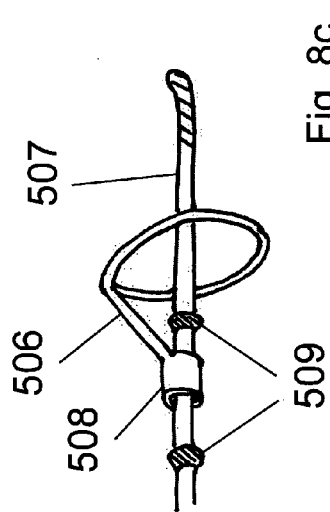
FIG. 8c shows a clot retrieval device frame mounted between stops on a guidewire.
Figure 8E:
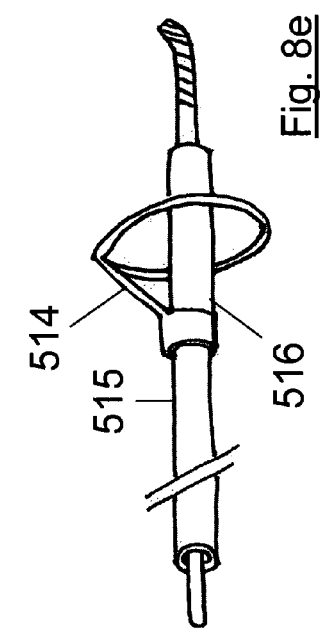
FIG. 8e shows a clot retrieval device frame connected to a tubular element mounted a guidewire.

FIGS. 8a-f show a variety of frame mounting constructions that could be employed in the creation of a device similar to that described in FIG. 6. FIG. 8a shows a frame 501 constructed from a guidewire 502. FIG. 8b shows a frame 503 fixedly attached to guidewire 504 at proximal collar 505. FIG. 8c shows a frame 506 connected to a guidewire 507 in such a way that the collar 508 of the frame can translate and rotate along and around the guidewire between the two stops 509, which are fixedly attached to the guidewire, or an integral part of the guidewire. FIG. 8d shows a frame 510 whose proximal end is attached to tube 511, which is slideably mounted on guidewire 513 proximal to stop 512. FIG. 8e shows a frame 514 which is attached to tube 516, which is slideably mounted on guidewire 515 such that the tube and frame can be advanced or retracted over the guidewire and the guidewire can be moved or exchanged through the tube. FIG. 8f shows a variant of the design shown in FIG. 8e, in which frame 517 is attached to tube 518 and tube 518 is connected to a proximal shaft 519 at the guidewire exit port 520. Such a design would facilitate the deployment of the device over a shorter "rapid exchange" guidewire In other embodiments alternative stop configurations to those shown in FIG. 8c may be employed, in order to facilitate and control movement of the clot retrieval device relative to the guidewire, and/or in order to control the manner in which force may be transmitted to the device during delivery, retrieval and general use. Some of these alternative configurations are shown in various figures throughout this document. It will also be understood that the many other frame designs disclosed in previous and subsequent figures, although illustrated in a certain configuration, may be configured in any of the other configurations depicted in FIGS. 8a-f.

Figures 9A, 9B, 9C, 9D, 9E, 9F, 9G, 9H, 9I:
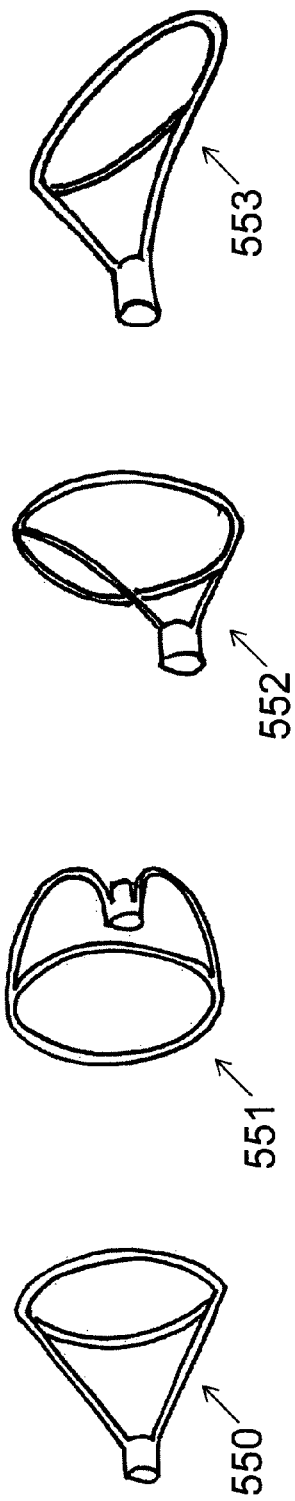
FIG. 9a shows the frame of a clot retrieval device in the expanded state.
FIG. 9b shows the frame of a clot retrieval device in the expanded state.
FIG. 9c shows the frame of a clot retrieval device in the expanded state.
FIG. 9d shows the frame of a clot retrieval device in the expanded state.
FIG. 9e shows the frame of a clot retrieval device in the expanded state.
FIG. 9f shows the frame of a clot retrieval device in the expanded state.
FIG. 9g shows the frame of a clot retrieval device in the expanded state.
FIG. 9h shows the frame of a clot retrieval device in the expanded state.
FIG. 9i shows the frame of a clot retrieval device in the expanded state.

FIGS. 9a-i show a variety of frame designs that could be employed in the creation of a clot capture device. Frame 550 in FIG. 9a has a generally circular perimeter with which to appose the vessel wall, and two proximal arms which taper outward distally from a proximal terminus. Such a design could be constructed from wire or from a cut tube or by other means, and could be made from any of the materials described later as suitable for the manufacture of frame 64 in FIG. 10a. Frame 551 in FIG. 9b is similar to frame 550 except that the inner terminus of the proximal arms is positioned distal to the outer circumferential portion of the frame. Frame 552 in FIG. 9c is similar to frame 550 except that the frame arms are of unequal lengths and/or angles, such that an offset is created between the centreline of the vessel and the proximal neck of the frame. Frame 553 in FIG. 9d is similar to frame 550 except that the frame arms are of unequal lengths and/or angles, such that the circumferential portion of the frame is inclined at an angle relative to the centreline of the vessel. Frame 554 in FIG. 9e is similar to frame 553 except that the frame has only one proximal arm. Frame 555 in FIG. 9f is similar to frame 550 except that the frame has three proximal arms. Frame 556 in FIG. 9g is similar to frame 550 except that the frame has four proximal arms. Frame 557 in FIG. 9h is similar to frame 554 except that the frame has an additional arm that tapers distally inwards from the outer circumferential portion. Frame 558 in FIG. 9i is similar to frame 501 of FIG. 8a except that the frame is not constructed directly from the guidewire itself, but from a separate material.

Another clot retrieval device 61 is shown in FIG. 10a-e. The clot retrieval device 61 shown in FIG. 10a comprises a frame 64, a guidewire 62, proximal collar 63, distal collar 66, support struts 60 and capture fibers 65. With this embodiment the frame 64 forms a three dimensional shape in its expanded configuration. The three dimensional shape is such that the outer surface of the frame in its expanded configuration can oppose the wall of a generally cylindrical vessel. The frame is preferably cut from a hypotube and is preferably metallic. Preferably the frame is nitinol, stainless steel, tantalum, MP35N, L604, a memory material, spring steel, or another high strength alloy. The frame comprises a number of segments 67. In a preferred embodiment the frame comprises pairs of segments. Each pair of segments are arranged at an angle and the angle of arrangement gets smaller as the frame is collapsed and increases as the frame is expanded. The pairs of segments are interconnected to from a 3D structure. In the embodiment shown two pairs of segments are shown. Three pairs of segments or more is also possible. The frame 64 is connected to the guidewire with support struts 60. In the embodiment shown the support struts 60 are attached to the frame 64 at its proximal end. The support struts 60 however are positioned underneath the frame 64 in the expanded configuration. This ensures that the frame 64 has maximum support when the guidewire 62 is being advanced proximally as the support struts 60 act generally to expand the frame. With this embodiment the frame is advanced proximally with a push force transmitted from the distal side. The force is transmitted along support struts 60 and has two components. One component acts to push the frame in the proximal direction while the other force acts to push the frame against the wall of the vessel. This makes it difficult for clot to escape around the outside of the frame 64. The support struts 60 are connected to the guidewire 62 through proximal collar 63. The support struts 60 may be connected to the frame in a number of ways.

The support struts 60 may be laser cut from the same tube as the frame 67 and as such would be integral with the frame 67.

Figure 10A:
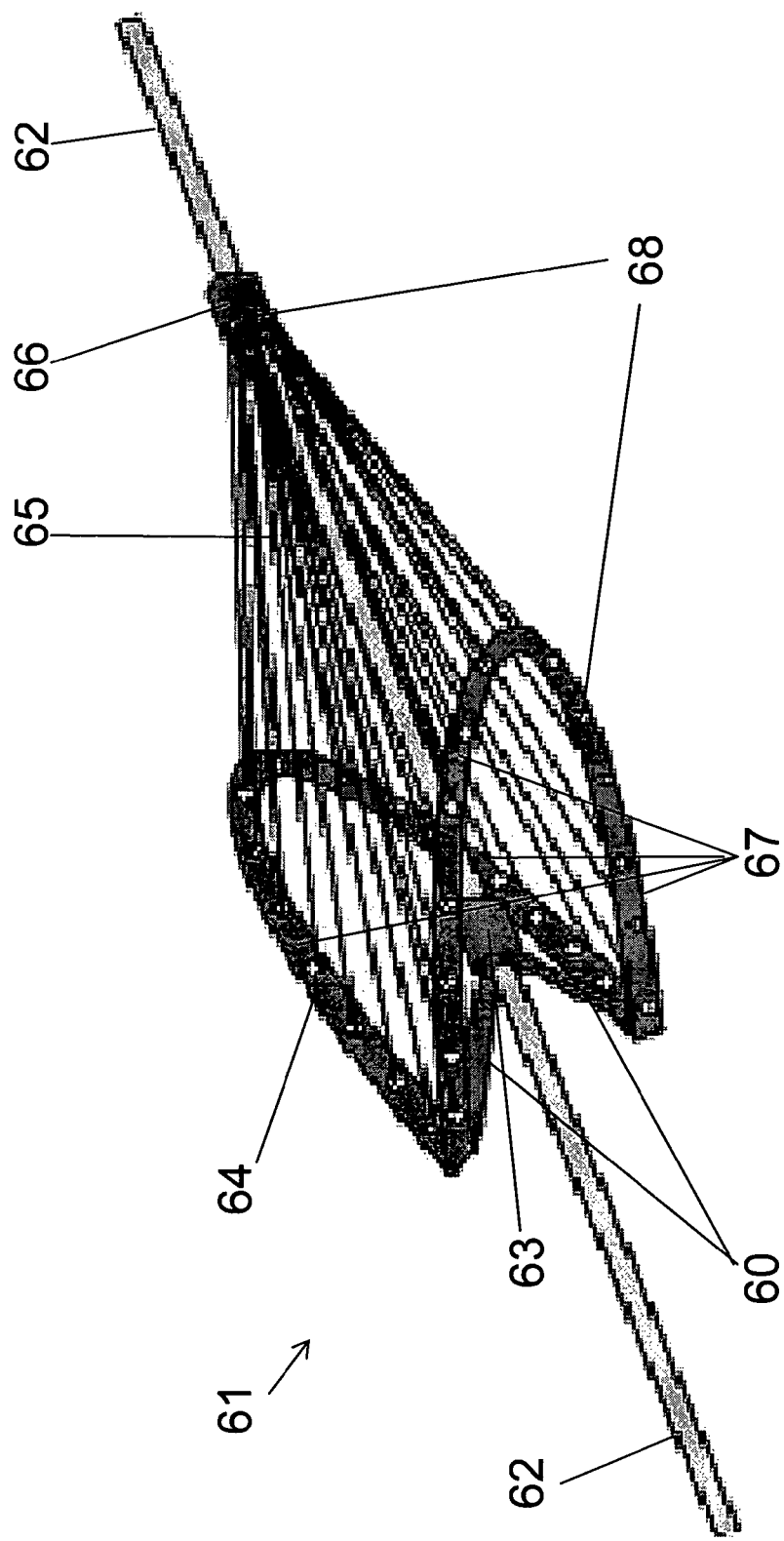
FIG. 10 shows a clot retrieval device in its expanded state.

FIG. 10b-e show a clot retrieval device 61 where the proximal collar 63, the support struts 60, and the frame are cut from a single piece of tubing which may be a hypotube. FIG. 10b is similar to FIG. 10a except that the proximal collar, the support struts and the frame are a single component. In order to manufacture such a complex component the metal used may be elastic. In one embodiment spring steel or a nitinol alloy is used. Preferably nitinol is used to make the frame. FIG. 10c shows an elevation of the one piece frame component 64 in the collapsed (as cut) configuration. The proximal collar 63 is simply a segment of the original hypotube and should be kept as short as possible. A pair of support struts 60 extends from proximal collar 63 and connects the proximal collar 63 with the struts 67 of the frame 64. The support struts 60 are positioned diametrically opposite (thus only one is visible in the elevation view). The interface 87 between the support struts 60 and the collar 63 is an area of high strain when the device is expanded. The wall thickness of the support struts 60 may be locally thinned to reduce strain in this area. At the distal end each support strut 60 bifurcates to form two struts 67 of frame 64. The two struts are of the same length and reconnect at their distal end. The bifurcation 85 is also an area of high strain during expansion and the stress is relieved in this area by reducing locally the width of the struts. The junction 86 at the distal end is another area of high stress during expansion and the stress is relieved in this area by locally reducing the width of the strut in the region of the junction 86. FIG. 10d shows an end-view looking at the collar 63 end. FIG. 10e shows a sectional view at a-a. This sectional view shows the arrangement of the four struts 67, and the cut gap 88 between the struts. The construction of junction area 86 where neighboring struts 67 are connected is further highlighted.

In another embodiment the support struts 60 may be separate components that are joined to the frame 67. The support struts 60 may be connected to the frame by a hinge. The resistance of the hinge to movement is much less than the resistance of the frame or support struts to bending movements. The hinge may be formed by an interconnection between the support strut 60 and the frame 64. In another embodiment a suture or fiber(s) is used to create the hinge. With this embodiment the flexibility of the suture/fiber allows the strut to move relative to the frame while their points of connection are relatively constrained.

The capture fibers 65 of this embodiment are of similar size to those described earlier. The capture fibers 65 are attached to the frame 64 and the distal collar 66 through eyelets 68. Preferably the fibers are highly oriented fibers. This high orientation results in fibers that are anisotropic and these fibers are particularly preferred. These fibers are very strong along the axis of the fiber and less strong in other directions. The distal collar 66 contains eyelets 68 through which the capture fibers are threaded. In one embodiment the distal collar 66 is fixed to the guidewire. In another embodiment the distal collar 66 is integral with the guidewire. In yet another embodiment the guidewire is a hypotube and the eyelet holes are made in the guidewire hypotube thus eliminating the need for a separate distal collar. In yet other embodiments the fibres are attached to a collar or directly to the guidewire or to each other by bonding, welding or other methods.

Yet another embodiment of the invention is shown in FIG. 11a-11c. The clot retrieval device 71 comprises a frame 74, a guidewire 72, proximal collar 73, intermediate collar 70 a distal collar 76, support struts 79 and capture fibers 75. With this embodiment the frame comprises a hoop subtended at an angle relative to the guidewire 72. The hoop is held relative to the wire by two support struts 79 a proximal collar 73 and an intermediate collar 70. In one embodiment the proximal collar is fixed and the distal collar slides on the guidewire. In another embodiment the distal collar is fixed and the proximal collar slides on the Guidewire. In yet another embodiment both collars are slidable on the guidewire and a stop or stops are used to enable a force to be applied through the guidewire to either collar, such as illustrated in FIGS. 7, 48 and 50. FIG. 11b shows the clot retrieval device 71 in the collapsed crossing configuration. In this illustration the capture fibers 75 are not shown (for clarity). The support struts 79 are positioned distal and proximal of the frame in the collapsed configuration. The crossing catheter 80 is preferably a micro-catheter. Preferably the crossing catheter 80 is 2.3 French or less in its distal diameter 82. Preferably the crossing catheter 80 has a distal diameter 82 of 1.9 French or less. More preferably the crossing catheter 80 has a distal diameter 82 of 1.6 French or less. The tip 83 of the crossing catheter is preferably made of a soft material and has a smooth transition. FIG. 11c shows the clot retrieval device 71 and the crossing catheter 80 of FIG. 11b, with the exception that the capture fibers 75 are also shown. The diameter of the capture fibers 75 is so small as they exert only a minor influence on the profile.

FIG. 12a and FIG. 12b show another embodiment of the invention. This embodiment is similar to that of FIG. 11a-11c except that the frame 94 is circular rather than elliptical and the support struts 99 make an angle with the guidewire that is closer to a right angle. In the expanded position the proximal collar 93 and the intermediate collar 90 are adjacent each other. The support struts 99 are connected to the frame in a hinged configuration. This hinged configuration is important as the support strut moves through a large angle during device expansion. In one embodiment the support strut moves through an angle of greater than 60'. Preferably the support strut moves through an angle of at least 80'. More preferably the support strut moves through an angle of at least 90'. This large angle of movement has the effect of reducing the length of the device in the collapsed configuration and this shorter device is more deliverable.

For example: For a device with an expanded diameter of 3 mm, changing the strut angle from 45' to 90' has the effect of shortening the device by 1.24 mm. In the neurovascular territory where vessel diameters are small and vessel tortuousity is high this is a very significant reduction. In one embodiment the hinge comprises three elements, a strut element 99 a frame element 94 and a hinge element 104. The frame element 94 and the strut element 99 are connected with the hinge element 104. The hinge element allows the frame 94 and strut 99 to change angle relative to each other with little resistance. In one embodiment the hinge element is a pin. In another the hinge element 104 is a fiber, a filament, a multifilament or a suture. In another embodiment the strut 99 and the frame 94 are connected and the hinge is integral of the connection. In another embodiment the hinge comprises a weakness in the structure at the area where the strut 99 and frame 94 meet. In another embodiment the hinge between the strut 99 and frame 94 is adjacent a hinge in the frame.

In one embodiment the intermediate collar is fixed to the wire. With this embodiment the intermediate collar 90 provides a movement stop to the proximal collar 93. This configuration provides a particularly stiff frame construction even for a low profile device. In another embodiment the proximal collar is fixed and the intermediate collar 90 can move axially. In one embodiment the proximal collar 93, intermediate collar 90 and distal collar are radiopaque. With this embodiment the collars are made from or coated with a material that absorbs X-Rays. Typically this involves using materials that have a high atomic mass. Materials with a concentration of gold, platinum, iridium, tungsten, and tantalum are especially suited. It will be appreciated that a variety of other metals, alloys or compounds could be employed. Such radiopaque features may be used in any of the devices described herein.

FIG. 12b shows the clot retrieval device 91 in the delivery configuration. A crossing catheter 100 is used to constrain the device 91 in the collapsed state during delivery and crossing of the obstruction. The catheter has a proximal end 101 and a distal end 102. The guidewire extends proximally through a lumen of the crossing catheter 100 and exits at either the proximal end of the crossing catheter 100 or through an exit port in the wall of the crossing catheter 100. The capture fibers are arranged as previously described although they are not shown in FIG. 12a or 12b.

Figure 13A:
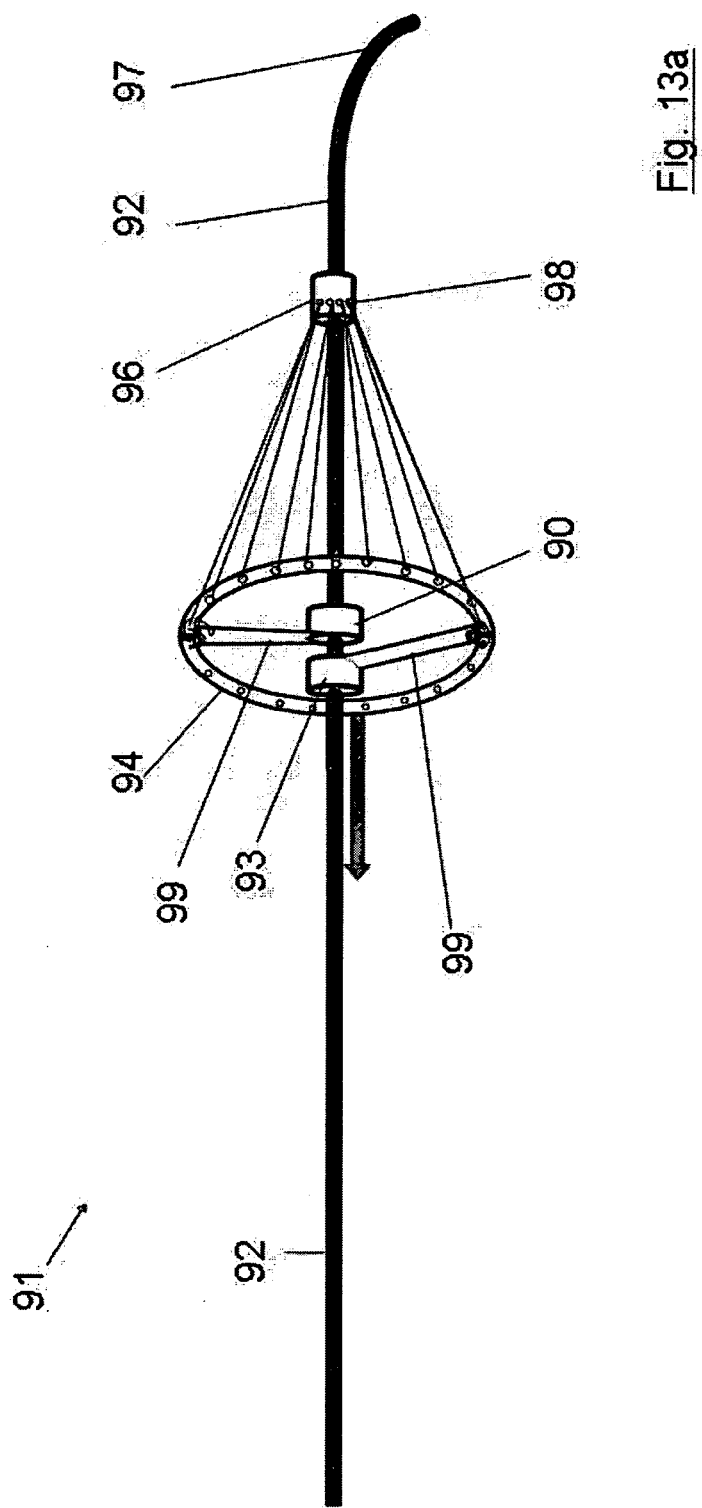
FIG. 13a shows a clot retrieval device in its expanded state.
Figure 15:
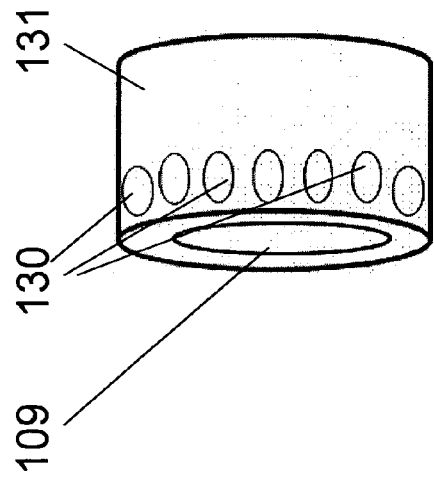
FIG. 15 shows a distal collar with eyelets for fiber alignment and/or attachment.

FIG. 13a shows the clot retrieval device of FIG. 12 except that the capture fibers 95 are shown. FIG. 13 also shows the collar arrangement whereby the intermediate collar 90 is fixed relative to guidewire 92 and the proximal collar 93 is slidable relative to guidewire 92. In another embodiment the proximal collar 93 and intermediate collar 90 are rotatable relative to guidewire 92. FIG. 13b to FIG. 13e show views of the proximal collar, intermediate collar and support struts of FIG. 12 and FIG. 13a. The collar 105 could be either a proximal collar or an intermediate collar. In the embodiments shown the strut 106 and collar 105 are integral. In one embodiment they are formed from a single piece of hypotube. Preferably the tube is nitinol and the shape of the strut 106 is set by heat treatment. FIG. 13b and FIG. 13d show an arrangement where the strut is in the delivery configuration. This is also the pre-heat treatment configuration. The lumen 108 is sized to fit over the guidewire of the earlier embodiments. FIG. 13d and FIG. 13e show the collar 105 and strut 106 in the expanded configuration. The hole 107 allows for the creation of a hinge feature with the frame of earlier embodiments.

Figure 17:
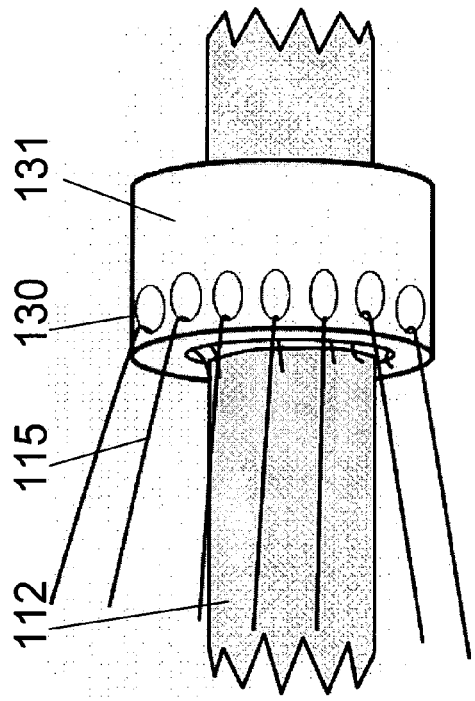
FIG. 17 shows a distal collar mounted on a guidewire with eyelets for fiber alignment and/or attachment.
Figure 14:
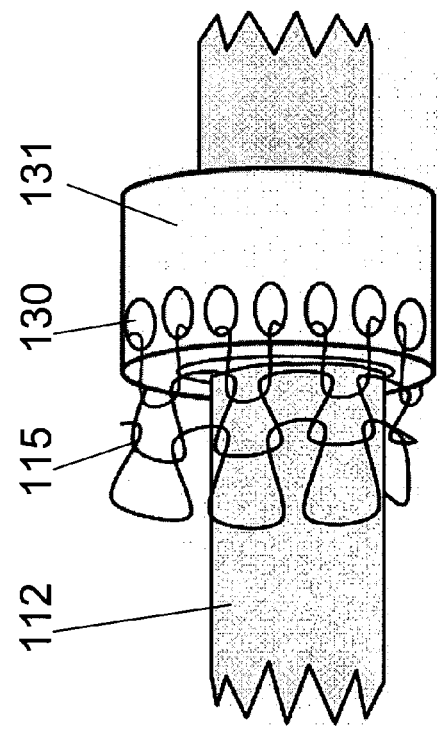
FIG. 14 shows a distal collar mounted on a guidewire with eyelets for fiber alignment and/or attachment.
Figure 16:
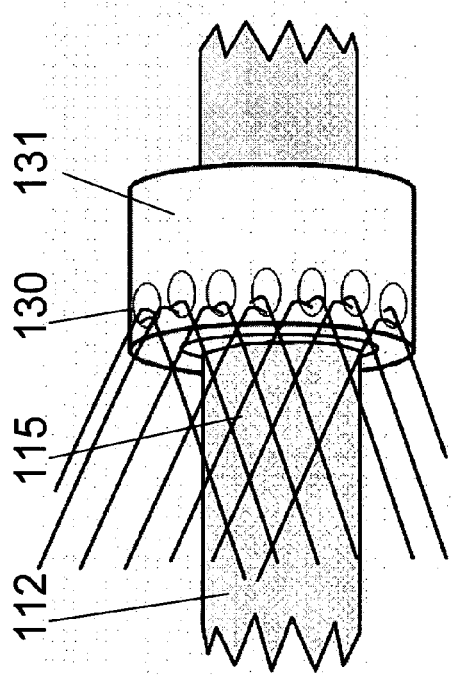
FIG. 16 shows a distal collar mounted on a guidewire with eyelets for fiber alignment and/or attachment.

Some examples of intermediate or distal collars 131 associated with the clot retrieval devices of the invention are shown in FIGS. 14 to FIG. 17. FIG. 14, FIG. 16 and FIG. 17 shows collar 131 with lumen 109 mounted on guidewire 112. The collar comprises eyelets 130 for attachment of capture fibers 115. In FIG. 14 the capture fibers form a knitted structure and are connected to the collar in a series of loops through the eyelets 130. In FIG. 16 the capture fibers 115 are arranged in a weaved configuration and are attached to the eyelets through a series of loops. The capture fiber may be looped between one eyelet 130 and a neighboring eyelet or it may be looped through the eyelet and the body of the collar 131.

FIG. 18 and FIG. 19 show the clot retrieval device 91 of FIG. 12 and FIG. 13 in use. The device 91 is shown deployed distal of obstructive clot 100. The device is advanced proximally in order to capture the clot as shown in FIG. 19.

Now with reference to FIG. 20 through to FIG. 23 there is shown another clot retrieval device of the invention. This device is constructed from a series of sub-elements that work together through a series of hinge elements. For the purpose of describing the hinge features of this invention, hinges will be classified in terms of the number of axis of freedom available to the hinge. One axis of freedom shall mean that the hinge movement is limited to a single plane of movement. An example of a hinge with one axis of freedom is the human knee joint. Two axis of freedom shall mean that the hinge movement is limited to a two planes of movement and the two planes are normal to each other (X,Y). An example of a hinge with two axis of freedom is the human hip joint.

With reference to FIG. 20a-h there is shown a number of sub-elements to the frames of the clot retrieval devices of the invention. FIG. 20a and FIG. 20b show a strut element 150 with curved ends 152 and a hinge hole 151 located concentric with curved ends. Curved ends 152 may be curved in one axis or two axes depending on whether the hinge has one axis of freedom or two axis of freedom. FIG. 20c shows the strut 150 in a curved configuration. FIG. 20d shows a schematic of the construction of a hinge between two struts 150. The end curves 152 of two struts are brought into contact and a hinge element 153 secures the strut ends 152 relative to each other. Since both ends are curved in two planes this configuration creates a hinge with two axis of freedom. In one embodiment the hinge element 153 is a ring element. In another embodiment the hinge element 153 is a fiber, monofilament, multifilament, a wire or a suture. FIG. 20d also shows eyelets 154 on the strut for attachment of capture fibers.

FIG. 20e shows another hinge configuration of the clot retrieval devices of the invention whereby two struts or a strut and a support member are joined in a hinged configuration. The strut 150 has two curved ends 152 and each curved end 152 has two hinge holes 151. Each hinge hole is fastened to its neighboring hinge hole to create a hinge that has one axis of freedom. A frame 164 for a clot retrieval device is shown in FIG. 20f and FIG. 20g. The frame comprises four struts 150 configured in a circular arrangement. Each strut comprises curved ends 152 and hinge holes 151 adjacent said curved ends. The frame 164 is supported by support members. In one embodiment proximal support members 157 and distal support members 156 are employed. Proximal support members 157 are connected to the guidewire proximally. Distal support members 156 are connected to the guidewire distally. In one embodiment the proximal support member 157 and/or the distal support member 156 is connected to the guidewire 172 via a collar 155. In one embodiment the support member 156/157 is integral with the collar 155. In another embodiment the support member 156/157 is connected to the collar with a hinge arrangement.

Preferably the hinge arrangement comprises a hinge with one axis of freedom. In one embodiment the support member 156/157 and the collar are integral and the hinge is made by thinning out the wall of the support member in the plane of bending adjacent the collar. Thinning the wall reduces plastic strain in the wall during hinging and allows large angles of movement. In one embodiment the support member 156/157 contacts the frame on its inner surface. In another embodiment the support member 157 contacts the frame intermediate the inner and outer surfaces.

FIG. 20h shows the arrangement of a frame support 165. The frame support comprises a collar 155 and support members 157. The collar comprises an inner lumen 166 and an outer surface. The support members 157 comprise a curved end 158 and a hinge hole 151.

FIG. 20i to FIG. 20k show how the hinges 167/168 allow the support frame to collapse. It will be noted that pairs of hinges facilitate most efficient collapse of the frame of the clot retrieval device. In the delivery configuration the curve of the struts 150 is straightened. This is illustrated in FIG. 20j where all of the hinges 168/167 are in the collapsed state and the struts 150 are straightened and lie substantially parallel to the axis of the guidewire 172.

FIG. 21a-c shows the frame elements of FIG. 20a-j assembled and mounted on a guidewire. FIG. 21a shows the frame 164 of FIG. 20j integrated with proximal and distal frame supports 165 of FIG. 20h. FIG. 21b shows the frame 164 of FIG. 20j integrated with proximal and distal frame supports 165 of FIG. 20h and all of this mounted on guidewire 172. FIG. 21c shows the clot retrieval device 175 assembled and in the collapsed configuration with capture fibers 171 included.

The hinges 167/168 associated with the body of frame 164 provide no bias for the frame. The hinges 167/168 thus provide no significant resistance to either expansion or collapse. The frame can thus be expanded from a collapsed state in one of the following ways.

In one embodiment the frame 164 is expanded and collapsed by movement of the more proximally located collar 155a relative to the more distal collar 155b. In one embodiment either the more proximally located collar 155a or the more distally located collar 155b is fixed to the guidewire 172. If the more distally located collar 155b is fixed longitudinally, then, advancing the more proximally located collar 155a distally expands the frame 164. In one embodiment movement of the collar 155a is achieved using a bumper catheter 173 as shown in FIG. 21c. The bumper catheter 173 has an outside diameter, a lumen and a distal face. The bumper catheter 173 is advanced over the Guidewire 172 until its distal face is adjacent the proximal end of collar 155a. The bumper catheter is further advanced and engages with the collar 155a and causes collar 155a to advance distally. As collar 155a advances distally the frame 164 expands. With the frame 164 in the expanded state, and the bumper catheter 173 held in position the clot retrieval device 175 and bumper catheter 173 are advanced proximally to capture the clot. When the clot is captured the bumper catheter 173 is disengaged from the collar 155a. The clot retrieval device 175 is retrieved. This may be achieved using a retrieval catheter, a micro-catheter, a sheath or guide catheter or the lumen of another catheter. Alternatively the clot retrieval device 175 can be withdrawn proximally into the procedural catheter.

In another embodiment the bumper catheter is connected to the collar 155a. In this way advancing the bumper catheter distally causes the frame 164 of the clot retrieval device 175 to expand, while advancing the bumper catheter proximally causes the frame 164 to collapse. In another embodiment the bumper catheter 173 is detachably coupled to the clot retrieval device 175 through collar 155a.

In another embodiment the support members 157/156 of frame support 165 are biased to the expanded state. For delivery the frame 164 is stored inside the pod of a delivery catheter. Upon deployment distal and proximal frame supports 165 acts on hinge points 167/168 and cause these to move radially outward. As these move outward the frame 164 of the clot retrieval device expands. On full expansion the frame 164 assumes a 3 dimensional ring-like configuration. With this embodiment, when the clot retrieval device 175 is deployed and the frame 164 is expanded the clot is captured by proximally advancing the clot retrieval device 175. After the clot is captured the clot retrieval device 175 is retrieved using a retrieval catheter, a micro-catheter, a sheath or guide catheter or the lumen of another catheter. Alternatively the clot retrieval device 175 can be withdrawn proximally into the procedural catheter.

A capture fiber collar 169 is located distal of the collars 155a/155b and this collar 169 provides an anchor site for the capture fibers distally. The capture fiber collar 169 may be fixed on the wire 172 or may be slidable and/or rotatable on the wire 172. In a preferred embodiment the capture fiber collar 169 has a limited range of movement. The movement may be limited proximally by abutment with the collar 155b of the frame support 165, or it may be limited by a stop (not shown) on the Guidewire 172. The movement of the capture fiber collar 169 may be limited distally by the capture fibers or by a stop on the wire 172. In yet another embodiment the distal tip of the guidewire ends proximal of collar 169, and collar 169 is therefore not engaged with the guidewire, but still acts as a distal terminus for the capture fibers.

Figure 22:
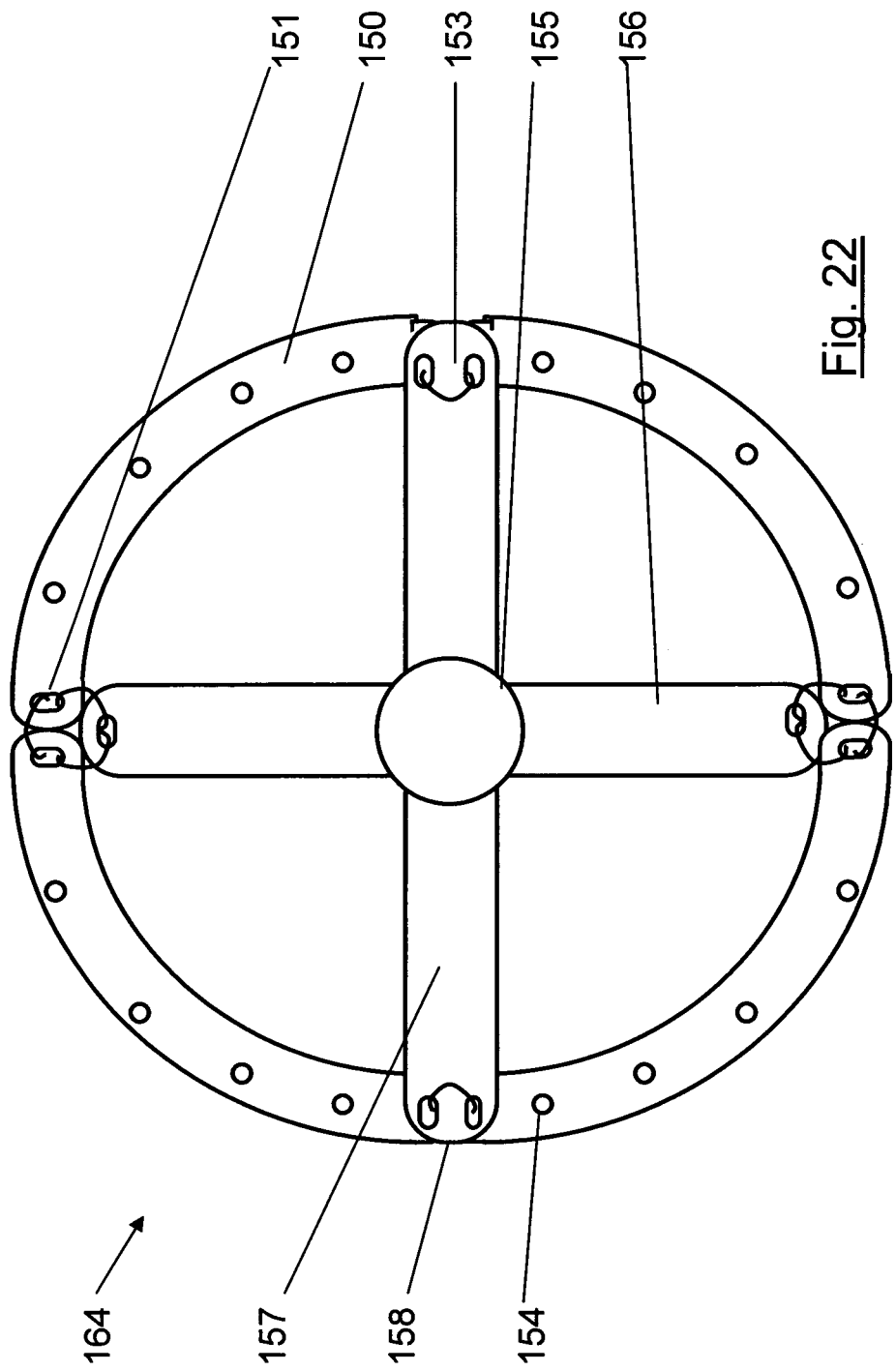
FIG. 22 shows an enlarged view of a hinged support frame with eyelets for fiber attachment.
Figure 25B:
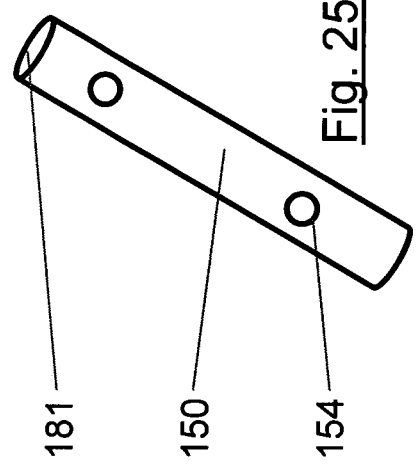
FIG. 25b shows a section of a strut of a clot retrieval device.
Figure 25D:
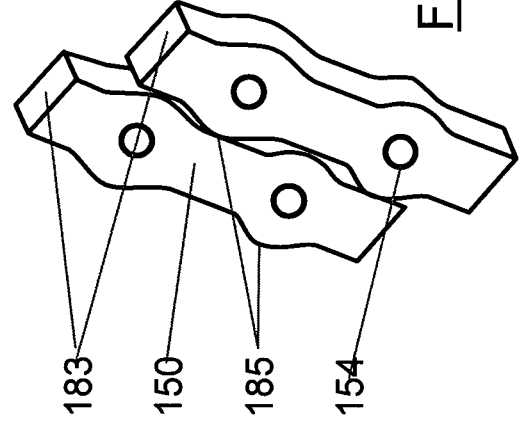
FIG. 25d shows two sections of two adjacent struts of a clot retrieval device nesting together.
Figure 25A:
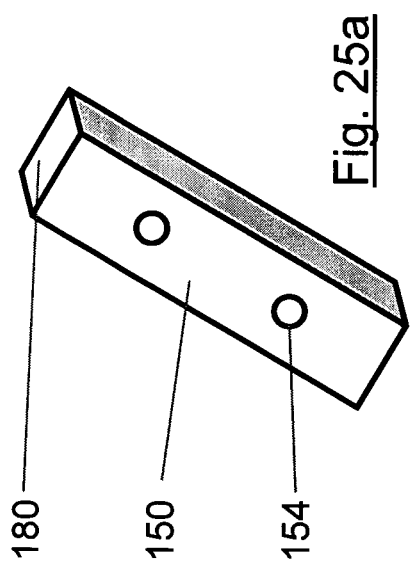
FIG. 25a shows a section of a strut of a clot retrieval device.
Figure 25C:
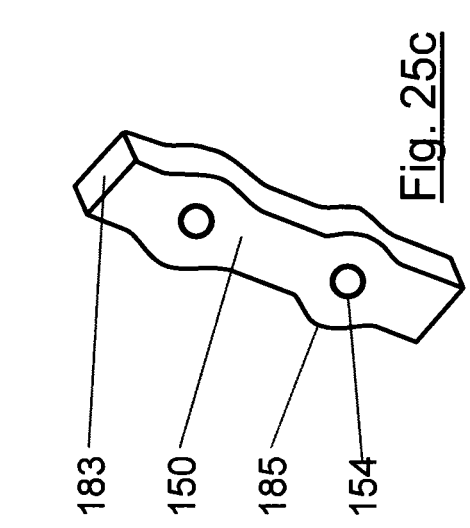
FIG. 25c shows a section of a strut of a clot retrieval device.

FIG. 22 shows the frame 164 of the invention when viewed from the proximal end in its expanded configuration. The struts 150, the support members 157/156 and the collars 155a/155b/169 are preferably manufactured from a metal. Preferably the material is nitinol, stainless steel, MP35N, L604, Tantalum, a mixture of the above or another alloy with similar mechanical attributes. The optimum choice of materials is dependant on the design and operating mechanism of the frame. In the case of a self expanding frame as illustrated in FIGS. 10a-d it will be advantageous to select a material which can recover from the high strains that may be induced in collapsing the frame for delivery through a small diameter catheter. Such strains will be design dependant, but selection of a superelastic material such as nitinol, which can recover from strains as high as 8%, will enable more compact geometries for areas 85 and 86 to be adopted. In the case of a frame that is expanded by an external force as described in relation to FIG. 21c, greater flexibility in material choice is made possible. In the case of hinged designs, as for example is shown in FIG. 22, still greater material choice is afforded, as significant strains are not induced in the hinged areas.

A frame 164 of a clot retrieval device of the invention is shown in FIG. 23a-23c at various levels of expansion. In FIG. 23a the frame 164 is shown in the fully expanded configuration. Struts 150 form a circular ring and these are supported by support members 157/156. The proximal collar 155a and support member 157 support the frame 164 at two opposing hinge points 168. The more distally located collar 155b and support members 156 support the frame at the two remaining opposing hinge points 167. The frame 164 is shown in the partially collapsed state in FIG. 28b. The proximal collar 155a has moved proximally relative to the more distally located collar 155b. In the partially collapsed (or expanded) configuration the struts form a zigzag pattern in three dimensions. The zigzag pattern is defined on a cylindrical surface in 3D space.

The frame 164 is shown in the fully collapsed state in FIG. 23c. The collar 155a has moved even more proximally and the strut 150 is substantially parallel to the axis of the guidewire 172.

FIG. 24a-24c shows the device of FIG. 23 with the capture fibers 171 in place. It will be appreciated that other capture fiber arrangements described in this invention could be used with the frames 164 and clot retrieval devices of FIG. 20-28.

FIG. 25a-d and FIG. 26a-f show more detailed views of aspects of the struts 150 of the frames 164. In one embodiment the struts are rectangular in cross-section 180. In another the cross-section 181 of the struts 150 is circular. In another embodiment the strut 150 comprises a number of eyelets 154 and the strut 150 comprises a thickened section 185 adjacent the eyelet 154. The eyelets 154 and thickened sections 185 are staggered on neighboring struts such that the struts stack more efficiently in the collapsed configuration. In one embodiment the eyelets 154 are circular. In another embodiment the eyelets 154 are centered on the neutral axis 195 of the strut 150. The neutral axis 195 of the strut 150 is defined as the portion of the strut that undergoes zero strain when the strut is loaded in bending. In another embodiment the eyelets 190 are elliptically shaped and the major axis of the elliptical eyelets 190 is substantially parallel with the neutral axis 195 of the strut 150. In another embodiment the eyelet 191 is elongated and the axis of elongation is approximately parallel to the neutral axis 195 of the strut 150. Capture fibers 192 are looped through eyelets 150. In one embodiment the capture fiber 192 makes a single loop through the eyelets 150. In another embodiment the capture fiber 193 makes a double loop through the eyelet 190. In another embodiment multiple capture fibers are looped through eyelets 191 or a single capture fiber 194 is looped multiple times.

The eyelets of this invention could be configured in a variety of shapes including elliptical, square, oblong, rectangular, polyhedral, or combinations or variations of the above. The eyelets are typically very small in diameter and are preferably processed by laser machining. The eyelets have a minor axis and a major axis. For the purpose of this invention the dimension of the minor axis is defined as the largest diameter of cylindrical pin guage (gage) that will fit into the eyelet without deforming the eyelet. Per this invention it is desired that the eyelet dimension be as small as possible. Preferably the eyelet has a minor axis that is less than 100 micrometers. More preferably the eyelet has a minor axis that is less than 50 micrometers. More preferably the eyelet has a minor axis that is less than 30 micrometers. Most preferably the eyelet has a minor axis that is less than 20 micrometers. When the major axis of the eyelet is positioned on the neutral axis of the strut then it is the size of the minor axis that dictates the loss of mechanical properties of the strut. It is therefore an object of this invention to minimize the loss of mechanical integrity of the struts while allowing high strength fibers to be secured to the frame. In another embodiment the capture fiber has a flattened aspect. The fiber may be elliptical or flattened in cross section or the fiber may be multifilament fiber.

The capture fibers used with the clot capture devices of this invention have special properties. In order to deliver the capture device through a micro catheter the capture fibers are exceedingly small. Fibers with a diameter of less than 100 micrometers are desired. More preferably the diameter of the fibers is less than 50 micrometers. Even more preferably the diameter of the fiber is less than 30 micrometers. Most preferably the diameter of the fiber is less than 20 micrometers.

The capture fibers 35 of this invention are exceptionally strong in order to achieve the really low delivery profiles of the invention. Suitable fibers include Ultra High molecular weight polyethylene fibers, PET fibers, stainless steel fibers, MP35N fibers, PTFE fibers, Polypropylene fibers, nylon fibers, Kevlar fibers and PEEK fibers. More preferably the fibers are polymeric fibers. More preferably the fibers are Nylon, PET, Kevlar or UHMWPE. Most preferably the fibers are made from ultra high molecular weight polyethylene (UHMWPE) or Kevlar. UHMWPE has a very long molecular chain and can therefore have molecular weights from 3 million to as high as 10 million atomic units, as opposed to approximately 500,000 atomic units for standard HDPE. This gives it excellent abrasion resistance as well as strength, making it an excellent choice for a capture net fiber. An exemplary UHMWPE capture fiber is supplied by DSM Dyneema BV, Urmond, The Netherlands.

Tables 1 and 2 below compare the properties of a range of material fibers. The strength of a specific fiber strand is proportional to ultimate tensile strength of its material and to the square of the fiber diameter. Therefore a big reduction in strength is caused by a relatively small reduction in diameter. For example with reference to table 1, reducing the diameter of a Dyneema UHMWPE fiber from 30 microns to 15 microns results in a four-fold decrease in fiber strength from 1.86N to 0.46N. For this reason while it is desirable for profile reasons to use a low fiber diameter, it is also desirable to use a fiber with a high ultimate tensile strength. The fibers used are sufficiently strong to withstand the loads that will be experienced during device delivery and clot retrieval, and also to facilitate device manufacturability. Inadequate fiber strength in manual, automated or semi-automated assembly processes is likely to result in frequent breakages and low yields. Preferably an individual fiber strength will be greater than 0.25N. More preferably an individual fiber strength will be greater than 0.35N. Most preferably an individual fiber strength will be greater than 0.5N. While PET is generally considered a high strength polymer, particularly when highly oriented, it can be seen from Table 2 that to achieve a 0.5N fiber strength a PET fiber diameter of over 25 microns is required, while the same strength can be achieved with UHMWPE or Kevlar fibers in diameters of less than 20 microns.

TABLE 1

Fiber Strengths (in Newtons) for specific fiber diameters

| Fiber material | Fiber diameter (microns) | | | | | UTS |
| --- | --- | --- | --- | --- | --- | --- |
|  | 15.00 | 20.00 | 25.00 | 30.00 | 50.00 | (Mpa) |
| UHMWPE - Dyneema | 0.46 | 0.82 | 1.29 | 1.85 | 5.14 | 2620 |
| UHMWPE - Celanese | 0.23 | 0.41 | 0.64 | 0.92 | 2.55 | 1300 |
| UHMWPE - Spectra 1000 | 0.51 | 0.90 | 1.41 | 2.03 | 5.64 | 2870 |
| UHMWPE - Tekmilon | 0.43 | 0.77 | 1.20 | 1.73 | 4.81 | 2450 |
| PET | 0.18 | 0.31 | 0.49 | 0.71 | 1.96 | 1000 |
| Nylon | 0.14 | 0.25 | 0.39 | 0.57 | 1.57 | 800 |
| Kevlar | 0.53 | 0.94 | 1.47 | 2.12 | 5.89 | 3000 |
| 302 SS (50% CW) | 0.27 | 0.48 | 0.74 | 1.07 | 2.98 | 1516 |
| 302 SS (90% CW) | 0.42 | 0.75 | 1.17 | 1.68 | 4.67 | 2378 |
| MP35N (95% CW) | 0.44 | 0.78 | 1.22 | 1.76 | 4.90 | 2495 |
| 35NLT (90% CW) | 0.45 | 0.80 | 1.25 | 1.80 | 5.01 | 2551 |
| L604 (50% CW) | 0.40 | 0.70 | 1.10 | 1.58 | 4.40 | 2241 |
| Nitinol | 0.26 | 0.45 | 0.71 | 1.02 | 2.84 | 1448 |

TABLE 2

Fiber diameters (in microns) for specific fiber strengths

| Fiber material | Fiber strength required (N) | | | | | UTS |
| --- | --- | --- | --- | --- | --- | --- |
|  | 0.20 | 0.50 | 1.00 | 5.00 | 10.00 | (Mpa) |
| UHMWPE - Dyneema | 9.86 | 15.59 | 22.04 | 49.29 | 69.71 | 2620 |
| UHMWPE - Celanese | 14.00 | 22.13 | 31.30 | 69.98 | 98.97 | 1300 |
| UHMWPE - Spectra 1000 | 9.42 | 14.89 | 21.06 | 47.10 | 66.61 | 2870 |
| UHMWPE - Tekmilon | 10.19 | 16.12 | 22.80 | 50.97 | 72.09 | 2450 |
| PET | 15.96 | 25.23 | 35.68 | 79.79 | 112.84 | 1000 |
| Nylon | 17.84 | 28.21 | 39.89 | 89.21 | 126.16 | 800 |
| Kevlar | 9.21 | 14.57 | 20.60 | 46.07 | 65.15 | 3000 |
| 302 SS (50% CW) | 12.96 | 20.49 | 28.98 | 64.80 | 91.64 | 1516 |
| 302 SS (90% CW) | 10.35 | 16.36 | 23.14 | 51.74 | 73.17 | 2378 |
| MP35N (95% CW) | 10.10 | 15.97 | 22.59 | 50.51 | 71.44 | 2495 |
| 35NLT (90% CW) | 9.99 | 15.80 | 22.34 | 49.96 | 70.65 | 2551 |
| L604 (50% CW) | 10.66 | 16.85 | 23.84 | 53.30 | 75.38 | 2241 |
| Nitinol | 13.26 | 20.97 | 29.65 | 66.31 | 93.77 | 1448 |

While UHMWPE fibers are extremely strong they are difficult to bond. The present invention overcomes these difficulties by allowing one single fiber to be used to manufacture the entire capture net. Furthermore the arrangement of the frame eyelets and collar eyelets allows a single fiber to be threaded over and over. Single loops can be made through the eyelets or multiple loops can be made. Multiple loops can be used to terminate a fiber. A small drop of adhesive can be used to fix the end of the fibers in the eyelets. Even though it is difficult to bond to the surface of UHMWPE fibers the adhesive acts as a mechanical constraint that prevents the loops from unraveling. Further since the load is carried by multiple fibers and multiple loops it is dispersed.

In another embodiment the capture fiber is a multifilament fiber. In yet another embodiment the fiber is a flat fiber or an oblong fiber.

In one embodiment the eyelets are positioned on the neutral axis of the strut of the frame. The neutral axis is generally at the center of the strut and corresponds to the line or plane in the strut that sees zero strain when the strut is loaded in bending. The advantage of putting the eyelet on the neutral axis is that it reduced the weakening effect of the eyelet. Where the eyelet has a major and a minor axis it is preferred that the major axis is as close to the neutral axis of the strut as possible.

Figure 27A:
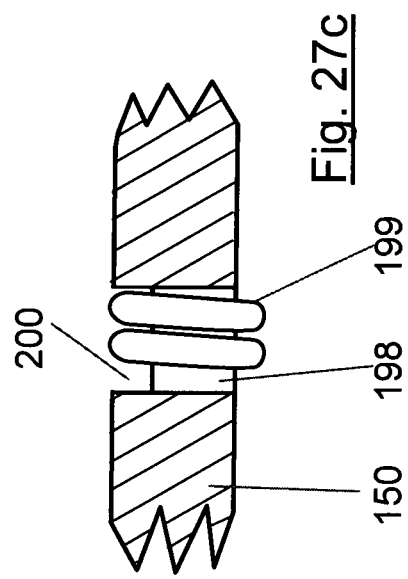
FIG. 27a shows a cross section of a strut with a capture fibre threaded through an eyelet.
Figure 27B:
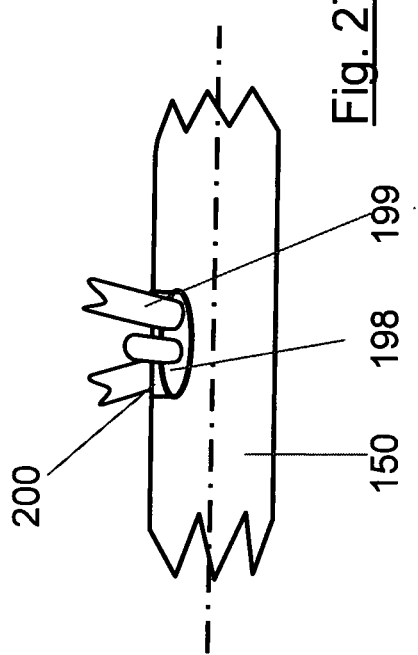
FIG. 27b shows a strut with a capture fibre threaded through an eyelet.

FIG. 27a shows a cross-sectional view of a strut 150. The cross section shows an eyelet 197 and a capture fiber threaded through the eyelet. FIG. 27b shows a plan view of the same strut 150, eyelet 197 and capture fiber 196 arrangement.

Figure 27C:
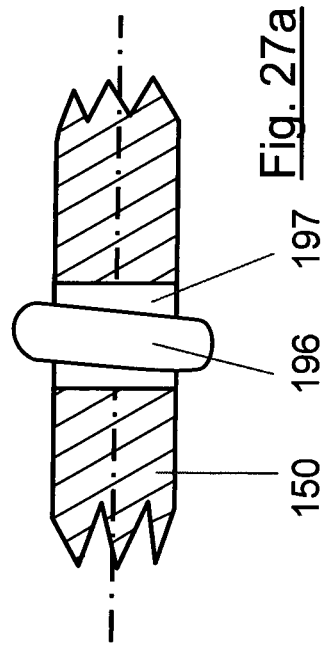
FIG. 27c shows a cross section of a strut with a capture fibre threaded through an eyelet.
Figure 27D:
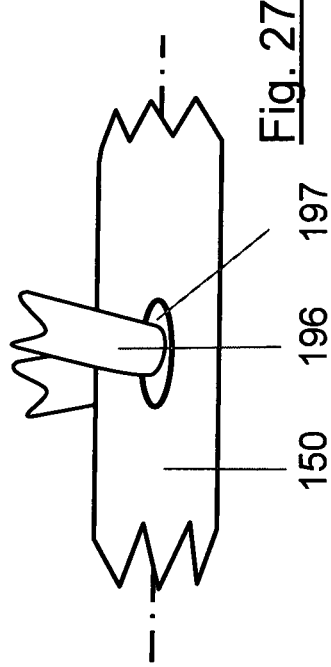
FIG. 27d shows a strut with a capture fibre threaded through an eyelet.

FIG. 27c shows another arrangement of strut 150, eyelet 198 and capture fibers 199. This time the eyelet is offset relative to the neutral axis of the strut 150. The eyelet is positioned close to one wall of the strut. A relief section 200 is also shown. This relief section 200 is created by partially machining material in the area where the capture fiber lies. In the embodiment shown the relief section 200 is created on the outer surface of the device. This ensures that the capture fibers do not add to the profile of the device as they loop about the frame. A plan view of the strut 150, eyelet 198, capture fiber 199 and relief section 200 is shown in FIG. 27d. It will be noted that the capture fiber 199 loops around the strut section twice in this schematic.

It will be appreciated that the capture fibers of this invention and the eyelets of the invention are both very small and assembling both presents a challenge. FIG. 28a shows a view of a segment of a strut 150 with eyelet 154. FIG. 28b shows a cross sectional view of the strut 150 taken through eyelet 154 along section line a-a. FIG. 28c shows a representation of a fixture device that allows the assembly of the capture fibers In another embodiment the eyelet is positioned close to the edge of the strut. With this embodiment the strut may be thickened on the side opposite the eyelet to compensate for any weakening.

FIGS. 29a-i show additional eyelets and fiber path defining features to those previously described in FIGS. 25-28. The purpose of these features is to provide points or areas of engagement between the frame and the fibers that help to define the configuration of the fiber or fibers. Frame 600 in FIG. 29a has eyelets 601 and 602 similar to those described in frames 26a and 26b. Frame 603 in FIG. 29b has a circular offset eyelet 604. Frame 605 in FIG. 29c has an assymetrical offset eyelet 606. Frame 607 in FIG. 29d has an inflexion 608 which creates a feature to provide a preferential seat for fiber attachment. FIG. 29e shows two variations of raised features 610 and 611, pairs of which may be used to define a fiber attachment point to the frame 609. FIG. 29f shows recessed features 613 which may be used to define fiber attachment points to the frame 612. FIG. 29g shows recessed features 615 which may be used to define fiber attachment points to the round wire of frame 614. Frame 616 in FIG. 29h is similar to frame 614, except that its raised features are separate components, which in one embodiment are radiopaque marker bands, and in another embodiment are of other metallic or polymeric materials. Element 619 in FIG. 29i is wrapped around frame 618 in such a way as to leave defined spaces 620 in which to attach fibers to the frame. In one embodiment element 619 is a radiopaque platinum wire, but in other embodiments may also be of other materials or in the shape of a coil. The recesses and raised areas illustrated may be created by a laser machining process, or by other mechanical, electrical or chemical means.

Now with reference to FIGS. 30a-e there are shown various frame features which may assist the attachment of a distal fiber or fiber structure to a frame structure. FIG. 30a illustrates a frame 650 with an external sleeve 651, which provides an attachment surface to which fibers may be more easily bonded or a higher friction surface on which fibers will slip less easily if tied in place. Attachment surface 651 may be a polymer sleeve, which may be placed prior to forming the frame shape and may also be bonded or heat shrunk into position. Alternatively the attachment surface may be a coating 652, as shown in FIG. 30b. FIGS. 30c-e describe variants in which connection elements are used to join distal fibers to a frame. These connection elements may be fibers also, and may be used with any of the frame designs disclosed elsewhere, particularly those with features as shown in FIGS. 25-30. Fiber 655 in FIG. 30c is connected to frame 653 by connection element 654, which is itself wrapped around frame 653. Fiber 655 is shown connected to the eyelets of frame 656 by discrete connection elements 657 in FIG. 30d, and by a continuous connection element 658 in FIG. 30e.

FIGS. 31a and 31c show two fiber configurations that may be employed to reduce the size of embolus that can pass through the fiber net. The weave or braid configuration 700 shown in FIG. 31a is constructed from multiple fibers, which is advantageous in that if one fiber breaks the integrity of the entire structure is not significantly affected; however this structure leaves multiple loose fiber ends 701 at each end. FIG. 31b shows a design which deals with this challenge by folding the woven net around the frame 703 and joining the loose ends together at a distal junction 704. In another embodiment the woven net may be folded around a connecting element which is in turn connected to the frame, or may be connected to the frame in a similar fashion to that described in FIGS. 30c-e. FIG. 31c shows a knitted net 705, which can be formed from a single fiber, and thus does not have the disadvantage of multiple loose ends. Such a net may be joined to the frame in a multitude of ways, many of which have been previously described in FIGS. 25-30.

FIG. 32a-e illustrates a number of fibre types that may be employed in the construction of a fiber net. A monofilament fiber 750 is shown in FIG. 32a. A multifilament twisted fiber 751 is shown in FIG. 32b. A multifilament braided fiber 752 is shown in FIG. 32c. A multifilament fiber with an outer sleeve 753 is shown in FIG. 32d. A multilayer fiber 754 is shown in FIG. 32e. Any of these fibers may be used to construct the net designs shown in FIGS. 33a-d. FIGS. 33a and 33b show how a porosity gradient may be created with either a knitted 756 or braided 757 design, which may be advantageous in efficiently balancing wrapped profile and effective particle retention. FIGS. 33c and 33d show a clot retrieval device constructed with axial fibers 758, which also create a similar porosity gradient. FIG. 33d illustrates a similar design to FIG. 33c, except that a stiffening element 759 is provided, which serves to control the wrapped configuration of the net during delivery and retrieval.

Now with reference to FIG. 34a-f there is shown a clot retrieval device 218 which comprises a frame assembly 225 and a catheter 211. The frame assembly 225 further comprises strut section 214 with eyelets 212, capture fibers 215, a fiber junction 217, an expansion cable 213, and a guidewire 210. The frame assembly 225 is shown in its expanded state in FIG. 34a and in its delivery state in FIG. 34b. The strut section 214 lies substantially parallel to the axis of the catheter 211 in the delivery configuration. The strut section 214 expands to a ring shape when it is not constrained. The strut section 214 is deployed from the catheter 211 by advancing the guidewire 210 relative to the catheter 211. In order to deliver the device 218 into very small vessels it is necessary that the profile (diameter) of the device is very small. In retrieving obstructive clots from the brain it is desired that the device can be delivered through a micro-catheter. Typical commercially available micro catheters have profiles of 1.2 F to 1.9 F (1 F=0.333 mm=0.013"). The inner lumen of a 1.9 F micro-catheter is approximately 0.016" (0.41 mm). In order for the clot retrieval device to fit into this space the cross-sectional area of the strut section needs to be very small. However in order to capture clot effectively larger strut sections are desired. The strut section 214 of FIG. 34 has a cross sectional area that can fit into a micro-catheter. The expansion cable 213 is a flexible yet strong cable and it is fastened to the strut section 214 at anchor point 223. The anchor point 223 is at the distal most portion of strut section 214. The other end of expansion cable 213 is fastened to the distal end 216 of catheter 211. The expansion cable is strong, flexible and very small in diameter. The cable may be manufactured from polymeric or metallic cable materials. Preferably the cable is made from polyester, nylon, olefin, fluoropolymer, stainless steel or other similar cables. The expansion cable may be monofilament or multifilament. PET, Nylon, UHMWPE, Kevlar and PEN fibers are especially preferred. When the strut section 214 is deployed it expands to form a ring. The strut section 214 is connected to the guidewire section 210 at the distal section 229 of guidewire. The strut section 214 and distal section 229 of guidewire are adapted such that the strut section 214 sits at an angle transverse to the axis of the vessel. In one embodiment the strut section 214 and/or/not the distal section of guidewire 210 have a preset shape that causes the strut section 214 to sit transverse to the axis of the vessel. In another embodiment the expansion cable 213 is tensioned by advancing the catheter 211 proximally relative to frame assembly 225. When the expansion cable is tensioned it causes the strut section 214 to move more transversely in the vessel. It will be appreciated that this mechanism allows the user to modify the shape of the strut section 214 as well as controlling the resistance of the strut section to collapse during clot capture. It will also be appreciated that this allows the device to be delivered through micro-catheters as the cross sectional area of the strut section can be reduced significantly. In another embodiment more than one expansion cable 213 is employed. With this embodiment the expansion cables are preferably attached to opposite sides of the strut section 214. Both cables are attached to the distal end of catheter 211 and both cables are tensioned by a proximal advancement of the catheter 211 relative to the frame assembly 225. With two cables the position of attachment 223 to the strut section can be varied. However some displacement relative to distal section 229 of guidewire is desired as this reduces the force required to bias the strut section 214.

In another embodiment the tensioning of the expansion cable 213 is controlled by a handle, at the user end. The handle comprises means for locking to the guidewire, means for locking to the catheter 211 and a mechanism to control fine axial motion of the catheter 211 and guidewire 210. In one embodiment the fine axial motion is controlled by a helical mechanism such as a thread or coil. In another embodiment the fine axial motion is achieved with a gear arrangement such as a rack and pinion. In one embodiment the guidewire locking mechanism comprises a pin vice. In another embodiment the expansion cable is fastened to the proximal end of catheter 211. In another embodiment the expansion cable is releasably attached to the proximal end of catheter. In yet another embodiment the expansion cable 213 can be released from catheter 211 and catheter 211 can be removed from the guidewire 210 leaving the frame assembly and the expansion cable behind. With this embodiment the strut section can be activated directly by the user by tensioning the expansion cable. In another embodiment the expansion cable has a grip section attached to its proximal end.

In the embodiment shown in FIG. 34a-b the strut section 214 is shown delivered inside the distal end 216 of catheter 211. The catheter 211 with strut section 214 collapsed are delivered to the target location through a procedural catheter. The lumen at the distal end 216 of catheter 211 is sized to accommodate the frame assembly 225 in its collapsed state.

With reference to FIG. 34c-f there is shown some detailed embodiments of the frame assembly 225 of the invention. FIG. 34c shows a frame assemble 225 comprising a strut section 214 and guidewire 210. The strut section 214 is ring shaped and is integral with the distal end 228 of guidewire 210. The guidewire 210 comprises a proximal section 226 and a distal section 228. The proximal and distal segments are joined at junction section 227. In one embodiment the proximal section at least partially comprises a tube and said tube engages with junction section 227 to connect the proximal 226 and distal 228 sections of the guidewire 210. The joint between the proximal 226 and distal 228 sections of the guidewire may be further reinforced by any of a variety of conventional joining techniques including screw joint, welding, soldering brazing, adhesive bonding, crimping, swaging or combinations of the above. The guidewire 210 extends from the strut section 214 back to the user in use and is thus much longer than depicted. The strut section 214 may be any of a variety of cross-sectional shapes including circular, elliptical, rectangular, square, polyhedral, and multifilament. Circular or rectangular are preferred. The strut section further comprises eyelets 212. The eyelets 212 are as described earlier in FIG. 30-33. The expansion cable 213 is connected to the strut section 214 at its distal end. An eyelet 223 may be used to effect cable attachment. The cross sectional area of the distal end of the guidewire 210 may be locally modified to improve the shaping of the frame by the expansion cables. The guidewire 210 may be flattened so as to create a directional bias for strut section 214 when expansion cable 213 is activated. A flattened cross section in this area has the effect of keeping the strut section 214 in plane during expansion. The strut section 214 of FIG. 34c may be cut from a hypotube. The shape may be cut from a small diameter tube and expanded or it may be cut directly from a large diameter tube.

FIG. 34d shows an alternative construction of the frame assembly 225. The guidewire 210 and frame assembly 214 are manufactured from a single piece of wire. The strut section 214 forms a ring shape and comprises eyelets 212 and an expansion cable 213 attachment eyelet 223. The strut section 214 is made from a wire that is looped and joined to itself. The joint area 219 is at the distal end of guidewire 210. A smooth transition 224 is effected between the joint area 219 and the distal end of the guidewire 210. The distal portion 229 of the joint area 219 may be locally thinned or flattened to create a bias for strut section expansion. FIG. 34e-f show segments of strut sections 214 of the invention wherein the strut sections 214 have either a circular or rectangular cross section.

The method of use of clot retrieval device 218 of FIG. 34a-f is highlighted in FIG. 35a-i. FIG. 35a shows a vessel 220 and an obstructive clot 221. The clot retrieval device 218 is shown in its collapsed state crossing the obstructive clot 221. The distal tip 216 of catheter 211 is advanced across obstructive clot 221 with strut section collapsed inside the lumen of the catheter distal tip 216. The guidewire extends proximally and is operably moveable relative to catheter 211 to deploy the strut section 214. The strut section 214 is deployed by advancing catheter 211 proximally while holding the guidewire 210 fixed (FIG. 35c-d). The strut section assumes its remembered ring shape in the vessel. The clot retrieval device is advanced proximally until its strut section 214 is adjacent the obstructive clot 221. At this point the catheter 211 is advanced proximally relative to the guidewire 210 until the expansion cable 213 is tensioned (FIG. 35e). This step can be controlled with a handle mechanism at the proximal end as described elsewhere. Increasing the tension in expansion cable 213 changes the angle that the strut frame 214 makes relative to the axis of the vessel 220. This in effect changes the size of the capture opening of the clot retrieval device 218. As the capture opening increases the strut frame 214 achieves better apposition with the walls of the vessel 220. It will be appreciated that these features allow the user to achieve very efficient clot capture. However overly tensioning the expansion cable 213 is not desirable as this will induce trauma to the vessel. Rather the expansion cable 213 is tightened to the point where the strut section 214 has achieved apposition with the vessel and the catheter 211 is then locked relative to the guidewire at the user end. The clot retrieval device 218 is now advanced proximally to capture obstructive clot 221 (FIG. 35f). With the obstructive clot captured the lock between catheter 211 and guidewire 210 is released. The guidewire is advanced proximally relative to catheter 211 and at least the proximal portion of strut section is drawn into the lumen at the distal end 216 of catheter 211 (FIG. 35g-h). This step reduces the diameter of the strut section and makes removal of the clot 221 and clot retrieval device 218 easier. The clot retrieval device 218 and clot 221 are removed from the body (FIG. 35i).

In another embodiment the lumen at the distal end 216 of catheter 211 is sized only to accommodate guidewire 210. With this embodiment the strut section 214 cannot be collapsed inside catheter 211. Instead, the frame assembly 225 and catheter 211 are delivered through the lumen of a micro catheter. The tip of the micro-catheter is placed across the obstructive clot. The strut section 214 is collapsed and while restrained in the collapsed state the frame assembly 225 and catheter 211 are advanced into the proximal lumen of the micro-catheter. The clot retrieval device is advanced through the lumen of the micro-catheter and deployed distal of the tip of the micro-catheter. When the device is deployed the micro-catheter is advanced proximally. Subsequently the clot retrieval device is advanced until the strut section is adjacent the obstructive clot. The catheter 211 is advanced proximally and expansion cable 213 is activated. When the frame section is expanded to the desired shape, the expansion cable 213 and catheter 211 are locked relative to guidewire 210. The clot retrieval device 218 is advanced proximally to capture the clot. The micro-catheter is again advanced until its distal tip engages with the strut section 214 of the clot retrieval device 218. The micro catheter is advanced further and partially collapses the strut section. The micro-catheter and clot retrieval device 218 are withdrawn from the vessel together.

Yet another embodiment is shown in FIG. 36a-b. The clot retrieval device 218 is the same as the clot retrieval device of FIG. 35. However in the embodiment shown in FIG. 36 the lumen of catheter 211 accommodates a separate crossing guidewire 222. The crossing guidewire 222 runs parallel the guidewire 210 of the clot retrieval device. The crossing guidewire 222 may sit side by side with the collapsed clot retrieval device. Alternatively catheter 211 has a separate lumen for crossing guidewire 222. The crossing guidewire is free to move axially and rotationally relative the clot retrieval device. The crossing guidewire 222 is preferably a conventional guidewire and its tip can be shaped to access target vessels. This allows the crossing guidewire 222 to be used in conjunction with catheter 211 to access difficult to reach locations by advancing the crossing guidewire 222 relative to the catheter 211 and torqueing it as necessary to achieve access. When the tip section of crossing guidewire 222 has accessed a side branch the catheter 211 can be advanced over the crossing guidewire. When the clot retrieval device 218 is delivered to the target location the crossing guidewire may be removed. Alternatively the crossing guidewire may be left in the target vessel.

FIG. 36a shows a crossing guidewire 222 with its distal tip across the capture fibers 215 of clot retrieval device 218. The capture fibers are arranged in a fashion that a small diameter device can be pushed through the gaps in the capture fibers 215. The ability of low profile devices to cross the capture fibers allows other devices to be used with the clot retrieval device.

Another embodiment of the invention is shown in FIG. 37a-e. FIG. 37a shows a conventional guidewire 230. The guidewire comprises a proximal end 231, a distal end 232 and a tip 234. The tip 234 is flexible and atraumatic to vessels. Many of the features of the clot retrieval device 250 of this embodiment are achieved by modifying the area 233 adjacent the tip 234 of conventional Guidewires 230. With reference to FIG. 37b there is shown a guidewire 233 which has been modified proximal of the tip in order to create clot retrieval device 250. The guidewire 233 comprises an inner shaft 235 and an outer shaft 236. The inner shaft and the outer shaft are fixed together. Proximal of the tip of the guidewire 230 the outer shaft 236 has substantially longitudinal cuts 238 so as to create strut elements 237. The strut elements 237 are cut so as to create ring elements 247. One or more ring elements may be created with strut elements 237. In the embodiment shown two ring elements 247 are created by cutting two pairs of strut elements 237 and connecting the strut elements 237 at their distal ends. In one embodiment the segment of the outer shaft 236 adjacent the tip 234 is made from an elastic, a super elastic or a shape memory material. Preferably said elastic material is nitinol or a spring steel. Most preferably the outer shaft 236 is made from nitinol. FIG. 37c shows the clot retrieval device 250 in its expanded state. It can be seen that a number of elements have been added to the modified guidewire of FIG. 37b to create the clot retrieval device 250. The strut elements 237 have a collapsed state and an expanded state. FIG. 37b shows the strut section 237 in it's as machined (laser cut) state. The strut section 237 is shown in its expanded state in FIG. 37c. In the expanded state the strut sections 237 form a capture frame 247. In the embodiment shown the capture frame 247 comprises two D-shaped elements. The capture frame comprises radial strut sections 246 and body strut sections 248. The body strut sections interface with the vessel wall in the expanded state and provide a line of apposition around the circumference of the vessel. The radial strut section 246 connects the body strut section to guidewire shaft 236. Eyelets 244 are provided on at least the body strut section 248 and capture fibers 241 are fixed to the capture frame 247 using said eyelets 244. The capture fibers 241 are fixed to collar 243 distally. Collar 243 is fixed to the distal portion of the guidewire. In another embodiment the distal eyelets are cut into the outer shaft 236 of the guidewire 230. This eliminates the need for collar 243 and reduces the distal profile of the device. When the strut section 237 is in the expanded state a recess area 240 is created in the wall of the guidewire. The integrity of the guidewire is maintained by the presence of connector elements 242. The connector element 242 is a portion of the outer shaft 236 that lies adjacent the recess area and connects the distal part 232 of the outer tube 236 with the proximal part 231 of the outer shaft 236. The connection between the proximal portion 231 and the distal portion 232 of the guidewire 230 is further reinforced with the inner shaft 235. In one embodiment the inner shaft 235 is fixed to the outer shaft 236. In one embodiment the connector element 242 is fixed to the inner shaft 235. When the strut section 237 is in the collapsed state it packs into the recess area 240. This keeps the delivery profile of the clot retrieval device 250 extremely low. Since the capture fibers are made from a highly oriented fiber such as Dyneema (UHMWPE), and since the recess space 240 is larger than the strut section the attachment of the capture fibers to the strut section 237 will not adversely impact the profile of the strut section 237 of the clot retrieval device 250 in the collapsed configuration.

The clot retrieval device 250 is shown in the delivery configuration in FIG. 37d. The delivery catheter 245 is of an extremely low profile. Preferably the delivery catheter is less than 2 F (0.66 mm). More preferably the delivery catheter profile is less than 1.9 F. Even more preferably the delivery catheter is less than 1.6 F.

FIG. 37e shows an end view of the device 250 in the expanded state. The view is as seen from distal of the expanded strut section 237. The inner core 235 is visible with two connector elements 242 diagonally opposite. The strut section 237 is shown expanded to from capture frame 247. The capture frame 247 comprises a double-D shape. The capture frame 247 further comprises radial strut sections 246 and body strut sections 248. The strut sections 237 are provided with eyelets 238 for capture fiber attachment.

In yet another embodiment the clot retrieval device 250 is delivered to the target site without the need for a delivery catheter. With this embodiment the inner shaft 235 and the outer shaft 236 are moveable relative to each other. The strut section 237 is connected to the inner shaft 235 in the delivery configuration and said connection restrains the strut section 237 in the collapsed state. Upon reaching the target site relative movement of the inner shaft relative to the outer shaft releases the connection and allows the strut section 237 to expand. In one embodiment the connection comprises a tether that is attached to both the strut section 237 and the inner shaft 235. In the collapsed configuration the tether is under tension as it restrains the strut section 237. The inner shaft 235 is either advanced or rotated to relax the tension in the tether and this allows the strut section 237 to expand. In another embodiment an engagement between the inner shaft 235 and the strut section 237 retains the strut section 237 in the collapsed state. The inner shaft 235 is either rotated or advanced to disengage with the strut section 237 and this allows the strut section 237 to expand. The engagement may be a frictional engagement, a snap engagement, a clip engagement feature, a hook engagement or other similar engagements.

Now with reference to FIGS. 38-39 there is shown another low profile clot retrieval device 280. FIG. 38a-b shows modifications to guidewire 260 necessary to create clot retrieval device 280 of FIG. 39a-b. The modified guidewire 260 comprises a tubular shaft 261 which has a proximal end 266 and a distal end, an outer surface and an inner lumen. The distal end of tubular shaft 261 comprises a strut section 267 and an expansion cable 265. The strut section is shown in the 'as cut' state in FIG. 38a-b. The strut section 267 comprises at least one pair of generally longitudinal struts 264 and a strut connection 268 at the distal end of longitudinal struts 264. Where the strut segment 267 comprises a single pair of longitudinal struts 264 then in the expanded configuration the axis of the outer shaft adjacent the strut section 267 will be offset relative to the axis of the vessel (as shown in FIG. 39a-b). However where the strut segment 267 comprises two pairs (or more) of longitudinal struts 264 then in the expanded configuration the axis of the outer shaft adjacent the strut section 267 will be generally coaxial with the axis of the vessel. In one embodiment the strut connection is a short strut like element. In a preferred embodiment the strut connection 268 has a curved aspect. The curved aspect helps to distribute stress as the strut section is expanded to from a ring. Preferably the strut connection has an inner curve and an outer curve wherein the inner curve has a smaller radius than the outer curve. Preferably the difference in radius of the inner curve versus the outer curve is less than the width of the strut sections 267. Preferably the strut connection comprises a strain relief feature. In another embodiment the strut connection 268 comprises an element that is curved in at least two dimensions.

The expansion cable is attached to the frame section 267 at attachment point 269 and extends proximally to the user. The expansion cable 265 enters the lumen of the tubular shaft 261 at port 262 and extends through the lumen back to the user. The expansion cable can be tensioned by the user at the proximal end of the guidewire shaft 261. In one embodiment the expansion cable is attached to a fine adjustment mechanism at the user end. This allows the user to control the level of tension in the expansion cable 265 and thus the resistance of the strut section 267 to collapse during clot capture. The port 262 position along the tubular shaft 261 may be varied. In one embodiment the distal opening of the lumen of the tubular shaft 261 is used as the port 262.

In the embodiment shown in FIG. 38 the eyelets 270 are shown along the length of strut section 267. Eyelets may also be placed at the distal end of the tubular shaft 261. The eyelets 270 may be created in a variety of configurations as previously described. Likewise, the attachment of the capture fibers 279 is as described earlier.

In another embodiment the width of struts 264 is sufficiently great that an expansion cable is not needed in order for the strut section 267 to effectively capture the obstructive clot.

The clot retrieval device 280 is shown assembled and in the expanded state in FIG. 39a-b. The capture fibers and the distal collar 282 have been added to FIG. 38 and the strut section 267 has been expanded. The strut section 267 is preferably made from an elastic material, a super elastic material or a shape memory material. The strut section 267 forms a ring in the expanded state and the ring shaped strut section 267 apposes the vessel in the expanded state. In use the expanded strut section 267 is advanced proximally to capture the clot. The expansion fiber 265 is used to add stiffness to the frame and prevent its partial collapse during clot capture. The large open mouth of the strut section in the expanded state makes this embodiment an effective clot capture device. The capture fibers are terminated at a distal junction 281 with a collar as previously described. The distal collar comprises eyelets for capture fiber attachment. In another embodiment the distal junction 281 is formed by the joining of the distal ends of the capture fibers 280 to each other. In one embodiment a knot arrangement is used, in another embodiment the capture fibers are bonded or welded together.

In the embodiment shown in FIG. 39 the distal junction 281 is free to move proximally as it is not constrained relative to the guidewire 261. In another embodiment at least one of the capture fibers has a bias. Preferably said bias generally pushes the distal junction 281 distal of the strut section. Preferably the biased capture fiber is elastic, super elastic or shape memory. Preferably said biased capture fiber is metallic. Preferably said capture fiber is nitinol, or stainless steel.

FIG. 39c shows the clot retrieval device 280 in the delivery configuration. The strut section 267 is shown in the collapsed configuration inside a pod 285 of delivery catheter 284. The guidewire shaft 261 extends proximally through the lumen of catheter 284. In one embodiment the catheter 284 and guidewire 261 are arranged in an over the wire fashion. In another embodiment the catheter 284 and guidewire 261 are arranged in a rapid exchange fashion. The catheter shaft is preferably made from a thin walled flexible material. Preferably the catheter is made from an olefin, nylon, a PEBAX, polyester, polyurethane or a fluoropolymer. The delivery catheter may be made from a combination of these materials. The catheter may be made with two or more layers and at least one of these layers comprise at least one of the above list of materials.

FIG. 40a-b shows a clot retrieval device 290 that is very similar to the clot retrieval device 280 of FIG. 39. The clot retrieval device 290 has a first difference in that the distal junction is connected to strut tip 287. The strut tip is created during the machining of the strut section 267. The strut tip is formed from a portion of the wall of the tubular shaft 261 that lies between longitudinal struts 264. The strut tip is designed to be mechanically similar to the core of a guidewire tip. The strut tip tapers distally and has an atraumatic element 287 at its distal end. The strut tip 287 provides a site upon which the distal junction 281 can be connected. In the embodiment shown a collar is used as the distal junction 281 and the collar has limited movement relative to the strut tip 287. In one embodiment the collar is fixed relative to the strut tip. A second difference between the clot retrieval device 280 of FIG. 39 and clot retrieval device 290 of FIG. 40 is that the distal end of the tubular shaft 261 has machined slots 286 to improve the trackability of the device. In one embodiment the slots run transverse to the axis of the tubular shaft and run only part of the circumference. In another embodiment pairs of transverse slots 286 are arranged on opposite sides of the tubular shaft 261. In another embodiment the slots 286 are arranged in a continuous helix along a portion of the distal end of the tubular shaft 261. In another embodiment the clot retrieval device comprises a supporting strut 288. The supporting strut 288 extends distally and substantially parallel of the axis of the tubular shaft 261 and comprises a restraining feature. The supporting strut 288 is configured to restrain the strut section 267 in the collapsed state during delivery. The restraining feature may comprise a tether arrangement, an interconnection between the supporting strut and the strut section 267, an interlock between the supporting strut and the strut section 267, or a coupling between the supporting strut 288 and the strut section 267. The restraining feature may be deactivated when the clot retrieval device 290 is at the site of the occlusion causing the strut section 267 to expand to its remembered expanded state. The deactivation may be brought about by means of a release cable, use of an inner core which may be advanced or retracted to free the strut section or advancement or retraction of an outer tubular member or a combination of these mechanisms. In another variant the restraining feature may be configured such that the strut section is firstly restrained to itself and secondly restrained to the supporting strut and that both restraints are decoupled either simultaneously or in series when the clot retrieval device 290 is at the site of occlusion. The clot retrieval device 290 is otherwise the same as clot retrieval device 280 and similar numbers shall have the same meaning for both devices.

Figure 43:
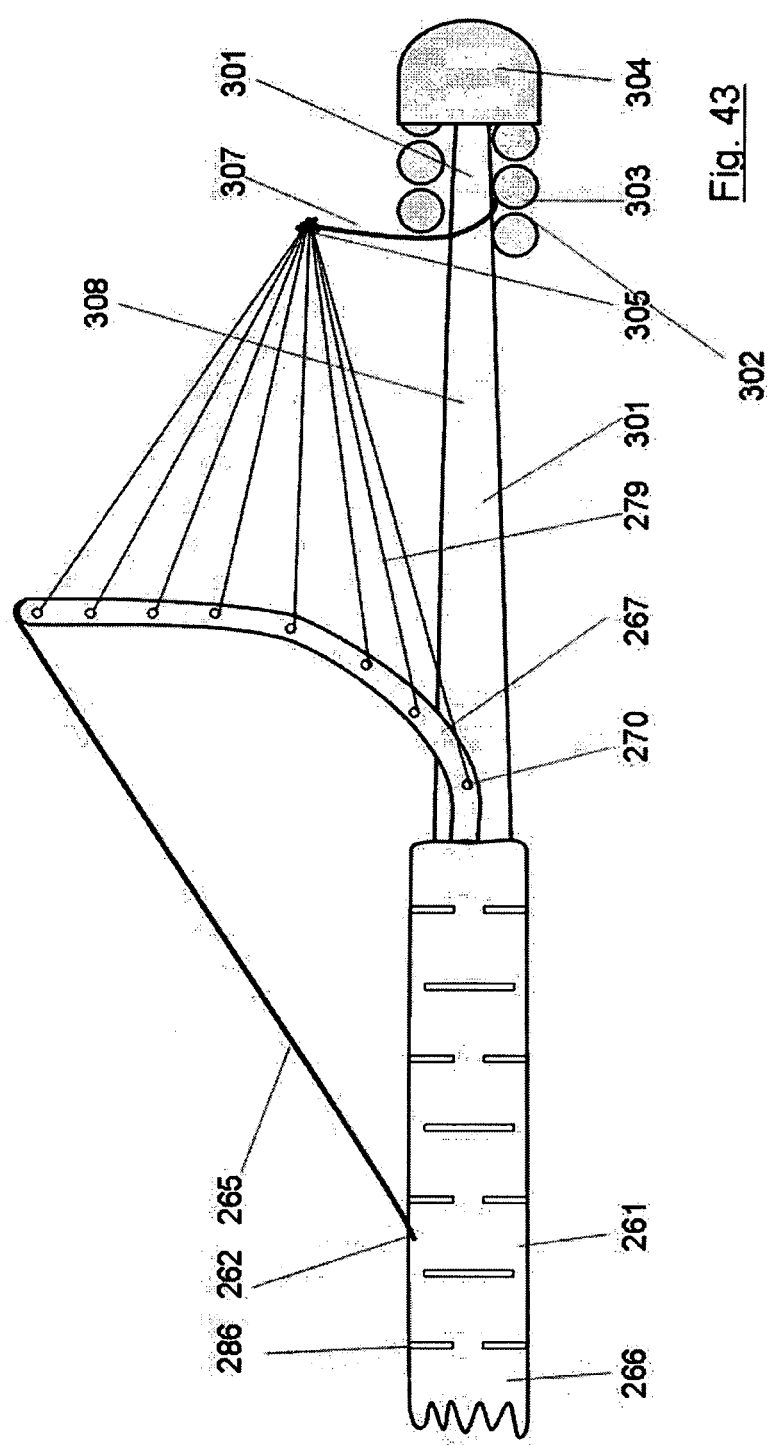

The clot retrieval devices of FIG. 41-43 are very similar to the clot retrieval devices shown in FIG. 39 and FIG. 40. With FIG. 41 the strut tip is cut substantially parallel to the longitudinal struts 264 of strut section 267. The longitudinal strut extends distal of the strut section and connects the tubular shaft proximally 261 with a distal segment of tubular shaft 291. The distal segment of the tubular shaft 291 is modified to make it atraumatic to vessels. The modification may comprise a spiral cut or slots as described previously. The distal tip 293 of the tubular shaft 291 is smooth soft and atraumatic. The distal junction 268 is connected to the distal shaft 291 as previously described.

FIG. 42a-b shows an inner core 301 adapted to from a guidewire like tip to the clot retrieval device 300. The inner core has proximal diameter that allows it to fit inside the lumen of the tubular shaft 261. The inner core 301 may be fixed relative to outer shaft 261 or it may be moveable relative to outer shaft 261. The distal portion of the inner core tapers distally and has an atraumatic tip 302. The atraumatic tip 302 comprises a rounded tip 304 and a coil segment 303. The rounded tip 304, the distal tip of the inner core 301 and the coils are preferably fastened together. The distal junction 268 is positioned proximal of the distal end of the core wire. In one embodiment the distal junction comprises a collar with eyelets for capture fiber attachment. The proximal end of inner core may be terminated distal of port 262. Alternatively the inner core extends proximally but provides clearance for the expansion cable. In yet another embodiment the inner core 301 and the expansion cable 265 are connected proximal of port 262 and the inner core 301 movement is used to tension the expansion cable 265. In another embodiment the inner core 301 distal end is shapeable.

In another embodiment the clot retrieval devices of this invention are adopted for use as embolic protection devices. With this embodiment the delivery catheter is removed after deployment and the guidewire is employed to deliver treatment devices. A greater number of capture fibers are employed and the capture fibers are arranged so as to create distal pores of less than 200 microns.

Another embodiment of the invention is shown in FIG. 44-46 wherein the clot retrieval device comprises a guidewire 330, a clot capture ring 320, and capture fibers 333. With reference to FIG. 44a there is shown a clot capture ring 320 of clot retrieval device 350. The clot capture ring is characterized in that it is cut from a tube and formed. The strut section 321 is shown in its as cut configuration and provides strong vessel apposition. The strut section is attached to the guidewire with a collar element 322. The collar element is cut from the same tube as the strut section 321 but it is formed into a collar after cutting. The collar element 322 comprises at least one finger element 323. The finger element is formed into a tubular segment such that it can be attached to the guidewire. Preferably one or more finger elements wrap around the guidewire diameter and make a secure attachment. Multiple finger elements are preferred over one wide finger element to ensure the device is trackable while distributing forces to the guidewire. The collar element may be welded or bonded to the guidewire. Alternatively the collar element may be a force fit with the guidewire. FIG. 44b shows a view of the collar element 322 and a portion of the strut section 321 in the as cut configuration. In this embodiment pairs of fingers 323 are located on either side of member 326. The collar element 322 is connected to the strut section by a connector element 325. The connector element 325 has a curved interface with the strut section 321. The connector element 325 is designed such that it distributes strain loads it has to endure during collapse and delivery. The curved interface helps to distribute the loads. Preferably the connector element comprises strain distributing features as described. The eyelets 327 are shown on the strut section and these function as previously described.

FIG. 44c shows the clot retrieval device 350 in the expanded configuration mounted on guidewire 330. The guidewire comprises a shaft, a proximal end 331, a distal end 332 and a tip 329. The capture ring 320 is connected to the guidewire adjacent the distal end 332. The capture ring is secured to the guidewire 330 using collar element 322. Capture fibers 333 are attached to the strut section using eyelets 327 and are attached to the distal end of the guidewire at distal attachment point 328. Distal attachment point comprises at least one eyelet in the guidewire. The guidewire may be tubular in this area or at least one micro-hole may be drilled through the wall of the guidewire to create an attachment. Alternatively the capture fibers may be bonded or mechanically fastened to the guidewire.

The clot retrieval device 350 is shown in the collapsed configuration inside the distal lumen of delivery catheter 335 in FIG. 44*d*. The clot retrieval device is deployed by advancing the guidewire 330 relative to the delivery catheter 335.

FIG. 45*a-c* shows a variation in the embodiments shown in FIG. 44. This time the connector element 340 is longer than previously described. This allows better strain relief to be achieved in the area of bending during collapse and it also allows the offset of the guidewire position to be controlled. In the embodiment shown the guidewire position is close to the strut frame but there is still a gap between the guidewire and the wall. This partial offset feature allows for a large capture opening.

Another variation of the embodiments described in FIG. 44-45 is shown in FIG. 46. This time an expansion cable 341 is employed to help frame expansion. The device is shown with the expansion cable in the tensioned configuration with the frame expanded into a ring. The expansion cable allows the angle of the ring to the vessel to be controlled by the user. In the embodiment shown the angle is greater than 90'. This makes the resistance of the frame to collapse very difficult during clot capture. The guidewire shaft has a port 342 and an inner lumen 343 through which the expansion cable runs. The proximal end of the expansion cable exits the lumen 343 at the proximal end of the guidewire 331.

With reference to FIG. 47*a-d* there is shown another clot retrieval device 360 which is constructed from a guidewire 364, capture fibers 365 and a fiber anchor 367. The guidewire comprises a proximal end 363, a distal end 368, a distal tip 369 and a frame section 361. The proximal end of the guidewire 363, comprises a tube section with an expansion cable 362 extending from the frame section 361 to a point proximal and external of the guidewire 364. The proximal end of the guidewire 363, in use, is external of the patient. The expansion cable is attached to the distal end of the distal frame section 371. The distal tip 369 has an atraumatic tip to prevent vessel injury. The frame section 361 further comprises a distal frame section 371 and a proximal frame section 370. The frame section 361 has an expanded configuration and a collapsed configuration. In the collapsed configuration the frame section comprises an elongate element. In the expanded configuration the proximal frame section 370 and distal frame section 371 forms a ring that orients transverse to the axis of the vessel.

In a first embodiment the frame section 361 is a substantially elongate element in its relaxed state. When the expansion cable 362 is tensioned the shape of frame section 361 changes from its relaxed elongate state to its expanded ring configuration. This shape change is controlled by compression slots 375 in the tubular wall of the guidewire shaft 364. The compression slots 375 allow the shaft 364 to compress preferentially on one side and this allows the shaft to adopt a curved configuration. Where all the slots are on one side of the tube then the tube will bend into a simple curve when loaded in compression. Complex curves can be achieved by using multiple slots and moving the position of the slots around the axis of the tube. FIG. 47*d* shows a section 364 of a guidewire shaft with slots designed to create both simple and complex curves. In the center of the slotted section all the slots 375 are in a line and this construction will allow for a simple curve when the shaft is compressed. At both the proximal and distal end of the section, the slot position changes as we move along the shaft. This creates a curve in two dimensions (Y & Z). In order to create the ring shown in FIG. 47*a* two complex curves ('a' in FIG. 47*d*) at either end of a simple curve ('b' in FIG. 47*d*) are required.

In another embodiment the frame section 361 is ring shaped in its relaxed state. In this configuration the device is collapsed for delivery using a delivery catheter 372. The collapsed device is stored in the lumen of the delivery catheter and advanced across the obstruction. It is deployed distal of the obstruction and opposes the vessel wall. The expansion cable may be employed in order to improve the stiffness of the device in the expanded configuration. Since the expansion cable effectively locks the distal end of the distal frame section 371 to the proximal end of the proximal frame section it greatly increases the resistance of the frame section to collapse.

In another embodiment two or more expansion cables are used. The first expansion cable is used as described above. The second expansion cable is attached to the frame section 361 between the distal frame section 371 and the proximal frame section 370. The expansion cable extends proximally until it enters the lumen of the guidewire 364 proximal of the frame section through a port in the wall. This second expansion cable when tensioned prevents the frame from collapsing distally when capturing clot.

With each of these embodiments the capture fibers 365 are attached to the frame section 361 at the proximal end and to the fiber anchor 367 at the distal end. Preferably the capture fibers 365 are slidably attached to the fiber anchor 367. In one embodiment the capture fibers 365 are connected to the compression slots 375. In another embodiment the frame section 361 comprises eyelets as previously described and the capture fibers are attached to the eyelets. In either scenario the attachment points of the capture fibers 365 are spaced apart along the length of the frame section 361. Preferably the capture fibers 365 are evenly spaced apart along the frame section 361. The fiber anchor 367 at the distal end provides for secure fiber attachment to the distal shaft 368 while allowing the capture fibers 365 to slide at the fiber anchor. The ability of the fibers to slide is important in allowing the frame section to collapse efficiently. Fibers attached to the distal part of distal frame section 371 require very little slack in order to allow that portion of the frame to move from an expanded state to a collapsed state. However, fibers at the proximal end of the proximal section of the frame 370 require considerable slack in order to allow that portion of the frame to collapse unconstrained. In order to minimize the amount of capture fiber 365 slack it is preferred that fibers connected to the distal section of the distal frame section 371 be looped through the fiber anchor and connected back to the proximal end of the proximal frame section 370. By taking this approach throughout the frame the level of capture fiber slack can be minimized. It will be appreciated that in order to allow for this fiber slack to be distributed the fibers need to slide through the fiber anchor with ease. Preferably the size of the opening on the distal anchor for fiber attachment is a clearance fit for the capture fibers. In one embodiment the anchor 367 comprises a ring with an inner diameter. The inner diameter is larger than the diameter of the guidewire and one or more attachment legs 376 fix the ring relative to the guidewire.

FIG. 48*a* shows a clot Retrieval device 800 in the expanded state. FIG. 48*b* shows the same device loaded into a microcatheter 812 for delivery to the target site. Frame 804 is similar to frame 361 in FIG. 47a, but in this case is not formed from the guidewire. Frame 804 expands to a generally circular shape in end view, but elongates and twists into a longitudinal element when collapsed for delivery and retrieval as shown in FIG. 48b. The proximal 807 and distal 806 ends of the frame 804, are mounted to tubular elements 808 and 805 respectively. These elements are mounted on the guidewire 809, allowing rotation and translation of the frame relative to the guidewire. Stops 801, 802 and 803 are positioned on the guidewire to allow the user to apply a push or pull force to appropriate elements of the device to facilitate its advancement or withdrawal. Stop 803 prevents the frame from elongating during clot retrieval, and together with stop 802 acts against the frame during clot capture and retrieval. Stop 802 apposes element 805 during device advancement through and from a delivery microcatheter 812 as shown in FIG. 48b. Apposing the distal end of the frame in this way keeps the frame 804 in tension rather than compression as would be the case if force were applied to element 807 to facilitate advancement. Keeping the frame in tension reduces the lateral forces applied to the lumen of the microcatheter, and thus reduces the force required to advance the clot retrieval device through the microcatheter. In one embodiment of this design a delivery assist catheter 811, with proximal element 810, may be used to transmit a push force to stop 801, which in turn transmits a push force through the guidewire to stop 802 and thus to the distal end of the frame. This method of advancement eliminates the need for that element of the guidewire proximal of stop 801 to transmit push, and therefore permits the use of a more flexible wire. In another embodiment (not shown) stop 801 is not present and delivery assist catheter 811 is not required as push force can be transmitted through the guidewire to stop 802 and thus to the frame.

FIGS. 49a-b illustrate another clot retrieval device 850 similar to device 360 shown in FIG. 47a, but employing an additional tether element 853. Frame 851 is configured to tend to adopt a curved profile and appose the vessel wall when released from the constraints of the delivery microcatheter 854 shown in FIG. 49b. When placed in tension the tether element 853 provides additional integrity to the frame, and acts against the tendency of the frame to elongate when meeting resistance such as during clot capture. Once the target clot has been successfully captured the tether element may be relaxed so as to allow the frame to elongate again for ease of retrieval. Alternatively the tether element may be kept in tension to maintain the frame and capture net 852 in a more preferential configuration for retention of captured clot during retrieval from the body.

FIGS. 50a-c show another clot retrieval device 870. FIG. 50a shows the device in its deployed state. Frame 871 is connected to guidewire 875 by element 873, which allows the frame to rotate and translate relative to the guidewire. Distal capture net 872 is connected to frame 871 and is also connected at its distal end to collar 874. FIG. 50b shows the device encapsulated in microcatheter 878 just prior to deployment from the microcatheter. To effect deployment the guidewire 875 on which the device is mounted is fitted with a stop 877, which apposes collar 874 when the microcatheter is retracted, preventing the clot retrieval device from retracting with the catheter. This configuration also holds the capture net in tension, with the associated benefits described previously in relation to FIG. 48a and b. In the embodiment shown a second guidewire stop 876 is provided, which apposes proximal frame element 873 during retraction and retrieval of the device. Such a design allows the length of guidewire protruding distal to stop 877 to be limited or eliminated. In another embodiment (not shown) only one guidewire stop is provided which acts in both deployment and retrieval.

FIG. 51a shows a clot retrieval device 890 configured in such a way that it may be used in conjunction with a variety of suitably sized guidewires 891. The device 890 has a shaft 892 which is sized to be able to advance or retract over guidewire 890. FIG. 51b shows a similar device 894 mounted on a shaft 895 which has a guidewire exit port 896, so that the device may be used with any suitably sized short length guidewires.

FIG. 52a shows a clot retrieval device 2010. The clot retrieval device 2010 comprises guidewire 2020 and a clot capture basket 2011. The clot capture basket comprises a frame 2012, and a net 2015. The clot retrieval device 2010 has an expanded state for engagement and capture of clots and a collapsed state for delivery through the vasculature. The frame 2012 comprises a collar 2023 for mounting the frame 2012 on the guidewire 2020, a hoop 2014 composed of struts 2009 and at least one connector element 2013 to connect the collar 2023 and the hoop 2014. Preferably the frame 2012 is made from a superelastic or shape memory material. The frame further comprises a bifurcation point 2022 where the connector 2013 splits to form two struts 2009. In this embodiment the connector 2013 has greater width than the struts 2009. In another embodiment the connector 2013 has greater width over most of its length than tha strut 2009 except in the region just proximal to the bifurcation. In this area the width of the connector 2013 is significantly reduced. This allows the connector 2013 to hinge at this point and so respond to vessel asymmetry or asymmetry in the guidewire access.

In one embodiment the clot capture basket 11 is fixed to the guidewire. In another embodiment the clot capture basket 2011 is slidable on the guidewire 2020.

FIG. 53 shows another clot retrieval device 2010 which is almost identical to the clot retrieval device of FIG. 2002 except that the connector comprises a pair of parallel struts 2025. The pair of parallel struts 2025 allows the connector to contribute strongly to the engagement force of the device while providing greater lateral flexibility. The capture basket 2011 further comprises a basket mounting tube 2019. The basket mounting tube 2019 extends from the proximal end of the basket 2011 to the distal end of the net 2015. The net is attached to the mounting tube 2019. The mounting tube may be fixed relative to the collar 2023 or it may slide relative to the collar 2023. The distal end of mounting tube is configured to engage with the stop 2017.

FIG. 54 shows a frame 2012 of FIG. 52 as a sub-component. The frame 2014 comprises three segments; the proximal segment comprises a collar 2023 which is a short tube for mounting on the guidewire 2020, the intermediate segment comprises two connectors 2013 and the distal segment comprises a plurality of struts that form a hoop 2014. Ideally there are four struts that each form a quadrant of the hoop. The frame 2014 is preferably made from a super elastic or a shape memory alloy.

FIG. 55 shows another clot retrieval device 2030, which is similar to the clot retrieval devices of FIGS. 52-54, and similar numerals are used to describe similar elements. The clot retrieval device is shown with a microcatheter 2031. The clot retrieval device is delivered through the lumen of a microcatheter and is moveable relative to the microcatheter 2031. The movement of the clot retrieval device 2030 relative to the microcatheter is effected by the movement element 2019. In one embodiment movement element 2019 comprises a tubular element which is slidable over the guidewire. The tubular element may be fixed to the collar 2023 of the capture basket 2011 and can thus control movement of the capture basket 2011 in both directions relative to the guidewire or the microcatheter. Alternatively the tubular element 2019 is separate fro the capture basket and advances the capture basket as a bumper tube. With this embodiment the bumper tube can advance the clot capture basket 2011 but can not withdraw the basket. In this embodiment the capture basket is withdrawn by engaging the step at the distal end of the guidewire.

Alternatively the movement element 2019 is a guidewire. With this embodiment the capture basket 2011 if fixed to the guidewire 2019 and thus movement of the capture basket is controlled by the guidewire. Forward and backward movement of the capture basket 2011 are controlled by the guidewire 2019.

FIG. 56 shows another clot retrieval device 2040, which is similar to the clot retrieval devices of FIGS. 52-55, and similar numerals are used to describe similar elements. With this embodiment the capture basket 2011 is deployed from a reception space 2046 at the distal end 2047 of the microcatheter 2041. The guidewire 2020 is moveable relative to the capture basket 2011. The microcatheter is connected to the capture basket 2011 by a telescoping tube 2048 which is fixed the collar 2023. The telescoping tube 2048 further comprises a stop 2043 which engages with a microcatheter stop 2044 to prevent complete separation of the basket 2011 and the microcatheter 2041. A bumper tube (not shown) is used to deploy the capture basket 2011 from the reception space 2046. The capture basket 2011 is removed at the end of the procedure by withdrawing the guidewire 2020 so as to engage the guidewire distal stop 2017 with the body tube 2021. This forces the telescoping tube 2048 and the capture basket back into the reception space for removal.

FIG. 57 shows another clot retrieval device 2060, which is similar to the clot retrieval devices of FIGS. 52-56, and similar numerals are used to describe similar elements. With this embodiment a bumper tube 2048 is used to advance the clot capture basket 2011 over the guidewire. The bumper tube further comprises a rapid exchange feature. The bumper tube comprises a lumen with a proximal exit port 2061 from which the guidewire exits. A control element 2063 is connected to the proximal end of bumper tube 2048. The control element 2063 extends proximal of the microcatheter 2041 and out of the patient. The user controls the position of the clot capture basket 2011 using a control handle 2065 at the proximal end 2064 of the control element 2063.

FIG. 58 shows another clot retrieval device 2080, which is similar to the clot retrieval devices of FIGS. 52-57, and similar numerals are used to describe similar elements. With this embodiment a tether 2042 extends between the collar 2023 of the capture basket 2011 and the microcatheter 2041. The tether 2042 has a relaxed configuration as shown in FIG. 58a and a taut configuration as shown in FIG. 58b. The proximal end of the tether 2042 extends proximally. In one embodiment the tether 2042 is controlled by the user. In another embodiment the proximal end of the tether 2042 is connected to the microcatheter. The tether 2042 allows the capture basket 2011 to move relative to the microcatheter within a certain limit.

FIG. 59a-h shows the devices as described in FIGS. 52-58 and similar numerals are used to describe similar elements. FIG. 59a-h also shows some of the methods of use of the clot retrieval devices described in the earlier drawings. These figures also disclose a clot debonding device 2091, which may be used in conjunction with the clot retrieval designs described herein. The clot debonding device is designed to assist in the removal of obstructions from a vessel by providing an abutment surface which may be used to appose one side of the obstruction so that a force may be applied to the other side of the obstruction without said force being transmitted to the vessel in which the obstruction is placed. It therefore enables a clot retrieval device or other similar device to more effectively engage and capture clot or other such vessel obstructions.

It will be appreciated that such a device also has applications beyond its use with the clot retrieval device described herein. Such a clot debonder may be effectively used to aid the disengagment and removal of vessel obstructions in conjunction with other clot retrieval devices or with thrombectomy devices or aspiration devices.

FIG. 59a shows a guidewire 2020 with a step 2017 at its distal end. The tip of the guidewire is placed in a vessel (not shown) distal of an occlusive clot (not shown). In FIG. 59b a microcatheter 2041 is advanced over the guidewire 2020 until its tip is also distal of the occlusive clot. A clot retrieval basket 2011 is advanced through the lumen of the microcatheter 2041 in FIG. 59c. In FIG. 59c the clot capture basket 2011 is being advanced using the distal end of a clot debonding device 2091. The clot debonding device 2091 comprises an expandable engagement element 2093 at its distal end. The expandable engagement element 2093 has an expanded configuration for engaging with a clot and debonding the clot and a collapsed state for delivery through a microcatheter. The expandable engagement element 2093 comprises a number of struts or wire segments 2094. In one embodiment the clot debonding element is cut from a hypo tube and the struts are expanded to the desired expanded shape and heat treated to remember that shape. Preferably the expandable engagement element 2093 is made from a shape memory alloy, a super elastic alloy. In one embodiment the expandable engagement element 2093 is made of Nitinol. The clot debonding device 2091 comprises a lumen extending from its distal end. The expandable engagement element 2093 comprises a channel or a lumen in both the expanded and collapsed states. In one embodiment the struts or wires of the expandable engagement element 2093 assume a collapsed state which maintains a channel (or lumen) over the distal end of the expandable engagement element 2093. In another embodiment the expandable engagement element 2093 comprises a collar 2095 and said collar comprises a lumen.

The clot debonding device 2091 further comprises a proximal shaft 2096. The proximal shaft 2096 is connected to the expandable engagement element 2093 and facilitates advancing and withdrawing the expandable engagement element 2091. In one embodiment the proximal shaft is connected directly to the expandable engagement element 2093. In another embodiment the proximal shaft 2096 is connected to the collar 2095 which in turn is connected to the expandable engagement element 2093. In one embodiment the expandable engagement element is integral with the collar 2095. In another embodiment the expandable engagement element is integral with the proximal shaft 2096. The proximal shaft 2096 comprises a lumen 2099 which is connected with the lumen or channel of the expandable engagement element and extends proximally to an exit port 2100. In FIG. 59 the exit port is shown at the proximal end of the shaft 2096. However, it will be appreciated that the exit port could be distal of the proximal end of the shaft 2096. The exit port may be towards the distal end of the shaft 2096. In one embodiment the exit port comprises an opening in the sidewall of the shaft. In another embodiment the shaft 2096 comprises a construction of at least two elements. The distal element comprises a tubing with a lumen and the proximal end comprises a connector element to connect the user with the distal lumen.

In one embodiment (not shown) the clot capture basket is advanced with a bumper tube which is removed upon deployment. When the clot capture basket 2090 is deployed distal of the occlusive clot then the clot debonding device is advanced over the proximal section of the guidewire 2020 and through the lumen of the microcatheter 2041 and it is deployed proximal of the occlusive clot. With this embodiment the rest of the procedure is as described in FIG. 59a-59h.

The clot debonding device 2091 comprises an engagement surface. The engagement surface is configured to engage with clot and comprises an expanded state and a collapsed state. The engagement surface is configured to achieve a low profile in the collapsed state and it is further configured to be highly trackable such that it can easily navigate the pathway to tortuous neurovascular vessels. In one embodiment the engagement surface comprises a substantially tubular structure for advancement through the vasculature in the collapsed state. Preferably in the collapsed state the tubular structure comprises a short tubular structure. The engagement surface in one embodiment comprises a cylindrical surface in the collapsed state.

In the expanded state the engagement surface is preferably configured for the transmission of force or pressure to the clot. The engagement surface may comprise an annular surface. With this embodiment the engagement surface has an outer diameter and an inner diameter. In one embodiment the outer diameter is sized to be similar to the diameter of the vessel or to the diameter of the clot and the inner diameter is similar in diameter to the dimensions of the guidewire 2020.

In one embodiment the engagement surface comprises a flared surface. In another embodiment the engagement surface comprises a plurality of struts said struts configured to apply pressure to the clot over a substantial portion of the cross-section of the vessel. In one embodiment the engagement surface of the clot debonding device is configured to apply an axial displacement to the entire body of the clot. Preferably the engagement surface of the clot debonding device is configured to displace the clot without fragmenting the clot.

In one embodiment the engagement surface comprises a plurality of elongate struts. In the delivery configuration the elongate struts are substantially aligned with the axis of the vessel while in the expanded configuration the struts project radially outward from the axis of the vessel. In one embodiment the struts are connected to each other. In one embodiment the struts of the engagement surface comprises an outer ring member and a plurality of radial struts connected to said outer ring member. In another embodiment the strut arrangement of the engagement surface comprises a plurality of cells. In another embodiment the engagement surface comprises an outer ring member and an inner ring member.

The inner ring member may be connected to or separate of the outer ring member. In one embodiment the outer ring member is connected to the collar 2095 by a plurality of radial struts. In one embodiment the outer ring member comprises a plurality of zig zag strut elements. In one embodiment the struts are cut from a tube and the tube comprises an 'as cut' configuration and an expanded configuration.

In another embodiment the engagement surface comprises a plurality of wires. The wires comprise a collapsed state and an expanded state and in the collapsed delivery state the wires are substantially aligned with the axis of the vessel. In the expanded state the wires project radially outwardly of the axis of the clot debonding device. In this or in any of the other embodiments the engagement surface may expand concentrically about its axis, or may take up an eccentric configuration.

FIG. 59d shows the clot capture basket 2090 in its deployed state distal of the occlusive clot. The deployment is effected by advancing the clot debonding device 2091. The expandable engagement element 2093 abuts the collar 2023 of the basket 2090 and deploys the basket 2090. The expandable engagement element 2093 remains in the collapsed state at the distal end of the microcatheter 2041. The microcatheter 2041 is withdrawn until its distal end is proximal of the occlusive clot.

With reference to FIG. 59e, the system further comprises a tether 2092 which limits the movement of the clot retrieval basket relative to either the microcatheter 2041 or the clot debonding device 2091. In the embodiment shown the tether 2092 is attached to the clot debonding device 2091. As the microcatheter 2041 is withdrawn the distance between the clot engagement device and the microcatheter 2041 increases until all the slack in the tether 2092 is removed.

With reference to FIG. 59f, the tip of the microcatheter is proximal of the occlusive clot, the basket 2090 is deployed distal of the clot and the expandable engagement element 2093 is deployed. This is achieved by advancing the proximal shaft 2096 relative to the microcatheter 2041. Upon deployment the struts or wires 2094 of the expandable engagement element 2093 expanded to their remembered expanded state. The guidewire is now moved proximally until the step engages with the clot capture basket 2090 and then both the basket 2090 and guidewire 2020 move proximally until the basket frame 2012 engages with the distal side of the occlusive clot. At this point the clot debonding device is advanced until the expanded struts 2094 engage with the proximal side of the occlusive clot. With the occlusive clot engaged at both ends the clot debonding device is advanced while holding the capture basket 2090 steadfast. This breaks the bonds between the clot and the vessel without applying any force to the distal vessels. This arrangement ensures that most of the forces of clot debonding are contained in the segment of the vessel where the clot is adherent. This is usually a segment of a few millimeters and the forces applied are shear forces rather than tensile forces. It may be necessary to adjust the position of the basket 2090 during the debonding step to continue to keep vessel tensile forces very low.

It will be appreciated that in order to remove an occlusive clot from a vessel that two sets of forces need to be dealt with. Firstly there is a blood pressure drop that lodges the clot in the vessel. More importantly, the presence of an initial clot results in platelet activation and inflammation at the site. During the inflammatory response a complex series of reactions are occurring including the cross linking of blood soluble fibrinogen into fibrin (a blood insoluble macromolecule that is the main component of clot) and the formation of platelet bridges. These reactions result in the progressive formation of chemical bonds between the clot and the vessel wall. Over time the clot becomes more rigidly fixed or bonded at the site of occlusion. In order to break these bonds a force needs to be applied and as the inflammation process progresses these bonds become more difficult to break. Furthermore, where a mechanical force is applied to the clot there is automatically a reaction force which is equal in size but acting in the opposite direction. With conventional devices this force is absorbed by the vessel. It is an object of this invention to prevent significant force being applied to the vessel during clot debonding.

In another embodiment the clot debonding device 2091 is deployed in the clot and a first portion of the clot is debonded from the vessel wall. It will be appreciated that this step could be repeated until all the clot has been debonded and captured in the clot capture basket 2090.

In an alternative method both the clot capture basket 2090 and the clot debonding device 2091 are both engaged with the occlusive clot as described above. Then the clot capture basket 2090 is pulled proximally while the clot debonding device is held steadfast. Which ever method is employed one element (either the clot debonding device, or the clot capture basket) is held steadfast and this element absorbs the reaction forces of clot debonding and thus prevents force being transmitted to the vessel.

With reference to FIG. 59*g*, after the clot has been debonded and captured in the clot capture basket 2090 the clot debonding device 2091 can be collapsed. This is achieved by pulling the device proximally such that the microcatheter tip collapses the struts 2094 of the expandable engagement element 2093. As the clot debonding device 2091 is pulled proximally the tether 2092 becomes taut and the clot capture basket is also drawn proximally.

In FIG. 59*h* the clot debonding device is withdrawn to the point where at least a portion of the frame 2012 of the clot capture basket 2090 is inside the distal end of the microcatheter 2041. The clot debonding device 2091 and the clot capture basket 2090 can be withdrawn from the patient at this point. Because of the tether between the clot debonding device 2091 and the capture basket 2090 the clot capture basket 2090 can be removed without removing the Guidewire 2020. The guidewire 2020 is left behind (not shown) for a final angiogram before also being removed if no further intervention is required.

FIGS. 60*a-b* show end views of the clot debonding devices of this invention. The clot debonding element 2110 of FIG. 60*a* comprises a lumen 2113 sized to accommodate a guidewire, a plurality of struts or wires 2111 which have an expanded state and a collapsed state, and a tubular element 2095. In the expanded state the struts or wires 2095 project at least partially radially outward with respect to the tubular member. In the collapsed state the struts or wires 2095 assume a somewhat tubular configuration when collapsed inside a microcatheter. In the collapsed state the struts or wires are substantially aligned with the longitudinal axis of the microcatheter and comprise a channel or lumen that can accommodate a guidewire. The pattern of the expandable portion 2112 can be varied greatly. In the figures shown two patterns are shown. However it will be appreciated that a myriad of other patterns are possible. These patterns may comprise some of the following elements: Single struts, bifurcated struts, bifurcated wires, struts or wires with curved segments, curved struts or wires with points of inflection, struts or wires connected with tethers, struts or wires that are configured to create a closed cell, a combination of at least one open and one closed cell, closed cells with multiple curved segments, struts or wires configured to create a cell with multiple curved segments, struts or wires configured to create a planar cell, and/or struts or wires configured to create a non-planar cell.

The pattern of the clot debonding element 2110 of FIG. 60*a* has overlapping wires. The use of crossing wires provides for better engagement with the clot. In this case the wires over lap to achieve the cross. However where the struts are cut from hypotube, junctions can be created without the need to cross the wires, as shown in the pattern in FIGS. 62*a-c*.

FIG. 60*b* shows a pattern with no cross overs. This pattern may be manufactured from a hypotube. In the fully expanded state the clot debonder may comprise an outer rim 2116. With the embodiment shown in FIGS. 60*a* and 60*b* the outer rim 2116 comprises a plurality of curved segments. Each pair of radially projecting struts 2095 meet at their distal end and this region is characterised in that it comprises a curved atraumatic region. This curved region is preferably curved in the circumferential direction.

FIG. 61 *a-c* show another clot debonder pattern 900 which features multiple longitudinal slots 902 which enable the distal end of tubular element 901 to expand radially outward to create an abutment surface as shown in side view in FIG. 61*b* and in end view in FIG. 61*c*. Tubular element 901 is preferentially cylindrical, and may be made from either a metallic or polymeric material, but preferentially metallic, and most preferentially nitinol.

In one embodiment the engagement surface comprises an axial strut segment 903, a curved strut segment 904 and a radial strut segment 905. With this embodiment the engagement surface 906 is connected to a tubular member 901 at its proximal end. The axial strut section 903 defines the point of connection between the engagement surface 906 and the tubular member 901. In the expanded configuration the struts of the axial segment 903 are oriented substantially parallel to the axis of the clot debonding device. However the axial segment 903 is preferably extremely short. Immediately distal of the axial segment 903 comprises the curved segment 904. In the expanded state this segment is curved such that the struts assume a radial configuration. The radial section 905 preferably comprises most of the engagement surface 906 and provides a high area surface for the transmission of force to the clot.

It will be appreciated that the clot debonding element is designed to transmit force over the entire surface of the clot and this ensures that the clot is debonded in one piece. The clot debonder is further configured such that the clot does not snag on its surface and it is further configured to push the clot into the opening of the clot capture basket.

The clot debonder engagement surface is configured such that upon withdrawal it disengages from the clot without snagging, or fragmenting the clot and without removing the clot from the capture basket.

In another embodiment the engagement surface 906 of FIG. 61*a-c* comprises a plurality of wires. With this embodiment the engagement surface 906 comprises an axial wire segment 903 which is connected to the collar 2095. Preferably the connection between the wire and the collar is configured so as to orient the wire parallel to the axis of the clot debonding device. While the connection point with the collar is aligned with the axis of the vessel the segment of the wire immediately distal of the collar (curved wire segment) comprises a curve in the expanded configuration. The wire is curved so as to orient the wire radially and create an abutment surface. The intermediate segment of the wire is distal of the curved segment and is characterised in that the wire is substantially radial relative to the axis of the clot debonder. This plurality of radial wire segments is configured to deliver and distribute pressure to one face of the clot. The distal segment of the wires comprises a second curved segment 908. This second curved segment 908 defines an outer rim 2116 of the clot engagement surface 906. The curved segment 908 also presents an atraumatic surface to the vessel. This second curved segment 908 is curved in the circumferential direction.

In one variation the engagement surface 906 comprises a plurality of first wires and a plurality of second wires and said first and second wires are connected at the distal most point. In the embodiment described above said first and second wires may be integral and may comprise a single formed wire. With this embodiment the wire engagement surface comprises a plurality of petal like engagement elements. Each petal comprises a radial clot engagement element and a circumferential clot engagement element. Because the engagement surface 906 comprises radial and circumferential engagement elements force is transmitted to the surface in a manner similar to that of a piston.

In another embodiment the struts or wires of the engagement surface 906 comprise an articulation region. With this embodiment the engagement surface 906 assumes the expanded state by an articulation of the struts or wires about the articulation region.

FIG. 62*a-e* shows side views of a number of clot debonding devices. These devices could be employed with any of the clot retrieval devices described in FIG. 52-59 or FIG. 79-80. FIG. 62*a* shows a colt debonding device 2126 wherein the device comprises an expandable portion 2112, a collar 2095 connecting said expandable portion 2112 with the tubular member 2114. In use the tubular member 2114 extends from the site of occlusion proximally through the vasculature and extends outside the patient such that it can be manipulated by the user. The tubular member comprises a lumen 2113 extending over its entire length.

FIG. 62*b* shows an alternative configuration of the clot debonding device 2115. This device also comprises an expandable section 2112, struts or wires 2111, a connecting collar 2095 and a tubular member 2114. In this case the tubular member 2114 is shorter than in FIG. 62*a*. In use the tubular member extends from the site of occlusion only partially through the vasculature. In this case the user controls clot engagement using the connector element 2117. The connector element 2117 if fixed to the tubular member 2114 at an attachment point 2119. The lumen 2113 of the tubular member 2114 is sized to accommodate a guidewire. This embodiment has the advantage of providing single user wire exchange (a rapid exchange feature).

FIG. 62*c* shows an alternative configuration which is similar to that of FIG. 62*b* except that no collar is employed. The tubular member 2114 is connected directly with the expandable section 2112. The proximal end of tubular member 2114 comprises an exit port 2120 to facilitate rapid exchange delivery. FIG. 62*d* shows an alternative configuration which is similar to that of FIG. 62*b* except that no tubular member is employed. In this case the connector element 2117 is connected directly with the collar 2095.

FIG. 62*e* shows yet another configuration which is similar to that of FIG. 62*d* except that no collar is employed. The connector element 2117 is connected directly with the expandable section 2112.

FIGS. 63, 64 and 65 show three designs of clot debonders that can alter the shape of their distal ends to create an abutment surface to facilitate capture of clot into a clot retrieval device. FIG. 63*a* shows device 910 with an inflatable distal cuff 911, which is shown in the inflated state in FIG. 63*b*. Inflation may be with a liquid, such as saline or contrast media or a mix of the two, or may be with a gas such as carbon dioxide. The inflating media is injected from the proximal end of the device through a lumen (not shown) in the wall of tube 912.

FIG. 64*a* shows device 920 with an expandable section 924, which is shown in the expanded state in FIG. 64*b*. The expandable section 924 is formed from wound or braided elements, which form a structure which tends to increase in diameter when compressed, and reduce in diameter when elongated. Expansion of this cuff is effected by advancement of outer member 921 relative to inner member 922, which is connected to the distal end of the expandable section by means of distal cuff 923. Retraction of outer member 921 reverses the effect by elongating the expandable section and reducing it to its original diameter.

FIG. 65*a-b* show a clot debonder 915 with an expansile distal cuff 916 of a similar design to that of device 920, but in which no actuation is required to effect the expansion. The expansile distal cuff is configured to preferentially adopt the expansile state depicted in FIG. 65*b*, and is held in the unexpanded state by the constraint provided by the lumen of the catheter (not shown) through which it is advanced to the target site.

FIGS. 66 and 67 show two examples of self-expanding clot debonders that expand upon advancement past the end of an outer constraining surface such as that of the lumen of a microcatheter 926. Debonder 925 is shown in the constrained state in FIG. 66*a*, in the partially expanded state in FIG. 66*b*, and in the fully expanded state in end view in FIG. 66*c*. FIG. 67*a* and *b* show a similar design to FIG. 66, wherein an additional element is employed to create a greater abutment surface area and perimeter.

FIGS. 68*a-c* show views of another clot debonding device, which could be employed with any of the clot retrieval devices described herein. FIG. 68*a* shows a side view of the debonder 950 in its unexpanded state. FIG. 68*b* shows a side view of the debonder in a partially expanded state. FIG. 68*c* shows an end view of the debonder in its fully expanded state. Device 950 contains multiple expandable portions 952, created by the addition of a plurality of longitudinal slots 953 to tubular member 954. An actuating element 951 is attached to the distal end of member 954, and runs within member 954 from the distal to the proximal end of the device. Retraction of the actuating element applies a compressive force to expandable portions 952 defined by slots 953. Controlled buckling of areas 956 is facilitated by the presence of crease lines 956. Tubular member 954 may be configured in a similar manner to member 954 in FIGS. 62*a* or FIG. 62*c*, such that the debonder is used as an "over the wire" or "rapid exchange" device. In one embodiment the clot debonder lumen 955 is sized so that it may be advanced through a pre-placed access microcatheter to the target site. In another embodiment the clot debonder lumen 955 is sized so that it may be backloaded onto a microcatheter prior to insertion of the microcatheter, and can then be advanced over the microcatheter to the target site.

FIGS. 69*a* and 69*b* show the clot debonder 950 depicted in FIG. 68 in use in conjunction with a clot retrieval device 961 and microcatheter 963. FIG. 69*b* shows the clot debonder advanced past the end of the microcatheter 963 and the actuator 951 retracted to expand the expandable distal area 952, which is shown in abutment with clot 962 just prior to retrieval of the clot into the clot retrieval device 961.

FIGS. 70-73 show the clot retrieval device of FIGS. 12 and 13 being used in conjunction with clot retrieval assist device 119. With this embodiment the clot retrieval device 91 is delivered across the obstructive clot and deployed as previously described. The clot retrieval assist device is delivered over the proximal section of the guidewire 92 until its distal tip is proximal of the obstructive clot. The clot retrieval assist device comprises a catheter 116 with a lumen, an expandable element(s) 117 wherein the expandable element 117 comprises a wire frame 118 that defines an inner space 132. The wire frame 118 has a remembered expanded configuration and a collapsed delivery configuration. In one embodiment the wire frame 118 defines an inner space 132 that has a paddle like expanded shape. In another the wire frame defines a circular inner space 132. In another embodiment the wire frame 118 defines a kidney shaped inner space 132. With the clot retrieval assist device 91 proximal of the occlusive clot 103 the expandable element 117 is deployed. The size of the expanded element 117 is controlled by the degree of deployment. When the expandable element 117 is at least partially deployed it is advanced against the occlusive clot 103 and forces the clot 103 into the clot retrieval device 91. In another embodiment the clot retrieval assist device 119 is held stationary with its expandable element 117 in the at least partially expanded state and clot retrieval device 91 is advanced proximally to capture the occlusive clot 103.

In another embodiment the clot retrieval device comprises a frame 94 a proximal collar 93 and a distal collar 90 and two connector elements 99. The proximal 93 and distal 90 collars are associated with the guidewire 92 and the connectors 99 connect the proximal and distal collars to the Guidewire 92. At least one of said proximal and distal collars is slidable relative to the guidewire 92.

FIG. 74 shows an alternative clot retrieval assist device 110. With this device 110 the expandable element 113 comprises a helical element and is attached to inner shaft 112. In the delivery configuration inner shaft 112 is retracted and both the inner shaft and expandable element 113 are housed inside the lumen of delivery catheter 111. With this embodiment advancement of the clot may be achieved by pushing as described with FIG. 19 or alternatively by rotation. With the rotation embodiment the expandable element 113 is either deployed in the body of the occlusive clot 103 or it is advanced in its expanded state until it is in the body of the occlusive clot. The inner shaft is rotated and the helical frame acts like an auger to move the occlusive clot into the clot retrieval device 91.

An alternative clot retrieval assist device 110 is shown in FIG. 75. With this device the expandable element 113 comprises multiple coil elements. An inner helical element 115 and outer element 114 are both connected to inner shaft 112 and rotation of inner shaft 112 rotates both coil elements.

Yet another clot retrieval assist device 120 is shown in FIG. 76*a* and FIG. 76*b*. The clot retrieval device is delivered over the proximal end 127 of guidewire 92. The clot retrieval assist device comprises an inner shaft 122, an expandable element 123 and a delivery catheter (not shown).

The expandable element 113 comprises a wire formed into a spiral. The spiral has a gradually increasing diameter. An inner coil of the spiral 124 has a smaller diameter than outer coil 125. In the expanded configuration the clot retrieval assist device 120 is advanced distally over the guidewire 92 and the expandable element 113 engages the obstructive clot 100 and forces the clot 100 into the clot retrieval device 91. Alternatively the clot retrieval device 91 may be advanced proximally while the clot retrieval assist device 120 remains stationary and limits the proximal movement of the clot 100 and thus forces the clot into the clot retrieval device 91.

An alternative clot retrieval system is shown in FIG. 77*a-b*. The clot retrieval system 2160 comprises a clot capture basket 2154 mounted on a guidewire 2162. The clot retrieval system 2160 further comprises a clot debonding element 2161 mounted on the guidewire 2162. The clot capture basket 2163 comprises a frame 2164 a collar 2168 mounted on the guidewire 2162 and at least one connector 2167 connecting the collar 2168 with the frame 2164. The frame 2164 comprises one or more pairs of struts 2166. In one embodiment the struts comprise a series of net attachment points 2175. The attachment points 2175 comprise a change in the cross section of the strut 2166 and provide a location for the attachment of a fibre of the net 2163 to the frame 2164. In one embodiment the attachment point 2175 comprises an eyelet. In another the point of attachment comprises a recess or a nick, or a reduction in the strut dimension.

The collar 2168 may be fixedly mounted on the guidewire 2162. In the embodiment shown the collar 2168 is rotationally mounted on the guidewire 2162. This is achieved by the use of a proximal stop 2170 and distal stop 172 mounted on either side of the collar 2168. The capture net 2163 is connected to the guidewire distal of the collar 2168. In one embodiment a distal collar 2169 is employed to provide an attachment point between the net 2163 and the guidewire 2162.

The frame 2164 has a collapsed state and an expanded state and in the expanded state (shown) comprises a hoop 2165. The hoop 2165 allows the frame to effectively engage with the outer bonded surface of the clot. The hoop 2165 is created by constructing that portion of the frame with at least one pairs of struts 2166. The pairs of struts form segments of a hoop 2165 in the expanded state but lay adjacent each other and parallel to the guidewire in the collapsed state.

The clot debonding element comprises at least one strut 2173 and it also has an expanded configuration (shown) and a collapsed configuration. In the collapsed state the struts 2173 of the clot debonding element 2161 lie adjacent and substantially parallel to the guidewire 2162. The at least one strut 2173 comprises a strut distal end 2178 and a strut proximal end 2177. At least one of said distal 2178 and proximal 2177 strut ends is slidable relative to the guidewire 2162. Furthermore, at least one of said distal strut ends 2178 or proximal strut ends 2177 are restricted from rotational motion relative to the guidewire 2162. The ability of at least one strut end to slide relative to the guidewire provides a first means of allowing the clot debonding element to assume an expanded configuration when not constrained. On the other hand preventing at least one strut end from rotating relative to the guidewire 2162 allows torque transmitted from the proximal end of the guidewire to be applied to the occlusive clot 2001 and debond said clot from the vessel wall 2002.

In the collapsed state both the basket and the clot debonding element collapse inside a microcatheter 2041 (not shown) in a fashion similar to that described earlier.

It will be appreciated that the clot debonding element as described with reference to FIG. 77 could equally be employed with any of the baskets described in any of the other clot capture basket devices of the invention.

With reference to FIG. 78 there is shown a schematic representation of a vessel with an acute occlusion with a piece of thrombus (clot). The clot may be embolic in origin or it may be thrombotic. Embolic occlusions of cerebral vessels are responsible for between 20% and 35% of all strokes. Embolic strokes are most frequently of cardiogenic origin with carotid and aortic disease also being major contributors. Thrombotic occlusions occur when thrombus forms in the vessel usually in response to underlying vascular disease. Thrombotic occlusions are responsible for between 45% and 50% of all strokes. The acute occlusion 2001 of FIG. 78*a* is fixed in the vessel 2002 primarily by the forces of blood pressure acting on the proximal side and force fitting it in a tapered vessel 2002.

However, the presence of the clot causes an inflammatory response at the site and platelets 2003 in the area are activated (FIG. 78*b*). The inflammatory response results in the formation of more thrombus and bonds 2004 start to form between the occlusive thrombus 2001 and the vessel wall 2002. Over time the bonding forces between the clot and the vessel wall become more significant and make removal of the clot more difficult. FIG. 78*c* shows a schematic representation of the occlusive clot 2001 after a time has passed with further thrombus deposited at the site and bonds 2004 formed between the clot 2001 and the vessel wall 2002.

FIG. 79*a*-I shows a method of using the devices of this invention. FIG. 79*a* shows a vessel 2002 with an occlusive clot 2001. The vessel 2002 has a proximal end 2005 and a distal end. The procedure to treat the occlusion per this invention comprises firstly gaining access to the vasculature. This is carried out by conventional means (the Seldenger technique). A guide catheter is placed in a large vessel proximal of the occlusion (not shown). A procedural guidewire 2020 is advanced through the guide catheter or sheath and is advanced across the occlusive clot 2001 as in FIG. 79*b*. When the guidewire 2020 is in place a microcatheter is advanced over the guidewire until the tip of the microcatheter is across the occlusion (FIG. 79*c*). As can be seen with reference to FIG. 79*d* the guidewire 2020 is now removed thus leaving the microcatheter 2041 in place with its tip 2047 across the occlusion 2001 and an empty lumen prepared for device advancement. With reference to FIG. 79*e*, the clot retrieval device 2130 is advanced in its collapsed state through the lumen of the microcatheter 2041 until it is deployed out of the distal end of the microcatheter 2041. Upon deployment the frame 2012 of the clot retrieval device 2130 causes the basket to expands. In the embodiment described in FIG. 79*e*, the frame 2012 is attached to the wire. The frame may be fixedly attached to the guidewire or it may be rotationally attached to the guidewire or it may be attached such that it has at least some rotational and/or some translational freedom.

With reference to FIG. 79*f*, the microcatheter is withdrawn to the proximal side of the occlusion 2001 when the clot capture device 2130 is deployed. The clot capture device 2130 is manipulated to ensure that it is fully engaged with the vessel wall. The clot debonding device 2091 is now advanced through the lumen of the microcatheter and its distal end is advanced distal of the microcatheter tip 2047. When the distal portion of the clot debonding device exits the microcatheter 2041 the expandable segment 2112 expands to its remembered expanded state. In the expanded state the clot debonding device 2091 is advanced until it engages with the proximal portion of the clot 2001 (FIG. 79*h*). At this point the clot capture basket 2130 is advanced proximally while the clot debonding device 2091 is held steadfast. This action breaks the bonds between the clot and the vessel and the clot 2001 is forced into the capture basket 2130. The clot debonding device 2091 can now be removed. This is achieved by withdrawing it back into the lumen of the microcatheter 2041. In its expanded state the clot debonding device has a conical aspect and this facilitates the retrieval of the device 2091 into the microcatheter 2041 (FIG. 79*i*). The clot debonding device 2091 can be fully withdrawn through the lumen of the microcatheter or it can be advanced a sufficient distance proximally to allow recovery of the clot capture basket 2130.

The clot capture basket recovery steps are described with reference to FIGS. 79*j* and 79*k*. The microcatheter distal end 2047 is engaged with the frame 2012 of the capture basket 2130. The guidewire is pulled proximally to force the proximal section of the frame 2012 into the lumen of the microcatheter. As the proximal section of the frame enters the microcatheter the frame struts 2009 collapse and the mouth of the basket closes. This allows the basket to be withdrawn from the vessel without the frame engaging with the vessel wall. The capture basket 2130, the microcatheter 2041 and the guidewire 2020 are removed together. The capture net 2015 scaffolds the clot during removal and prevents fragments from embolizing. The capture basket 2130, the microcatheter 2041 and the guidewire 2020 are withdrawn through the lumen of the guide catheter or sheath and removed from the patient. The net allows the clot to deform and change shape as it is pulled into the guide catheter or sheath without allowing particles or fragments to embolize.

FIG. 80*a-m* shows another method of using the devices of this invention. FIG. 80*a* shows a vessel 2002 with an occlusive clot 2001. The vessel 2002 has a proximal end 2005 and a distal end. The procedure to treat the occlusion per this invention comprises firstly gaining access to the vasculature. This is carried out by conventional means (the Seldenger technique). A guide catheter is placed in a large vessel proximal of the occlusion (not shown). A procedural guidewire 2020 is advanced through the guide catheter or sheath and is advanced across the occlusive clot 2001 as in FIG. 80*b*. When the guidewire 2020 is in place a microcatheter is advanced over the guidewire until the tip of the microcatheter is across the occlusion (FIG. 80*c*). As can be seen with reference to FIG. 80*d* the guidewire 2020 is removed thus leaving the microcatheter 2041 in place with its tip 2047 across the occlusion 2001 and an empty lumen prepared for device advancement. With reference to FIG. 80*e*, a special clot retrieval guidewire 2142 is advanced through the microcatheter until its distal tip is distal of the microcatheter 2041. The clot retrieval guidewire 2142 has a stop 2144 at its distal end. The stop 2142 limits the movement of the clot capture basket 2140 on the wire and prevents the clot capture device 2140 from sliding off the distal end of the guidewire 2142.

The clot retrieval device 2140 is advanced over the guidewire 2142 in its collapsed state through the lumen of the microcatheter 2041 until it is deployed out of the distal end of the microcatheter 2041. Upon deployment the frame 2012 of the clot retrieval device 2140 causes the basket to expand. In the embodiment described in FIG. 80*f*, the capture basket 2140 is slidable on the clot capture guidewire 2142.

With reference to FIG. 80*g*, the microcatheter 2041 is withdrawn to the proximal side of the occlusion 2001 when the clot capture device 2140 is deployed. The clot capture device 2140 may be manipulated to ensure that it is fully engaged with the vessel wall 2002. The clot debonding device 2091 is now advanced through the lumen of the microcatheter 2041 and its distal end is advanced distal of the microcatheter tip 2047. When the distal portion of the clot debonding device 2091 exits the microcatheter 2041 the expandable segment 2112 expands to its remembered expanded state. In the expanded state the clot debonding device 2091 is advanced until it engages with the proximal portion of the clot 2001 (FIG. 80*i*). At this point the clot capture guidewire 2142 is advanced proximally until the stop 2144 engages with the capture basket 2140. In one embodiment the stop 2144 engages with either the collar 2023 of the capture basket 2140. In another the stop 2144 engages with a tube extending from the proximal end of the basket. Further withdrawal of the guidewire 2142 causes the clot capture basket 2140 to advance proximally. The guidewire 2142 is advanced proximally until the capture basket engages with the distal end of the occlusive clot 2001. With the clot debonding device 2091 held steadfast the basket is withdrawn proximally until the clot is debonded and enters the basket.

The clot debonding device 2091 can now be removed. This is achieved by withdrawing it back into the lumen of the microcatheter 2041. In its expanded state the clot debonding device has a conical aspect and this facilitates the retrieval of the device 2091 into the microcatheter 2041 (FIG. 80*j*). The clot debonding device 2091 can be fully withdrawn through the lumen of the microcatheter or it can be advanced a sufficient distance proximally to allow recovery of the clot capture basket 2130.

The clot capture basket recovery steps are described with reference to FIGS. 80*k* to 80*m*. The microcatheter distal end 2047 is engaged with the frame 2012 of the capture basket 2140. The guidewire is pulled proximally to force the proximal section of the frame 2012 into the lumen of the microcatheter 2041. As the proximal section of the frame enters the microcatheter the frame struts 2009 collapse and the mouth of the basket closes. This allows the basket 2140 to be withdrawn from the vessel without the frame 2012 engaging with the vessel wall 2002. In this embodiment the capture basket 2140 and the microcatheter 2041 are removed together. The guidewire is left in the vessel until the very end of the procedure. This has the advantage of allowing the physician carry out final imaging steps prior to loosing access to the vessel. The capture net 2015 scaffolds the clot during removal and prevents fragments from embolizing. The capture basket 2140, the microcatheter 2041 and the clot 2001 are withdrawn through the lumen of the guide catheter or sheath and removed from the patient. The net allows the clot 2001 to deform and change shape as it is pulled into the guide catheter or sheath without allowing particles or fragments to embolize.

It will be appreciated that the various features illustrated and/or described herein may be used as appropriate with any of the devices, methods or systems described.

The invention is not limited to the embodiments hereinbefore described which may be varied in detail.

The invention claimed is:

1. A clot removal device for restoring blood flow to a vessel occluded by an obstructive clot, the device having an expanded deployed configuration, and a retracted delivery configuration in which it may be advanced across said obstructive clot, the device comprising:
    an expandable clot retrieval portion configured for deployment on a distal side of the clot, the clot retrieval portion having a plurality of struts forming at least one hoop;
    an expandable portion configured for deployment on a proximal side of the clot, the expandable portion having a plurality of struts and a proximally tapering portion at a proximal end of the expandable portion, and the expandable portion being connected to the clot retrieval portion by a plurality of connecting elements;
    a clot receiving space between the clot retrieval portion and the expandable portion; and
    a longitudinally-extending member extending through the clot receiving space and coupled to the clot retrieval portion, wherein a central axis of the longitudinally-extending member is located along a central axis of both the clot retrieval portion and the expandable portion, wherein
    the clot removal device includes a clot retrieval configuration during withdrawal of the expandable clot retrieval portion into a catheter that is smaller than the expanded deployed configuration of the expanded clot removal device, the clot retrieval configuration maintaining the clot receiving space between the clot retrieval portion and the expandable portion.

2. The clot removal device of claim 1, wherein the clot receiving space in the clot retrieval configuration corresponds to a length of the plurality of connecting elements from a proximal-most end to a distal-most end.

3. The clot removal device of claim 1, wherein the clot retrieval portion includes a distally tapering distal end portion.

4. The clot removal device of claim 1, wherein the plurality of struts of the expandable portion are formed by a distal end portion of a tubular member, the plurality of struts defining openings through the expandable portion between the plurality of struts.

5. The clot removal device of claim 1, wherein the expandable portion is connected to the clot retrieval portion by two connecting elements.

6. The clot removal device of claim 1, wherein the expandable portion includes a circumferential zig zag structure, and the plurality of connecting elements are coupled at a base of the zig zag structure.

7. The clot removal device of claim 6, wherein the plurality of connecting elements are connected to a proximal-most portion of the clot retrieval portion.

8. The clot removal device of claim 1, wherein the longitudinally-extending member extends distally beyond the distal end of the clot retrieval portion.

9. A clot removal device for restoring blood flow to a vessel occluded by an obstructive clot, the device having an expanded deployed configuration, and a retracted delivery configuration in which it may be advanced across said obstructive clot, the device comprising:
    an expandable clot retrieval portion configured for deployment on a distal side of the clot, the clot retrieval portion having a plurality of struts forming at least one hoop;
    an expandable portion configured for deployment on a proximal side of the clot, the expandable portion having a plurality of struts and a proximally tapering portion at a proximal end of the expandable portion, and the expandable portion being directly connected to the clot retrieval portion by a plurality of connecting elements;
    a clot receiving space between the clot retrieval portion and the expandable portion; and
    a longitudinally-extending member extending through the clot receiving space and coupled to the clot retrieval portion, wherein a central axis of the longitudinally-extending member is located along a central axis of both the clot retrieval portion and the expandable portion, wherein
    the clot removal device includes a clot retrieval configuration during withdrawal of the expandable clot retrieval portion into a catheter that is smaller than the expanded deployed configuration of the expanded clot removal device, the clot retrieval configuration maintaining the clot receiving space between the clot retrieval portion and the expandable portion.

10. The clot removal device of claim 9, wherein the clot receiving space in the clot retrieval configuration corresponds to a length of the plurality of connecting elements from a proximal-most end to a distal-most end.

11. The clot removal device of claim 9, wherein the clot retrieval portion includes a distally tapering distal end portion.

12. The clot removal device of claim 9, wherein the expandable portion includes a plurality of struts formed by a distal end portion of a tubular member, the plurality of struts defining openings through the expandable portion between the plurality of struts.

13. The clot removal device of claim 9, wherein the expandable portion is connected to the clot retrieval portion by two connecting elements.

14. The clot removal device of claim 9, wherein the expandable portion includes a circumferential zig zag structure, and the plurality of connecting elements are coupled at a base of the zig zag structure.

15. The clot removal device of claim 14, wherein the plurality of connecting elements are connected to a proximal-most portion of the clot retrieval portion.

16. The clot removal device of claim 9, wherein the longitudinally-extending member extends distally beyond the distal end of the clot retrieval portion.

* * * * *